(12) United States Patent
Subbian et al.

(10) Patent No.: US 8,778,652 B2
(45) Date of Patent: Jul. 15, 2014

(54) PENTOSE FERMENTATION BY A RECOMBINANT MICROORGANISM

(75) Inventors: Ezhilkani Subbian, Mountain View, CA (US); John H. Grate, Los Altos, CA (US); Catherine M. Cho, Redwood City, CA (US); Benjamin Mijts, Belmont, CA (US); Jeanne Bonomo Benoit, Menlo Park, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 13/530,311

(22) Filed: Jun. 22, 2012

(65) Prior Publication Data

US 2013/0004998 A1 Jan. 3, 2013

Related U.S. Application Data

(60) Provisional application No. 61/503,304, filed on Jun. 30, 2011.

(51) Int. Cl.
*C12N 9/90* (2006.01)

(52) U.S. Cl.
USPC .......................................................... 435/233

(58) Field of Classification Search
USPC ................................... 435/183, 233; 530/350
See application file for complete search history.

(56) References Cited

U.S. PATENT DOCUMENTS

| | | | |
|---|---|---|---|
| 4,486,553 A | 12/1984 | Wesch | |
| 5,605,793 A | 2/1997 | Stemmer | |
| 5,811,238 A | 9/1998 | Stemmer et al. | |
| 5,830,721 A | 11/1998 | Stemmer et al. | |
| 5,834,252 A | 11/1998 | Stemmer et al. | |
| 5,837,458 A | 11/1998 | Minshull et al. | |
| 5,928,905 A | 7/1999 | Stemmer et al. | |
| 6,096,548 A | 8/2000 | Stemmer | |
| 6,117,679 A | 9/2000 | Stemmer | |
| 6,132,970 A | 10/2000 | Stemmer | |
| 6,165,793 A | 12/2000 | Stemmer | |
| 6,180,406 B1 | 1/2001 | Stemmer | |
| 6,251,674 B1 | 6/2001 | Tobin et al. | |
| 6,277,638 B1 | 8/2001 | Stemmer | |
| 6,287,861 B1 | 9/2001 | Stemmer et al. | |
| 6,287,862 B1 | 9/2001 | delCardayre et al. | |
| 6,291,242 B1 | 9/2001 | Stemmer | |
| 6,297,053 B1 | 10/2001 | Stemmer | |
| 6,303,344 B1 | 10/2001 | Patten et al. | |
| 6,309,883 B1 | 10/2001 | Minshull et al. | |
| 6,319,713 B1 | 11/2001 | Patten et al. | |
| 6,319,714 B1 | 11/2001 | Crameri et al. | |
| 6,323,030 B1 | 11/2001 | Stemmer | |
| 6,326,204 B1 | 12/2001 | delCardayre et al. | |
| 6,335,160 B1 | 1/2002 | Patten et al. | |
| 6,335,198 B1 | 1/2002 | delCardayre et al. | |
| 6,344,356 B1 | 2/2002 | Stemmer | |
| 6,352,859 B1 | 3/2002 | delCardayre et al. | |
| 6,355,484 B1 | 3/2002 | Patten et al. | |
| 6,358,740 B1 | 3/2002 | Patten et al. | |
| 6,358,742 B1 | 3/2002 | Stemmer | |
| 6,365,377 B1 | 4/2002 | Patten et al. | |
| 6,365,408 B1 | 4/2002 | Stemmer | |
| 6,368,861 B1 | 4/2002 | Crameri et al. | |
| 6,372,497 B1 | 4/2002 | Stemmer | |
| 6,376,246 B1 | 4/2002 | Crameri et al. | |
| 6,379,964 B1 | 4/2002 | delCardayre et al. | |
| 6,387,702 B1 | 5/2002 | Stemmer | |
| 6,391,552 B2 | 5/2002 | Stemmer | |
| 6,391,640 B1 | 5/2002 | Minshull et al. | |
| 6,395,547 B1 | 5/2002 | Stemmer | |
| 6,406,855 B1 | 6/2002 | Patten et al. | |
| 6,406,910 B1 | 6/2002 | Patten et al. | |
| 6,413,745 B1 | 7/2002 | Patten et al. | |
| 6,413,774 B1 | 7/2002 | Stemmer | |
| 6,420,175 B1 | 7/2002 | Stemmer | |
| 6,423,542 B1 | 7/2002 | Crameri et al. | |
| 6,426,224 B1 | 7/2002 | Crameri et al. | |
| 6,436,675 B1 | 8/2002 | Welch et al. | |
| 6,444,468 B1 | 9/2002 | Stemmer et al. | |
| 6,455,253 B1 | 9/2002 | Patten et al. | |
| 6,479,652 B1 | 11/2002 | Crameri et al. | |
| 6,482,647 B1 | 11/2002 | Stemmer | |
| 6,489,146 B2 | 12/2002 | Stemmer et al. | |
| 6,506,602 B1 | 1/2003 | Stemmer | |
| 6,506,603 B1 | 1/2003 | Stemmer | |
| 6,519,065 B1 | 2/2003 | Colbourne et al. | |
| 6,521,453 B1 | 2/2003 | Crameri et al. | |
| 6,528,311 B1 | 3/2003 | delCardayre et al. | |
| 6,573,098 B1 | 6/2003 | Stemmer | |

(Continued)

FOREIGN PATENT DOCUMENTS

| | | |
|---|---|---|
| EP | 0 137 280 B1 | 3/1992 |
| WO | 93/03159 A1 | 2/1993 |

(Continued)

OTHER PUBLICATIONS

Altschul, S.F., et al., "Gapped BLAST and PSI-BLAST: a new generation of protein database search programs," Nucleic Acids Res., 25(17):3389-3402 [1997].
Amore, R., et al., "The fermentation of xylose—an analysis of the expression of *Bacillus* and *Actinoplanes* xylose isomerase genes in yeast," Appl. Microbiol. Biotechnol., 30:351-357 [1989].
Blaiseau, P-L., et al., "Primary structure of a chitinase-encoding gene (chi1) from the filamentous fungus *Aphanocladium album*: similarity to bacterial chitinases," Gene, 120:243-248 [1992].
Boel, E., et al., "Two different types of intervening sequences in the glucoamylase gene from *Aspergillus niger*," EMBO J., 3:1581-85 [1984].
Botstein, D., et al., "Strategies and Applications of in Vitro Mutagenesis," Science, 229(4719):1193-1201 [1985].
Brat, D., et al., "Functional Expression of a Bacterial Xylose Isomerase in *Saccharomyces cerevisiae*," Appl. Environ. Microbiol. 75(8):2304-2311 [Feb. 13, 2009].
Brigham, J.S., et al., "Hemicellulases: Diversity and Applications," in Handbook on Bioethanol (C. Wyman ed.) pp. 119-141, Taylor and Francis, Washington DC, (1995).

(Continued)

*Primary Examiner* — Maryam Monshipouri
(74) *Attorney, Agent, or Firm* — Codexis, Inc.

(57) ABSTRACT

The present invention provides recombinant nucleic acid constructs comprising a xylose isomerase polynucleotide, a recombinant fungal host cell comprising a recombinant xylose isomerase polynucleotide, and related methods.

1 Claim, 5 Drawing Sheets

(56) References Cited

U.S. PATENT DOCUMENTS

| | | |
|---|---|---|
| 6,576,467 B1 | 6/2003 | Stemmer |
| 6,579,678 B1 | 6/2003 | Patten et al. |
| 6,586,182 B1 | 7/2003 | Patten et al. |
| 6,602,986 B1 | 8/2003 | Stemmer et al. |
| 6,613,514 B2 | 9/2003 | Patten et al. |
| 6,653,072 B1 | 11/2003 | Patten et al. |
| 6,716,631 B1 | 4/2004 | delCardayre et al. |
| 6,946,296 B2 | 9/2005 | Patten et al. |
| 6,961,664 B2 | 11/2005 | Selifonov et al. |
| 6,995,017 B1 | 2/2006 | Stemmer |
| 7,024,312 B1 | 4/2006 | Selifonov et al. |
| 7,058,515 B1 | 6/2006 | Selifonov et al. |
| 7,105,297 B2 | 9/2006 | Minshull et al. |
| 7,148,054 B2 | 12/2006 | delCardayre et al. |
| 7,288,375 B2 | 10/2007 | Stemmer et al. |
| 7,421,347 B2 | 9/2008 | Selifonov et al. |
| 7,430,477 B2 | 9/2008 | Selifonov et al. |
| 7,534,564 B2 | 5/2009 | Patten et al. |
| 7,620,500 B2 | 11/2009 | Mundorff et al. |
| 7,620,502 B2 | 11/2009 | Selifonov et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,776,598 B2 | 8/2010 | Patten et al. |
| 7,783,428 B2 | 8/2010 | Gustafsson et al. |
| 7,795,030 B2 | 9/2010 | Minshull et al. |
| 7,853,410 B2 | 12/2010 | Selifonov et al. |
| 7,868,138 B2 | 1/2011 | Stemmer et al. |
| 7,873,499 B2 | 1/2011 | Selifonov et al. |
| 7,904,249 B2 | 3/2011 | Selifonov et al. |
| 7,957,912 B2 | 6/2011 | Selifonov et al. |
| 8,143,050 B2 | 3/2012 | Yang et al. |
| 2008/0057541 A1 | 3/2008 | Hill et al. |
| 2008/0220990 A1 | 9/2008 | Fox |
| 2009/0061484 A1 | 3/2009 | Scott et al. |
| 2009/0209009 A1 | 8/2009 | Tolan et al. |
| 2009/0312196 A1 | 12/2009 | Colbeck et al. |
| 2012/0003703 A1 | 1/2012 | Mitchell et al. |
| 2012/0045793 A1 | 2/2012 | Shock et al. |
| 2012/0077216 A1 | 3/2012 | Zhang et al. |
| 2012/0083019 A1 | 4/2012 | Baidyaroy et al. |
| 2012/0088271 A1 | 4/2012 | Haerizadeh et al. |
| 2012/0107881 A1 | 5/2012 | Dhawan et al. |
| 2012/0184020 A1* | 7/2012 | Picataggio et al. ...... 435/254.21 |

FOREIGN PATENT DOCUMENTS

| | | |
|---|---|---|
| WO | 95/22625 A1 | 8/1995 |
| WO | 96/00787 A1 | 1/1996 |
| WO | 97/00078 A1 | 1/1997 |
| WO | 97/35966 A1 | 10/1997 |
| WO | 98/27230 A1 | 6/1998 |
| WO | 98/31837 A1 | 7/1998 |
| WO | 00/04190 A1 | 1/2000 |
| WO | 01/75767 A2 | 10/2001 |
| WO | 2007/136762 A2 | 11/2007 |
| WO | 2009/152336 A1 | 12/2009 |
| WO | 2010/148148 A1 | 12/2010 |
| WO | 2011/006136 A2 | 1/2011 |
| WO | 2011/041594 A1 | 4/2011 |
| WO | 2011/066457 A2 | 6/2011 |
| WO | 2011/143632 A2 | 11/2011 |
| WO | 2011/150318 A1 | 12/2011 |
| WO | 2012/024662 A2 | 2/2012 |
| WO | 2012/024698 A1 | 2/2012 |
| WO | 2012/027282 A2 | 3/2012 |
| WO | 2012/044868 A1 | 4/2012 |
| WO | 2012/061432 A1 | 5/2012 |

OTHER PUBLICATIONS

Carter, P., "Site-directed mutagenesis," Biochem. J., 237:1-7 [1986].
Case, M.E, et al., "Efficient transformation of *Neurospora crassa* by utilizing hybrid plasmid DNA," Proc. Natl. Acad. Sci. USA, 76(10):5259-5263 [1979].
Christians, F.C., et al., "Directed evolution of thymidine kinase for AZT phosphorylation using DNA family shuffling," Nat. Biotechnol., 17:259-264 [1999].
Crameri A., et al., "DNA shuffling of a family of genes from diverse species accelerates directed evolution," Nature, 391:288-291 [1998].
Crameri, A., et al., "Improved green fluorescent protein by molecular evolution using DNA shuffling," Nat. Biotechnol., 14:315-319 [1996].
Crameri, A., et al., "Molecular evolution of an arsenate detoxification pathway by DNA shuffling," Nat. Biotechnol., 15:436-438 [1997].
Dale, S.J. et al., "Oligonucleotide-Directed Random Mutagenesis Using the Phosphorothioate Method," Meth. Mol. Biol., 57:369-74 [1996].
Dayhoff, M.O. et al., In Atlas of Protein Sequence and Structure, "A model of evolutionary change in proteins," vol. 5, Suppl. 3, Natl. Biomed. Res. Round, Washington D.C. [1978], pp. 345-352.
Dupont, A.-L., et al., "Comprehensive characterisation of cellulose- and lignocellulosedegradation products in aged papers: Capillary zone electrophoresis of low-molar mass organic acids, carbohydrates, and aromatic lignin derivatives," Carbohydr. Polym., 68:1-16 [2007].
Foreman, P.K., et al., "Transcriptional Regulation of Biomass-degrading Enzymes in the Filamentous Fungus *Trichoderma reesei*," J. Biol. Chem., 278(34):31988-31997 (2003).
Gardonyi, M., et al., "The *Streptomyces rubiginosus* xylose isomerase is misfolded when expressed in *Saccharomyces cerevisiae*," Enzyme Microb. Technol., 32:252-259 [2003].
Glenn, J.K., et al., "Mn(II) Oxidation is the Principal Function of the Extracellular Mn-Peroxidase from *Phanerochaete chrysosporium*'," Arch. Biochem. Biophys., 251(2):688-696 [1986].
Harvey, P.J., et al., "Veratryl alcohol as a mediator and the role of radical cations in lignin biodegradation by *Phanerochaete chrysosporium*," FEBS Lett., 195(1,2):242-246 [1986].
Henaut and Danchin in Neidhardt et al. [eds.], *Escherichia coli* and *Salmonella*, "Analysis and predictions from *Escherichia coli* Sequences, or *E. coli* in silico," ASM Press, Washington D.C., [1987], pp. 2047-2066.
Henikoff, S., et al., "Amino acid substitution matrices from protein blocks," Proc. Natl. Acad. Sci. USA, 89:10915-10919 [1992].
Henriksen, A.L.S., et al., "Study of the glucoamylase promoter in *Aspergillus niger* using green fluorescent protein," Microbiol., 145:729-34 [1999].
"Hjersted, J.L., et al.,""Genome-Scale Analysis of *Saccharomyces cerevisiae* Metabolism and Ethanol Productionin Fed-Batch Culture,""Biotechnol. Bioengineer., 97(5):1190-1204 [2007].".
Johnstone, I.L., et al., "Cloning an *Aspergillus nidulans* developmental gene by transformation," EMBO J.,4 (5):1307-1311 [1985].
Kelly, J.M., et al., "Transformation of *Asoergillus niger* by the amdS gene of *Aspergillus nidulans*," EMBO J., 4 (2):475-479 [1985].
Kinsey, J.A., et al., "Transformation of *Neurospora crassa* with the Cloned am (Glutamate Dehydrogenase) Gene," Mol. Cell. Biol., 4:117-122 [1984].
Kramer, B., et al., "Different base/base mismatches are corrected with different efficiencies by the methyl-directed DNA mismatch-repair system of *E. coli*," Cell, 38:879-887 [1984].
Kuyper, M., et al., "High-level functional expression of a fungal xylose isomerase: the key to e/cient ethanolic fermentation of xylose by *Saccharomyces cerevisiae*?," FEMS Yeast Res., 4:69-78 [2003].
Kuyper, M., et al., "Metabolic engineering of a xylose-isomerase-expressing *Saccharomyces cerevisiae* strain for rapid anaerobic xylose fermentation," FEMS Yeast Res., A445:399-409 [2005].
Limon, C., et al., "Primary structure and expression pattern of the 33-kDa chitinase gene from the nucoparasitic fungus *Trichocherma harzianum*," Curr. Genet., 28:478-83 [1995].
Ling, M.M., et al., "Approaches to DNA Mutagenesis: An Overview," Anal. Biochem., 254(2):157-78 [1997].
Madhaven, A., et al., "Alcoholic fermentation of xylose and mixed sugars using recombinant *Saccharomyces cerevisiae* engineered for xylose utilization," Appl. Microbiol. Biotechnol., 82:1067-1078 [2009].

(56) References Cited

OTHER PUBLICATIONS

Manivasakam, P., et al., "Nonhomologous End Joining during Restriction Enzyme-Mediated DNA Integration in *Saccharomyces cerevisiae*," Mol. Cell Biol., 18(3):1736-1745 [1998].A46.

Matsushika, A., et al., "Ethanol production from xylose in engineered *Saccharomyces cerevisiae* strains: current state and perspectives," Appl. Microbiol. Biotechnol., 84:37-53 [2009].

McInerney, J.O., "GCUA: general codon usage analysis," Bioinformatics, 14(4):372-73, 1998.

Minshull, J., et al., "Protein evolution by molecular breeding," Curr. Op. Chem. Biol., 3:284-290 [1999].

Moes, C.J. et al. "Cloning and Expression of the *Clostridium thermosulfurogenes* D-Xylose Isomerase Gene (xyk4) in *Saccharomyces cerevisiae*," Biotech. Lett.,18(3):269-274 [1996].

Nakamura, Y., et al., "Codon usage tabulated from international DNA sequence databases: status for the year 2000," Nucl. Acids Res., 28:292 [2000].

Nunberg, J.H., et al., "Molecular Cloning and Characterization of the Glucoamylase Gene of *Aspergillus* awamori," Mol. Cell Biol., 4(11):2306-2315 [1984].

Park, J.B., et al., "The human glutaredoxin gene: determination of its organization, transcription start point, and promoter analysis," Gene, 197:189-93 [1997].

Romanos, M.A., et al., "Foreign Gene Expression in Yeast: a Review," Yeast 8:423-488 [1992].

Salheimo, M., et al., "Swollenin, a *Trichoderma reesei* protein with sequence similarity to the plant expansins, exhibits disruption activity on cellulosic materials," Eur. J. Biochem., 269:4202-4211 [2002].

Sarthy, A. V., et al., "Expression of the *Escherichia coli* Xylose Isomerase Gene in *Saccharomyces cerevisiae*," Appl. Environ. Microbiol., 53(9):1996-2000 [1987].

Sauer, U., "Evolutionary Engineering of Industrially Important Microbial Phenotypes," Adv. Biochem. Engineer. Biotechnol., 73:129-169 [2001].

Sedlak, M., et al., "Characterization of the effectiveness of hexose transporters for transporting xylose during glucose and xylose co-fermentation by a recombinant*Saccharomyces* yeast," Yeast 21:671-684 [2004].

Sheir-Neiss, G., et al., "Characterization of the secreted cellulases of *Trichoderma reesei* wild type and mutants during controlled fermentations," Appl. Microbiol. Biotechnol., 20:46-53 [1984].

Smith, M., "In Vitro Mutagenesis," Ann. Rev. Genet., 19:423-462 [1985].

Sonderegger, M., et al., "Molecular Basis for Anaerobic Growth of *Saccharomyces cerevisiae* on Xylose, Investigated by Global Gene Expression and Metabolic Flux Analysis," Appl. Environ. Microbiol., 70(4):2307-2317 [2004].

Stemmer, W.P.C., "DNA shuffling by random fragmentation and reassembly: In vitro recombination for molecular evolution," Proc. Nat. Acad. Sci. USA, 91:10747-10751 [1994].

Stemmer, W.P.C., "Rapid evolution of a protein in vitro by DNA shuffling," Nature, 370:389-391 [1994].

Stenico, M., et al., "Codon usage in *Caenorhabditis elegans*: delineation of translational selection and mutational biases," Nucl. Acids Res. 22(13):2437-46 [1994].

Teixiera, M.C., et al., "Genome-Wide Identification of *Saccharomyces cerevisiae* Genes Required for Maximal Tolerance to Ethanol," Appl. Environ. Microbiol., 75(18):5761-5772 [2009].

Tilburn, J., et al., "Transformation by integration in *Aspergillus nidulans*," Gene 26:205-221 [1983].

Tiwari, S., et al., "Prediction of probable genes by Fourier analysis of genomic sequences," Comput. Appl. Biosci. 13 (3):263-270 [1997].

Uberbacher, E.C., et al., "Discovering and Understanding Genes in Human DNA Sequence Using GRAIL," Methods Enzymol., 266:259-281 [1996].

Viikari, L., et al., "Thermostable enzymes in lignocellulose hydrolysis," Adv. Biochem. Eng. Biotechnol., 108:121-45 [2007].

Wada, K., et al., "Codon usage tabulated from the GenBank genetic sequence data," Nucl. Acids Res., 20:2111-2118 [1992].

Walfridsson, M., et al., "Ethanolic Fermentation of Xylose with *Saccharomyces cerevisiae* Harboring the *Thermus thermophilus* xyIA Gene, Which Expresses an Active Xylose (Glucose) Isomerase," Appl. Environ. Microbiol., 62 (12):4648-4651 [1996].

Wells, J.A., et al., "Cassette mutagenesis: an efficient method for generation of multiple mutations at defined sites," Gene, 34:315-323 [1985].

Wenger, J.W., et al.,"Bulk Segregant Analysis by High-Throughput Sequencing Reveals a Novel Xylose Utilization Gene from *Saccharomyces cerevisiae*," PLoS Genet., 6(5):1-17 [2010].

Wisselink, H.W., et al., "Novel Evolutionary Engineering Approach for Accelerated Utilization of Glucose, Xylose, and Arabinose Mixtures by Engineered *Saccharomyces cerevisiae* Strains," Appl. Environ. Microbiol., 75(4):907-914 [2009].

Wright, A., et al., "Diverse Plasmid DNA Vectors by Directed Molecular Evolution of Cytomegalovirus Promoters," Hum. Gene Ther., 16:881-892 [2005].

Wright, F., "The 'effective number of codons' used in a gene," Gene 87:23-29 [1990].

Yelton, M.M., et al., "Transformation of *Aspergillus nidulans* by using a trpC plasmid," Proc. Natl. Acad. Sci. USA, 81:1480-1474 [1984].

Zhang, J.-H., et al., "Directed evolution of a fucosidase from a galactosidase by DNA shuffling and screening" Proc. Nat. Acad. Sci. U.S.A., 94:4504-4509 [1997].

Zhu, T., et al., "Construction of two Gateway vectors for gene expression in fungi," Plasmid 62:128-33 [2009].

\* cited by examiner

SEQUENCE LISTING

<160> NUMBER OF SEQ ID NOS: 33

<210> SEQ ID NO 1
<211> LENGTH: 1317
<212> TYPE: DNA
<213> ORGANISM: Ruminococcus flavefaciens

<400> SEQUENCE: 1

```
atggaatttt tcagcaatat cggtaaaatt cagtatcagg gaccaaaaag tactgatcct      60
ctctcattta agtactataa ccctgaagaa gtcatcaacg gaaagacaat gcgcgagcat     120
ctgaagttcg ctctttcatg gtggcacaca atgggcggcg acggaacaga tatgttcggc     180
tgcggcacaa cagacaagac ctggggacag tccgatcccg ctgcaagagc aaaggctaag     240
gttgacgcag cattcgagat catggataag ctctccattg actactattg tttccacgat     300
cgcgatcttt ctcccgagta tggcagcctc aaggctacca acgatcagct tgacatagtt     360
acagactata tcaaggagaa gcagggcgac aagttcaagt gcctctgggg tacagcaaag     420
tgcttcgatc atccaagatt catgcacggt gcaggtacat ctccttctgc tgatgtattc     480
gctttctcag ctgctcagat caagaaggct ctcgagtcaa cagtaaagct cggcggtaac     540
ggttacgttt tctggggcgg acgtgaaggc tatgagacac ttcttaatac aaatatggga     600
ctcgaactcg acaatatggc tcgtcttatg aagatggctg ttgagtatgg acgttcgatc     660
ggcttcaagg gcgacttcta tatcgagccc aagcccaagg agcccacaaa gcatcagtac     720
gatttcgata cagctactgt tctgggattc ctcagaaagt acggtctcga taaggatttc     780
aagatgaata tcgaagctaa ccacgctaca cttgctcagc atacattcca gcatgagctc     840
cgtgttgcaa gagacaatgg tgtgttcggt tctatcgacg caaaccaggg cgacgttctt     900
cttggatggg atacagacca gttccccaca aatatctacg atacaacaat gtgtatgtat     960
gaagttatca aggcaggcgg cttcacaaac ggcggtctca acttcgacgc taaggcacgc    1020
agagggagct tcactcccga ggatatcttc tacagctata tcgcaggtat ggatgcattt    1080
gctctgggct tcagagctgc tctcaagctt atcgaagacg gacgtatcga caagttcgtt    1140
gctgacagat acgcttcatg gaataccggt atcggtgcag acataatcgc aggtaaggca    1200
gatttcgcat ctcttgaaaa gtatgctctt gaaaagggcg aggttacagc ttcactctca    1260
agcggcagac aggaaatgct ggagtctatc gtaaataacg ttcttttcag tctgtaa      1317
```

<210> SEQ ID NO 2
<211> LENGTH: 438
<212> TYPE: PRT
<213> ORGANISM: Ruminococcus flavefaciens

<400> SEQUENCE: 2

Met Glu Phe Phe Ser Asn Ile Gly Lys Ile Gln Tyr Gln Gly Pro Lys
1               5                   10                  15

Ser Thr Asp Pro Leu Ser Phe Lys Tyr Tyr Asn Pro Glu Glu Val Ile

```
            20              25              30
Asn Gly Lys Thr Met Arg Glu His Leu Lys Phe Ala Leu Ser Trp Trp
            35              40              45
His Thr Met Gly Gly Asp Gly Thr Asp Met Phe Gly Cys Gly Thr Thr
            50              55              60
Asp Lys Thr Trp Gly Gln Ser Asp Pro Ala Arg Ala Lys Ala Lys
65              70              75              80
Val Asp Ala Ala Phe Glu Ile Met Asp Lys Leu Ser Ile Asp Tyr Tyr
                85              90              95
Cys Phe His Asp Arg Asp Leu Ser Pro Glu Tyr Gly Ser Leu Lys Ala
            100             105             110
Thr Asn Asp Gln Leu Asp Ile Val Thr Asp Tyr Ile Lys Glu Lys Gln
            115             120             125
Gly Asp Lys Phe Lys Cys Leu Trp Gly Thr Ala Lys Cys Phe Asp His
            130             135             140
Pro Arg Phe Met His Gly Ala Gly Thr Ser Pro Ser Ala Asp Val Phe
145             150             155             160
Ala Phe Ser Ala Ala Gln Ile Lys Lys Ala Leu Glu Ser Thr Val Lys
            165             170             175
Leu Gly Gly Asn Gly Tyr Val Phe Trp Gly Gly Arg Glu Gly Tyr Glu
            180             185             190
Thr Leu Leu Asn Thr Asn Met Gly Leu Glu Leu Asp Asn Met Ala Arg
            195             200             205
Leu Met Lys Met Ala Val Glu Tyr Gly Arg Ser Ile Gly Phe Lys Gly
            210             215             220
Asp Phe Tyr Ile Glu Pro Lys Pro Lys Glu Pro Thr Lys His Gln Tyr
225             230             235             240
Asp Phe Asp Thr Ala Thr Val Leu Gly Phe Leu Arg Lys Tyr Gly Leu
            245             250             255
Asp Lys Asp Phe Lys Met Asn Ile Glu Ala Asn His Ala Thr Leu Ala
            260             265             270
Gln His Thr Phe Gln His Glu Leu Arg Val Ala Arg Asp Asn Gly Val
            275             280             285
Phe Gly Ser Ile Asp Ala Asn Gln Gly Asp Val Leu Leu Gly Trp Asp
            290             295             300
Thr Asp Gln Phe Pro Thr Asn Ile Tyr Asp Thr Thr Met Cys Met Tyr
305             310             315             320
Glu Val Ile Lys Ala Gly Gly Phe Thr Asn Gly Gly Leu Asn Phe Asp
            325             330             335
Ala Lys Ala Arg Arg Gly Ser Phe Thr Pro Glu Asp Ile Phe Tyr Ser
            340             345             350
Tyr Ile Ala Gly Met Asp Ala Phe Ala Leu Gly Phe Arg Ala Ala Leu
            355             360             365
Lys Leu Ile Glu Asp Gly Arg Ile Asp Lys Phe Val Ala Asp Arg Tyr
            370             375             380
Ala Ser Trp Asn Thr Gly Ile Gly Ala Asp Ile Ile Ala Gly Lys Ala
385             390             395             400
Asp Phe Ala Ser Leu Glu Lys Tyr Ala Leu Glu Lys Gly Glu Val Thr
            405             410             415
Ala Ser Leu Ser Ser Gly Arg Gln Glu Met Leu Glu Ser Ile Val Asn
            420             425             430
Asn Val Leu Phe Ser Leu
            435
```

<210> SEQ ID NO 3
<211> LENGTH: 1317
<212> TYPE: DNA
<213> ORGANISM: Clostridium phytofermentans

<400> SEQUENCE: 3

```
atgaagaact atttccccaa cgtcccagaa gtcaaatacg aaggtccaaa ctccacaaat      60
cctttcgctt ttaaatatta tgatgctaat aaagtagtcg ccggtaagac catgaaggag     120
cattgtagat tcgctctatc ctggtggcac actttgtgtg ccggtggtgc tgatccattc     180
ggagtaacta ctatggacag gacctacggt aacattaccg acccaatgga actagctaag     240
gccaaagttg atgctggttt cgaactgatg actaagctgg gcatcgagtt cttctgcttc     300
catgatgccg acattgctcc agaaggtgac accttcgaag agtccaagaa gaatctgttc     360
gagattgttg attacatcaa ggagaagatg gaccaaaccg gcatcaagtt gttatggggc     420
actgctaaca actttagtca ccccaggttc atgcacggtg catcaacttc ttgtaatgcc     480
gatgttttcg cttatgctgc tgcgaaaata aagaacgctt tagatgcgac catcaagttg     540
ggcggtaagg ttatgtcttt tggggtggt agagaaggtt acgagaccct gctgaatact     600
gacctgggct tagaactgga caacatggct aggctaatga gatggccgt agaatacggt     660
agggctaatg gattcgacgg tgacttctac atcgagccta acccaaggaa acctactaag     720
caccagtacg acttcgacac tgctaccgta ttagcttttt taaggaagta cgggttggaa     780
aaagacttca agatgaacat cgaagccaat cacgccacac tagcaggcca cacattcgag     840
catgagttag ctatggctag ggtaaacggt gcattcggtt ctgttgatgc taaccaaggt     900
gacccaaact taggatggga cacggatcaa ttccccacag acgttcattc tgctactctt     960
gctatgctgg aggtcttgaa agccggtggt ttcacaaatg gcggcctgaa ctttgatgcg    1020
aaagttcgta ggggttcatt cgagtttgac gatattgcct atggttacat tgctggtatg    1080
gatactttcg cgttagggtt aattaaagct gctgaaatca ttgatgacgg tagaattgcc    1140
aagtttgtgg atgacaggta tgcctcttac aagaccggta ttggtaaagc gatcgttgac    1200
ggaactacct ctttggaaga attggaacaa tacgtgttga ctcattctga acctgtcatg    1260
caatctggta gacaagaggt tctggaaact attgtcaaca acatattgtt tagataa       1317
```

<210> SEQ ID NO 4
<211> LENGTH: 438
<212> TYPE: PRT
<213> ORGANISM: Clostridium phytofermentans

<400> SEQUENCE: 4

```
Met Lys Asn Tyr Phe Pro Asn Val Pro Glu Val Lys Tyr Glu Gly Pro
1               5                   10                  15

Asn Ser Thr Asn Pro Phe Ala Phe Lys Tyr Tyr Asp Ala Asn Lys Val
            20                  25                  30

Val Ala Gly Lys Thr Met Lys Glu His Cys Arg Phe Ala Leu Ser Trp
        35                  40                  45

Trp His Thr Leu Cys Ala Gly Gly Ala Asp Pro Phe Gly Val Thr Thr
    50                  55                  60

Met Asp Arg Thr Tyr Gly Asn Ile Thr Asp Pro Met Glu Leu Ala Lys
65                  70                  75                  80

Ala Lys Val Asp Ala Gly Phe Glu Leu Met Thr Lys Leu Gly Ile Glu
                85                  90                  95
```

```
Phe Phe Cys Phe His Asp Ala Asp Ile Ala Pro Glu Gly Asp Thr Phe
            100                 105                 110
Glu Glu Ser Lys Lys Asn Leu Phe Glu Ile Val Asp Tyr Ile Lys Glu
            115                 120                 125
Lys Met Asp Gln Thr Gly Ile Lys Leu Leu Trp Gly Thr Ala Asn Asn
130                 135                 140
Phe Ser His Pro Arg Phe Met His Gly Ala Ser Thr Ser Cys Asn Ala
145                 150                 155                 160
Asp Val Phe Ala Tyr Ala Ala Lys Ile Lys Asn Ala Leu Asp Ala
            165                 170                 175
Thr Ile Lys Leu Gly Gly Lys Gly Tyr Val Phe Trp Gly Gly Arg Glu
            180                 185                 190
Gly Tyr Glu Thr Leu Leu Asn Thr Asp Leu Gly Leu Glu Leu Asp Asn
            195                 200                 205
Met Ala Arg Leu Met Lys Met Ala Val Glu Tyr Gly Arg Ala Asn Gly
210                 215                 220
Phe Asp Gly Asp Phe Tyr Ile Glu Pro Lys Pro Lys Glu Pro Thr Lys
225                 230                 235                 240
His Gln Tyr Asp Phe Asp Thr Ala Thr Val Leu Ala Phe Leu Arg Lys
            245                 250                 255
Tyr Gly Leu Glu Lys Asp Phe Lys Met Asn Ile Glu Ala Asn His Ala
            260                 265                 270
Thr Leu Ala Gly His Thr Phe Glu His Glu Leu Ala Met Ala Arg Val
            275                 280                 285
Asn Gly Ala Phe Gly Ser Val Asp Ala Asn Gln Gly Asp Pro Asn Leu
            290                 295                 300
Gly Trp Asp Thr Asp Gln Phe Pro Thr Asp Val His Ser Ala Thr Leu
305                 310                 315                 320
Ala Met Leu Glu Val Leu Lys Ala Gly Gly Phe Thr Asn Gly Gly Leu
            325                 330                 335
Asn Phe Asp Ala Lys Val Arg Arg Gly Ser Phe Glu Phe Asp Asp Ile
            340                 345                 350
Ala Tyr Gly Tyr Ile Ala Gly Met Asp Thr Phe Ala Leu Gly Leu Ile
            355                 360                 365
Lys Ala Ala Glu Ile Ile Asp Asp Gly Arg Ile Ala Lys Phe Val Asp
            370                 375                 380
Asp Arg Tyr Ala Ser Tyr Lys Thr Gly Ile Gly Lys Ala Ile Val Asp
385                 390                 395                 400
Gly Thr Thr Ser Leu Glu Glu Leu Glu Gln Tyr Val Leu Thr His Ser
            405                 410                 415
Glu Pro Val Met Gln Ser Gly Arg Gln Glu Val Leu Glu Thr Ile Val
            420                 425                 430
Asn Asn Ile Leu Phe Arg
            435

<210> SEQ ID NO 5
<211> LENGTH: 1326
<212> TYPE: DNA
<213> ORGANISM: Abiotrophia defectiva

<400> SEQUENCE: 5
atgagtgaat tgttccaaaa catcccaaaa atcaaatacg aaggtgcaaa ttccaaaaat      60
cctttggctt ttcattatta tgatgctgaa aaaatagtcc tcggtaagac catgaaggag     120
catttgccat tcgctatggc atggtggcac aatttgtgtg ccgctggtac tgatatgttc     180
```

-continued

```
ggacgtgata ctgcggacaa gtcctttggt ttggaaaaag gctcaatgga acatgctaag      240
gccaaagttg atgctggttt cgaatttatg gaaaagctgg gcattaaata cttctgcttc      300
catgatgtag accttgttcc agaagcttgc gacattaaag agaccaattc tcgactggac      360
gaaatttctg attacatctt ggagaagatg aagggcactg atattaagtg tttatggggc      420
actgctaata tgttttctaa ccccaggttc gtgaacggtg caggatctac taatagtgcc      480
gatgtttact gttttgctgc tgcgcaaata aagaaagcat tagatattac cgtcaagttg      540
ggcggtagag gttatgtctt tggggtggt agagaaggtt acgagaccct gctgaatact      600
gacgtgaaat ttgaacagga aaacattgct aatctaatga gatggccgt agaatacggt      660 aggtctattg gattcaaagg tgacttctac atcgagccta acccaagga acctatgaag      720 caccagtacg acttcgacgc tgctaccgca ataggttttt taaggcagta cgggttggat      780
aaagacttca aattgaacat cgaagccaat cacgccacac tagcaggaca ctcattccag      840
catgagttac gtatttctag tattaacggt atgttgggtt ctgttgatgc taaccaaggt      900
gacatgttgt taggatggga cacggatgaa tttcccttg acgtttatga tactactatg      960
tgtatgtatg aggtccttaa aaacggtggt ttgacaggcg gctttaactt tgatgcgaaa     1020
aatcgtaggc cttcatacac gtatgaagat atgttctatg gtttcattct tggtatggat     1080
tctttcgcgt tagggttgat aaaagctgct aaattgattg aagaaggtac acttgacaat     1140
tttattaagg aaaggtataa atcttttgaa tccgaaattg gtaaaaaaat tagatccaaa     1200
tcagcctctt tgcaagaatt ggcagcttat gctgaggaaa tgggtgctcc cgcgatgccg     1260
ggttcaggta ggcaagagta tctgcaagct gctctcaacc aaaatttgtt tggtgaagtg     1320
taataa                                                                1326
```

<210> SEQ ID NO 6
<211> LENGTH: 440
<212> TYPE: PRT
<213> ORGANISM: Abiotrophia defectiva

<400> SEQUENCE: 6

```
Met Ser Glu Leu Phe Gln Asn Ile Pro Lys Ile Lys Tyr Glu Gly Ala
1               5                   10                  15

Asn Ser Lys Asn Pro Leu Ala Phe His Tyr Tyr Asp Ala Glu Lys Ile
            20                  25                  30

Val Leu Gly Lys Thr Met Lys Glu His Leu Pro Phe Ala Met Ala Trp
        35                  40                  45

Trp His Asn Leu Cys Ala Ala Gly Thr Asp Met Phe Gly Arg Asp Thr
    50                  55                  60

Ala Asp Lys Ser Phe Gly Leu Glu Lys Gly Ser Met Glu His Ala Lys
65                  70                  75                  80

Ala Lys Val Asp Ala Gly Phe Glu Phe Met Glu Lys Leu Gly Ile Lys
                85                  90                  95

Tyr Phe Cys Phe His Asp Val Asp Leu Val Pro Glu Ala Cys Asp Ile
            100                 105                 110

Lys Glu Thr Asn Ser Arg Leu Asp Glu Ile Ser Asp Tyr Ile Leu Glu
        115                 120                 125

Lys Met Lys Gly Thr Asp Ile Lys Cys Leu Trp Gly Thr Ala Asn Met
    130                 135                 140

Phe Ser Asn Pro Arg Phe Val Asn Gly Ala Gly Ser Thr Asn Ser Ala
145                 150                 155                 160
```

Asp Val Tyr Cys Phe Ala Ala Gln Ile Lys Lys Ala Leu Asp Ile
            165                 170                 175

Thr Val Lys Leu Gly Gly Arg Gly Tyr Val Phe Trp Gly Gly Arg Glu
        180                 185                 190

Gly Tyr Glu Thr Leu Leu Asn Thr Asp Val Lys Phe Glu Gln Glu Asn
            195                 200                 205

Ile Ala Asn Leu Met Lys Met Ala Val Glu Tyr Gly Arg Ser Ile Gly
        210                 215                 220

Phe Lys Gly Asp Phe Tyr Ile Glu Pro Lys Pro Lys Glu Pro Met Lys
225                 230                 235                 240

His Gln Tyr Asp Phe Asp Ala Ala Thr Ala Ile Gly Phe Leu Arg Gln
            245                 250                 255

Tyr Gly Leu Asp Lys Asp Phe Lys Leu Asn Ile Glu Ala Asn His Ala
        260                 265                 270

Thr Leu Ala Gly His Ser Phe Gln His Glu Leu Arg Ile Ser Ser Ile
    275                 280                 285

Asn Gly Met Leu Gly Ser Val Asp Ala Asn Gln Gly Asp Met Leu Leu
        290                 295                 300

Gly Trp Asp Thr Asp Glu Phe Pro Phe Asp Val Tyr Asp Thr Thr Met
305                 310                 315                 320

Cys Met Tyr Glu Val Leu Lys Asn Gly Gly Leu Thr Gly Gly Phe Asn
            325                 330                 335

Phe Asp Ala Lys Asn Arg Arg Pro Ser Tyr Thr Tyr Glu Asp Met Phe
        340                 345                 350

Tyr Gly Phe Ile Leu Gly Met Asp Ser Phe Ala Leu Gly Leu Ile Lys
    355                 360                 365

Ala Ala Lys Leu Ile Glu Glu Gly Thr Leu Asp Asn Phe Ile Lys Glu
        370                 375                 380

Arg Tyr Lys Ser Phe Glu Ser Glu Ile Gly Lys Lys Ile Arg Ser Lys
385                 390                 395                 400

Ser Ala Ser Leu Gln Glu Leu Ala Ala Tyr Ala Glu Glu Met Gly Ala
            405                 410                 415

Pro Ala Met Pro Gly Ser Gly Arg Gln Glu Tyr Leu Gly Ala Ala Leu
        420                 425                 430

Asn Gln Asn Leu Phe Gly Glu Val
    435                 440

<210> SEQ ID NO 7
<211> LENGTH: 1323
<212> TYPE: DNA
<213> ORGANISM: Ruminococcus champanellensis 18P13

<400> SEQUENCE: 7 atggaattttt tcaagaacat ctctaagata ccatacgaag gcaaagactc taccaatcca      60
ttagcattca agtactacaa tcctgacgaa gtaatcgacg gtaagaagat gagagacatc     120
atgaagtttg ctttgtcttg gtggcatact atgggaggtg atggtactga tatgtttggc     180
tgtggtactg ctgataagac atggggcgag aatgatccag ctgctagagc taaagctaaa     240
gttgatgccg catttgaaat catgcagaag ttatccattg attacttctg cttccatgat     300
agagatttgt ctccagagta cggttctttg aaggacacaa cgctcaatt ggacattgtc     360 actgactaca tcaaggctaa acaagctgaa accggtttga atgtctttg gggtactgct     420 aagtgcttcg accatccaag attcatgcac ggtgctggta cttctccttc agcggatgtc     480
ttcgcattct cagctgctca aatcaagaaa gctctggaat ctaccgtcaa gttgggtgga     540

-continued

```
actggttatg tcttctgggg tggtagagaa ggatatgaaa cgttgttgaa tactaacatg      600
ggacttgaat tggacaacat ggctaggttg atgaagatgg ccgttgagta tggtaggtct      660
attggtttca aggtgacttc ctacattgaa cctaagccaa aggaaccaac taagcatcaa      720
tacgactttg acactgctac agtcttgggc tttctgagaa agtacggcct ggacaaagac      780
ttcaagatga acatagaagc caatcatgca actttagcgc aacataccct ccagcacgaa      840
ttgtgtgtcg ccagaactaa tggtgctttc ggttctattg atgctaatca aggtgatccc      900
ttgttgggtt gggatacaga tcagtttcct acaaacatct atgatactac tatgtgcatg      960
tacgaagtta tcaaagctgg tggtttcact aatggtggtc ttaactttga tgctaaagct     1020
agaagaggtt ctttcactcc agaagatatt ttctattctt acattgctgg tatggatgct     1080
ttcgctttag gttacaaagc tgcttctaag ctaatcgctg atggtaggat tgatagcttc     1140
attagcgata gatatgcttc ttggtctgaa ggtattggtt tggacatcat ttccggcaaa     1200
gctgatatgg cggctttaga gaagtatgct ttggagaaag gagaggtcac tgattctatc     1260
tcttctggaa gacaggaact gttagagtcc attgttaaca acgtaatctt caacctataa     1320
taa                                                                   1323
```

<210> SEQ ID NO 8
<211> LENGTH: 439
<212> TYPE: PRT
<213> ORGANISM: Ruminococcus champanellensis 18P13

<400> SEQUENCE: 8

```
Met Glu Phe Phe Lys Asn Ile Ser Lys Ile Pro Tyr Glu Gly Lys Asp
1               5                   10                  15

Ser Thr Asn Pro Leu Ala Phe Lys Tyr Tyr Asn Pro Asp Glu Val Ile
            20                  25                  30

Asp Gly Lys Lys Met Arg Asp Ile Met Lys Phe Ala Leu Ser Trp Trp
        35                  40                  45

His Thr Met Gly Gly Asp Gly Thr Asp Met Phe Gly Cys Gly Thr Ala
    50                  55                  60

Asp Lys Thr Trp Gly Glu Asn Asp Pro Ala Ala Arg Ala Lys Ala Lys
65                  70                  75                  80

Val Asp Ala Ala Phe Glu Ile Met Gln Lys Leu Ser Ile Asp Tyr Phe
                85                  90                  95

Cys Phe His Asp Arg Asp Leu Ser Pro Glu Tyr Gly Ser Leu Lys Asp
            100                 105                 110

Thr Asn Ala Gln Leu Asp Ile Val Thr Asp Tyr Ile Lys Ala Lys Gln
        115                 120                 125

Ala Glu Thr Gly Leu Lys Cys Leu Trp Gly Thr Ala Lys Cys Phe Asp
    130                 135                 140

His Pro Arg Phe Met His Gly Ala Gly Thr Ser Pro Ser Ala Asp Val
145                 150                 155                 160

Phe Ala Phe Ser Ala Ala Gln Ile Lys Lys Ala Leu Glu Ser Thr Val
                165                 170                 175

Lys Leu Gly Gly Thr Gly Tyr Val Phe Trp Gly Gly Arg Glu Gly Tyr
            180                 185                 190

Glu Thr Leu Leu Asn Thr Asn Met Gly Leu Glu Leu Asp Asn Met Ala
        195                 200                 205

Arg Leu Met Lys Met Ala Val Glu Tyr Gly Arg Ser Ile Gly Phe Lys
    210                 215                 220
```

```
Gly Asp Phe Tyr Ile Glu Pro Lys Pro Lys Glu Pro Thr Lys His Gln
225                 230                 235                 240

Tyr Asp Phe Asp Thr Ala Thr Val Leu Gly Phe Leu Arg Lys Tyr Gly
                245                 250                 255

Leu Asp Lys Asp Phe Lys Met Asn Ile Glu Ala Asn His Ala Thr Leu
            260                 265                 270

Ala Gln His Thr Phe Gln His Glu Leu Cys Val Ala Arg Thr Asn Gly
        275                 280                 285

Ala Phe Gly Ser Ile Asp Ala Asn Gln Gly Asp Pro Leu Leu Gly Trp
    290                 295                 300

Asp Thr Asp Gln Phe Pro Thr Asn Ile Tyr Asp Thr Thr Met Cys Met
305                 310                 315                 320

Tyr Glu Val Ile Lys Ala Gly Gly Phe Thr Asn Gly Gly Leu Asn Phe
                325                 330                 335

Asp Ala Lys Ala Arg Arg Gly Ser Phe Thr Pro Glu Asp Ile Phe Tyr
            340                 345                 350

Ser Tyr Ile Ala Gly Met Asp Ala Phe Ala Leu Gly Tyr Lys Ala Ala
        355                 360                 365

Ser Lys Leu Ile Ala Asp Gly Arg Ile Asp Ser Phe Ile Ser Asp Arg
    370                 375                 380

Tyr Ala Ser Trp Ser Glu Gly Ile Gly Leu Asp Ile Ile Ser Gly Lys
385                 390                 395                 400

Ala Asp Met Ala Ala Leu Glu Lys Tyr Ala Leu Glu Lys Gly Glu Val
                405                 410                 415

Thr Asp Ser Ile Ser Ser Gly Arg Gln Glu Leu Leu Glu Ser Ile Val
            420                 425                 430

Asn Asn Val Ile Phe Asn Leu
        435
```

<210> SEQ ID NO 9
<211> LENGTH: 1410
<212> TYPE: DNA
<213> ORGANISM: Phytophora infestans

<400> SEQUENCE: 9

```
atgcaacatc aagtgaaaga atatttccca aacgtcccaa aaatcacatt cgaaggtcaa      60
aatgccaaaa gtgttttggc ttatcgtgaa tataatgctt cagaagtaat catgggtaag     120
accatggagg agtggtgtag attcgctgtg tgttattggc acacttttgg taactctggt     180
tctgatccgt tcggaggtga aacttatacc aatagattgt ggaatgaatc attggaaaga     240
gctaatattt cttctaggga aagattgttg gaagctgcta agtgcaaagc tgatgctgct     300
ttcgaaactt ttacaaagct gggcgttaaa tactacacct tccatgatgt agaccttatt     360
tcagaaggtg ccaaccttga agagtcccaa tctctactgg acgaaatttc tgattacttg     420
ttggataagc agaatcaaac tggtgttagg tgtttatggg gcactactaa tttgtttggt     480
cacagaaggt tcatgaacgg tgcatcaact aatcctgata tgaaagtttt cgctcatgct     540
gctgcgagag taaagaaagc aatggaaatt accttgaagt tgggcggtca aaattttgtc     600
ttttggggtg gtagagaagg tttccagtcc attctgaata ctgacatgaa aactgaactg     660
gatcacatgg ctgctttttt taagttggtc gtagcataca aaaaggaact tggagccaca     720
tttcaattct tggtcgagcc taaacccagg gaacctatga agcaccagta cgactacgac     780
gctgctaccg tagtagcttt tttacatacg tacgggttgc aaaatgactt caaattgaac     840
atcgaaccca atcacaccac actagcagga cacgattacg agcatgatat atattatgct     900
```

-continued

```
gctagttaca aaatgttggg ttctgttgat tgtaacacag gtgacccgtt ggtaggatgg    960
gacacggatc aattttttgat ggacgaaaaa aaagctgttt tggttatgaa aaagatcgtt   1020
gaaatcggtg gtttggcacc aggcggcttg aactttgatg cgaaagttcg tagggaatca   1080
accgatttgg aagatatttt cattgctcac attggtagta tggattgttt cgcgagaggg   1140
ttgagacaag ctgctaaatt gcttgaaaaa aatgaacttg gcgaattggt taagcaaagg   1200
tatgcatctt ggaaatccac acttggtgaa agaattgaac aaggacaagc cactttggaa   1260
gaagtggcag cttatgctaa ggaaagtggt gaacccgatc atgtgtcagg taagcaagag   1320
ttggcggaac ttatgtggag cacagttgcg ttggctacag ggatttggca agatcatgtt   1380
acttgttctt tgactaaaaa ttggtgttaa                                     1410
```

<210> SEQ ID NO 10
<211> LENGTH: 469
<212> TYPE: PRT
<213> ORGANISM: Phytophora infestans

<400> SEQUENCE: 10

```
Met Gln His Gln Val Lys Glu Tyr Phe Pro Asn Val Pro Lys Ile Thr
1               5                   10                  15

Phe Glu Gly Gln Asn Ala Lys Ser Val Leu Ala Tyr Arg Glu Tyr Asn
                20                  25                  30

Ala Ser Glu Val Ile Met Gly Lys Thr Met Glu Glu Trp Cys Arg Phe
            35                  40                  45

Ala Val Cys Tyr Trp His Thr Phe Gly Asn Ser Gly Ser Asp Pro Phe
        50                  55                  60

Gly Gly Glu Thr Tyr Thr Asn Arg Leu Trp Asn Glu Ser Leu Glu Arg
65                  70                  75                  80

Ala Asn Ile Ser Ser Arg Glu Arg Leu Leu Glu Ala Ala Lys Cys Lys
                85                  90                  95

Ala Asp Ala Ala Phe Glu Thr Phe Thr Lys Leu Gly Val Lys Tyr Tyr
            100                 105                 110

Thr Phe His Asp Val Asp Leu Ile Ser Glu Gly Ala Asn Leu Glu Glu
        115                 120                 125

Ser Gln Ser Leu Leu Asp Glu Ile Ser Asp Tyr Leu Leu Asp Lys Gln
    130                 135                 140

Asn Gln Thr Gly Val Arg Cys Leu Trp Gly Thr Thr Asn Leu Phe Gly
145                 150                 155                 160

His Arg Arg Phe Met Asn Gly Ala Ser Thr Asn Pro Asp Met Lys Val
                165                 170                 175

Phe Ala His Ala Ala Arg Val Lys Lys Ala Met Glu Ile Thr Leu
            180                 185                 190

Lys Leu Gly Gly Gln Asn Phe Val Phe Trp Gly Gly Arg Glu Gly Phe
        195                 200                 205

Gln Ser Ile Leu Asn Thr Asp Met Lys Thr Glu Leu Asp His Met Ala
    210                 215                 220

Ala Phe Phe Lys Leu Val Val Ala Tyr Lys Lys Glu Leu Gly Ala Thr
225                 230                 235                 240

Phe Gln Phe Leu Val Glu Pro Lys Pro Arg Glu Pro Met Lys His Gln
                245                 250                 255

Tyr Asp Tyr Asp Ala Ala Thr Val Val Ala Phe Leu His Thr Tyr Gly
            260                 265                 270

Leu Gln Asn Asp Phe Lys Leu Asn Ile Glu Pro Asn His Thr Thr Leu
```

```
              275                 280                 285
Ala Gly His Asp Tyr Glu His Asp Ile Tyr Ala Ala Ser Tyr Lys
    290                 295                 300

Met Leu Gly Ser Val Asp Cys Asn Thr Gly Asp Pro Leu Val Gly Trp
305                 310                 315                 320

Asp Thr Asp Gln Phe Leu Met Asp Glu Lys Lys Ala Val Leu Val Met
                325                 330                 335

Lys Lys Ile Val Glu Ile Gly Gly Leu Ala Pro Gly Gly Leu Asn Phe
            340                 345                 350

Asp Ala Lys Val Arg Arg Glu Ser Thr Asp Leu Glu Asp Ile Phe Ile
        355                 360                 365

Ala His Ile Gly Ser Met Asp Cys Phe Ala Arg Gly Leu Arg Gln Ala
    370                 375                 380

Ala Lys Leu Leu Glu Lys Asn Glu Leu Gly Glu Leu Val Lys Gln Arg
385                 390                 395                 400

Tyr Ala Ser Trp Lys Ser Thr Leu Gly Glu Arg Ile Glu Gln Gly Gln
                405                 410                 415

Ala Thr Leu Glu Glu Val Ala Ala Tyr Ala Lys Glu Ser Gly Glu Pro
            420                 425                 430

Asp His Val Ser Gly Lys Gln Glu Leu Ala Glu Leu Met Trp Ser Thr
        435                 440                 445

Val Ala Leu Ala Thr Gly Ile Trp Gln Asp His Val Thr Cys Ser Leu
    450                 455                 460

Thr Lys Asn Trp Cys
465

<210> SEQ ID NO 11
<211> LENGTH: 14
<212> TYPE: DNA
<213> ORGANISM: Artificial Sequence
<220> FEATURE:
<223> OTHER INFORMATION: Synthetic DNA oligonucleotide

<400> SEQUENCE: 11
ggatcccaaa caaa                                                        14

<210> SEQ ID NO 12
<211> LENGTH: 9
<212> TYPE: DNA
<213> ORGANISM: Artificial Sequence
<220> FEATURE:
<223> OTHER INFORMATION: Synthetic DNA oligonucleotide

<400> SEQUENCE: 12 taacatatg                                                              9

<210> SEQ ID NO 13
<211> LENGTH: 88
<212> TYPE: DNA
<213> ORGANISM: Artificial Sequence
<220> FEATURE:
<223> OTHER INFORMATION: Synthetic DNA oligonucleotide

<400> SEQUENCE: 13
gagctcacgg atccgtcata tgctagatct ctgaattctt actagttcga cgtctaccta     60
ggcagtcgac acgcggccgc ttctcgag                                        88

<210> SEQ ID NO 14
<211> LENGTH: 1082
```

```
<212> TYPE: DNA
<213> ORGANISM: Artificial Sequence
<220> FEATURE:
<223> OTHER INFORMATION: Synthetic DNA truncated sequence

<400> SEQUENCE: 14
atggaatttt tctccaacat cggaaaaatc caataccaag gtccaaaatc cacagatcct      60
ttgtcttta  aatattataa tcctgaagaa gtaatcaacg gtaagaccat gagggagcat     120
ttgaaattcg ctctatcctg gtggcacact atgggtggcg atggtactga tatgttcgga    180
tgtggtacta cggacaagac ctggggtcaa tccgacccag cggcaagagc taaggccaaa    240
gttgatgctg ctttcgaaat tatggataag ctgagcattg attactactg cttccatgat    300
agagaccttt ctccagaata tggctccttg aaagcgacca atgatcaact ggacattgtt    360
actgattaca tcaaggagaa gcagggcgat aaattcaagt gtttatgggg cactgctaaa    420
tgctttgatc accccaggtt catgcacggt gcaggaactt ctcctagtgc cgatgttttc    480
gcttttctg  ctgcgcaaat aaagaaagca ttagaatcta ccgtcaagtt gggcggtaat    540
ggttatgtct tttggggtgg tagagaaggt tacgagaccc tgctgaatac taacatgggc    600
ttagaactgg acaacatggc taggctaatg aagatggccg tagaatacgg taggtctatt    660
ggattcaaag gtgacttcta catcgagcct aaacccaagg aacctactaa gcaccagtac    720
gacttcgaca ctgctaccgt attaggtttt taaggaagt  acgggttgga taaagacttc    780
aagatgaaca tcgaagccaa tcacgccaca ctagcacaac acacattcca gcatgagtta    840
cgtgtggcta gggataacgg tgtattcggt tctattgatg ctaaccaagg tgacgtattg    900
ttaggatggg acacggatca attccccaca aacatttatg atactactat gtgtatgtat    960
gaggtcatta aagccggtgg tttcacaaat ggcggcctga actttgatgc gaaagctcgt   1020
aggggttcat tcacgcctga agatatttc  tatagttaca ttgctggtat ggatgctttc   1080
gc                                                                  1082

<210> SEQ ID NO 15
<211> LENGTH: 748
<212> TYPE: DNA
<213> ORGANISM: Artificial Sequence
<220> FEATURE:
<223> OTHER INFORMATION: Synthetic DNA truncated sequence

<400> SEQUENCE: 15
ttacgagacc ctgctgaata ctaacatggg cttagaactg gacaacatgg ctaggctaat     60
gaagatggcc gtagaatacg gtaggtctat tggattcaaa ggtgacttct acatcgagcc    120
taaacccaag gaacctacta agcaccagta cgacttcgac actgctaccg tattaggttt    180
tttaaggaag tacgggttgg ataaagactt caagatgaac atcgaagcca atcacgccac    240
actagcacaa cacacattcc agcatgagtt acgtgtggct agggataacg gtgtattcgg    300
ttctattgat gctaaccaag gtgacgtatt gttaggatgg gacacggatc aattccccac    360
aaacatttat gatactacta tgtgtatgta tgaggtcatt aaagccggtg gtttcacaaa    420
tggcggcctg aactttgatg cgaaagctcg taggggttca ttcacgcctg aagatatttt    480
ctatagttac attgctggta tggatgcttt cgcgttaggg tttagagcag ctcttaaatt    540
gattgaagac ggtagaattg acaagtttgt ggctgacagg tatgcctctt ggaataccgg    600
tattggtgca gatattattg ccggaaaagc cgatttgca  tcattggaaa atatgctttt    660
ggaaaaaggt gaagttaccg cgtcattgtc ttctggtaga caagagatgc tggaatctat    720
```

```
tgtcaacaac gtattgttta gtttgtaa                                           748
```

<210> SEQ ID NO 16
<211> LENGTH: 731
<212> TYPE: DNA
<213> ORGANISM: Artificial Sequence
<220> FEATURE:
<223> OTHER INFORMATION: Synthetic DNA truncated sequence

<400> SEQUENCE: 16

```
atgaagaact atttccccaa cgtcccagaa gtcaaatacg aaggtccaaa ctccacaaat    60
cctttcgctt ttaaatatta tgatgctaat aaagtagtcg ccggtaagac catgaaggag   120
cattgtagat tcgctctatc ctggtggcac actttgtgtg ccggtggtgc tgatccattc   180
ggagtaacta ctatggacag gacctacggt aacattaccg acccaatgga actagctaag   240
gccaaagttg atgctggttt cgaactgatg actaagctgg gcatcgagtt cttctgcttc   300
catgatgccg acattgctcc agaaggtgac accttcgaag agtccaagaa gaatctgttc   360
gagattgttg attacatcaa ggagaagatg gaccaaaccg catcaagtt gttatggggc    420
actgctaaca ctttagtca ccccaggttc atgcacggtg catcaacttc ttgtaatgcc    480
gatgttttcg cttatgctgc tgcgaaaata agaacgctt tagatgcgac catcaagttg    540
ggcggtaagg ttatgtctt ttggggtggt agagaaggtt acgagaccct gctgaatact    600
gacctgggct tagaactgga caacatggct aggctaatga agatgccgt agaatacggt    660
agggctaatg gattcgacgg tgacttctac atcgagccta acccaagga acctactaag    720
caccagtacg a                                                         731
```

<210> SEQ ID NO 17
<211> LENGTH: 766
<212> TYPE: DNA
<213> ORGANISM: Artificial Sequence
<220> FEATURE:
<223> OTHER INFORMATION: Synthetic DNA truncated sequence

<400> SEQUENCE: 17

```
ttatgtcttt tggggtggta gagaaggtta cgagaccctg ctgaatactg acctgggctt    60
agaactggac aacatggcta ggctaatgaa gatggccgta gaatacggta gggctaatgg   120
attcgacggt gacttctaca tcgagcctaa acccaaggaa cctactaagc accagtacga   180
cttcgacact gctaccgtat tagcttttt aaggaagtac gggttggaaa aagacttcaa   240
gatgaacatc gaagccaatc acgccacact agcaggccac acattcgagc atgagttagc   300
tatggctagg gtaaacggtg cattcggttc tgttgatgct aaccaaggtg acccaaactt   360
aggatgggac acgatcaat tccccacaga cgttcattct gctactcttg ctatgctgga   420
ggtcttgaaa gccggtggtt tcacaaatgg cggcctgaac tttgatgcga agttcgtag    480
gggttcattc gagtttgacg atattgccta tggttacatt gctggtatgg atactttcgc   540
gttagggtta attaaagctg ctgaaatcat tgatgacggt agaattgcca gtttgtgga    600
tgacaggtat gcctcttaca agaccggtat tggtaaagcg atcgttgacg gaactacctc   660
tttggaagaa ttggaacaat acgtgttgac tcattctgaa cctgtcatgc aatctggtag   720
acaagaggtt ctggaaacta ttgtcaacaa catattgttt agataa                  766
```

<210> SEQ ID NO 18
<211> LENGTH: 1088
<212> TYPE: DNA
<213> ORGANISM: Artificial Sequence
<220> FEATURE:
<223> OTHER INFORMATION: Synthetic DNA truncated sequence

<400> SEQUENCE: 18

```
atgagtgaat tgttccaaaa catcccaaaa atcaaatacg aaggtgcaaa ttccaaaaat      60
cctttggctt ttcattatta tgatgctgaa aaaatagtcc tcggtaagac catgaaggag     120
catttgccat cgctatggc atggtggcac aatttgtgtg ccgctggtac tgatatgttc     180
ggacgtgata ctgcggacaa gtcctttggt ttggaaaaag gctcaatgga acatgctaag     240
gccaaagttg atgctggttt cgaatttatg gaaaagctgg gcattaaata cttctgcttc     300
catgatgtag accttgttcc agaagcttgc gacattaaag agaccaattc tcgactggac     360
gaaatttctg attacatctt ggagaagatg aagggcactg atattaagtg tttatggggc     420
actgctaata tgttttctaa ccccaggttc gtgaacggtg caggatctac taatagtgcc     480
gatgtttact gttttgctgc tgcgcaaata agaaagcat agatattac cgtcaagttg     540
ggcggtagag gttatgtctt ttggggtggt agagaaggtt acgagaccct gctgaatact     600
gacgtgaaat ttgaacagga aaacattgct aatctaatga agatggccgt agaatacggt     660
aggtctattg gattcaaagg tgacttctac atcgagccta acccaagga acctatgaag     720
caccagtacg acttcgacgc tgctaccgca ataggtttt taaggcagta cgggttggat     780
aaagacttca aattgaacat cgaagccaat acgccacac tagcaggaca ctcattccag     840
catgagttac gtatttctag tattaacggt atgttgggtt ctgttgatgc taaccaaggt     900
gacatgttgt taggatggga cacggatgaa tttccctttg acgtttatga tactactatg     960
tgtatgtatg aggtccttaa aaacggtggt ttgacaggcg gctttaactt tgatgcgaaa    1020
aatcgtaggc cttcatacac gtatgaagat atgttctatg gtttcattct tggtatggat    1080
tctttcgc                                                              1088
```

<210> SEQ ID NO 19
<211> LENGTH: 775
<212> TYPE: DNA
<213> ORGANISM: Artificial Sequence
<220> FEATURE:
<223> OTHER INFORMATION: Synthetic DNA truncated sequence

<400> SEQUENCE: 19

```
ttatgtcttt tggggtggta gagaaggtta cgagaccctg ctgaatactg acgtgaaatt     60
tgaacaggaa aacattgcta atctaatgaa gatggccgta gaatacggta ggtctattgg    120
attcaaaggt gacttctaca tcgagcctaa acccaaggaa cctatgaagc accagtacga    180
cttcgacgct gctaccgcaa taggttttt aaggcagtac gggttggata aagacttcaa    240
attgaacatc gaagccaatc acgccacact agcaggacac tcattccagc atgagttacg    300
tatttctagt attaacggta tgttgggttc tgttgatgct aaccaaggtg acatgttgtt    360
aggatgggac acggatgaat ttccctttga cgtttatgat actactatgt gtatgtatga    420
ggtccttaaa aacggtggtt tgacaggcgg ctttaacttt gatgcgaaaa atcgtaggcc    480
ttcatacacg tatgaagata tgttctatgg tttcattctt ggtatggatt ctttcgcgtt    540
agggttgata aagctgcta aattgattga agaaggtaca cttgacaatt ttattaagga    600
aaggtataaa tcttttgaat ccgaaattgg taaaaaaatt agatccaaat cagcctcttt    660
gcaagaattg gcagcttatg ctgaggaaat gggtgctccc gcgatgccgg ttcaggtag    720
gcaagagtat ctgcaagctg ctctcaacca aaatttgttt ggtgaagtgt aataa         775
```

<210> SEQ ID NO 20
<211> LENGTH: 1085
<212> TYPE: DNA
<213> ORGANISM: Artificial Sequence
<220> FEATURE:
<223> OTHER INFORMATION: Synthetic DNA truncated sequence

<400> SEQUENCE: 20

| | | | | | |
|---|---|---|---|---|---|
| atggaatttt | tcaagaacat | ctctaagata | ccatacgaag | gcaaagactc | taccaatcca | 60 |
| ttagcattca | agtactacaa | tcctgacgaa | gtaatcgacg | gtaagaagat | gagagacatc | 120 |
| atgaagtttg | ctttgtcttg | gtggcatact | atgggaggtg | atggtactga | tatgtttggc | 180 |
| tgtggtactg | ctgataagac | atggggcgag | aatgatccag | ctgctagagc | taaagctaaa | 240 |
| gttgatgccg | catttgaaat | catgcagaag | ttatccattg | attacttctg | cttccatgat | 300 |
| agagatttgt | ctccagagta | cggttctttg | aaggacacaa | cgctcaatt | ggacattgtc | 360 |
| actgactaca | tcaaggctaa | acaagctgaa | accggtttga | atgtctttg | gggtactgct | 420 |
| aagtgcttcg | accatccaag | attcatgcac | ggtgctggta | cttctccttc | agcggatgtc | 480 |
| ttcgcattct | cagctgctca | aatcaagaaa | gctctggaat | ctaccgtcaa | gttgggtgga | 540 |
| actggttatg | tcttctgggg | tggtagagaa | ggatatgaaa | cgttgttgaa | tactaacatg | 600 |
| ggacttgaat | tggacaacat | ggctaggttg | atgaagatgg | ccgttgagta | tggtaggtct | 660 |
| attggtttca | aggtgacttt | ctacattgaa | cctaagccaa | aggaaccaac | taagcatcaa | 720 |
| tacgactttg | acactgctac | agtcttgggc | tttctgagaa | agtacggcct | ggacaaagac | 780 |
| ttcaagatga | acatagaagc | caatcatgca | actttagcgc | aacataccct | tccagcacga | 840 |
| ttgtgtgtcg | ccagaactaa | tggtgctttc | ggttctattg | atgctaatca | aggtgatccc | 900 |
| ttgttgggtt | gggatacaga | tcagtttcct | acaaacatct | atgatactac | tatgtgcatg | 960 |
| tacgaagtta | tcaaagctgg | tggtttcact | aatggtggtc | ttaactttga | tgctaaagct | 1020 |
| agaagaggtt | ctttcactcc | agaagatatt | ttctattctt | acattgctgg | tatggatgct | 1080 |
| ttcgc | | | | | | 1085 |

<210> SEQ ID NO 21
<211> LENGTH: 769
<212> TYPE: DNA
<213> ORGANISM: Artificial Sequence
<220> FEATURE:
<223> OTHER INFORMATION: Synthetic DNA truncated sequence

<400> SEQUENCE: 21

| | | | | | |
|---|---|---|---|---|---|
| tgtcttctgg | ggtggtagag | aaggatatga | aacgttgttg | aatactaaca | tgggacttga | 60 |
| attggacaac | atggctaggt | tgatgaagat | ggccgttgag | tatggtaggt | ctattggttt | 120 |
| caaaggtgac | ttctacattg | aacctaagcc | aaaggaacca | actaagcatc | aatacgactt | 180 |
| tgacactgct | acagtcttgg | gctttctgag | aaagtacggc | ctggacaaag | acttcaagat | 240 |
| gaacatagaa | gccaatcatg | caactttagc | gcaacatacc | ttccagcacg | aattgtgtgt | 300 |
| cgccagaact | aatggtgctt | tcggttctat | tgatgctaat | caaggtgatc | ccttgttggg | 360 |
| ttgggataca | gatcagtttc | ctacaaacat | ctatgatact | actatgtgca | tgtacgaagt | 420 |
| tatcaaagct | ggtggtttca | ctaatggtgg | tcttaacttt | gatgctaaag | ctagaagagg | 480 |
| ttctttcact | ccagaagata | ttttctattc | ttacattgct | ggtatggatg | ctttcgcttt | 540 |
| aggttacaaa | gctgcttcta | agctaatcgc | tgatggtagg | attgatagct | tcattagcga | 600 |
| tagatatgct | tcttggtctg | aaggtattgg | tttggacatc | atttccggca | aagctgatat | 660 |

```
ggcggcttta gagaagtatg ctttggagaa aggagaggtc actgattcta tctcttctgg    720
aagacaggaa ctgttagagt ccattgttaa caacgtaatc ttcaaccta                769

<210> SEQ ID NO 22
<211> LENGTH: 1323
<212> TYPE: DNA
<213> ORGANISM: Artificial Sequence
<220> FEATURE:
<223> OTHER INFORMATION: Synthetic DNA sequence for Variant No 2

<400> SEQUENCE: 22
atgagtgaat tgttccaaaa catcccaaaa atcaaatacg aaagtgcaaa ttccaaaaat     60
cctttggctt ttcattatta tgatgctgaa aaaatagtcc tcggtaagac catgaaggag    120
catttgccat tcgctatggc atggtggcac aatttgtgtg ccgctggtac tgatatgttc    180
ggacgtgata ctgcggacaa gtcccttggt ttggaaaaag gctcaatgga acatgctaag    240
gccaaagttg atgctggttt cgaatttatg gaaaagctgg gcattaaata cttctgcttc    300
catgatgtag accttgttcc agaagcttgc gacattaaag agaccaattc tcgactggac    360
gaaatttctg attacatctt ggagaagatg aagggcactg atattaagtg tttatggggc    420
actgctaata tgttttctaa ccccaggttc gtgaacggtg caggatctac taatagtgcc    480
gatgtttact gttttgctgc tgcgcaaata aagaaagcat tagatattac cgtcaagttg    540
ggcggtagag gttatgtctt tggggtggt agagaaggtt acgagaccct gctgaatact    600
aacgttggct tagaactgga caacatggct aggctaatga agatggccgt agaatacggt    660
aggtctattg gattcaaagg tgacttctac atcgagccta acccaaggga acctgcaaag    720
caccagtacg acttcgacac tgctaccgta ttaggttttt taaggaagta cgggttggat    780
aaagacttca agatgaacat cgaagccaat cacgccacac tagcaggaca ctcattccag    840
catgagttac gtatttctag tattaacggt atgttgggtt ctgttgatgc taaccaaggt    900
gacatgttgt aggatggga cacggatgaa tttcccttg acgtttatga tactactatg    960
tgtatgtatg aggtccttaa aaacggtggt ttgacaggcg gctttaactt tgatgcgaaa   1020
aatcgtaggc cttcatacac gtatgaagat atgttctatg gtttcattct tggtatggat   1080
tctttcgcgt tagggtttag agcagctctt aaattgattg aagacggtag aattgacaag   1140
tttgtggctg acaggtatgc ctcttggaat accggtattg gtgcagatat tattgccgga   1200
aaagccgatt tgcatcatt ggaaaaatat gctttggaaa aggtgaagt taccgcgtca   1260 ttgtcttctg gtagacaaga gatgctggaa tctattgtca caacgtatt gtttagtttg   1320 taa                                                               1323

<210> SEQ ID NO 23
<211> LENGTH: 440
<212> TYPE: PRT
<213> ORGANISM: Artificial Sequence
<220> FEATURE:
<223> OTHER INFORMATION: Synthetic polypeptide sequence for Variant No 2

<400> SEQUENCE: 23

Met Ser Glu Leu Phe Gln Asn Ile Pro Lys Ile Lys Tyr Glu Ser Ala
1               5                   10                  15

Asn Ser Lys Asn Pro Leu Ala Phe His Tyr Tyr Asp Ala Glu Lys Ile
            20                  25                  30

Val Leu Gly Lys Thr Met Lys Glu His Leu Pro Phe Ala Met Ala Trp
        35                  40                  45
```

```
Trp His Asn Leu Cys Ala Ala Gly Thr Asp Met Phe Gly Arg Asp Thr
 50                  55                  60

Ala Asp Lys Ser Leu Gly Leu Glu Lys Gly Ser Met Glu His Ala Lys
 65                  70                  75                  80

Ala Lys Val Asp Ala Gly Phe Glu Phe Met Glu Lys Leu Gly Ile Lys
                 85                  90                  95

Tyr Phe Cys Phe His Asp Val Asp Leu Val Pro Glu Ala Cys Asp Ile
                100                 105                 110

Lys Glu Thr Asn Ser Arg Leu Asp Glu Ile Ser Asp Tyr Ile Leu Glu
            115                 120                 125

Lys Met Lys Gly Thr Asp Ile Lys Cys Leu Trp Gly Thr Ala Asn Met
130                 135                 140

Phe Ser Asn Pro Arg Phe Val Asn Gly Ala Gly Ser Thr Asn Ser Ala
145                 150                 155                 160

Asp Val Tyr Cys Phe Ala Ala Ala Gln Ile Lys Lys Ala Leu Asp Ile
                165                 170                 175

Thr Val Lys Leu Gly Gly Arg Gly Tyr Val Phe Trp Gly Gly Arg Glu
                180                 185                 190

Gly Tyr Glu Thr Leu Leu Asn Thr Asn Val Gly Leu Glu Leu Asp Asn
            195                 200                 205

Met Ala Arg Leu Met Lys Met Ala Val Glu Tyr Gly Arg Ser Ile Gly
210                 215                 220

Phe Lys Gly Asp Phe Tyr Ile Glu Pro Lys Pro Lys Glu Pro Ala Lys
225                 230                 235                 240

His Gln Tyr Asp Phe Asp Thr Ala Thr Val Leu Gly Phe Leu Arg Lys
                245                 250                 255

Tyr Gly Leu Asp Lys Asp Phe Lys Met Asn Ile Glu Ala Asn His Ala
                260                 265                 270

Thr Leu Ala Gly His Ser Phe Gln His Glu Leu Arg Ile Ser Ser Ile
            275                 280                 285

Asn Gly Met Leu Gly Ser Val Asp Ala Asn Gln Gly Asp Met Leu Leu
290                 295                 300

Gly Trp Asp Thr Asp Glu Phe Pro Phe Asp Val Tyr Thr Thr Met
305                 310                 315                 320

Cys Met Tyr Glu Val Leu Lys Asn Gly Gly Leu Thr Gly Gly Phe Asn
                325                 330                 335

Phe Asp Ala Lys Asn Arg Arg Pro Ser Tyr Thr Tyr Glu Asp Met Phe
            340                 345                 350

Tyr Gly Phe Ile Leu Gly Met Asp Ser Phe Ala Leu Gly Phe Arg Ala
                355                 360                 365

Ala Leu Lys Leu Ile Glu Asp Gly Arg Ile Asp Lys Phe Val Ala Asp
370                 375                 380

Arg Tyr Ala Ser Trp Asn Thr Gly Ile Gly Ala Asp Ile Ile Ala Gly
385                 390                 395                 400

Lys Ala Asp Phe Ala Ser Leu Glu Lys Tyr Ala Leu Glu Lys Gly Glu
                405                 410                 415

Val Thr Ala Ser Leu Ser Ser Gly Arg Gln Glu Met Leu Glu Ser Ile
            420                 425                 430

Val Asn Asn Val Leu Phe Ser Leu
            435                 440

<210> SEQ ID NO 24
<211> LENGTH: 1311
```

<212> TYPE: DNA
<213> ORGANISM: Artificial Sequence
<220> FEATURE:
<223> OTHER INFORMATION: Synthetic DNA sequence for Variant No 3

<400> SEQUENCE: 24

```
atggaattttt tcaagaacat ctctaagata ccatacgaag gcaaagactc taccaatcca      60
ttagcattca agtactacaa tcctgacgaa gtaatcgacg gtaagaagat gagagacatc     120
atgaagtttg ctttgtcttg gtggcatact atgggaggtg atggtactga tatgtttggc     180
tgtggtactg ctgataagac atggggcgag aatgatccag ctgctagagc taaagctaaa     240
gttgatgccg catttgaaat catgcagaag ttatccattg attacttctg cttccatgat     300
agagatttgt ctccagagta cggttctttg aaggacacaa acgctcaatt ggacgttgtc     360
actgactaca tcaaggctaa acaagctgaa accggtttga atgtctttg ggtactgct      420
aagtgcttcg accatccaag attcatgcac ggtgctggta cttctccttc agcggatgtc     480
ttcgcattct cagctgctca aatcaagaaa gctctggaat ctaccgtcaa gttgggtgga     540
actggttatg tcttttgggg tggtagagaa ggttacgaga ccctgctgaa tactaacatg     600
ggcttagaac tggacaacat ggctaggcta atgaagatgg ccgtagaata cggtagggct     660
aatggattca aggtgacttt ctacatcgag cctaaaccca aggaaccaac taagcatcaa     720
tacgactttg acactgctac agtcttgggc tttctgagaa agtacggcct ggacaaagac     780
ttcaagatga acatcgaacc caatcacacc acactagcag gacactcatt cgagcatgag     840
ttagctatgg ctagggtaaa cggtgcattc ggttctgttg atgctaacca aggtgacgta     900
ttgttaggat gggacacggg tcaattcccc acagacgttc attctgctac tcttgctatg     960
ctggaggtct tgaaagccgg tggtttcaca aatggcggcc tgaactttga tgcgaaagct    1020
cgtagggggtt cattcgagtt tgacgatatt gcctatggtt acattgctgg tatggatact    1080
ttcgcgttag ggttaattaa agctgctgaa atcattgatg acggtagaat tgccaagttt    1140
gtggatgaca ggtatgcctc ttacaagacc ggtattggta aagcgatcgt tgacggaact    1200
acctcttttgg aagaattgga acaatacgtg ttgactcatt ctgaacctgt catgcaatct    1260
ggtggacaag aggttctgga aactattgtc aacaacgtat tgtttagata a             1311
```

<210> SEQ ID NO 25
<211> LENGTH: 436
<212> TYPE: PRT
<213> ORGANISM: Artificial Sequence
<220> FEATURE:
<223> OTHER INFORMATION: Synthetic polypeptide sequence for Variant No 3

<400> SEQUENCE: 25

```
Met Glu Phe Phe Lys Asn Ile Ser Lys Ile Pro Tyr Glu Gly Lys Asp
1               5                   10                  15

Ser Thr Asn Pro Leu Ala Phe Lys Tyr Tyr Asn Pro Asp Glu Val Ile
            20                  25                  30

Asp Gly Lys Lys Met Arg Asp Ile Met Lys Phe Ala Leu Ser Trp Trp
        35                  40                  45

His Thr Met Gly Gly Asp Gly Thr Asp Met Phe Gly Cys Gly Thr Ala
    50                  55                  60

Asp Lys Thr Trp Gly Glu Asn Asp Pro Ala Ala Arg Ala Lys Ala Lys
65                  70                  75                  80

Val Asp Ala Ala Phe Glu Ile Met Gln Lys Leu Ser Ile Asp Tyr Phe
                85                  90                  95
```

```
Cys Phe His Asp Arg Asp Leu Ser Pro Glu Tyr Gly Ser Leu Lys Asp
                100                 105                 110

Thr Asn Ala Gln Leu Asp Val Val Thr Asp Tyr Ile Lys Ala Lys Gln
            115                 120                 125

Ala Glu Thr Gly Leu Lys Cys Leu Trp Gly Thr Ala Lys Cys Phe Asp
130                 135                 140

His Pro Arg Phe Met His Gly Ala Gly Thr Ser Pro Ser Ala Asp Val
145                 150                 155                 160

Phe Ala Phe Ser Ala Ala Gln Ile Lys Lys Ala Leu Glu Ser Thr Val
                165                 170                 175

Lys Leu Gly Gly Thr Gly Tyr Val Phe Trp Gly Gly Arg Glu Gly Tyr
            180                 185                 190

Glu Thr Leu Leu Asn Thr Asn Met Gly Leu Glu Leu Asp Asn Met Ala
        195                 200                 205

Arg Leu Met Lys Met Ala Val Glu Tyr Gly Arg Ala Asn Gly Phe Lys
    210                 215                 220

Gly Asp Phe Tyr Ile Glu Pro Lys Pro Lys Glu Pro Thr Lys His Gln
225                 230                 235                 240

Tyr Asp Phe Asp Thr Ala Thr Val Leu Gly Phe Leu Arg Lys Tyr Gly
                245                 250                 255

Leu Asp Lys Asp Phe Lys Met Asn Ile Glu Pro Asn His Thr Thr Leu
            260                 265                 270

Ala Gly His Ser Phe Glu His Glu Leu Ala Met Ala Arg Val Asn Gly
        275                 280                 285

Ala Phe Gly Ser Val Asp Ala Asn Gln Gly Asp Val Leu Leu Gly Trp
    290                 295                 300

Asp Thr Gly Gln Phe Pro Thr Asp Val His Ser Ala Thr Leu Ala Met
305                 310                 315                 320

Leu Glu Val Leu Lys Ala Gly Phe Thr Asn Gly Gly Leu Asn Phe
                325                 330                 335

Asp Ala Lys Ala Arg Arg Gly Ser Phe Glu Phe Asp Asp Ile Ala Tyr
            340                 345                 350

Gly Tyr Ile Ala Gly Met Asp Thr Phe Ala Leu Gly Leu Ile Lys Ala
        355                 360                 365

Ala Glu Ile Ile Asp Asp Gly Arg Ile Ala Lys Phe Val Asp Asp Arg
    370                 375                 380

Tyr Ala Ser Tyr Lys Thr Gly Ile Gly Lys Ala Ile Val Asp Gly Thr
385                 390                 395                 400

Thr Ser Leu Glu Glu Leu Glu Gln Tyr Val Leu Thr His Ser Glu Pro
                405                 410                 415

Val Met Gln Ser Gly Gly Gln Glu Val Leu Glu Thr Ile Val Asn Asn
            420                 425                 430

Val Leu Phe Arg
        435

<210> SEQ ID NO 26
<211> LENGTH: 1326
<212> TYPE: DNA
<213> ORGANISM: Artificial Sequence
<220> FEATURE:
<223> OTHER INFORMATION: Synthetic DNA sequence for Variant No 42

<400> SEQUENCE: 26
atgaagaact atttccccaa cgtcccagaa gtcaaatacg aaggtccaaa ctccacaaat      60
cctttcgctt ttaaatatta tgatgctaat aaagtagtcg ccggtaagac catgaaggag     120
```

```
cattgtagat tcgctctatc ctggtggcac actttgtgtg ccggtggtgc tgatccattc    180
ggagtaacta ctatggacag gacctacggt aacattaccg acccaatgga actagctaag    240
gccaaagttg atgctggttt cgaactgatg actaagctgg catcgagtt cttctgcttc     300 catgatgccg acattgctcc agaaggtgac accttcgaag agtccaagaa gaatctgttc    360
gagattgttg attacatcaa ggagaagatg gaccaaaccg gcatcaagtt gttatggggc    420
actgctaaca actttagtca ccccaggttc atgcacggtg caggaacttc tcctagtgcc    480
gatgttttcg cttatgctgc tgcgaaaata aagaacgctt tagatgcgac catcaagttg    540
ggcggtagag gttatgtctt tggggtggt agagaaggtt acgagaccct gctgaatact     600
aacatgggct tagaactgga caacatggct aggttgatga gatggccgt tgagtatggt      660 aggtctattg gattcaaagg tgacttctac atcgagccta acccaaggaa acctatgaag    720
caccagtacg acttcgacac tgctaccgta ttaggttttt taaggcagta cgggttggat    780
aaagacttca aattgaacat cgaagccaat cacgccacac tagcaggaca ctcattccag    840
catgagttac gtatttctag tattaacggt atgttgggtt ctgttgatgc taaccaaggt    900
gacgtattgt taggatggga cacggatcaa ttccccacaa acatttatga tactactatg    960
tgtatgtatg aggtcattaa agccggtggt ttcacaaatg gcggcctgaa ctttgatgct    1020
aaagctagaa gaggttcatt cacgcctgaa gatatttct attcttacat tgctggtatg    1080
gatgctttcg cgttagggtt tagagcagct cttaaattga ttgaagacgg tagaattgac    1140
aagtttgtgg ctgacaggta tgcctcttgg aataccggta ttggtgcaga tattattgcc    1200
ggaaaagccg attttgcatc attggaaaaa tatgctttgg agaaaggaga ggttaccgcg    1260
tcattgtctt ctggtagaca agagatgctg gaatctattg tcaacaacgt attgtttagt    1320
ttgtaa                                                              1326
```

<210> SEQ ID NO 27
<211> LENGTH: 441
<212> TYPE: PRT
<213> ORGANISM: Artificial Sequence
<220> FEATURE:
<223> OTHER INFORMATION: Synthetic polypeptide sequence for Variant No
      42

<400> SEQUENCE: 27

```
Met Lys Asn Tyr Phe Pro Asn Val Pro Glu Val Lys Tyr Glu Gly Pro
1               5                   10                  15

Asn Ser Thr Asn Pro Phe Ala Phe Lys Tyr Tyr Asp Ala Asn Lys Val
            20                  25                  30

Val Ala Gly Lys Thr Met Lys Glu His Cys Arg Phe Ala Leu Ser Trp
        35                  40                  45

Trp His Thr Leu Cys Ala Gly Gly Ala Asp Pro Phe Gly Val Thr Thr
    50                  55                  60

Met Asp Arg Thr Tyr Gly Asn Ile Thr Asp Pro Met Glu Leu Ala Lys
65                  70                  75                  80

Ala Lys Val Asp Ala Gly Phe Glu Leu Met Thr Lys Leu Gly Ile Glu
                85                  90                  95

Phe Phe Cys Phe His Asp Ala Asp Ile Ala Pro Glu Gly Asp Thr Phe
            100                 105                 110

Glu Glu Ser Lys Lys Asn Leu Phe Glu Ile Val Asp Tyr Ile Lys Glu
        115                 120                 125

Lys Met Asp Gln Thr Gly Ile Lys Leu Leu Trp Gly Thr Ala Asn Asn
```

```
                 130                 135                 140
Phe Ser His Pro Arg Phe Met His Gly Ala Gly Thr Ser Pro Ser Ala
145                 150                 155                 160

Asp Val Phe Ala Tyr Ala Ala Ala Lys Ile Lys Asn Ala Leu Asp Ala
                165                 170                 175

Thr Ile Lys Leu Gly Gly Arg Gly Tyr Val Phe Trp Gly Gly Arg Glu
            180                 185                 190

Gly Tyr Glu Thr Leu Leu Asn Thr Asn Met Gly Leu Glu Leu Asp Asn
                195                 200                 205

Met Ala Arg Leu Met Lys Met Ala Val Glu Tyr Gly Arg Ser Ile Gly
            210                 215                 220

Phe Lys Gly Asp Phe Tyr Ile Glu Pro Lys Pro Lys Glu Pro Met Lys
225                 230                 235                 240

His Gln Tyr Asp Phe Asp Thr Ala Thr Val Leu Gly Phe Leu Arg Gln
                245                 250                 255

Tyr Gly Leu Asp Lys Asp Phe Lys Leu Asn Ile Glu Ala Asn His Ala
            260                 265                 270

Thr Leu Ala Gly His Ser Phe Gln His Glu Leu Arg Ile Ser Ser Ile
        275                 280                 285

Asn Gly Met Leu Gly Ser Val Asp Ala Asn Gln Gly Asp Val Leu Leu
        290                 295                 300

Gly Trp Asp Thr Asp Gln Phe Pro Thr Asn Ile Tyr Asp Thr Thr Met
305                 310                 315                 320

Cys Met Tyr Glu Val Ile Lys Ala Gly Gly Phe Thr Asn Gly Gly Leu
                325                 330                 335

Asn Phe Asp Ala Lys Ala Arg Arg Gly Ser Phe Thr Pro Glu Asp Ile
            340                 345                 350

Phe Tyr Ser Tyr Ile Ala Gly Met Asp Ala Phe Ala Leu Gly Phe Arg
        355                 360                 365

Ala Ala Leu Lys Leu Ile Glu Asp Gly Arg Ile Asp Lys Phe Val Ala
        370                 375                 380

Asp Arg Tyr Ala Ser Trp Asn Thr Gly Ile Gly Ala Asp Ile Ile Ala
385                 390                 395                 400

Gly Lys Ala Asp Phe Ala Ser Leu Glu Lys Tyr Ala Leu Glu Lys Gly
                405                 410                 415

Glu Val Thr Ala Ser Leu Ser Ser Gly Arg Gln Glu Met Leu Glu Ser
            420                 425                 430

Ile Val Asn Asn Val Leu Phe Ser Leu
        435                 440

<210> SEQ ID NO 28
<211> LENGTH: 1317
<212> TYPE: DNA
<213> ORGANISM: Artificial Sequence
<220> FEATURE:
<223> OTHER INFORMATION: Synthetic DNA sequence for Variant No 48

<400> SEQUENCE: 28
atgaagaact atttccccaa cgtcccagaa gtcaaatacg aaggtccaaa ctccacaaat      60
cctttcgctt ttaaatatta tgatgctaat aaagtagtcg ccggtaagac catgaaggag     120
cattgtagat tcgctctatc ctggtggcac actttgtgtg ccggtggtgc tgatccattc     180
ggagtaacta ctatggacag gacctacggt aacattaccg acccaatgga actagctaag     240
gccaaagttg atgctggttt cgaactgatg actaagctgg gcatcgagtt cttctgcttc     300
```

-continued

```
catgatgccg acattgctcc agaaggtgac accttcgaag agtccaagaa gaatctgttc     360
gagattgttg attacatcaa ggagaagatg gaccaaaccg gcatcaagtt gttatggggc     420
actgctaaca actttagtca ccccaggttc atgcacggtg catcaacttc ttgtaatgcc     480
gatgttttcg cttatgctgc tgcgaaaata aagaacgctt taggtgcgac catcaagttg     540
ggcggtagag gttatgtctt tggggtggt agagaaggat atgaaacgtt gttgaatact      600
aacatgggac ttgaattgga caacatggct aggttgatga agatggccgt tgagtatggt     660
aggtctattg gtttcaaagg tgacttctac atcgagccta acccaagga acctactaag      720
caccagtacg acttcgacgc tgctaccgca ataggttttt taaggcagta cgggttggac     780
aaagacttca aattgaacat cgaagccaat cacgccacac tagcaggaca ctcattccag     840
catgagttac gtatttctag tattaacggt atgttgggtt ctgttgatgc taaccaaggt     900
gacccaaaact taggatggga cacggatcaa ttccccacag acgttcattc tgctactctt    960
gctatgctgg aggtcttgaa agccggtggt ttcacaaatg gcggcctgaa ctttgatgcg    1020
aaagttcgta ggggttcatt cgagtttgac gatattgcct atggttacat tgctggtatg    1080
gatgctttcg cgttagggtt aattaaagct gctgaaatca ttgatgacgg tagaattgcc    1140
aagtttgtgg atgacaggta tgcctcttac aagaccggca ttggtaaagc gatcgttgac    1200
ggaactacct ctttggaaga attggaacaa tacgtgttga ctcattctga acctgtcatg    1260
caatctggta gacaagaggt tctggaaact attgtcaaca acatattgtt tagataa       1317
```

<210> SEQ ID NO 29
<211> LENGTH: 438
<212> TYPE: PRT
<213> ORGANISM: Artificial Sequence
<220> FEATURE:
<223> OTHER INFORMATION: Synthetic polypeptide sequence for Variant No 48

<400> SEQUENCE: 29

```
Met Lys Asn Tyr Phe Pro Asn Val Pro Glu Val Lys Tyr Glu Gly Pro
1               5                   10                  15

Asn Ser Thr Asn Pro Phe Ala Phe Lys Tyr Tyr Asp Ala Asn Lys Val
            20                  25                  30

Val Ala Gly Lys Thr Met Lys Glu His Cys Arg Phe Ala Leu Ser Trp
        35                  40                  45

Trp His Thr Leu Cys Ala Gly Gly Ala Asp Pro Phe Gly Val Thr Thr
    50                  55                  60

Met Asp Arg Thr Tyr Gly Asn Ile Thr Asp Pro Met Glu Leu Ala Lys
65                  70                  75                  80

Ala Lys Val Asp Ala Gly Phe Glu Leu Met Thr Lys Leu Gly Ile Glu
                85                  90                  95

Phe Phe Cys Phe His Asp Ala Asp Ile Ala Pro Glu Gly Asp Thr Phe
            100                 105                 110

Glu Glu Ser Lys Lys Asn Leu Phe Glu Ile Val Asp Tyr Ile Lys Glu
        115                 120                 125

Lys Met Asp Gln Thr Gly Ile Lys Leu Leu Trp Gly Thr Ala Asn Asn
    130                 135                 140

Phe Ser His Pro Arg Phe Met His Gly Ala Ser Thr Ser Cys Asn Ala
145                 150                 155                 160

Asp Val Phe Ala Tyr Ala Ala Ala Lys Ile Lys Asn Ala Leu Gly Ala
                165                 170                 175

Thr Ile Lys Leu Gly Gly Arg Gly Tyr Val Phe Trp Gly Gly Arg Glu
```

```
              180                 185                 190
Gly Tyr Glu Thr Leu Leu Asn Thr Asn Met Gly Leu Glu Leu Asp Asn
                    195                 200                 205

Met Ala Arg Leu Met Lys Met Ala Val Glu Tyr Gly Arg Ser Ile Gly
            210                 215                 220

Phe Lys Gly Asp Phe Tyr Ile Glu Pro Lys Pro Lys Glu Pro Thr Lys
225                 230                 235                 240

His Gln Tyr Asp Phe Asp Ala Ala Thr Ala Ile Gly Phe Leu Arg Gln
                245                 250                 255

Tyr Gly Leu Asp Lys Asp Phe Lys Leu Asn Ile Glu Ala Asn His Ala
            260                 265                 270

Thr Leu Ala Gly His Ser Phe Gln His Glu Leu Arg Ile Ser Ser Ile
        275                 280                 285

Asn Gly Met Leu Gly Ser Val Asp Ala Asn Gln Gly Asp Pro Asn Leu
            290                 295                 300

Gly Trp Asp Thr Asp Gln Phe Pro Thr Asp Val His Ser Ala Thr Leu
305                 310                 315                 320

Ala Met Leu Glu Val Leu Lys Ala Gly Gly Phe Thr Asn Gly Gly Leu
                325                 330                 335

Asn Phe Asp Ala Lys Val Arg Arg Gly Ser Phe Glu Phe Asp Asp Ile
            340                 345                 350

Ala Tyr Gly Tyr Ile Ala Gly Met Asp Ala Phe Ala Leu Gly Leu Ile
        355                 360                 365

Lys Ala Ala Glu Ile Ile Asp Asp Gly Arg Ile Ala Lys Phe Val Asp
    370                 375                 380

Asp Arg Tyr Ala Ser Tyr Lys Thr Gly Ile Gly Lys Ala Ile Val Asp
385                 390                 395                 400

Gly Thr Thr Ser Leu Glu Glu Leu Glu Gln Tyr Val Leu Thr His Ser
                405                 410                 415

Glu Pro Val Met Gln Ser Gly Arg Gln Glu Val Leu Thr Ile Val
            420                 425                 430

Asn Asn Ile Leu Phe Arg
        435

<210> SEQ ID NO 30
<211> LENGTH: 1326
<212> TYPE: DNA
<213> ORGANISM: Artificial Sequence
<220> FEATURE:
<223> OTHER INFORMATION: Synthetic DNA sequence for Variant No 56

<400> SEQUENCE: 30
atgaagaact atttccccaa cgtcccagaa gtcaaatacg aaggtccaaa ctccacaaat    60
cctttcgctt ttaaatatta tgatgctaat aaagtagtcg ccggtaagac catgaaggag   120
cattgtagat tcgctctatc ctggtggcac actttgtgtg ccggtggtgc tgatccattc   180
ggagtaacta ctatggacag gacctacggt aacattaccg acccaatgga actagctaag   240
gccaaagttg atgctggttt cgaactgatg actaagctgg gcatcgagtt cttctgcttc   300
catgatgccg acattgctcc agaaggtgac accttcgaag agtccaagaa gaatctgttc   360
gagattgttg attacatcaa ggagaagatg gaccaaaccg gcatcaagtt gttatgggc   420 actgctaaca actttagtca ccccaggttc atgcacggtg caggaacttc ttgtaatgcc   480
gatgttttcg cttatgctgc tgcgaaaata aagaacgctt tagatgcgac catcaagttg   540
ggcggtagag gttatgtctt tggggtggt agagaaggtt acgagaccct gctgaatact   600
```

```
aacatgggct tagaactgga caacatggct aggctaatga agatggccgt agaatacggt    660
aggtctattg gattcaaagg tgacttctac attgaaccta aacccaagga acctactaag    720
caccagtacg acttcgacac tgctaccgta ttaggttttt taaggaagta cgggttggat    780
aaagacttca agatgaacat cgaagccaat cacgccacac tagcaggaca ctcattccag    840
catgagttac gtgtggctag ggataacggt gtattcggtt ctattgatgc taaccaaggt    900
gacgtattgt taggatggga cacgatcaa ttccccacaa acatttatga tactactatg    960
tgtatgtatg aggtcattaa agccggcggt tcacaaatg gcggcctgaa ctttgatgcg    1020
aaagctcgta ggggttcatt cacgcctgaa gatattttct atagttacat tgctggtatg    1080
gatgctttcg cgttagggtt tagagcagct cttaaattga ttgaagacgg tagaattgac    1140
aagtttgtgg ctgacaggta tgcctcttgg aataccggta ttggtgcaga tattattgcc    1200
ggaaaagccg attttgcatc attggaaaaa tatgctttgg aaaaaggtga agttgccgcg    1260
tcattgtctt ctggtagaca agagatgctg gaatctattg tcaacaacgt attgtttagt    1320
ttgtaa                                                               1326
```

<210> SEQ ID NO 31
<211> LENGTH: 441
<212> TYPE: PRT
<213> ORGANISM: Artificial Sequence
<220> FEATURE:
<223> OTHER INFORMATION: Synthetic polypeptide sequence for Variant No 56

<400> SEQUENCE: 31

```
Met Lys Asn Tyr Phe Pro Asn Val Pro Glu Val Lys Tyr Glu Gly Pro
1               5                   10                  15

Asn Ser Thr Asn Pro Phe Ala Phe Lys Tyr Tyr Asp Ala Asn Lys Val
            20                  25                  30

Val Ala Gly Lys Thr Met Lys Glu His Cys Arg Phe Ala Leu Ser Trp
        35                  40                  45

Trp His Thr Leu Cys Ala Gly Ala Asp Pro Phe Gly Val Thr Thr
    50                  55                  60

Met Asp Arg Thr Tyr Gly Asn Ile Thr Asp Pro Met Glu Leu Ala Lys
65                  70                  75                  80

Ala Lys Val Asp Ala Gly Phe Glu Leu Met Thr Lys Leu Gly Ile Glu
                85                  90                  95

Phe Phe Cys Phe His Asp Ala Asp Ile Ala Pro Glu Gly Asp Thr Phe
            100                 105                 110

Glu Glu Ser Lys Lys Asn Leu Phe Glu Ile Val Asp Tyr Ile Lys Glu
        115                 120                 125

Lys Met Asp Gln Thr Gly Ile Lys Leu Leu Trp Gly Thr Ala Asn Asn
    130                 135                 140

Phe Ser His Pro Arg Phe Met His Gly Ala Gly Thr Ser Cys Asn Ala
145                 150                 155                 160

Asp Val Phe Ala Tyr Ala Ala Ala Lys Ile Lys Asn Ala Leu Asp Ala
                165                 170                 175

Thr Ile Lys Leu Gly Gly Arg Gly Tyr Val Phe Trp Gly Gly Arg Glu
            180                 185                 190

Gly Tyr Glu Thr Leu Leu Asn Thr Asn Met Gly Leu Glu Leu Asp Asn
        195                 200                 205

Met Ala Arg Leu Met Lys Met Ala Val Glu Tyr Gly Arg Ser Ile Gly
    210                 215                 220
```

```
Phe Lys Gly Asp Phe Tyr Ile Glu Pro Lys Pro Lys Glu Pro Thr Lys
225                 230                 235                 240

His Gln Tyr Asp Phe Asp Thr Ala Thr Val Leu Gly Phe Leu Arg Lys
            245                 250                 255

Tyr Gly Leu Asp Lys Asp Phe Lys Met Asn Ile Glu Ala Asn His Ala
        260                 265                 270

Thr Leu Ala Gly His Ser Phe Gln His Glu Leu Arg Val Ala Arg Asp
    275                 280                 285

Asn Gly Val Phe Gly Ser Ile Asp Ala Asn Gln Gly Asp Val Leu Leu
290                 295                 300

Gly Trp Asp Thr Asp Gln Phe Pro Thr Asn Ile Tyr Asp Thr Thr Met
305                 310                 315                 320

Cys Met Tyr Glu Val Ile Lys Ala Gly Gly Phe Thr Asn Gly Gly Leu
                325                 330                 335

Asn Phe Asp Ala Lys Ala Arg Arg Gly Ser Phe Thr Pro Glu Asp Ile
            340                 345                 350

Phe Tyr Ser Tyr Ile Ala Gly Met Asp Ala Phe Ala Leu Gly Phe Arg
        355                 360                 365

Ala Ala Leu Lys Leu Ile Glu Asp Gly Arg Ile Asp Lys Phe Val Ala
    370                 375                 380

Asp Arg Tyr Ala Ser Trp Asn Thr Gly Ile Gly Ala Asp Ile Ile Ala
385                 390                 395                 400

Gly Lys Ala Asp Phe Ala Ser Leu Glu Lys Tyr Ala Leu Glu Lys Gly
                405                 410                 415

Glu Val Ala Ala Ser Leu Ser Ser Gly Arg Gln Glu Met Leu Glu Ser
            420                 425                 430

Ile Val Asn Asn Val Leu Phe Ser Leu
        435                 440

<210> SEQ ID NO 32
<211> LENGTH: 1326
<212> TYPE: DNA
<213> ORGANISM: Artificial Sequence
<220> FEATURE:
<223> OTHER INFORMATION: Synthetic DNA sequence for Variant No 62

<400> SEQUENCE: 32
atgaagaact atttccccaa cgtcccagaa gtcaaatacg aaggtccaaa ctccacaaat      60
cctttcgctt ttaaatatta tgatgctaat aaagtagtcg ccggtaagac catgaaggag     120
cattgtagat tcgctctatc ctggtggcac actttgtgtg ccgtggtgc tgatccattc      180 ggagtaacta ctatggacag gacctacggt aacattaccg acccaatgga catgctaag     240 gccaaagttg atgctggttt cgaactgatg actaagctgg catcgagtt cttctgcttc     300 catgatgccg acattgctcc agaaggtgac accttcgaag agtccaagaa gaatctgttc     360
gagattgttg attacatcaa ggagaagatg gaccaaaccg gcatcaagtt gttatggggc     420
actgctaaca actttagtca ccccaggttc atgcacggtg catcaacttc ttgtaatgcc     480
gatgttttcg cttatgctgc tgcgaaaata aagaacgctc tagatgcgac catcaagttg     540
ggcggtaagg gttatgtctt tggggtggt agagaaggtt acgagaccct gctgaatact      600
aacatgggct tagaactgga caacatggct aggctaatga gatggccgt agaatacggt      660 aggtctattg gattcgacgg tgacttctac atcgagccta aacccaagga acctactaag     720
caccagtacg acttcgacac tgctaccgta ttaggtttttt taaggaagta cgggttggat    780
```

```
aaagacttca agatgaacat cgaagccaat cacgccacac tagcaggaca ctcattccag    840
catgagttac gtatttctag tattaacggt atgttgggtt ctgttgatgc taaccaaggt    900
gacatgttgt taggatggga cacggatcaa ttccccacaa acatttatga tactactatg    960
tgtatgtatg aggtcattaa agccggtggt ttcacaaatg gcggcctgaa ctttgatgcg   1020
aaagctcgta gaggttcttt cactccagaa gatattttct attcttacat tgctggtatg   1080
gatgctttcg cgttagggtt tagggcagct cttaaattga ttgaagacgg tagaattgac   1140
aagtttgtgg ctgacaggta tgcctcttgg aataccggta ttggtgcaga tattattgcc   1200
ggaaaagccg attttgcatc attggaaaaa tatgctttgg aaaaaggtga agttaccgcg   1260
tcattgtctt ctggtagaca agagatgctg gaatctattg tcaacaacgt attgtttagt   1320
ttgtaa                                                              1326
```

<210> SEQ ID NO 33
<211> LENGTH: 441
<212> TYPE: PRT
<213> ORGANISM: Artificial Sequence
<220> FEATURE:
<223> OTHER INFORMATION: Synthetic polypeptide sequence for Variant No 62

<400> SEQUENCE: 33

```
Met Lys Asn Tyr Phe Pro Asn Val Pro Glu Val Lys Tyr Glu Gly Pro
 1               5                  10                  15

Asn Ser Thr Asn Pro Phe Ala Phe Lys Tyr Tyr Asp Ala Asn Lys Val
            20                  25                  30

Val Ala Gly Lys Thr Met Lys Glu His Cys Arg Phe Ala Leu Ser Trp
        35                  40                  45

Trp His Thr Leu Cys Ala Gly Gly Ala Asp Pro Phe Gly Val Thr Thr
    50                  55                  60

Met Asp Arg Thr Tyr Gly Asn Ile Thr Asp Pro Met Glu His Ala Lys
65                  70                  75                  80

Ala Lys Val Asp Ala Gly Phe Glu Leu Met Thr Lys Leu Gly Ile Glu
                85                  90                  95

Phe Phe Cys Phe His Asp Ala Asp Ile Ala Pro Glu Gly Asp Thr Phe
            100                 105                 110

Glu Glu Ser Lys Lys Asn Leu Phe Glu Ile Val Asp Tyr Ile Lys Glu
        115                 120                 125

Lys Met Asp Gln Thr Gly Ile Lys Leu Leu Trp Gly Thr Ala Asn Asn
    130                 135                 140

Phe Ser His Pro Arg Phe Met His Gly Ala Ser Thr Ser Cys Asn Ala
145                 150                 155                 160

Asp Val Phe Ala Tyr Ala Ala Ala Lys Ile Lys Asn Ala Leu Asp Ala
                165                 170                 175

Thr Ile Lys Leu Gly Gly Lys Gly Tyr Val Phe Trp Gly Gly Arg Glu
            180                 185                 190

Gly Tyr Glu Thr Leu Leu Asn Thr Asn Met Gly Leu Glu Leu Asp Asn
        195                 200                 205

Met Ala Arg Leu Met Lys Met Ala Val Glu Tyr Gly Arg Ser Ile Gly
    210                 215                 220

Phe Asp Gly Asp Phe Tyr Ile Glu Pro Lys Pro Lys Glu Pro Thr Lys
225                 230                 235                 240

His Gln Tyr Asp Phe Asp Thr Ala Thr Val Leu Gly Phe Leu Arg Lys
                245                 250                 255
```

```
Tyr Gly Leu Asp Lys Asp Phe Lys Met Asn Ile Glu Ala Asn His Ala
            260             265             270

Thr Leu Ala Gly His Ser Phe Gln His Glu Leu Arg Ile Ser Ser Ile
        275             280             285

Asn Gly Met Leu Gly Ser Val Asp Ala Asn Gln Gly Asp Met Leu Leu
    290             295             300

Gly Trp Asp Thr Asp Gln Phe Pro Thr Asn Ile Tyr Asp Thr Thr Met
305             310             315             320

Cys Met Tyr Glu Val Ile Lys Ala Gly Gly Phe Thr Asn Gly Gly Leu
            325             330             335

Asn Phe Asp Ala Lys Ala Arg Arg Gly Ser Phe Thr Pro Glu Asp Ile
            340             345             350

Phe Tyr Ser Tyr Ile Ala Gly Met Asp Ala Phe Ala Leu Gly Phe Arg
            355             360             365

Ala Ala Leu Lys Leu Ile Glu Asp Gly Arg Ile Asp Lys Phe Val Ala
        370             375             380

Asp Arg Tyr Ala Ser Trp Asn Thr Gly Ile Gly Ala Asp Ile Ile Ala
385             390             395             400

Gly Lys Ala Asp Phe Ala Ser Leu Glu Lys Tyr Ala Leu Glu Lys Gly
            405             410             415

Glu Val Thr Ala Ser Leu Ser Ser Gly Arg Gln Glu Met Leu Glu Ser
            420             425             430

Ile Val Asn Asn Val Leu Phe Ser Leu
            435             440
```

US 8,778,652 B2

PENTOSE FERMENTATION BY A RECOMBINANT MICROORGANISM

The present application claims priority to U.S. Provisional Application No. 61/503,304, filed Jun. 30, 2011, the entire content of which is incorporated herein by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file CX3-091US1_ST25.TXT, created on Jul. 26, 2012, 75,020 bytes, machine format IBM-PC, MS-Windows operating system, is hereby incorporated by reference.

FIELD OF THE INVENTION

The present invention provides methods and compositions suitable for use in the isomerization of xylose to xylulose.

BACKGROUND

Ethanol and ethanol fuel blends are widely used in Brazil and in the United States as a transportation fuel. Combustion of these fuels is believed to produce fewer of the harmful exhaust emissions (e.g., hydrocarbons, nitrogen oxide, and volatile organic compounds (VOCs)) that are generated by the combustion of petroleum. Bioethanol is a particularly favored form of ethanol because the plant biomass from which it is produced utilizes sunlight, an energy source that is renewable. In the United States, ethanol is used in gasoline blends that are from 5% to 85% ethanol. Blends of up to 10% ethanol (E10) are approved for use in all gasoline vehicles in the U.S. and blends of up to 85% ethanol (E85) can be utilized in specially engineered flexible-fuel vehicles (FFV). The Brazilian government has mandated the use of ethanol-gasoline blends as a vehicle fuel, and the mandatory blend has been 25% ethanol (E25) since 2007.

Bioethanol is currently produced by the fermentation of hexose sugars that are obtained from carbon feedstocks. Currently, only the sugar from sugar cane and starch from feedstock such as corn can be economically converted. There is, however, much interest in using lignocellulosic feedstocks where the cellulose part of a plant is broken down to sugars and subsequently converted to ethanol. Lignocellulosic biomass is made up of cellulose, hemicelluloses, and lignin. Cellulose and hemicellulose can be hydrolyzed in a saccharification process to sugars that can be subsequently converted to ethanol via fermentation. The major fermentable sugars from lignocelluloses are glucose and xylose. For economical ethanol yields, a strain that can effectively convert all the major sugars present in cellulosic feedstock would be highly desirable.

SUMMARY OF THE INVENTION

The present invention provides methods and compositions suitable for use in the isomerization of xylose to xylulose.

In some embodiments, the present invention provides recombinant nucleic acid constructs comprising at least one polynucleotide sequence encoding a polypeptide that is capable of catalyzing the isomerization of D-xylose directly to D-xylulose, wherein the polynucleotide is a polynucleotide that encodes a polypeptide comprising an amino acid sequence having at least about 70%, at least 75%, at least 80%, at least 85%, at least 90%, or at least 95% identity to SEQ ID NO:23; 25, 27, 29, 31, or 33, or a polynucleotide that hybridizes under stringent hybridization conditions to the complement of a polynucleotide that encodes a polypeptide having the amino acid sequence of SEQ ID NO: 23; 25, 27, 29, 31, and/or 33. In some embodiments, at least one polynucleotide sequence encodes a polypeptide comprising the amino acid sequence of SEQ ID NO: 23; 25, 27, 29, 31, and/or 33, while in some alternative embodiments, the polynucleotide sequence encodes a polypeptide comprising the amino acid sequence of SEQ ID NO: 23; 25, 27, 29, 31, and/or 33. In some additional embodiments, the present invention also provides recombinant nucleic acid constructs comprising at least one polynucleotide sequence that encodes a polypeptide that is capable of catalyzing the isomerization of D-xylose directly to D-xylulose, wherein the polynucleotide is a polynucleotide that encodes a polypeptide comprising an amino acid sequence having at least 60%, at least 65%, at least 70%, at least 75%, at least 80%, at least 85%, at least 90%, at least 95%, at least 96%, at least 97%, at least 98%, or at least 99% identity to at least one chimeric xylose isomerase variant set forth in Table 3-1. In some further embodiments, the nucleic acid constructs comprise at least one polynucleotide sequence comprising at least one mutation and/or mutation set selected from those set forth in Table 3-1, wherein the mutation and/or mutation set comprise either or both amino acid or nucleic acid mutations and/or mutation sets. In some embodiments, the nucleic acid constructs comprise at least one polypeptide comprising a chimeric xylose isomerase.

The present invention also provides nucleic acid constructs comprising polynucleotide sequences encoding polypeptides having amino acid sequences that comprise at least one mutation (and/or mutation set) at the following position and/or positions: 3/5/8/11/13/14/15/16/18/19/22/24/27/28/30/31/32/33/38/42/45/46/50/51/52/53/54/61/62/64/67/68/70/71/72/73/74/75/76/84/87/89/92/94/96/101/104/107/108/109/110/112/115/116/119/120/121/125/128/130/131/132/140/141/143/144/148/149/153/154/155/160/161/163/172/173/180/199/236/273/275/282/283/284/285/288/289/292/299/307/310/311/312/323/325/328/330/333/339/342/344/346/349/352/353/355/359; 5/8/11/13/15/16/19/22/29/33/36/39/40/41/64/70/71/89/96/112/115/119/126/129/130/131/132/180/219/220/266/269/273/275/277/281/282/285/288/292/306/311/312/313/314/315/317/318/320/323/345/346/347/350/352/359/364/365/366/368/369/370/372/377/381/387/388/393/394/396/397/399/400/401/402/403/404/407/409/411/412/413/415/416/417/418/419/420/423/426/429/437/438; 5/8/11/13/15/16/19/22/29/33/36/39/40/41/64/70/71/89/96/112/115/126/129/130/131/132/180/281/285/288/299/364/365/368/372/378/380/381/388/389/393/397/402/404/417/419/426/435/437; 2/3/5/7/8/9/10/11/13/16/19/21/22/27/28/29/30/32/33/38/41/42/51/52/53/54/56/58/61/62/64/66/68/70/71/74/75/76/84/87/89/92/94/95/96/101/103/104/107/108/109/110/111/112/113/114/115/116/118/119/120/121/128/129/130/131/132/134/140/141/143/152/155/156/162/163/166/169/172/173/175/180/219/220/223/249/257/273/311/312/313/314/315/317/318/320/323/339/345/346/347/350/364/365/366/368/369/370/372/377/381/387/388/393/394/396/397/399/400/401/402/403/404/407/409/411/412/413/415/416/417/418/419/420/426/429/434/437/438; 2/3/5/7/8/9/10/11/13/16/18/19/21/22/27/28/29/30/32/33/38/41/42/51/52/53/54/56/58/61/62/64/66/68/70/71/74/75/76/84/87/89/94/95/96/101/103/104/107/108/109/110/111/112/113/114/115/116/118/119/120/121/128/129/130/131/132/134/140/141/143/152/155/156/162/163/166/169/172/173/175/180/273/277/281/282/285/288/292/299/300/311/312/313/314/315/317/318/320/323/335/339/345/346/347/350/

352/359/364/365/366/368/369/370/372/377/381/387/388/
393/394/396/397/399/400/401/402/403/404/407/409/411/
412/413/415/416/417/418/419/420/426/429/434/437/438;
2/3/5/7/8/9/10/11/13/16/19/21/22/27/28/29/30/32/33/38/41/
42/51/52/53/54/56/58/61/62/64/66/68/70/71/74/75/76/84/
134/140/141/143/152/155/156/162/163/166/169/172/173/
175/180/198/199/206/219/220/223/249/257/273/277/281/
282/292/299/300/311/312/313/314/315/317/318/320/323/
339/345/346/347/350/352/359/364/365/366/368/369/370/
372/377/381/387/388/393/394/396/397/399/400/401/402/
403/404/407/409/411/412/413/415/416/417/418/419/420/
426/429/434/437/438; 2/3/5/7/8/9/10/11/13/16/19/21/22/27/
28/29/30/32/33/38/41/42/51/52/53/54/56/58/61/62/64/66/
68/70/71/74/75/76/87/89/92/94/95/96/101/103/104/107/
108/109/110/111/112/113/114/115/116/118/119/120/121/
128/129/130/131/132/134/140/141/143/152/155/156/162/
163/166/169/172/173/175/180/198/199/249/273/277/281/
282/285/288/292/299/300/311/312/313/314/315/317/318/
320/323/339/345/346/347/350/352/359/364/365/366/368/
369/370/372/377/381/387/388/393/394/396/397/399/400/
401/402/403/404/407/409/411/412/413/415/416/417/418/
419/420/426/429/434/437/438; 2/3/5/8/11/13/15/16/18/19/
22/24/27/28/30/31/32/33/38/42/45/46/50/51/52/53/54/61/
62/64/67/68/70/71/72/73/74/75/76/84/87/89/92/94/96/101/
104/107/108/109/110/112/113/115/116/119/120/121/125/
128/130/131/132/140/141/143/144/148/149/153/154/155/
160/161/163/172/173/180/198/199/200/201/203/204/206/
208/236/244/247/248/253/262/273/275/282/283/284/285/
288/289/292/299/307/310/311/312/323/325/328/330/333/
339/342/344/346/349/352/353/355/359/364/365/366/368/
373/375/376/378/380/381/382/385/387/388/389/390/393/
394/396/397/398/399/401/402/403/404/406/407/410/412/
414/415/416/418/419/420/426/428/429/430/431/433/434/
437/438; 2/3/5/7/8/9/10/11/13/16/19/21/22/27/28/29/30/32/
33/38/41/42/51/52/53/54/56/58/61/62/64/66/68/70/71/74/
75/76/84/87/89/92/94/95/96/101/103/104/107/108/109/110/
111/112/113/114/115/116/118/119/120/121/128/129/130/
131/132/134/140/141/143/152/155/156/162/163/166/169/
172/173/175/180/244/247/248/253/262/273/275/282/283/
284/285/288/289/292/299/300/311/312/313/314/315/317/
318/320/323/339/345/346/347/350/352/364/365/366/368/
369/370/372/377/381/387/388/393/394/396/397/399/400/
401/402/403/404/407/409/411/412/413/415/416/417/418/
419/420/426/429/434/437/438; 2/3/5/7/8/9/10/11/13/16/19/
21/22/27/28/29/30/32/33/38/41/42/51/52/53/54/56/58/61/
62/64/66/68/70/71/74/75/76/84/87/89/92/94/95/96/101/103/
104/107/108/109/110/111/112/113/114/115/116/118/119/
120/121/128/129/130/131/132/134/140/141/143/152/155/
156/162/163/166/169/172/173/175/198/199/223/236/273/
277/281/282/285/288/292/299/300/311/312/313/314/315/
317/318/320/323/339/345/346/347/350/352/359/364/365/
366/368/369/370/372/377/381/387/388/393/394/396/397/
399/400/401/402/403/404/407/409/411/412/413/415/416/
417/418/419/420/426/429/434/437/438; 2/3/5/7/8/9/10/11/
13/16/19/21/22/27/28/29/30/32/33/38/41/42/51/52/53/54/
56/58/61/62/64/66/68/70/71/74/75/76/84/87/89/92/94/95/
96/101/103/104/107/108/109/110/111/112/113/114/115/
116/118/119/120/121/128/129/130/131/132/134/140/141/
143/152/155/156/162/163/166/169/172/173/175/180/198/
199/219/220/223/249/257/273/277/281/282/285/288/292/
299/300/311/312/313/314/315/317/318/320/323/339/345/
346/347/350/352/359/364/365/366/368/369/370/372/377/
381/387/388/393/394/396/397/399/400/401/402/403/404/
407/409/411/412/413/415/416/417/418/419/420/426/429/
434/437/438; 2/3/5/7/8/9/10/11/13/16/19/21/22/27/28/29/
30/32/33/38/41/42/51/52/53/54/56/58/61/62/64/66/68/70/
71/74/75/76/84/87/89/92/94/95/96/101/103/104/107/108/
109/110/111/112/113/114/115/116/118/119/120/121/128/
129/130/131/13277/381/387/388/393/394/396/397/399/
400/401/402/403/404/407/409/411/412/413/415/416/417/
418/419/420/426/429/434/437/438; 2/3/5/6/7/8/10/11/13/
16/19/21/22/27/28/29/30/32/33/38/41/42/51/52/53/54/56/
58/61/62/64/66/68/70/71/74/75/76/84/87/89/92/94/95/96/
101/103/104/107/108/109/110/111/112/113/114/115/116/
118/119/120/121/128/129/130/131/132/134/140/141/143/
152/155/156/162/163/166/169/172/173/175/180/198/199/
219/257/292/311/312/313/314/315/317/318/320/323/339/
345/346/347/350/352/359/364/365/366/368/369/370/372/
377/381/387/388/393/394/396/397/399/400/401/402/403/
404/407/409/411/412/413/415/416/417/418/419/420/426/
429/434/437/438; 2/3/5/7/8/9/10/11/13/16/19/21/22/27/28/
29/30/32/33/38/41/42/51/52/53/54/56/58/61/62/64/66/68/
70/71/74/75/76/84/87/89/92/94/95/96/101/103/104/107/
108/109/110/111/112/113/114/115/116/118/119/120/121/
128/129/130/131/132/134/140/141/143/152/155/156/166/
169/172/173/175/180/198/199/219/220/223/249/257/273/
277/281/282/285/288/292/299/300/311/312/313/314/315/
317/318/320/323/339/344/345/346/347/350/352/359/364/
365/366/368/369/370/372/377/381/387/388/393/394/396/
397/399/400/401/402/403/404/407/409/411/412/413/415/
416/417/418/419/420/426/429/434/437/438; 2/3/5/7/8/9/10/
11/13/16/19/21/22/27/28/29/30/32/33/38/41/42/51/52/53/
54/56/58/61/62/64/66/68/70/71/74/75/76/84/87/89/92/94/
95/96/101/103/104/107/108/109/110/111/112/113/114/115/
116/118/119/120/121/128/129/130/131/132/134/140/141/
143/152/155/156/162/163/166/169/172/173/175/180/219/
220/223/236/244/247/248/257/273/277/281/282/285/288/
292/299/300/311/312/313/314/315/317/318/320/323/339/
345/346/347/350/352/359/364/365/366/368/369/370/372/
377/381/387/388/393/394/396/397/399/400/401/402/403/
404/407/409/411/412/413/415/416/417/418/419/420/426/
429/434/437/438; 2/3/5/7/8/9/10/11/13/16/19/21/22/27/28/
29/30/32/33/38/41/42/51/52/53/54/56/58/61/62/64/66/68/
70/71/74/75/76/84/87/89/92/94/95/96/101/103/104/107/
108/109/110/111/112/113/114/115/116/118/119/120/121/
128/129/130/131/132/134/140/141/143/148/149/152/155/
156/162/163/166/169/172/173/175/180/198/199/219/220/
223/253/257/273/277/281/282/285/288/292/299/300/311/
312/313/314/315/317/318/320/323/339/345/346/347/350/
352/359/361/364/365/366/368/369/370/372/377/381/387/
388/393/394/396/397/399/400/401/402/403/404/407/409/
411/412/413/415/416/417/418/419/420/426/429/434/437/
438; 2/3/5/7/8/9/10/11/13/16/19/21/22/27/28/29/30/32/33/
38/41/42/51/52/53/54/56/58/61/62/64/66/68/70/71/74/75/
76/84/87/89/92/94/95/96/101/103/104/107/108/109/110/
111/112/113/114/115/116/118/119/120/121/128/129/130/
131/132/134/140/141/143/155/156/162/163/166/169/172/
173/175/180/273/275/416; 3/5/8/11/13/15/16/18/19/22/24/
27/28/30/31/32/33/38/42/45/46/50/51/52/53/54/61/62/64/
67/68/70/71/72/73/74/75/76/84/87/89/92/94/96/101/104/
107/108/109/110/112/115/116/119/120/121/125/128/130/
131/132/140/141/143/144/148/149/153/154/155/160/161/
163/172/173/180/198/199/200/201/203/204/206/208/236/
244/247/248/253/262/273/275/282/283/284/285/288/289/
292/299/307/310/311/312/323/325/328/330/333/339/342/
344/346/349/352/353/355/359/364/365/366/368/373/375/
376/378/380/381/382/385/387/388/389/390/393/394/396/
397/398/399/401/402/403/404/406/407/410/412/414/415/
416/418/419/420/426/428/429/430/431/433/434/437/438;
3/5/8/11/13/15/16/18/19/22/24/27/28/30/31/32/33/38/42/
45/46/50/51/52/53/54/61/62/64/67/68/70/71/72/73/74/75/
76/149/153/154/155/160/161/163/172/173/180/198/199/
200/201/203/204/206/208/236/244/247/248/253/262/273/
275/282/A283/284/285/288/289/292/299/307/310/311/312/

323/A325/328/330/333/A339/342/344/346/349/352/353/
A355/A359/364/365/A366/368/373/375/376/378/380/
A381/382/A385/387/388/389/390/A393/394/396/A397/
398/399/401/402/A403/404/406/407/410/412/414/415/416/
418/419/420/426/428/429/430/431/433/434/437/438; 236/
244/247/248/253/262/273/275/282/283/284/285/288/289/
292; 2/3/5/7/8/9/10/11/13/16/19/21/22/27/28/29/30/32/33/
38/41/42/51/52/53/54/56/58/61/62/64/66/68/70/71/74/75/
76/84/87/89/92/94/95/96/101/103/104/107/108/109/110/
111/112/113/114/115/116/118/119/120/121/128/129/130/
131/132/134/140/141/143/152/155/156/162/163/166/169/
172/173/175/180/208/219/220/223/273/277/281/282/285/
288/292/299/300/311/312/313/314/315/317/318/320/323/
334/339/345/346/347/350/352/359/364/365/366/368/369/
370/372/374/377/381/387/388/393/394/396/397/399/400/
401/402/403/404/407/409/411/412/413/415/416/417/418/
419/420/422/426/429/434/437/438; 2/3/5/7/8/9/10/11/13/
16/19/21/22/27/28/29/30/32/33/38/41/42/51/52/53/54/56/
58/61/62/64/66/68/70/71/74/75/76/84/87/89/92/94/95/96/
101/103/104/107/108/109/110/111/112/113/114/115/116/
118/119/120/121/128/129/130/131/132/134/140/141/143/
152/155/156/162/163/166/169/172/173/175/180/198/199/
273/277/281/282/285/288/292/299/300; 2/3/5/7/8/9/10/11/
13/16/19/21/22/27/28/29/30/32/33/38/41/42/51/52/53/54/
56/58/61/62/64/66/68/70/71/74/75/76/84/87/89/92/94/95/
96/101/103/104/107/108/109/110/111/112/113/114/115/
116/118/119/120/121/128/129/130/131/132/134/140/141/
143/152/155/156/162/163/166/169/172/173/175/180/223/
273/275/282/283/284/285/288/289/292/299; 2/3/5/7/8/9/10/
11/13/15/16/19/21/22/27/28/29/30/32/33/38/41/42/51/52/
53/54/56/58/61/62/64/66/68/70/71/74/75/76/84/87/89/92/
94/95/96/101/103/104/107/108/109/110/111/112/113/114/
115/116/118/119/120/121/128/129/130/131/132/134/140/
141/143/152/155/156/162/163/166/169/172/173/175/180/
219/220/223/257/273/277/281/282/285/288/292/299/300/
311/312/313/314/315/317/318/320/323/325/339/345/346/
347/350/352/A359/364/365/A366/368/369/370/372/377;
2/3/5/7/8/9/10/11/13/16/19/21/22/27/28/29/30/32/33/38/41/
42/51/52/53/54/56/58/61/62/64/66/68/70/71/74/75/76/84/
87/89/92/94/95/96/101/103/104/107/108/109/110/111/112/
113/114/115/116/118/119/120/121/128/129/130/131/132/
134/140/141/143/152/155/156/162/163/166/169/172/173/
175/180/223/273/282/283/284/285/288/289/292/299;
5/8/11/13/15/16/19/22/29/33/36/39/40/41/64/70/71/89/96/
112/115/126/129/130/131/132/198/199/219/220/223/247/
248/253/262/269/285/288/311/312/313/314/315/317/318/
320/323/339/345/346/347/350/352/359/364/365/366/368/
369/370/372/377/381/387/388/393/394/396/397/399/400/
401/402/403/404/407/409/411/412/413/415/416/417/418/
419/420/426/429/434/437/438; 2/3/5/7/8/9/10/11/13/16/19/
21/22/27/28/29/30/32/33/38/41/42/51/52/53/54/56/58/61/
62/64/66/68/70/71/74/75/76/84/87/89/92/94/95/96/101/103/
104/107/108/109/110/111/112/113/114/115/116/118/119/
120/121/128/129/130/131/132/134/140/141/143/152/155/
156/162/163/166/169/172/173/175/180/219/220/223/224/
249/257/273/277/281/282/285/288/292/299/300/311/312/
313/314/315/317/318/320/323/339/345/346/347/350/352/
359/364/365/366/368/369/370/372/377/381/387/388/393/
394/396/397/399/400/401/402/403/404/407/409/411/412/
413/415/416/417/418/419/420/426/429/434/437/438; 2/3/5/
7/8/9/10/11/13/16/19/21/22/27/28/29/30/32/33/38/41/42/
51/52/53/54/56/58/61/62/64/66/68/70/71/74/75/76/84/134/
140/141/143/146/152/155/156/162/163/166/169/172/173/
175/180/219/220/223/249/257/273/277/281/282/285/288/
292/299/300/311/312/313/314/315/317/318/320/323/339/
345/346/347/350/352/359/364/365/366/368/369/370/372/
377/381/387/388/393/394/396/397/399/400/401/402/403/
404/407/409/411/412/413/415/416/417/418/419/420/426/
429/434/437/438; 2/3/5/7/8/9/10/11/13/16/19/21/22/27/28/
29/30/32/33/38/41/42/51/52/53/54/56/58/61/62/64/66/68/
70/71/74/75/76/84/87/89/92/94/95/96/101/103/104/107/
108/109/111/112/113/114/115/116/118/119/120/121/128/
129/130/131/132/134/140/141/143/152/155/156/162/163/
166/169/172/173/175/180/219/220/223/273/275/282/283/
284/285/288/289/292/299; 2/3/5/7/8/9/10/11/13/16/19/21/
22/27/28/29/30/32/33/38/41/42/51/52/53/54/56/58/61/62/
64/66/68/70/71/74/75/76/84/87/89/92/94/95/96/101/103/
104/107/108/109/110/111/112/113/114/115/116/118/119/
120/121/128/129/130/131/132/134/140/141/143/152/155/
156/162/163/166/169/172/173/175/180/223/249/257/273/
277/281/282/285/288/292/299/300/311/312/313/314/315/
317/318/320/323/345/346/347/350/352/359/364/365/366/
368/369/370/372/377/381/387/388/393/394/396/397/399/
400/401/402/403/404/407/409/411/412/413/415/416/417/
418/419/420/426/429/434/437/438; 2/3/5/7/8/9/10/11/13/
16/19/21/22/27/28/29/30/32/33/38/42/45/46/50/51/52/53/
54/61/62/64/67/68/70/71/72/73/74/75/76/84/87/89/92/94/
96/101/104/107/108/109/110/112/115/116/119/120/121/
125/128/130/131/132/140/141/143/144/148/149/153/154/
155/160/161/163/172/173/180/198/199/219/236/244/247/
248/253/262/273/275/282/283/284/285/288/289/292/299/
307/310/311/312/323/325/328/330/333/339/342/344/346/
349/352/353/355/359/364/365/366/368/373/375/376/378/
380/381/382/385/387/388/389/390/393/394/396/397/398/
399/401/402/403/404/406/407/410/412/414/415/416/418/
419/420/426/428/429/430/431/433/434/437/438; 2/3/5/7/8/
9/10/11/13/16/19/21/22/27/28/29/30/32/33/38/41/42/51/52/
53/54/56/58/61/62/64/66/68/70/71/74/75/76/84/87/89/92/
94/95/96/101/103/104/107/108/109/110/111/112/113/114/
115/116/118/119/120/121/128/129/130/131/132/134/140/
141/143/152/155/156/162/163/166/169/172/173/175/180/
219/220/223/236/257/273/277/281/282/285/288/292/299/
300/311/312/313/314/315/317/318/320/323/339/359/364/
365/366/368/369/370/372/377/381/387/388/393/394/396/
397/399/400/401/402/403/404/407/409/411/412/413/415/
416/417/418/419/420/426/429/434/437/438; 2/3/5/7/8/9/10/
11/13/16/19/21/22/27/28/29/30/32/33/38/41/42/51/52/53/
54/56/58/61/62/64/66/68/70/71/74/75/76/84/87/89/92/94/
95/96/101/103/104/107/108/109/110/111/112/113/114/115/
116/118/119/120/121/128/129/130/131/132/134/140/141/
143/152/155/156/162/163/166/169/172/173/175/180/198/
199/236/244/247/248/253/262/273/277/281/282/285/288/
292/299/300/311/312/313/314/315/317/318/320/323/339/
345/346/347/349/350/352/359/364/365/366/368/369/370/
372/377/381; 2/3/5/7/8/9/10/11/13/16/19/21/22/27/28/29/
30/32/33/38/41/42/51/52/53/54/56/58/61/62/64/66/68/70/
71/74/75/76/84/87/89/92/94/95/96/101/103/104/107/108/
109/110/111/112/113/114/115/116/118/119/120/121/128/
129/130/131/132/134/140/141/143/152/155/156/162/163/
166/169/172/173/175/180/219/220/223/249/299/300/311/
312/313/314/315/317/318/320/323/339/345/346/347/350/
359/364/365/366/368/369/370/372/377/381/387/388/393/
394/396/397/399/400/401/402/403/404/407/409/411/412/
413/415/416/417/418/419/420/426/429/434/437/438; 2/3/5/
7/8/9/10/11/13/16/19/21/22/27/28/29/30/32/33/35/36/38/
41/42/51/52/53/54/56/58/61/62/64/66/68/70/71/74/75/76/
84/89/92/94/95/96/101/103/104/107/108/109/110/111/112/
113/114/115/116/118/119/120/121/128/129/130/131/132/
134/140/141/143/152/155/156/162/163/166/169/172/173/
175/180/236; 28/29/30/32/33/38/41/42/51/52/53/54/56/58/
61/62/64/66/68/70/71/74/75/76/84/87/89/92/94/95/96/101/
103/104/107/108/109/110/111/112/113/114/115/116/118/
119/120/121/128/129/130/131/132/134/140/141/143/152/
155/156/162/163/166/169/172/173/175/180/219/220/249/

299/300/339/345/346/347/350/352/359/364/365/366/368/
369/370/372/377; 2/3/5/7/8/9/10/11/13/16/19/21/22/27/28/
29/30/32/33/38/41/42/51/52/53/54/56/58/61/62/64/66/68/
70/71/74/75/76/84/87/89/92/94/95/96/101/103/104/107/
108/S109/110/111/112/113/114/115/116/118/119/120/121/
128/129/130/131/132/134/140/141/143/152/155/156/162/
163/166/169/172/173/175/180/198/199/219/220/223/249/
257/299/311/312/313/314/315/317/318/320/323/339/345/
346/347/350/352/359/364/365/366/368/369/370/372/377/
381/387/388/393/394/396/397/399/400/401/402/403/404/
407/409/411/412/413/415/416/417/418/419/420/426/429/
434/437/438; 2/3/5/7/8/9/10/11/13/16/19/21/22/27/28/29/
30/32/33/38/41/42/51/52/53/54/56/58/61/62/64/66/68/70/
71/74/75/76/84/87/89/92/94/95/96/101/103/104/107/108/
109/110/111/112/113/114/115/116/118/119/120/121/128/
129/130/131/132/134/140/141/143/152/155/156/162/163/
166/169/172/173/175/180/219/220/223/249/311/312/313/
314/315/317/318/320/323/339/345/346/347/350/352/359/
364/365/366/368/369/370/372/377/378/381/387/388/393/
394/396/397/399/400/401/402/403/404/407/409/411/412/
413/415/416/417/418/419/420/426/429/434/437/438; 5/8/
11/13/15/16/19/22/29/33/36/39/40/41/64/70/71/89/96/112/
115/126/129/130/131/132/180/198/199/24/247/248/253/
273/275/282/283/284/285/288/289/292/311/312/313/314/
315/317/318/320/323/387/388; 2/3/5/7/8/9/10/11/13/16/19/
21/22/27/28/29/30/32/33/38/41/42/51/52/53/54/56/58/61/
62/64/66/68/70/71/74/75/76/84/87/89/92/94/95/96/101/103/
104/107/108/109/110/111/112/113/114/115/116/118/119/
120/121/128/129/130/131/132/134/140/141/143/152/155/
156/162/163/166/169/172/173/175/180; 2/3/5/7/8/9/10/11/
13/16/19/21/22/27/28/29/30/32/33/38/41/42/51/52/53/54/
56/58/61/62/64/66/68/70/71/74/75/76/84/87/89/92/94/95/
96/101/103/104/107/108/109/110/111/112/113/114/115/
116/118/119/120/121/128/129/130/131/132/134/140/141/
143/152/155/156/162/163/166/169/172/173/175/180/198/
199/247/248/253/273/277/281/282/285/288/311/312/313/
314/315/317/318/319/320/323/339/345/346/347/350/352/
359/364/365/366/368/369/370/372/377/381/387/388/393/
394/396/397/399/400/401/402/403/404/407/409/411/412/
413/415/416/417/418/419/420/426/429/434/437/438; 2/3/5/
7/8/9/10/11/13/16/19/21/22/27/28/29/30/32/33/38/41/42/
51/52/53/54/56/58/61/62/64/66/68/70/71/74/75/76/84/87/
89/92/94/95/96/101/103/104/107/108/109/110/111/112/
113/114/115/116/118/119/120/121/128/129/130/131/132/
134/140N/141/143/152/155/156/162/163/166/169/172/173/
175/180/253/273/275; 2/3/5/7/8/9/10/11/13/16/19/21/22/27/
28/29/30/32/33/38/41/42/51/52/53/54/56/58/61/62/64/66/
68/70/71/74/75/76/84/87/89/92/94/95/96/101/103/104/106/
107/108/109/110/111/112/113/114/115/116/118/119/120/
121/123/128/129/130/131/132/134/140/141/143/152/155/
156/162/163/166/169/172/173/175/180/249/257/273/277/
281/282/285/288/292/299/300/311/312/313/314/315/317/
318/320/323/339/345/346/347/350/352/359/364/365/366/
368/369/370/372/377/32/3/5/7/8/9/10/11/13/16/19/21/22/
27/28/29/30/32/33/38/41/42/51/52/53/54/56/58/61/62/64/
66/68/70/71/74/75/76/84/87/89/92/94/95/96/101/103/104/
107/108/109/110/111/112/113/114/115/116/118/119/120/
121/128/129/130/131/132/294/396/397/399/400/401/402/
403/404/407/409/411/412/413/415/416/417/418/419/420/
426/429/434/437/438; 2/3/5/7/8/9/10/11/13/16/19/21/22/27/
28/29/30/32/33/38/41/42/51/52/53/54/56/58/61/62/64/66/
68/70/71/74/75/76/84/87/89/92/94/95/96/101/103/104/107/
108/109/110/111/112/113/114/115/116/118/119/120/121/
128/129/130/131/132/134/140/141/143/152/155/162/163/
166/169/172/173/175/180/198/199/299; 2/3/5/7/8/9/10/11/
13/16/19/21/22/27/28/29/30/32/33/38/41/42/51/52/53/54/
56/58/61/62/64/66/68/70/71/74/75/76/84/87/89/92/94/95/
96/101/103/104/107/108/109/110/111/112/113/114/115/
116/118/119/120/121/128/129/130/131/132/134/140/141/
143/152/155/156/162/163/166/169/172/173/175/180/198/
199/236/244/299/300/311/312/313/314/315/317/318/320/
323/339/345/346/347/350/352/359/364/365/366/368/369/
370/372/377/381/387/388/393/394/396/397/399/400/401/
402/403/404/407/409/411/412/413/415/416/417/418/419/
420/426/429/434/437/438; 2/3/5/7/8/9/10/11/13/16/19/21/
22/27/28/29/30/32/33/38/41/42/51/52/53/54/56/58/61/62/
64/66/68/70/71/74/75/76/84/87/89/92/94/95/96/101/103/
104/107/108/109/110/111/112/113/114/115/116/118/119/
120/121/128/129/130/131/132/134/140/141/143/152/155/
156/162/163/166/169/172/173/175/180/183/198/199/219/
220/257/311/312/313/314/315/317/318/320/323/339/345/
346/347/350/352/359/364/365/366/368/369/370/372/377/
381/387/388/393/394/396/397/399/400/401/402/403/404/
407/409/411/412/413/415/416/417/418/419/420/426/429/
434/437/438; 372; 5/8/11/13/15/16/19/22/29/33/36/39/40/
41/64/70/71/89/96/112/115/126/129/130/131/132/180/198/
199/219/220/236/249/257/273/277/281/282/285/288/292/
311/312/313/314/315/317/318/320/323/339/345/346/347/
350/352/359/364/365/366/368/369/370/372/377/381/387/
388/393/394/396/397/399/400/401/402/403/404/407/409/
411/412/413/415/416/417/418/419/420/426/429/434/437/
438; 2/3/5/7/8/9/10/11/13/16/19/21/22/27/28/29/30/32/33/
38/41/42/51/52/53/54/56/58/61/62/64/66/68/70/71/74/75/
76/84/87/89/92/94/95/96/101/103/104/107/108/109/110/
111/112/113/114/115/116/118/119/120/121/128/129/130/
131/132/134/140/141/143/152/155/156/162/163/166/169/
172/173/175/180/198/199/273/277/281/282/285/288/292/
299/300/311/312/313/314/315/317/318/320/323/328/339/
345/346/347/350/352/359/364/365/366/368/369/370/387/
388/393/394/396/397/399/400/401/402/403/404/407/409/
411/412/413/415/416/417/418/419/420/426/429/434/437/
438; and/or 2/3/5/7/8/9/10/11/13/16/19/21/22/27/28/29/30/
32/33/38/41/42/51/52/53/54/56/58/61/62/64/66/68/70/71/
74/75/76/84/87/89/92/94/95/96/101/103/104/107/108/109/
110/111/112/113/114/115/116/118/119/120/121/128/129/
130/131/132/134/140/141/143/152/155/156/162/163/166/
169/172/173/175/180/288/289/292; 2/3/5/7/8/9/10/11/13/
16/19/21/22/27/28/29/30/32/33/38/41/42/51/52/53/54/56/
58/61/62/64/66/68/70/71/74/75/76/84/87/89/92/94/95/96/
101/103/104/107/108/109/110/111/112/113/114/115/116/
118/119/120/121/128/129/130/131/132/134/140/141/143/
152/155/156/162/163/166/169/172/173/175/180/253/273/
275, wherein the positions are numbered by correspondence
with the amino acid sequence set forth in SEQ ID NO:2.

In some further embodiments, the nucleic acid constructs
comprise polynucleotide sequences encoding polypeptides
having amino acid sequences that comprise at least one mutation and/or mutation set selected from: F3/S5/G8/Q11/Q13/
G14/P15/K16/T18/D19/S22/K24/N27/P28/E30/V31/I32/
N33/R38/K42/L45/S46/T50/M51/G52/G53/D54/C61/G62/
T64/T67/W68/Q70/S71/D72/P73/A74/A75/R76/A84/I87/
D89/S92/D94/Y96/R101/S104/Y107/G108/S109/L110/
A112/D115/Q116/I119/V120/T121/K125/Q128/D130/
K131/F132/K140/C141/D143/H144/M148/H149/T153/
S154/P155/F160/A161/S163/E172/S173/N180/M199/
T236/Q273/T275/V282/A283/R284/D285/V288/F289/
I292/V299/Q307/T310/N311/I312/I323/A325/F328/N330/
L333/A339/G342/F344/P346/I349/S352/Y353/A355/A359;
S5/G8/Q11/Q13/P15/K16/D19/S22/E29/N33/T36/E39/
H40/L41/T64/Q70/S71/D89/Y96/A112/D115/I119/E126/
G129/D130/K131/F132/N180/S219/I220/A266/A269/
Q273/T275/Q277/R281/V282/D285/V288/I292/D306/
N311/I312/Y313/D314/T315/M317/C318/Y320/I323/
T345/P346/E347/F350/S352/A359/F364/R365/A366/L368/

K369/L370/E372/D377/A381/W387/N388/A393/D394/
I396/A397/K399/A400/D401/F402/A403/S404/K407/
A409/E411/K412/G413/V415/T416/A417/S418/L419/
S420/R423/M426/S429/S437/L438; S5/G8/Q11/Q13/P15/
K16/D19/S22/E29/N33/T36/E39/H40/L41/T64/Q70/S71/
D89/Y96/A112/D115/E126/G129/D130/K131/F132/N180/
R281/D285/V288/V299/F364/R365/L368/E372/K378/
V380/A381/N388/T389/A393/A397/F 402/S404/A417/
L419/M426/L435/S437; E2/F3/S5/I7/G8/K9/I10/Q11/Q13/
K16/D19/L21/S22/N27/P28/E29/E30/I32/N33/R38/L41/
K42/M51/G52/G53/D54/T56/M58/C61/G62/T64/K66/
W68/Q70/S71/A74/A75/R76/A84/I87/D89/S92/D94/Y95/
Y96/R101/L103/S104/Y107/G108/S109/L110/K111/A112/
T113/N114/D115/Q116/D118/I119/V120/T121/Q128/
G129/D130/K131/F132/C134/K140/C141/D143/G152/
P155/S156/F162/S163/Q166/K169/E172/S173/N175/
N180/S219/I220/K223/G249/D257/Q273/N311/I312/
Y313/D314/T315/M317/C318/Y320/I323/A339/T345/
P346/E347/F350/F364/R365/A366/L368/K369/L370/E372/
D377/A381/W387/N388/A393/D394/I396/A397/I399/
A400/D401/F402/A403/S404/K407/A409/E411/K412/
G413/V415/T416/A417/S418/L419/S420/M426/S429/
V434/S437/L438; E2/F3/S5/I7/G8/K9/I10/Q11/Q13/K16/
T18/D19/L21/S22/N27/P28/E29/E30/I32/N33/R38/L41/
K42/M51/G52/G53/D54/T56/M58/C61/G62/T64/K66/
W68/Q70/S71/A74/A75/R76/A84/I87/D89/D94/Y95/Y96/
R101/L103/S104/Y107/G108/S109/L110/K111/A112/
T113/N114/D115/Q116/D118/I119/V120/T121/Q128/
G129/D130/K131/F132/C134/K140/C141/D143/G152/
P155/S156/F162/S163/Q166/K169/E172/S173/V175/
N180/Q273/Q277/R281/V282/D285/V288/I292/V299/
L300/N311/I312/Y313/D314/T315/M317/C318/Y320/
I323/F335/A339/T345/P346/E347/F350/S352/A359/F364/
R365/A366/L368/K369/L370/E372/D377/A381/W387/
N388/A393/D394/I396/A397/K399/A400/D401/F402/
A403/S404/K407/A409/E411/K412/G413/V415/T416/
A417/S418/L419/S420/M426/S429/V434/S437/L438;
E2/F3/S5/I7/G8/K9/I10/Q11/Q13/K16/D19/L21/S22/N27/
P28/E29/E30/I32/N33/R38/L41/K42/M51/G52/G53/D54/
T56/M58/C61/G62/T64/K66/W68/Q70/S71/A74/A75/R76/
A84/I87/D89/S92/D94/Y95/Y96/R101/L103/S104/Y107/
G108/S109/L110/K111/A112/T113/N114/D115/Q116/
D118/I119/V120/T121/Q128/G129/D130/K131/F132/
C134/K140/C141/D143/G152/P155/S156/F162/S163/
Q166/K169/E172/S173/V175/N180/Q273/Q277/R281/
V282/D285/V288/I292/V299/L300/N311/I312/Y313/
D314/T315/M317/C318/Y320/I323/F335/A339/T345/
P346/E347/F350/S352/A359/F364/R365/A366/L368/
K369/L370/E372/D377/A381/W387/N388/A393/D394/
I396/A397/K399/A400/D401/F402/A403/S404/K407/
A409/E411/K412/G413/V415/T416/A417/S418/L419/
S420/M426/S429/V434/S437/L438; E2/F3/S5/I7/G8/K9/
I10/Q11/Q13/K16/D19/L21/S22/N27/P28/E29/E30/I32/
N33/R38/L41/K42/M51/G52/G53/D54/T56/M58/C61/G62/
T64/K66/W68/Q70/S71/A74/A75/R76/I87/D89/S92/D94/
Y95/Y96/R101/L103/S104/Y107/G108/S109/L110/K111/
A112/T113/N114/D115/Q116/D118/I119/V120/T121/
Q128/G129/D130/K131/F132/C134/K140/C141/D143/
G152/P155/S156/F162/S163/Q166/K169/E172/S173/
V175/N180/N198/M199/G249/Q273/Q277/R281/V282/
D285/V288/I292/V299/L300/N311/I312/Y313/D314/T315/
M317/C318/Y320/I323/A339/T345/P346/E347/F350/S352/
A359/F364/R365/A366/L368/K369/L370/E372/D377/
A381/W387/N388/A393/D394/I396/A397/K399/A400/
D401/F402/A403/S404/K407/A409/E411/K412/G413/
V415/T416/A417/S418/L419/S420/M426/S429/V434/
S437/L438; F3/S5/G8/Q11/Q13/P15/K16/T18/D19/S22/
K24/N27/P28/E30/V31/I32/N33/R38/K42/L45/S46/T50/
M51/G52/G53/D54/C61/G62/T64/T67/W68/Q70/S71/D72/
P73/A74/A75/R76/A84/I87/D89/S92/D94/Y96/R101/S104/
Y107/G108/S109/L110/A112/T113/D115/Q116/I119/
V120/T121/K125/Q128/D130/K131/F132/K140/C141/
D143/H144/M148/H149/T153/S154/P155/F160/A161/
S163/E172/S173/N180/N198/M199/G200/L201/L203/
D204/M206/R208/T236/T244/V247/L248/K253/M262/
Q273/T275/V282/A283/R284/D285/V288/F289/I292/
V299/Q307/T310/N311/I312/I323/A325/F328/N330/L333/
A339/G342/F344/P346/I349/S352/Y353/A355/A359/F364/
R365/A366/L368/D373/R375/I376/K378/V380I/A381/
D382/A385/W387/N388/T389/G390/A393/D394/I396/
A397/G398/K399/D401/F402/A403/S404/E406/K407/
L410/K412/E414/V415/T416/S418/L419/S420/M426/
E428/S429/I430/V431/N433/V434/S437/L438; E2/F3/S5/
I7/G8/K9/I10/Q11/Q13/K16/D19/L21/S22/N27/P28/E29/
E30/I32/N33/R38/L41/K42/M51/G52/G53/D54/T56/M58/
C61/G62/T64/K66/W68/Q70/S71/A74/A75/R76/A84/I87/
D89/S92/D94/Y95/Y96/R101/L103/S104/Y107/G108/
S109/L110/K111/A112/T113/N114/D115/Q116/D118/
I119/V120/T121/Q128/G129/D130/K131/F132/C134/
K140/C141/D143/G152/P155/S156/F162/S163/Q166/
K169/E172/S173/V175/N180/T244/V247/L248/K253/
M262/Q273/T275/V282/A283/R284/D285/V288/F289/
I292/V299/L300/N311/I312/Y313/D314/T315/M317/
C318/Y320/I323/A339/T345/P346/E347/F350/S352/F364/
R365/A366/L368/K369/L370/E372/D377/A381/W387/
N388/A393/D394/I396/A397/K399/A400/D401/F402/
A403/S404/K407/A409/E411/K412/G413/V415/T416/
A417/S418/L419/S420/M426/S429/V434/S437/L438;
E2/F3/S5/I7/G8/K9/I10/Q11/Q13/K16/D19/L21/S22/N27/
P28/E29/E30/I32/N33/R38/L41/K42/M51/G52/G53/D54/
T56/M58/C61/G62/T64/K66/W68/Q70/S71/A74/A75/R76/
A84/I87/D89/S92/D94/Y95/Y96/R101/L103/S104/Y107/
G108/S109/L110/K111/A112/T113/N114/D115/Q116/
D118/I119/V120/T121/Q128/G129/D130/K131/F132/
C134/K140/C141/D143/G152/P155/S156/F162/S163/
Q166/K169/E172/S173/V175/N198/M199/K223/T236/
Q273/Q277/R281/V282/D285/V288/I292/V299/L300/
N311/I312/Y313/D314/T315/M317/C318/Y320/I323/
A339/T345/P346/E347/F350/S352/A359/F364/R365/
A366/L368/K369/L370/E372/D377/A381/W387/N388/
A393/D394/I396/A397/K399/A400/D401/F402/A403/
S404/K407/A409/E411/K412/G413/V415/T416/A417/
S418/L419/S420/M426/S429/V434/S437/L438; E2/F3/S5/
I7/G8/K9/I10/Q11/Q13/K16/D19/L21/S22/N27/P28/E29/
E30/I32/N33/R38/L41/K42/M51/G52/G53/D54/T56/M58/
C61/G62/T64/K66/W68/Q70/S71/A74/A75/R76/A84/I87/
D89/S92/D94/Y95/Y96/R101/L103/S104/Y107/G108/
S109/L110/K111/A112/T113/N114/D115/Q116/D118/
I119/V120/T121/Q128/G129/D130/K131/F132/C134/
K140/C141/D143/G152/P155/S156/F162/S163/Q166/
K169/E172/S173/V175/N180/N198/M199/S219/I220/
K223/G249/D257/Q273/Q277/R281/V282/D285/V288/
I292/V299/L300/N311/I312/Y313/D314/T315/M317/
C318/Y320/I323/A339/T345/P346/E347/F350/S352/A359/
F364/R365/A366/L368/K369/L370/E372/D377/A381/
W387/N388/A 393/D394/I396/A397/K399/A400/D401/
F402/A403/S404/K407/A409/E411/K412/G413/V415/
T416/A417/S418/L419/S420/M426/S429/V434/S437/
L438; E2/F3/S5/I7/G8/K9/I10/Q11/Q13/K16/D19/L21/
S22/N27/P28/E29/E30/I32/N33/R38/L41/K42/M51/G52/
G53/D54/T56/M58/C61/G62/T64/K66/W68/Q70/S71/A74/
A75/R76/A84/I87/D89/S92/D94/Y95/Y96/R101/L103/
S104/Y107/G108/S109/L110/K111/A112/T113/N114/
D115/Q116/D118/I119/V120/T121/Q128/G129/D130/

K131/F132/C134/K140/C141/D143/G152/P155/S156/
F162/S163/Q166/K169/E172/S173/V175/N180/S219/I220/
K223/D257/Q273/Q277/R281/V282/D285/V288/I292/
V299/L300/N311/I312/Y313/D314/T315/M317/C318/
Y320/I323/A339/T345/P346/E347/F350/S352/A359/F364/
R365/A366/L368/K369/L370/E372/D373/D377/A381/
W387/N388/A393/D394/I396/A397/K399/A400/D401/
F402/A403/S404/K407/A409/E411/K412/G413/V415/
T416/A417/S418/L419/S420/M426/S429/V434/S437/
L438; E2/F3/S5/N6/I7/G8/I10/Q11/Q13/K16/D19/L21/
S22/N27/P28/E29/E30/I32/N33/R38/L41/K42/M51/G52/
G53/D54/T56/M58/C61/G62/T64/K66/W68/Q70/S71/A74/
A75/R76/A84/I87/D89/S92/D94/Y95/Y96/R101/L103/
S104/Y107/G108/S109/L110/K111/A112/T113/N114/
D115/Q116/D118/I119/V120/T121/Q128/G129/D130/
K131/F132/C134/K140/C141/D143/G152/P155/S156/
F162/S163/Q166/K169/E172/S173/V175/N180/N198/
M199/S219/D257/I292/N311/I312/Y313/D314/T315/
M317/C318/Y320/I323/A339/T345/P346/E347/F350/S352/
A359/F364/R365/A366/L368/K369/L370/E372/D377/
A381/W387/N388/A393/D394/I396/A397/K399/A400/
D401/F402/A403/S404/K407/A409/E411/K412/G413/
V415/T416/A417/S418/L419/S420/M426/S429/V434/
S437/L438; E2/F3/S5/I7/G8/K9/I10/Q11/Q13/K16/D19/
L21/S22/N27/P28/E29/E30/I32/N33/R38/L41/K42/M51/
G52/G53/D54/T56/M58/C61/G62/T64/K66/W68/Q70/S71/
A74/A75/R76/A84/I87/D89/S92/D94/Y95/Y96/R101/
L103/S104/Y107/G108/S109/L110/K111/A112/T113/
N114/D115/Q116/D118/I119/V120/T121/Q128/G129/
D130/K131/F132/C134/K140/C141/D143/G152/P155/
S156/Q166/K169/E172/S173/V175/N180/N198/M199/
S219/I220/K223/G249/D257/Q273/Q277/R281/V282/
D285/V288/I292/V299/L300/N311/I312/Y313/D314/T315/
M317/C318/Y320/I323/A339/F344/T345/P346/E347/F350/
S352/A359/F364/R365/A366/L368/K369/L370/E372/
D377/A381/W387/N388/A393/D394/I396/A397/K399/
A400/D401/F402/A403/S404/K407/A409/E411/K412/
G413/V415/T416/A417/S418/L419/S420/M426/S429/
V434/S437/L438; E2/F3/S5/I7/G8/K9/I10/Q11/Q13/K16/
D19/L21/S22/N27/P28/E29/E30/I32/N33/R38/L41/K42/
M51/G52/G53/D54/T56/M58/C61/G62/T64/K66/W68/
Q70/S71/A74/A75/R76/A84/I87/D89/S92/D94/Y95/Y96/
R101/L103/S104/Y107/G108/S109/L110/K111/A112/
T113/N114/D115/Q116/D118/I119/V120/T121/Q128/
G129/D130/K131/F132/C134/K140/C141/D143/G152/
P155/S156/F162/S163/Q166/K169/E172/S173/V175/
N180/S219/I220/K223/T236/T244/V247/L248/D257/
Q273/Q277/R281/V282/D285/V288/I292/V299/L300/
N311/I312/Y313/D314/T315/M317/C318/Y320/I323/
A339/T345/P346/E347/F350/S352/A359/F364/R365/
A366/L368/K369/L370/E372/D377/A381/W387/N388/
A393/D394/I396/A397/K399/A400/D401/F402/A403/
S404/K407/A409/E411/K412/G413/V415/T416/A417/
S418/L419/S420/M426/S429/V434/S437/L438; E2/F3/S5/
I7/G8/K9/I10/Q11/Q13/K16/D19/L21/S22/N27/P28/E29/
E30/I32/N33/R38/L41/K42/M51/G52/G53/D54/T56/M58/
C61/G62/T64/K66/W68/Q70/S71/A74/A75/R76/A84/I87/
D89/S92/D94/Y95/Y96/R101/L103/S104/Y107/G108/
S109/L110/K111/A112/T113/N114/D115/Q116/D118/
I119/V120/T121/Q128/G129/D130/K131/F132/C134/
K140/C141/D143/M148/H149/G152/P155/S156/F162/
S163/Q166/K169/E172/S173/V175/N180/N198/M199/
S219/I220/K223/K253/D257/Q273/Q277/R281/V282/
D285/V288/I292/V299/L300/N311/I312/Y313/D314/T315/
M317/C318/Y320/I323/A339/T345/P346/E347/F350/S352/
A359/A361/F364/R365/A366/L368/K369/L370/E372/
D377/A381/W387/N388/A393/D394/I396/A397/K399/
A400/D401/F402/A403/S404/K407/A409/E411/K412/
G413/V415/T416/A417/S418/L419/S420/M426/S429/
V434/S437/L438; E2/F3/S5/I7/G8/K9/I10/Q11/Q13/K16/
D19/L21/S22/N27/P28/E29/E30/I32/N33/R38/L41/K42/
M51/G52/G53/D54/T56/M58/C61/G62/T64/K66/W68/
Q70/S71/A74/A75/R76/A84/I87/D89/S92/D94/Y95/Y96/
R101/L103/S104/Y107/G108/S109/L110/K111/A112/
T113/N114/D115/Q116/D118/I119/V120/T121/Q128/
G129/D130/K131/F132/C134/K140/C141/D143/P155/
S156/F162/S163/Q166/K169/E172/S173/V175/N180/
Q273/T275/T416; F3/S5/G8/Q11/Q13/P15/K16/T18/D19/
S22/K24/N27/P28/E30/V31/I32/N33/R38/K42/L45/S46/
T50/M51/G52/G53/D54/C61/G62/T64/T67/W68/Q70/S71/
D72/P73/A74/A75/R76/A84/I87/D89/S92/D94/Y96/R101/
S104/Y107/G108/S109/L110/A112/D115/Q116/I119/
V120/T121/K125/Q128/D130/K131/F132/K140/C141/
D143/H144/M148/H149/T153/S154/P155/F160/A161/
S163/E172/S173/N180/N198/M199/G200/L201/L203/
D204/M206/R208/T236/T244/V247/L248/K253/M262/
Q273/T275/V282/A283/R284/D285/V288/F289/I292/
V299/Q307/T310/N311/I312/I323/A325/F328/N330/L333/
A339/G342/F344/P346/I349/S352/Y353/A355/A359/F364/
R365/A366/L368/D373/R375/I376/K378/V380/A381/
D382/A385/W387/N388/T389/G390/A393/D394/I396/
A397/G398/K399/D401/F402/A403/S404/E406/K407/
L410/K412/E414/V415/T416/S418/L419/S420/M426/
E428/S429/I430/V431/N433/V434/S437/L438; F3/S5/G8/
Q11/Q13/P15/K16/T18/D19/S22/K24/N27/P28/E30/V31/
I32/N33/R38/K42/L45/S46/T50/M51/G52/G53/D54/C61/
G62/T64/T67/W68/Q70/S71/D72/P73/A74/A75/R76/A84/
I87/D89/S92/D94/Y96/R101/S104/Y107/G108/S109/L110/
A112/D115/Q116/I119/V120/T121/K125/Q128/D130/
K131/F132/K140/C141/D143/H144/M148/H149/T153/
S154/P155/F160/A161/S163/E172/S173/N180/N198/
M199/G200/L201/L203/D204/M206/R208/T236/T244/
V247/L248/K253/M262/Q273/T275/V282/A283/R284/
D285/V288/F289/I292/V299/Q307/T310/N311/I312/I323/
A325/F328/N330/L333/A339/G342/F344/P346/I349/S352/
Y353/A355/A359/F364/R365/A366/L368/D373/R375/
I376/K378/V380/A381/D382/A385/W387/N388/T389/
G390/A393/D394/I396/A397/G398/K399/D401/F402/
A403/S404/E406/K407/L410/K412/E414/V415/T416/
S418/L419/S420/M426/E428/S429/I430/V431/N433/
V434/S437/L438; T236/T244/V247/L248/K253/M262/
Q273/T275/V282/A283/R284/D285/V288/F289/I292;
E2/F3/S5/I7/G8/K9/I10/Q11/Q13/K16/D19/L21/S22/N27/
P28/E29/E30/I32/N33/R38/L41/K42/M51/G52/G53/D54/
T56/M58/C61/G62/T64/K66/W68/Q70/S71/A74/A75/R76/
A84/I87/D89/S92/D94/Y95/Y96/R101/L103/S104/Y107/
G108/S109/L110/K111/A112/T113/N114/D115/Q116/
D118/I119/V120/T121/Q128/G129/D130/K131/F132/
C134/K140/C141/D143/G152/P155/S156/F162/S163/
Q166/K169/E172/S173/V175/N180/R208/S219/I220/
K223/Q273/Q277/R281/V282/D285/V288/I292/V299/
L300/N311/I312/Y313/D314/T315/M317/C318/Y320/I323/N334/A339/T345/P346/E347/F350/S352/A359/F364/R365/A366/L368/K369/L370/E372/G374/D377/A381/W387/N388/A393/D394/I396/A397/K399/A400/D401/F402/A403/S404/K407/A409/E411/K412/G413/V415/T416/A417/S418/L419/S420/G422/M426/S429/V434/S437/L438; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/S92/D94/Y95/Y96/R101/L103/S104/Y107/G108/S109/L110/K111/A112/T113/N114/D115/Q116/D118/I119/V120/T121/Q128/G129/D130/K131/F132/C134/K140/C141/D143/G152/P155/

S156/F162/S163/Q166/K169/E172/S173/V175/N180/
N198/M199/Q273/Q277/R281/V282/D285/V288/I292/
V299/L300; E2/F3/S5/I7/G8/K9/I10/Q11/Q13/K16/D19/
L21/S22/N27/P28/E29/E30/I32/N33/R38/L41/K42/M51/
G52/G53/D54/T56/M58/C61/G62/T64/K66/W68/Q70/S71/
A74/A75/R76/A84/I87/D89/S92/D94/Y95/Y96/R101/
L103/S104/Y107/G108/S109/L110/K111/A112/T113/
N114/D115/Q116/D118/I119/V120/T121/Q128/G129/
D130/K131/F132/C134/K140/C141/D143/G152/P155/
S156/F162/S163/Q166/K169/E172/S173/V175/N180/
K223/Q273/T275/V282/A283/R284/D285/V288/F289/
I292/V299; E2/F3/S5/I7/G8/K9/I10/Q11/Q13/P15/K16/
D19/L21/S22/N27/P28/E29/E30/I32/N33/R38/L41/K42/
M51/G52/G53/D54/T56/M58/C61/G62/T64/K66/W68/
Q70/S71/A74/A75/R76/A84/I87/D89/S92/D94/Y95/Y96/
R101/L103/S104/Y107/G108/S109/L110/K111/A112/
T113/N114/D115/Q116/D118/I119/V120/T121/Q128/
G129/D130/K131/F132/C134/K140/C141/D143/G152/
P155/S156/F162/S163/Q166/K169/E172/S173/V175/
N180/S219/I220/K223/D257/Q273/Q277/R281/V282/
D285/V288/I292/V299/L300/N311/I312/Y313/D314/T315/
M317/C318/Y320/I323/A325/A339/T345/P346/E347/
F350/S352/A359/F364/R365/A366/L368/K369/L370/
E372/D377; E2/F3/S5/I7/G8/K9/I10/Q11/Q13/K16/D19/
L21/S22/N27/P28/E29/E30/I32/N33/R38/L41/K42/M51/
G52/G53/D54/T56/M58/C61/G62/T64/K66/W68/Q70/S71/
A74/A75/R76/A84/I87/D89/S92/D94/Y95/Y96/R101/
L103/S104/Y107/G108/S109/L110/K111/A112/T113/
N114/D115/Q116/D118/I119/V120/T121/Q128/G129/
D130/K131/F132/C134/K140/C141/D143/G152/P155/
S156/F162/S163/Q166/K169/E172/S173/V175/N180/
K223/Q273/T275/V282/A283/R284/D285/V288/F289/
I292/V299; S5/G8/Q11/Q13/P15/K16/D19/S22/E29/N33/
T36/E39/H40/L41/T64/Q70/S71/D89/Y96/A112/D115/
E126/G129/D130/K131/F132/N198/M199/S219/I220/
K223/V247/L248/K253/M262/A269/D285/V288/N311/
I312/Y313/D314/T315/M317/C318/Y320/I323/A339/
T345/P346/E347/F350/S352/A359/F364/R365/A366/L368/
K369/L370/E372/D377/A381/W387/N388/A393/D394/
I396/A397/K399/A400/D401/F402/A403/S404/K407/
A409/E411/K412/G413/V415/T416/A417/S418/L419/
S420/M426/S429/V434/S437/L438; E2/F3/S5/I7/G8/K9/
I10/Q11/Q13/K16/D19/L21/S22/N27/P28/E29/E30/I32/
N33/R38/L41/K42/M51/G52/G53/D54/T56/M58/C61/G62/
T64/K66/W68/Q70/S71/A74/A75/R76/A84/I87/D89/S92/
D94/Y95/Y96/R101/L103/S104/Y107/G108/S109/L110/
K111/A112/T113/N114/D115/Q116/D118/I119/V120/
T121/Q128/G129/D130/K131/F132/C134/K140/C141/
D143/G152/P155/S156/F162/S163/Q166/K169/E172/
S173/V175/N180/S219/I220/K223/G224/G249/D257/
Q273/Q277/R281/V282/D285/V288/I292/V299/L300/
N311/I312/Y313/D314/T315/M317/C318/Y320/I323/
A339/T345/P346/E347/F350/S352/A359/F364/R365/
A366/L368/K369/L370/E372/D377/A381/W387/N388/
A393/D394/I396/A397/K399/A400/D401/F402/A403/
S404/K407/A409/E411/K412/G413/V415/T416/A417/
S418/L419/S420/M426/S429/V434/S437/L438; E2/F3/S5/
I7/G8/K9/I10/Q11/Q13/K16/D19/L21/S22/N27/P28/E29/
E30/I32/N33/R38/L41/K42/M51/G52/G53/D54/T56/M58/
C61/G62/T64/K66/W68/Q70/S71/A74/A75/R76/A84/I87/
D89/S92/D94/Y95/Y96/R101/L103/S104/Y107/G108/
S109/L110/K111/A112/T113/N114/D115/Q116/D118/
I119/V120/T121/Q128/G129/D130/K131/F132/C134/
K140/C141/D143/R146/G152/P155/S156/F162/S163/
Q166/K169/E172/S173/V175/N180/S219/I220/K223/
Q273/T275/V282/A283/R284/D285/V288/F289/I292/
V299; E2/F3/S5/I7/G8/K9/I10/Q11/Q13/K16/D19/L21/
S22/N27/P28/E29/E30/I32/N33/R38/L41/K42/M51/G52/
G53/D54/T56/M58/C61/G62/T64/K66/W68/Q70/S71/A74/
A75/R76/A84/I87/D89/S92/D94/Y95/Y96/R101/L103/
S104/Y107/G108/S109/K111/A112/T113/N114/D115/
Q116/D118/I119/V120/T121/Q128/G129/D130/K131/
F132/C134/K140/C141/D143/G152/P155/S156/F162/
S163/Q166/K169/E172/S173/V175/N180/K223/G249/
D257/Q273/Q277/R281/V282/D285/V288/I292/V299/
L300/N311/I312/Y313/D314/T315/M317/C318/Y320/
I323/T345/P346/E347/F350/S352/A359/F364/R365/A366/
L368/K369/L370/E372/D377/A381/W387/N388/A393/
D394/I396/A397/K399/A400/D401/F402/A403/S404/
K407/A409/E411/K412/G413/V415/T416/A417/S418/
L419/S420/M426/S429/V434/S437/L438; E2/F3/S5/I7/G8/
K9/I10/Q11/Q13/K16/D19/L21/S22/N27/P28/E29/E30/
I32/N33/R38/L41/K42/M51/G52/G53/D54/T56/M58/C61/
G62/T64/K66/W68/Q70/S71/A74/A75/R76/A84/I87/D89/
S92/D94/Y95/Y96/R101/L103/S104/Y107/G108/S109/
L110/A111/D115/Q116/D118/I119/V120/T121/K125/
Q128/D130/K131/F132/K140/C141/D143/H144/M148/
H149/T153/S154/P155/F160/A161/S163/E172/S173/N180/
N198/M199/S219/T236/T244/V247/L248/K253/M262/
Q273/T275/V282/A283/R284/D285/V288/F289/I292/
V299/Q307/T310/N311/I312/I323/A325/F328/N330/
L333/A 339/G342/F344/P346/I349/S352/Y353/A355/
A359/F364/R365/A366/L368/D373/R375/I376/K378/
V380/A381/D382/A385/W387/N388/T389/G390/A393/
D394/I396/A397/G398/K399/D401/F402/A403/S404/
E406/K407/L410/K412/E414/V415/T416/S418/L419/
S420/M426/E428/S429/I430/V431/N433/V434/S437/
L438; E2/F3/S5/I7/G8/K9/I10/Q11/Q13/K16/D19/L21/
S22/N27/P28/E29/E30/I32/N33/R38/L41/K42/M51/G52/
G53/D54/T56/M58/C61/G62/T64/K66/W68/Q70/S71/A74/
A75/R76/A84/I87/D89/S92/D94/Y95/Y96/R101/L103/
S104/Y107/G108/S109/L110/K111/A112/T113/N114/
D115/Q116/D118/I119/V120/T121/Q128/G129/D130/
K131/F132/C134/K140/C141/D143/G152/P155/S156/
F162/S163/Q166/K169/E172/S173/V175/N180/S219/I220/
K223/T236/D257/Q273/Q277/R281/V282/D285/V288/
I292/V299/L300/N311/I312/Y313/D314/T315/M317/
C318/Y320/I323/A339/A359/F364/R365/A366/L368/
K369/L370/E372/D377/A381/W387/N388/A393/D394/
I396/A397/K399/A400/D401/F402/A403/S404/K407/
A409/E411/K412/G413/V415/T416/A417/S418/L419/
S420/M426/S429/V434/S437/L438; E2/F3/S5/I7/G8/K9/
I10/Q11/Q13/K16/D19/L21/S22/N27/P28/E29/E30/I32/
N33/R38/L41/K42/M51/G52/G53/D54/T56/M58/C61/G62/
T64/K66/W68/Q70/S71/A74/A75/R76/A84/I87/D89/S92/
D94/Y95/Y96/R101/L103/S104/Y107/G108/S109/L110/
K111/A112/T113/N114/D115/Q116/D118/I119/V120/
T121/Q128/G129/D130/K131/F132/C134/K140/C141/
D143/G152/P155/S156/F162/S163/Q166/K169/E172/
S173/V175/N180/N198/M199/T236/T244/V247/L248/
K253/M262/Q273/Q277/R281/V282/D285/V288/I292/
V299/L300/N311/I312/Y313/D314/T315/M317/C318/
Y320/I323/A339/T345/P346/E347/I349/F350/S352/A359/
F364/R365/A366/L368/K369/L370/E372/D377/A381;
E2/F3/S5/I7/G8/K9/I10/Q11/Q13/K16/D19/L21/S22/N27/
P28/E29/E30/I32/N33/R38/L41/K42/M51/G52/G53/D54/
T56/M58/C61/G62/T64/K66/W68/Q70/S71/A74/A75/R76/
A84/I87/D89/S92/D94/Y95/Y96/R101/L103/S104/Y107/
G108/S109/L110/K111/A112/T113/N114/D115/Q116/
D118/I119/V120/T121/Q128/G129/D130/K131/F132/
C134/K140/C141/D143/G152/P155/S156/F162/S163/
Q166/K169/E172/S173/V175/N180/S219/I220/K223/
G249/V299/L300/N311/I312/Y313/D314/T315/M317/
C318/Y320/I323/A339/T345/P346/E347/F350/A359/F364/

R365/A366/L368/K369/L370/E372/D377/A381/W387/
N388/A393/D394/I396/A397/K399/A400/D401/F402/
A403/S404/K407/A409/E411/K412/G413/V415/T416/
A417/S418/L419/S420/M426/S429/V434/S437/L438;
E2/F3/S5/I7/G8/K9/I10/Q11/Q13/K16/D19/L21/S22/N27/
P28/E29/E30/I32/N33/K35/T36/R38/L41/K42/M51/G52/
G53/D54/T56/M58/C61/G62/T64/K66/W68/Q70/S71/A74/
A75/R76/A84/I87/D89/S92/D94/Y95/Y96/R101/L103/
S104/Y107/G108/S109/L110/K111/A112/T113/N114/
D115/Q116/D118/I119/V120/T121/Q128/G129/D130/
K131/F132/C134/K140/C141/D143/G152/P155/S156/
F162/S163/Q166/K169/E172/S173/V175/N180/T236; P28/
E29/E30/I32/N33/R38/L41/K42/M51/G52/G53/D54/T56/
M58/C61/G62/T64/K66/W68/Q70/S71/A74/A75/R76/A84/
I87/D89/S92/D94/Y95/Y96/R101/L103/S104/Y107/G108/
S109/L110/K111/A112/T113/N114/D115/Q116/D118/
I119/V120/T121/Q128/G129/D130/K131/F132/C134/
K140/C141/D143/G152/P155/S156/F162/S163/Q166/
K169/E172/S173/V175/N180/S219/I220/G249/V299/
L300/A339/T345/P346/E347/F350/S352/A359/F364/R365/
A366/L368/K369/L370/E372/D377;   E2/F3/S5/I7/G8/K9/
I10/Q11/Q13/K16/D19/L21/S22/N27/P28/E29/E30/I32/
N33/R38/L41/K42/M51/G52/G53/D54/T56/M58/C61/G62/
T64/K66/W68/Q70/S71/A74/A75/R76/A84/I87/D89/S92/
D94/Y95/Y96/R101/L103/S104/Y107/G108/S109/L110/
K111/A112/T113/N114/D115/Q116/D118/I119/V120/
T121/Q128/G129/D130/K131/F132/C134/K140/C141/
D143/G152/P155/S156/F162/S163/Q166/K169/E172/
S173/V175/N180/N198/M199/S219/I220/K223/G249/
D257/V299/N311/I312/Y313/D314/T315/M317/C318/
Y320/I323/A339/T345/P346/E347/F350/S352/A359/F364/
R365/A366/L368/K369/L370/E372/D377/A381/W387/
N388/A393/D394/I396/A397/K399/A400/D401/F402/
A403/S404/K407/A409/E411/K412/G413/V415/T416/
A417/S418/L419/S420/M426/S429/V434/S437/L438;
E2/F3/S5/I7/G8/K9/I10/Q11/Q13/K16/D19/L21/S22/N27/
P28/E29/E30/I32/N33/R38/L41/K42/M51/G52/G53/D54/
T56/M58/C61/G62/T64/K66/W68/Q70/S71/A74/A75/R76/
A84/I87/D89/S92/D94/Y95/Y96/R101/L103/S104/Y107/
G108/S109/L110/K111/A112/T113/N114/D115/Q116/
D118/I119/V120/T121/Q128/G129/D130/K131/F132/
C134/K140/C141/D143/G152/P155/S156/F162/S163/
Q166/K169/E172/S173/V175/N180;   E2/F3/S5/I7/G8/K9/
I10/Q11/Q13/K16/D19/L21/S22/N27/P28/E29/E30/I32/
N33/R38/L41/K42/M51/G52/G53/D54/T56/M58/C61/G62/
T64/K66/W68/Q70/S71/A74/A75/R76/A84/I87/D89/S92/
D94/Y95/Y96/R101/L103/S104/Y107/G108/S109/L110/
K111/A112/T113/N114/D115/Q116/D118/I119/V120/
T121/Q128/G129/D130/K131/F132/C134/K140/C141/
D143/G152/P155/S156/F162/S163/Q166/K169/E172/
S173/V175/N180/N198/M199/V247/L248/K253/Q273/
Q277/R281/V282/D285/V288/N311/I312/Y313/D314/
T315/M317/C318/M319/Y320/I323/A339/T345/P346/
E347/F350/S352/A359/F364/R365/A366/L368/K369/
L370/E372/D377/A381/W387/N388/A393/D394/I396/
A397/K399/A400/D401/F402/A403/S404/K407/A409/
E411/K412/G413/V415/T416/A417/S418/L419/S420/
M426/S429/V434/S437/L438;    E2/F3/S5/I7/G8/K9/I10/
Q11/Q13/K16/D19/L21/S22/N27/P28/E29/E30/I32/N33/
R38/L41/K42/M51/G52/G53/D54/T56/M58/C61/G62/T64/
K66/W68/Q70/S71/A74/A75/R76/A84/I87/D89/S92/D94/
Y95/Y96/R101/L103/S104/Y107/G108/S109/L110/K111/
A112/T113/N114/D115/Q116/D118/I119/V120/T121/
Q128/G129/D130/K131/F132/C134/K140N/C141/D143/
G152/P155/S156/F162/S163/Q166/K169/E172/S173/
V175/N180/K253/Q273/T275;    E2/F3/S5/I7/G8/K9/I10/
Q11/Q13/K16/D19/L21/S22/N27/P28/E29/E30/I32/N33/

R38/L41/K42/M51/G52/G53/D54/T56/M58/C61/G62/T64/
K66/W68/Q70/S71/A74/A75/R76/A84/I87/D89/S92/D94/
Y95/Y96/R101/L103/S104/E106/Y107/G108/S109/L110/
K111/A112/T113/N114/D115/Q116/D118/I119/V120/
T121/Y123/Q128/G129/D130/K131/F132/C134/K140/
C141/D143/G152/P155/S156/F162/S163/Q166/K169/
E172/S173/V175/N180/G249/D257/Q273/Q277/R281/
V282/D285/V288/I292/V299/L300/N311/I312/Y313/
D314/T315/M317/C318/Y320/I323/A339/T345/P346/
E347/F350/S352/A359/F364/R365/A366/L368/K369/
L370/E372/D377/A381; E2/F3/S5/I7/G8/K9/I10/Q11/Q13/
K16/D19/L21/S22/N27/P28/E29/E30/I32/N33/R38/L41/
K42/M51/G52/G53/D54/T56/M58/C61/G62/T64/K66/
W68/Q70/S71/A74/A75/R76/A84/I87/D89/S92/D94/Y95/
Y96/R101/L103/S104/Y107/G108/S109/L110/K111/A112/
T113/N114/D115/Q116/D118/I119/V120/T121/Q128/
G129/D130/K131/F132/C134/K140/C141/D143/G152/
P155/S156/F162/S163/Q166/K169/E172/S173/V175/
N198/M199/S219/I220/K223/G249/D257/I292/V299/
L300/N311/I312/Y313/D314/T315/M317/C318/Y320/
I323/A339/T345/P346/E347/F350/S352/A359/F364/R365/
A366/L368/K369/L370/E372/D377/A381/W387/N388/
A393/D394/I396/A397/K399/A400/D401/F402/A403/
S404/K407/A409/E411/K412/G413/V415/T416/A417/
S418/L419/S420/M426/S429/V434/S437/L438; E2/F3/S5/
I7/G8/K9/I10/Q11/Q13/K16/D19/L21/S22/N27/P28/E29/
E30/I32/N33/R38/L41/K42/M51/G52/G53/D54/T56/M58/
C61/G62/T64/K66/W68/Q70/S71/A74/A75/R76/A84/I87/
D89/S92/D94/Y95/Y96/R101/L103/S104/Y107/G108/
S109/L110/K111/A112/T113/N114/D115/Q116/D118/
I119/V120/T121/Q128/G129/D130/K131/F132/C134/
K140/C141/D143/G152/P155/F162/S163/Q166/K169/
E172/S173/V175/N180/N198/M199/V299;    E2/F3/S5/I7/
G8/K9/I10/Q11/Q13/K16/D19/L21/S22/N27/P28/E29/E30/
I32/N33/R38/L41/K42/M51/G52/G53/D54/T56/M58/C61/
G62/T64/K66/W68/Q70/S71/A74/A75/R76/A84/I87/D89/
S92/D94/Y95/Y96/R101/L103/S104/Y107/G108/S109/
L110/K111/A112/T113/N114/D115/Q116/D118/I119/
V120/T121/Q128/G129/D130/K131/F132/C134/K140/
C141/D143/G152/P155/S156/F162/S163/Q166/K169/
E172/S173/V175/N180/N198/M199/T236/T244/V299/
L300/N311/I312/Y313/D314/T315/M317/C318/Y320/
I323/A339/T345/P346/E347/F350/S352/A359/F364/R365/
A366/L368/K369/L370/E372/D377/A381/W387/N388/
A393/D394/I396/A397/K399/A400/D401/F402/A403/
S404/K407/A409/E411/K412/G413/V415/T416/A417/
S418/L419/S420/M426/S429/V434/S437/L438; E2/F3/S5/
I7/G8/K9/I10/Q11/Q13/K16/D19/L21/S22/N27/P28/E29/
E30/I32/N33/R38/L41/K42/M51/G52/G53/D54/T56/M58/
C61/G62/T64/K66/W68/Q70/S71/A74/A75/R76/A84/I87/
D89/S92/D94/Y95/Y96/R101/L103/S104/Y107/G108/
S109/L110/K111/A112/T113/N114/D115/Q116/D118/
I119/V120/T121/Q128/G129/D130/K131/F132/C134/
K140/C141/D143/G152/P155/S156/F162/S163/Q166/
K169/E172/S173/V175/N180/V183/N198/M199/S219/
I220/D257/N311/I312/Y313/D314/T315/M317/C318/
Y320/I323/A339/T345/P346/E347/F350/S352/A359/F364/
R365/A366/L368/K369/L370/E372/D377/A381/W387/
N388/A393/D394/I396/A397/K399/A400/D401/F402/
A403/S404/K407/A409/E411/K412/G413/V415/T416/
A417/S418/L419/S420/M426/S429/V434/S437/L438;
E372G; S5/G8/Q11/Q13/P15/K16/D19/S22/E29/N33/T36/
E39/H40/L41/T64/Q70/S71/D89/Y96/A112/D115/E126/
G129/D130/K131/F132/N180/N198/M199/S219/I220/
T236/G249/D257/Q273/Q277/R281/V282/D285/V288/
I292/N311/I312/Y313/D314/T315/M317/C318/Y320/I323/
A339/T345/P346/E347/F350/S352/A359/F364/R365/

A366/L368/K369/L370/E372/D377/A381/W387/N388/
A393/D394/I396/A397/K399/A400/D401/F402/A403/
S404/K407/A409/E411/K412/G413/V415/T416/A417/
S418/L419/S420/M426/S429/V434/S437/L438; E2/F3/S5/
I7/G8/K9/I10/Q11/Q13/K16/D19/L21/S22/N27/P28/E29/
E30/I32/N33/R38/L41/K42/M51/G52/G53/D54/T56/M58/
C61/G62/T64/K66/W68/Q70/S71/A74/A75/R76/A84/I87/
D89/S92/D94/Y95/Y96/R101/L103/S104/Y107/G108/
S109/L110/K111/A112/T113/N114/D115/Q116/D118/
I119/V120/T121/Q128/G129/D130/K131/F132/C134/
K140/C141/D143/G152/P155/S156/F162/S163/Q166/
K169/E172/S173/V175/N180/N198/M199/Q273/Q277/
R281/V282/D285/V288/I292/V299/L300/N311/I312/
Y313/D314/T315/M317/C318/Y320/I323/F328/A339/
T345/P346/E347/F350/S352/A359/F364/R365/A366/L368/
K369/L370/W387/N388/A393/D394/I396/A397/K399/
A400/D401/F402/A403/S404/K407/A409/E411/K412/
G413/V415/T416/A417/S418/L419/S420/M426/S429/
V434/S437/L438; E2/F3/S5/I7/G8/K9/I10/Q11/Q13/K16/
D19/L21/S22/N27/P28/E29/E30/I32/N33/R38/L41/K42/
M51/G52/G53/D54/T56/M58/C61/G62/T64/K66/W68/
Q70/S71/A74/A75/R76/A84/I87/D89/S92/D94/Y95/Y96/
R101/L103/S104/Y107/G108/S109/L110/K111/A112/
T113/N114/D115/Q116/D118/I119/V120/T121/Q128/
G129/D130/K131/F132/C134/K140/C141/D143/G152/
P155/S156/F162/S163/Q166/K169/E172/S173/V175/
N180/V288/F289/I292; and/or E2/F3/S5/I7/G8/K9/I10/
Q11/Q13/K16/D19/L21/S22/N27/P28/E29/E30/I32/N33/
R38/L41/K42/M51/G52/G53/D54/T56/M58/C61/G62/T64/
K66/W68/Q70/S71/A74/A75/R76/A84/I87/D89/S92/D94/
Y95/Y96/R101/L103/S104/Y107/G108/S109/L110/K111/
A112/T113/N114/D115/Q116/D118/I119/V120/T121/
Q128/G129/D130/K131/F132/C134/K140/C141/D143/
G152/P155/S156/F162/S163/Q166/K169/E172/S173/
V175/N180/K253/Q273/T275, wherein the positions are numbered by correspondence with the amino acid sequence set forth in SEQ ID NO:2.

In still some additional embodiments, the nucleic acid constructs comprise polynucleotide sequences encoding polypeptides having amino acid sequences that comprise at least one mutation and/or mutation set selected from: F3L/
S5Q/G8P/Q11K/Q13E/G14S/P15A/K16N/T18K/D19N/
S22A/K24H/N27D/P28A/E30K/V31I/I32V/N33L/R38K/
K42P/L45M/S46A/T50N/M51L/G52C/G53A/D54A/C61R/
G62D/T64A/T67S/W68L/Q70E/S71K/D72G/P73S/A74M/
A75E/R76H/A84G/I87F/D89E/S92G/D94K/Y96F/R101V/
S104V/Y107A/G108C/S109D/L110I/A112E/D115S/
Q116R/I119E/V120I/T121S/K125L/Q128K/D130T/
K131D/F132I/K140N/C141M/D143S/H144N/M148V/
H149 N/T153S/S154T/P155N/F160Y/A161C/S163A/
E172D/S173I/N180R/M199V/T236A/Q273G/T275S/
V282I/A283S/R284S/D285I/V288M/F289L/I292V/
V299M/Q307E/T310F/N311D/I312V/I323L/A325N/
F328L/N330-/L333F/A339N/G342P/F344Y/P346Y/
I349M/S352G/Y353F/A355L/A359S; S5K/G8S/Q11P/
Q13E/P15K/K16D/D19N/S22A/E29D/N33D/T36K/E39D/
H40I/L41M/T64A/Q70E/S71N/D89Q/Y96F/A112D/
D115A/I119V/E126A/G129A/D130E/K131T/F132L/
N180T/S219A/I220N/A266P/A269T/Q273G/T275
S/Q277E/R281A/V282M/D285V/V288A/I292V/D306G/
N311D/I312V/Y313H/D314S/T315A/M317L/C318A/
Y320L/I323L/T345E/P346F/E347D/F350A/S352G/
A359T/F364L/R365I/A366K/L368A/K369E/L370I/
E372D/D377A/A381D/W387Y/N388K/A393K/D394A/
I396V/A397D/K399T/A400T/D401S/F402L/A403E/
S404E/K407Q/A409V/E411T/K412H/G413/V415P/
T416V/A417-/S418-/L419M/S420Q/R423G/M426V/
S429T/S437R/L438-; S5K/G8S/Q11P/Q13E/P15K/K16D/
D19N/S22A/E29D/N33D/T36K/E39D/H40I/L41M/T64A/
Q70E/S71N/D89Q/Y 96F/A112D/D115A/E126A/G129A/
D130E/K131T/F132L/N180T/R281c/D285TN288A/
V299P/F364Y/R365K/L368S/E372A/K378SN3801/
A381S/N388S/T389E/A393L/A397S/F402M/S404A/
A417D/L419I/M426L/L4351/S437 N; E2K/F3Y/S5P/I7V/
G8P/K9E/I10V/Q11K/Q13E/K16N/D19N/L21F/S22A/
N27D/P28A/E29N/E30K/I32V/N33A/R38K/L41C/K42R/
M51L/G52C/G53A/D54G/T56A/M58P/C61V/G62T/
T64M/K66R/W68Y/Q70N/S71T/A74M/A75E/R76L/
A84G/I87L/D89T/S92G/D94E/Y95F/Y96F/R101A/L103I/
S104A/Y107G/G108D/S109T/L110F/K111E/A112E/
T113S/N114K/D115K/Q116N/D118F/I119V/V120I/T121V/
Q128M/G129D/D130Q/K131T/F132I/C134L/K140N/
C141N/D143S/G152S/P155C/S156N/F162Y/S163A/
Q166K/K169N/E172D/S173A/V175I/N180K/S219A/
I220N/K223D/G249A/D257E/Q273G/N311D/I312V/
Y313H/D314S/T315A/M317L/C318A/Y320L/I323L/
A339V/T345E/P346F/E347D/F350A/F364L/R365I/
A366K/L368A/K369E/L370I/E372D/D377A/A381D/
W387Y/N388K/A393K/D394A/I396V/A397D/K399T/
A400T/D401S/F402L/A403E/S404E/K407Q/A409V/
E411T/K412H/G413/V415P/T416V/A417-/S418-/
L419M/S420Q/M426V/S429T/V434I/S437R/L438-; E2K/
F3Y/S5P/I7V/G8P/K9E/I10V/Q11K/Q13E/K16N/T18A/
D19N/L21F/S22A/N27D/P28A/E29N/E30K/I32V/N33A/
R38K/L41C/K42R/M51L/G52C/G53A/D54G/T56A/
M58P/C61V/G62T/T64M/K66R/W68Y/Q70N/S71T/
A74M/A75E/R76L/A84G/I87L/D89T/D94E/Y95F/Y96F/
R101A/L103I/S104A/Y107G/G108D/S109T/L110F/
K111E/A112E/T113S/N114K/D115K/Q116N/D118F/
I119E/V120I/T121V/Q128M/G129D/D130Q/K131T/
F132I/C134L/K140N/C141N/D143S/G152S/P155C/
S156N/F162Y/S163A/Q166K/K169N/E172D/S173A/
V175I/N180K/Q273G/Q277E/R281A/V282M/D285V/
V288A/I292V/V299P/L300N/N311D/I312V/Y313H/
D3145/T315A/M317L/C318A/Y320L/I323L/F335L/
A339V/T345E/P346F/E347D/F350A/S352G/A359T/
F364L/R365I/A366K/L368A/K369E/L370I/E372D/
D377A/A381D/W387Y/N388K/A393K/D394A/I396V/
A397D/K399T/A400T/D401S/F402L/A403E/S404
E/K407Q/A409V/E411T/K412H/G413S/V415P/T416V/
A417-/S418-/L419M/S420Q/M426V/S429/V434I/S437R/
L438-; E2K/F3Y/S5P/I7V/G8P/K9E/I10V/Q11K/Q13E/
K16N/D19N/L21F/S22A/N27D/P28A/E29N/E30K/I32V/
N33A/R38K/L41C/K42R/M51L/G52C/G53A/D54G/
T56A/M58P/C61V/G62T/T64M/K66R/W68Y/Q70N/
S71A/A74M/A75E/R76L/A84G/I87L/D89T/S92G/D94E/
Y95F/Y96F/R101A/L103I/S104A/Y107G/G108D/S109T/
L110F/K111E/A112E/T113S/N114K/D115K/Q116N/
D118F/I119E/V120I/T121V/Q128M/G129D/D130Q/
K131T/F132I/C134L/K140N/C141N/D143S/G4525/
P155C/S156N/F162Y/S163A/Q166K/K169N/E172D/
S173A/V175I/N180K/N198D/M199L/M206T/S219A/
I220N/K223D/G249A/D257E/Q273G/Q277E/R281A/
V282M/I292V/V299P/L300N/N311D/I312V/Y313H/
D314S/T315A/M317L/C318A/Y320L/I323L/A339V/
T345E/P346F/E347D/F350A/S352G/A359T/F364L/R365I/
A366K/L368A/K369E/L370I/E372D/D377A/A381D/
W387Y/N388K/A393K/D394A/I396V/A397D/K399T/
A400T/D4015/F402L/A403E/S404E/K407Q/A409V/
E411T/K412H/G413S/V415P/T416V/A417-/S418-/
L419M/S420Q/M426V/S429T/V434I/S437R/L438-; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/

C61V/G62T/T64M/K66R/W68Y/Q70N/S71T/A74M/
A75E/R76L/I87L/D89T/S92G/D94E/Y95F/Y96F/R101A/
L103I/S104A/Y107G/G108D/S109T/L110F/K111E/
A112E/T113S/N114K/D115K/Q116N/D118F/I119E/
V120I/T121V/Q128M/G129D/D130Q/K131T/F132I/
C134L/K140N/C141N/D143S/G152S/P155C/S156N/
F162Y/S163A/Q166K/K169N/E172D/S173A/V175I/
N180R/N198D/M199L/G249A/Q273G/Q277E/R281A/
V282M/D285V/V288A/I292V/V299P/L300N/N311D/
I312V/Y313H/D3145/T315A/M317L/C318A/Y320L/
I323L/A339V/T345E/P346F/E347D/F350A/S352G/
A359T/F364L/R365I/A366K/L368A/K     369E/L370I/
E372D/D377A/A381D/W387Y/N388K/A393K/D394A/
I396V/A397D/K399T/A400T/D401S/F402L/A403E/
S404E/K407Q/A409V/E411T/K412H/G413S/V415P/
T416V/A417-/S418-/L419M/S420Q/M426V/S429/V434I/
S437R/L438-;     F3L/S5Q/G8P/Q11K/Q13E/P15A/K16N/
T18K/D19N/S22A/K24H/N27D/P28A/E30K/V31I/I32V/
N33L/R38K/K42P/L45M/S46A/T50N/M51L/G52C/G53A/
D54A/C61R/G62D/T64A/T67S/W68F/Q70E/S71K/D72G/
P73S/A74M/A75E/R76H/A84G/I87F/D89E/S92G/D94K/
Y96F/R101V/S104V/Y107A/G108C/S109D/L110I/
A112E/T113I/D115S/Q116R/I119E/V120I/T121S/K125L/
Q128K/D130T/K131D/F132I/K140N/C141M/D1435/
H144N/M148V/H149     N/T153S/S154T/P155N/F160Y/
A161C/S163A/E172D/S173I/N180R/N198D/M199V/
G200K/L201F/L203Q/D204E/M206I/R208N/T236M/
T244AN247A/L248I/K253Q/M262L/Q273G/T275S/
V282I/A283S/R284S/D285I/V288M/F289L/I292V/
V299M/Q307E/T310F/N311D/I312V/I323L/A325N/
F328L/N330-L333F/A339N/G342P/F344Y/P346Y/I349M/
S352G/Y353F/A355L/A359S/F364L/R365I/A366K/
L368A/D373E/R375T/I376L/K378V/V380I/A381K/
D382E/A385K/W387F/N388E/T389S/G390E/A393K/
D394K/I396R/A3975/G398K/K399S/D401S/F402L/
A403Q/S404E/E406A/K407A/L410E/K412M/E414-/
V415A/T416P/S418M/L419P/S420G/M426Y/E428Q/
S429A/I1430A/V431L/N433Q/V434N/S437E/L438V;
E2K/F3Y/S5P/I7V/G8P/K9E/I10V/Q11K/Q13E/K16N/D19N/L21F/S22A/N27D/P28A/E29N/E30K/I32V/N33A/R 38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D115K/Q116N/D118F/I119E/V120I/T121V/Q128M/G129D/D130Q/K131T/F132I/C134L/K140N/C141N/D143S/G152S/P155C/S156N/F162Y/S163A/Q166K/K169N/E172G/S173A/V175I/N180R/T244A/V247A/L2481/K253Q/M262L/Q273G/T275S/V282I/A283S/R284S/D285I/V288M/F289L/I292V/V299P/L300N/N311D/I312V/Y313H/D3145/T315A/M317L/C318A/Y320L/I323L/A339V/T345E/P346F/E347D/F350A/S352G/F364L/R365I/A366K/L368A/K369E/L370I/E372D/D377A/A381D/W387Y/N388K/A393K/D394A/I396V/A397D/K399T/A400T/D4015/F402L/A403E/S404E/K407Q/A409V/E411T/K412H/G413S/V415P/T416V/A417-/S418-/L419M/S420Q/M426V/S429/V434I/S437R/L438-; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D115K/Q116N/D118F/I119E/V120I/T121V/Q128M/G129D/D130Q/K131T/F132I/C134L/K140N/C141N/D143S/G152S/P155C/S156N/F162Y/S163A/Q166K/K169N/E172D/S173A/V175I/N198D/M199L/K223N/T236M/Q273G/Q277E/R281A/V282M/D285V/V288A/I292V/V299P/L300N/N311D/I312V/Y313H/D314S/T315A/M317L/C318A/Y320L/I323L/A339V/T345E/P346F/E347D/F350A/S352G/A359T/F364L/R365I/A366K/L368A/K369E/L370I/E372D/D377A/A381D/W387Y/N388K/A393K/D394A/I396V/A397D/K399T/A400T/D401S/F402L/A403E/S404E/K407Q/A409V/E411T/K412H/G413S/V415P/T416V/A417-/S418-/L419M/S420Q/M426V/S429/V434I/S437R/L438-; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D115K/Q116N/D118F/I119E/V120I/T121V/Q128M/G129D/D130Q/K131T/F132I/C134L/K140N/C141N/D143S/G152S/P155C/S156N/F162Y/S163A/Q166K/K169N/E172D/S173A/V175I/N180K/N198D/M199L/S219A/I220N/K223D/G249A/D257E/Q273G/Q277E/R281A/V282M/D285V/V288A/I292V299P/L300N/N311D/I312V/Y313H/D314S/T315A/M317L/C318A/Y320L/I323L/A339V/T345E/P346F/E347D/F350A/S352G/A359T/F364L/R365I/A366K/L368A/K369E/L370I/E372D/D377A/A381D/W387Y/N388K/A393K/D394A/I396V/A397D/K399T/A400T/D401S/F402L/A403E/S404E/K407Q/A409V/E411T/K412H/G413S/V415P/T416V/A417-/S418-/L419M/S420Q/M426V/S429T/V434I/S437R/L438-; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D115K/Q116N/D118F/I119E/V120I/T121V/Q128M/G129D/D130Q/K131T/F132I/C134/K140N/C141N/D143S/G152S/P55C/S156N/I66K/K169N/E 72D/S173A/V175/N180K/N198D/M199L/S219A/I220N/K223D/G249A/D257E/Q273G/Q277E/R281A/V282M/D285V/V288A/I292V/V299P/L300N/N311D/I312V/Y313H/D314S/T315A/M317L/C318A/Y320L/I323L/A339V/F344L/T345E/P346F/E347D/F350A/S352G/A359T/F364L/R365I/A366K/L368A/K369E/L370I/E372D/D377A/A381D/W387Y/N388K/A393K/D394A/I396V/A397D/K 399T/A400T/D401S/F402L/A403E/S404E/K407Q/A409V/E411T/K412H/G413S/V415P/T416V/A417-/S418-/L419M/S420Q/M426V/S429T/V434I/S437R/L438*; E2K/F3Y/S5P/I7V/G8P/K9E/I10V/Q11K/Q13E/K16N/D19N/L21F/S22A/N27D/P28A/E29N/E30K/I32V/N33A/R 38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D115K/Q116N/D118F/I119E/V120I/T121V/Q128M/G129D/D130Q/K131T/F132I/C134L/K140N/C141N/D143S/G152S/P155C/S156N/F162Y/S163A/Q166K/K169N/E172D/S173A/V175/N180K/S219A/I220N/K223D/T236M/T244A/V247A/L248I/D257E/Q273G/Q277E/R281A/V282M/D285V/V288A/I292V/V299P/L300N/N311D/I312V/Y313H/D314S/T315A/M317L/C318A/Y320L/I323L/A339V/T345E/P346F/E347D/F350A/S352G/A359I/F364L/R365I/A366K/L368A/K369E/L370I/E372D/D377A/A381D/W387Y/N388K/A393E/D394A/I1396V/A397D/K399T/

A400T/D401S/F402L/A403E/S404E/K407Q/A409V/
E411T/K412H/G413S/V415P/T416V/A417-/S418-/
L419M/S420Q/M426V/S429T/V434I/S437R/L438-; E2K/
F3Y/S5P/I7V/G8P/K9E/I10V/Q11K/Q13E/K16N/D19N/
L21F/S22A/N27D/P28A/E29N/E30K/I32V/N33A/R38K/
L41C/K42R/M51L/G52C/G53A/D54G/T56A/M58P/
C61V/G62T/T64M/K66R/W68Y/Q70N/S71T/A74M/
A75E/R76L/A84G/I87L/D89T/S92G/D94E/Y95F/Y96F/
R101A/L103I/S104A/Y107G/G108D/S109T/L110F/
K111E/A112E/T113S/N114K/D115K/Q116N/D118F/
I119E/V120I/T121V/Q128M/G129D/D130Q/K131T/
F132I/C134L/K140N/D143S/P155C/S163A56N/F166K/
K169N/E172D/S1173A/V175/N1800R/Q273G/T275S/
T416A; F3L/S5Q/G8P/Q11K/Q13E/P15A/K16N/T18K/
D19N/S22A/K24H/N27D/P28A/E30K/V31I/I32V/N33L/
R38K/K42P/L45M/S46A/T50N/M51L/G52C/G53A/
D54A/C61R/G62D/T64A/T67S/W68F/Q70E/S71K/D72G/
P73S/A74M/A75E/R76H/A84G/I87F/D89E/S92G/D94K/
Y96F/R101V/S104V/Y107A/G108C/S109D/L110I/
A112E/D115S/Q116R/I119E/V120I/T121S/K125L/
Q128K/D130T/K131D/F132I/K140N/C141M/D143S/
H144N/M148V/H149N/T153S/S154T/P155N/F160Y/
A161C/S163A/E172D/S173I/N18R/N198D/M199V/
G200K/L201F/L203Q/D204E/M206I/R208N/T236M/
T244A/V247A/L248I/K253Q/M262L/Q273G/T275S/
V282I/A283S/R284S/D285I/V288M/F289L/I292V/
V299M/Q307E/T3100F/N311D/I312V/I323L/A325N/
F328L/N330-/L333F/A339N/G342F/F344Y/P346Y/
I K253Q/M262L/A269G/D285V/V288A/N311D/I312V/
Y313H/D314S/T315A/M317L/C318A/Y320L/I323L/
A339V/T345E/P346F/E347D/F350A/S352G/A359T/
F364L/R365I/A366K/L368A/K369E/L370I/E372D/
D377A/A381D/W387Y/N388K/A393K/D394A/I396V/
A397D/K399T/A400T/D401S/F402L/A403E/S404E/
K407Q/A409V/E411T/K412H/G413S/V415P/T416V/
A417-/I418-/L419M/S420Q/M426V/S429T/V434I/S437R/
L438-; E2K/F3Y/S5P/I7V/G8P/K9E/I10V/Q11K/Q13E/
K16N/D19N/L21F/S22A/N27D/P28A/E29N/E30K/I32V/
N33A/R 38K/L41C/K42R/M51L/G52C/G53A/D54G/
T56A/M58P/C61V/G62T/T64M/K66R/W68Y/Q70N/
S71T/A74M/A75E/R76L/A84G/I87L/D89T/S92G/D94E/
Y95F/Y96F/R 101A/L103I/S104A/Y107G/G108D/S109T/
L110F/K111E/A112E/T113S/N114K/D115K/Q116N/
D118F/I119E/V120I/T121V/Q128M/G129D/D130Q/
K131T/F132I/C134L/K140N/C141N/D143S/R146G/
G152S/P55C/S156N/F162Y/S163A/Q166K/K169N/E72D/
S73A/V175I/N180K/S219A/I220N/K223D/G249A/D257E/
Q273G/Q277E/R281A/V282M/D285V/V288A/I292V/
V299P/L300N/N311D/I312V/Y313H/D314S/T315A/
M317L/C318A/Y320L/I323L/A339V/T345E/P346F/
E347D/F350A/S352G/A359T/F364L/R365I/A366K/
L368A/K369E/L370I/E372D/D377A/A381D/W387Y/
N388K/A393K/D394A/I396V/A397D/K 399T/A400T/
D401S/F402L/A403E/S404E/K407Q/A409V/E411T/
K412H/G413S/V415P/T416V/A417-/S418-/L419M/
S420Q/M426V/S429T/V434I/S437R/L438*; E2K/F3Y/
S5P/I7V/G8P/K9E/I10V/Q11K/Q13E/K16N/D19N/L21F/
S22A/N27D/P28A/E29N/E30K/I32V/N33A/R38K/L41C/
K42R/M51L/G52C/G53A/D54G/T56A/M58P/C61V/
G62T/T64M/K66R/W68Y/Q70N/S71T/A74M/A75E/
R76H/A84G/I87L/D89T/S92G/D94E/Y95F/Y96F/R101A/
L103/S104A/Y107G/G108D/S109T/K111E/A 112E/
T113S/N114K/D115K/Q116N/D118F/I119E/V120I/
T121V/Q128M/G129D/D130Q/K131T/F132I/C134L/
K140N/C141N/D143S/G152S/P155C/S156N/F162Y/
S163A/Q166K/K169N/E172D/S173A/V175I/N180K/
S219A/I220N/K 223D/Q273G/T275S/V282I/A283S/
R284S/D285I/V288M/F289L/I292V/V299M; E2K/F3Y/
S5P/I7V/G8P/K9E/I10V/Q11K/Q13E/K16N/D19N/L21F/
S22A/N27D/P28A/E29N/E30K/I32V/N33A/R38K/L41C/
K42R/M51L/G52C/G53A/D54G/T56A/M58P/C61V/
G62T/T64M/K66R/W68Y/Q70N/S71T/A74M/A75E/
R76L/A84G/I87L/D89T/S92G/D94E/Y95F/Y96F/R101A/
L103I/S104A/Y107G/G108D/S109T/L110F/K111E/
A112E/T113S/N114K/D115K/Q116N/D118F/I119E/
V120I/T121V/Q128M/G129D/D130Q/K131T/F132I/
C134L/K140N/C141N/D143S/G152S/P155C/S156N/
F62Y/S163A/Q166K/K169N/E172D/S173A/V175I/
N180K/K223D/G249A/D257E/Q273G/Q277E/R281A/
V282M/D285V/V288A/I292V/V299P/L300N/N311D/
I312V/Y313H/D314S/T315A/M317L/C318A/Y320L/
I323L/T345E/P346F/E347D/F350A/S352G/A359T/F364L/
R365I/A366K/L368A/K369E/L370I/E372D/D377A/
A381D/W387Y/N388K/A393K/D394A/I396V/A397D/
K399T/A400T/D401S/F402L/A403E/S404E/K407Q/
A409V/E411T/K412H/G413S/V415P/T416V/A417-/
S418-/L419M/S420Q/M426V/S429T/V434I/S437R/L438-;
E2K/F3Y/S5P/I7V/G8P/K9E/I10V/Q11K/Q13E/K16N/
D19N/L21F/S22A/N27D/P28A/E29N/E30K/I32V/N33A/
R38K/K42P/L45M/S46A/T50N/M51L/G52C/G53A/
D54G/C61R/G62D/T64A/T67S/W68F/Q70E/S71K/D72G/
P73S/A74M/A75E/R76H/A84G/I87F/D89E/S92G/D94K/
Y96F/R101V/S104A/Y107A/G108C/S109D/L101I/
A112E/D115S/Q116R/I119E/V120I/T121S/K125L/
Q128K/D130T/K131D/F132I/K140N/C141M/D143S/

H144N/M148V/H149N/T153S/S154T/P155N/F160Y/
A161C/S163A/E172D/S173I/N18R/N198D/M199L/
S219A/T236A/T244A/V247A/L248I/K253Q/M262L/
Q273G/T275S/V282I/A283S/R284S/D285/V288M/F289L/
I292V/V299M/Q307E/T310F/N311D/I312V/I323L/
A325F/F328L/N330-/L333F/A339N/G342P/F344Y/
P346Y/I349M/S352G/Y353F/A355L/A359S/F364L/
R365I/A366K/L368A/D373E/R 375T/I376L/K378N/
V380I/A381K/D382E/A385K/W387F/N388E/T389S/
G390E/A393K/D394K/I396R/A397S/G398K/K399S/
D401S/F402L/A403Q/S404E/E406A/K407A/L410E/
K412M/E414-/V415A/T416P/S418M/L419P/S420G/
M426Y/E428Q/S429A/I430A/V431L/N433Q/V434N/
S437E/L438V; E2K/F3Y/S5P/I7V/G8P/K9E/I10V/Q11K/
Q13E/K16N/D19N/L21F/S22A/N27D/P28A/E29N/E30K/
I32V/N33A/R38K/L41C/K42R/M51L/G52C/G53A/D54G/
T56A/M58P/C61V/G62T/T64V/K66R/W68Y/Q70N/S71T/
A74M/A75E/R76L/A84G/I87L/D89T/S92G/D94E/Y95F/
Y96F/R101A/L103/S104A/Y107G/G108D/S109T/L110F/
K111E/A 112E/T113S/N114K/D115K/Q116N/D118F/
I119E/V120I/T121V/Q128M/G129D/D130Q/K131T/
F132I/C134L/K140N/C141N/D143S/G152S/P155C/
S156N/F162Y/S163A/Q166K/K169N/E172D/S173A/
V175I/N180K/S219A/I220N/K223D/T236M/D257E/
Q273G/Q277E/R281A/V282M/D285V/V288A/I292V/
V299P/L300N/N311D/I312V/Y313H/D314S/T315A/
M317L/C318A/Y320L/I323L/A339V/A359T/F364L/
R365I/A366K/L368A/K369E/L370I/E372D/D377A/
A381D/W387Y/N388K/A393K/D394A/I396V/A397D/
K399T/A400T/D401S/F402L/A403E/S404E/K407Q/
A409V/E411T/K412H/G413S/V415P/T416V/A417-/
S418-/L419M/S420Q/M426V/S429T/V434I/S437R/L438-
E2K/F3Y/S5P/I7V/G8P/K9E/I10V/Q11K/Q13E/K16N/
D19N/L21F/S22A/N27D/P28A/E29N/E30K/I32V/N33A/
R38K/L41C/K42R/M51L/G52C/G53A/D54G/T56A/
M58P/C61V/G62T/T64M/K66R/W68Y/Q70N/S71T/
A74M/A75E/R76L/A84G/I87L/D89T/S92G/D94E/Y95F/
Y96F/R101A/L103I/S104A/Y107G/G108D/S109T/L110F/
K111E/A112E/T113S/N114K/D115K/Q116N/D118F/
I119E/V120I/T121V/Q128M/G129D/D130Q/K131T/
F132I/C134L/K140N/C141N/D143S/G152S/P155C/
S156N/F162Y/S163A/Q166K/K169N/E 172D/S73A/
V175I/N180K/N198D/M199V/T236M/T244A/V247A/
L248I/K253Q/M262L/Q273G/Q277E/R281A/V282M/
D285V/V288A/I292V/V299P/L300N/N311D/I312V/
Y313H/D314S/T315A/M317L/C318A/Y320L/I323L/
A339V/T345E/P346F/E347D/I349V/F350A/S352G/
A359T/F364L/R365I/A366K/L368A/K369E/L370I/
E372D/D377A/A381D; E2K/F3Y/S5P/I7V/G8P/K9E/
I10V/Q11K/Q13E/K16N/D19N/L21F/S22A/N27D/P28A/
E29N/E30K/I32V/N33A/R 38K/L41C/K42R/M51L/G52C/
G53A/D54G/T56A/M58P/C61V/G62T/T64M/K66R/
W68Y/Q70N/S71T/A74M/A75E/R76L/A84G/I87L/D89T/
S92G/D94E/Y95F/Y96F/R101A/L103I/S104A/Y107G/
G108D/S109T/L110F/K111E/A112E/T113S/N114K/
D115K/Q116N/D118F/I119E/V120I/T121V/Q128M/
G129D/D130Q/K131T/F132I/C134L/K140N/C141N/
D143S/G152S/P155C/S156N/F162Y/S163A/Q166K/
K169N/E172D/S173A/V175I/N18K/N198D/M199L/
S219A/I220N/K223D/G249A/D257E/V299M/N311D/
I312V/Y313H/D314S/T315A/M317L/C318A/Y320L/
I323L/A339V/T345E/P346F/E347D/F350A/S352G/A359T/F364L/R365I/A366K/L368A/K369E/L370I/E372D/D 377A/A381D/W387Y/N388K/A393K/D394A/I396V/A397D/K399T/A400T/D401S/F402L/A403E/S404E/K407Q/A409V/E411T/K412H/G413S/V415P/T416V/A417-/S418-/L419M/S420Q/M426V/S429T/

V434I/S437R/L438-; E2K/F3Y/S5P/I7V/G8P/K9E/I10V/
Q11K/Q13E/K16N/D19N/L21F/S22A/N27D/P28A/E29N/
E30K/I32V/N33A/R38K/L41C/K42R/M51L/G52C/G53A/
D54G/T56A/M58P/C61V/G62T/T64M/K66R/W68Y/
Q70N/S71T/A74M/A75E/R76L/A84G/I87L/D89T/S92G/
D94E/Y95F/Y96F/R101A/L103I/S104A/Y107G/G108D/
S109T/L110F/K111E/A112E/T113S/N114K/D115K/
Q116N/D118F/I119E/V120I/T121V/Q128M/G129D/
D130Q/K131T/F132I/C134L/K140N/D143S/G152S/
P155C/S156N/F162Y/S163A/Q166K/K169N/E172D/
S173A/V175I/N180K/S219A/I220N/K223D/G249A/
N311D/I312V/Y313H/D314S/T315A/M317L/C318A/
Y320L/I323L/A339V/T345E/P346F/E 347D/F350A/
S352G/A359T/F364L/R365/A366K/L368A/K369E/L370I/
E372D/D377A/K378E/A381D/W387Y/N388K/A393K/
D394A/I396V/A397D/K399T/A400T/D401S/F402L/
A403E/S404E/K407Q/A409V/E411T/K412H/G 413S/
V415P/T416V/A417-/S418-/L419M/S420Q/M426V/
S429T/V434I/S437R/L438*; S5K/G8S/Q11P/Q13E/
P15K/K 6D/D19N/S22A/E29D/N33D/T36K/E39D/H40I/
L41M/T64A/Q70E/S71N/D89Q/Y96F/A112D/D115A/
E126A/G129A/D130A/K131F/F132L/N180K/N198D/
M199V/T244A/V247A/L248I/K253Q/Q273G/T275S/
V282I/A283S/R D285I/V288M/F289L/I292V/N311D/
I312V/Y313H/D314S/T315A/M317L/C318A/Y320L/
I323L/W387Y/N388K; E2K/F3Y/S5P/I7V/G8P/K9E/I10V/
Q11K/Q13E/K16N/D19N/L21F/S22A/N27D/P28A/E29N/
E30K/I32V/N33A/R38K/L41C/K42R/M51L/G52C/G53A/
D54G/T56A/M58P/C61V/G62T/T64M/K66R/W68Y/
Q70N/S71T/A74M/A75E/R76L/A84G/I87L/D89T/S92G/
D94E/Y95F/Y96F/R101A/L103I/S104A/Y107G/G108D/S109T/L110F/K111E/A112E/T113S/N114K/D115K/Q116N/D118F/I119E/V120I/T121V/Q128M/G129D/D130Q/K131T/F132I/C134L/K140N/D143S/G152S/P155C/S156N/I63A/Q66K/K69N/E172D/S173A/V175/N18K; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D115K/Q116N/D118F/I119E/V120I/T121V/Q128M/G129D/D130Q/K131T/F132I/C134L/K140N/C141N/D143S/G152S/P155C/S156N/F162Y/S163A/Q166K/K169N/E172D/S173A/V175/N180K/N198D/M199L/V247A/L248I/K253Q/Q273G/Q277E/R281A/V282M/D285V/V288A/N311D/I312V/Y313H/D314S/T315A/M317L/C318A/M319T/Y320L/I323L/A339V/T345E/P346F/E347D/F350A/S352G/A359T/F364L/R365I/A366K/L368A/K369E/L370I/E372D/D377A/A381D/W387Y/N388K/A393K/D394A/I396V/A397D/K399T/A400T/D401S/F402L/A403E/S404E/K407Q/A409V/E411T/K412H/G413S/V415P/T416V/A417-/S418-/L419M/S420Q/M426V/S429T/V434I/S437R/L438-; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64V/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D115K/Q116N/D118F/I119E/V120I/T121V/Q128M/G129D/D130Q/K131T/F132I/C134L/K140N/C141N/D143S/G152S/P155C/S156N/F162Y/S163A/Q166K/K169N/E172D/S173A/V175I/N180K/K253Q/Q273G/T275S; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53T/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103/S104A/E106G/Y107G/G108D/S109T/L110F/K111E/A1112E/T113S/N114K/D115K/Q116N/D118F/I119E/V120I/T121V/Y123H/Q128M/G129D/D130Q/K131T/F132I/C34L/K40N/C141N/D143S/G152S/P55C/S56N/F62Y/S63A/Q166K/K169N/E 72D/S73A/V175I/N80K/G249A/D257E/Q273G/Q277E/R281A/V282M/D285V/V288A/I292V/V299P/L300N/N311D/I312V/Y313H/D 314S/T315A/M317L/C318A/Y320L/I323L/A339V/T345E/P346F/E347D/F350A/S352G/A359T/F364L/R365I/A366K/L368A/K369E/L370I/E372D/D377A/A381D; E2K/F3Y/S5P/I7V/G8P/K9E/I10V/Q11K/Q13E/K16N/D19N/L21F/S22A/N27D/P28A/E29N/E30K/I32V/N33A/R 38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D115K/Q116N/D118F/I119E/V120I/T121V/Q128M/G129D/D130Q/K131T/F132I/C134L/K140N/D143S/G152S/P155C/S156N/F162Y/S163A/Q166K/K169N/E172D/S173A/V175/N198D/M199L/S219A/I220N/K223D/G249A/D257E/I1292V/V299P/L300N/N311D/I312V/Y313H/D314S/T315A/M317L/C318A/Y320L/I323L/A339V/T345E/P346F/E347D/F350A/S352G/A359T/F364L/R365I/A366K/L368A/K369E/L370I/E372D/D377A/A381D/W387Y/N388K/A393K/D394A/I396V/A397D/K399T/A400T/D401S/F402L/A403E/S404E/K407Q/A409V/E411T/K412H/G413S/V415P/T416V/A417-/S418-/L419M/S420Q/M426V/S429T/V434I/S437R/L438-; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D115K/Q116N/D118F/I119E/V120I/T121V/Q128M/G129D/D130Q/K131T/F132I/C134L/K140N/C4N/D143S/G152S/P55C/F62Y69N/E72D/S63A/Q66K/K69N/I72D/S73A/V175/N180K/N198D/M199L/V299P; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D115K/Q116N/D118F/I119E/V120I/T121V/Q128M/G129D/D130Q/K131T/F132I/C134L/K140N/D143S/G152S/P155C/S156N/F162Y/S163A/Q166R/K169N/E 72D/S173A/V175/N180K/N98D/M199L/T236M/I244A/V299P/L300N/N311D/I312V/Y313H/D314S/T315A/M317L/C318A/Y320L/I323L/A339V/T345E/P346F/E347D/F350A/S352G/A359T/F364L/R365I/A366K/L368A/K369E/L370I/E372D/D377A/A381D/W387Y/N388K/A393K/D394A/I396V/A397D/K399T/A400T/D401S/F402L/A403E/S404E/K407Q/A409V/E411T/K412H/G413S/V415P/T416V/A417-/S418-/L419M/S420Q/M426V/S429T/V434I/S437R/L438-; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103/S104A/Y107G/

G108D/S109T/L110F/K111E/A112E/T113S/N114K/
D115K/Q116N/D118F/I119E/V120I/T121V/Q128M/
G129D/D130Q/K31T/F132I/C134L/K140N/C141N/
D143S/G152S/P155C/S156N/F162Y/S163A/Q166K/
K169N/E172D/S173A/V175I/N180K/V183A/N198D/
M199L/S219A/I220N/D257E/N311D/I312V/Y313H/
D314S/T315A/M317L/C318A/Y320L/I323L/A339V/
T345E/P346F/E347D/F350A/S352G/A359T/F364L/R365I/
A366K/L368A/K369E/L370I/E372D/D377A/A381D/
W387Y/N388K/A393K/D394A/I396V/A397D/K399T/
A400T/D401S/F402L/A403E/S404E/K407Q/A409V/
E411T/K412H/G413S/V415P/T416V/A417-/I418-/L419M/
S420Q/M426V/S429T/V434I/S437R/L438-; E372G; S5K/
G8S/Q11P/Q13E/P15K/K16D/D19N/S22A/E29D/N33D/
T36K/E39D/H40I/L41M/T64A/Q70E/S71N/D89Q/Y96F/
A112D/D115A/E126A/G129A/D130E/K131T/F132L/
N180T/N198D/M199L/S219A/I220N/T236M/G249A/
D257E/Q273G/Q277E/R281A/V282M/D285V/V288A/
I292V/N311D/I312V/Y313H/D314S/T315A/M317L/
C318A/Y320L/I323L/A339V/T345E/P346F/E347D/
F350A/S352G/A359T/F364L/R365I/A366K/L368A/
K369E/L370I/E372D/D377A/A381D/W387Y/N388K/
A393K/D394A/I396V/A397D/K399T/A400T/D401S/
F402L/A403E/S404E/K407Q/A409V/E411T/K412H/
G413S/V415P/T416V/A417-/S418-/L419M/S420Q/
M426V/S429T/V434I/S437R/L438-; E2K/F3Y/S5P/I7V/
G8P/K9E/I10V/Q11K/Q13E/K16N/D19N/L21F/S22A/
N27D/P28A/E29N/E30K/I32V/N33A/R38K/L41C/K42R/
M51L/G52C/G53A/D54G/T56A/M58P/C61V/G62T/
T64M/K66R/W68Y/Q70N/S71T/A74M/A75E/R76L/
A84G/I87L/D89T/S92G/D94E/Y95F/Y96F/R101A/L103/
S104A/Y107G/G108D/S109T/L110F/K111E/A112E/
T113S/N114K/D115K/Q116N/D118F/I119E/V120I/
T121V/Q128M/G129D/D130Q/K131T/F132I/C134L/
K140N/C141N/D143S/G152S/P155C/S156N/F162Y/
S163A/Q166K/K169N/E172D/S173A/V175I/N180K/
N198D/M199L/Q273G/Q277E/R281A/V282M/D285V/
V288A/I292V/V299P/L300N/N311D/I312V/Y313H/
D314S/T315A/M317L/C318A/Y320L/I323L/F328L/
A339V/T345E/P346F/E347D/F350A/S352G/A359T/
F364L/R365I/A366E/L    368A/K369E/L370I/W387Y/
N388K/A393K/D394A/I396V/A397D/K399T/A400T/
D401S/F402L/A403E/S404E/K407Q/A409V/E411T/
K412H/G413S/V415P/T416V/A417-/S418-/L419M/
S420Q/M426V/S429T/V434I/S437R/L438*; E2K/F3Y/
S5P/I7V/G8P/K9E/I10V/Q11K/Q13E/K16N/D19N/L21F/
S22A/N27D/P28A/E29N/E30K/I32V/N33A/R 38K/L41C/
K42R/M51L/G52C/G53A/D54G/T56A/M58P/C61V/
G62T/T64M/K66R/W68Y/Q70N/S71T/A74M/A75E/
R76H/A84G/I87L/D89T/S92G/D94E/Y95F/Y96F/R101A/
L103/S104A/Y107G/G108D/S109T/L110F/K111E/A112E/
T113S/N114K/D115K/Q116N/D118F/I119E/V120I/
T121V/Q128M/G129D/D130Q/K131T/F132I/C134L/
K140N/C141N/D143S/G152S/P55C/S156N/F162Y/S 63A/
Q166K/K169N/E172D/S173A/V175I/N180K/V288M/
F289L/I292V; and/or E2K/F3Y/S5P/I7V/G8P/K9E/I10V/
Q11K/Q13E/K16N/D19N/L21F/S22A/N27D/P28A/E29N/
E30K/I32V/N33A/R38K/L41C/K42R/M51L/G52C/G53A/
D54G/T56A/M58P/C61V/G62T/T64V/K66R/W68Y/
Q70N/S71T/A74M/A75E/R76L/A84G/I87L/D89T/S92G/
D94E/Y95F/Y96F/R    101A/L103/S104A/Y107G/G108D/
S109T/L110F/K111E/A112E/T113S/N114K/D115K/
Q116N/D118F/I119E/V120I/T121V/Q128M/G129D/
D130Q/K131T/F132I/C134L/K140N/C141N/D143S/
G152S/P55C/S156N/F62Y/S163A/Q166K/K169N/E172D/
S173A/V175I/N180K/K253Q/Q273G/T275S, wherein the positions are numbered by correspondence with the amino acid sequence set forth in SEQ ID NO:2.

In some additional embodiments, the nucleic acid constructs of the present invention further comprise a genetic element that facilitates stable integration into a fungal host genome. In some additional embodiments, the nucleic acid constructs of the present invention further comprise at least one genetic element that facilitates stable integration into a fungal host genome. In some embodiments, the genetic element or at least one genetic element facilitates integration into a fungal host genome by homologous recombination. In some further embodiments, the nucleic acid constructs comprise a fungal origin of replication. In some additional embodiments, the fungal origin of replication is a yeast origin of replication. In some further embodiments, the nucleic acid constructs comprise polynucleotide sequences operatively linked to promoter sequences that are functional in fungal cells. In some embodiments, the promoter sequence is a fungal promoter sequence. In some further embodiments, the fungal promoter sequence is a yeast promoter sequence. In some additional embodiments, the nucleic acid constructs comprise polynucleotide sequences operatively linked to a transcription termination sequences that are functional in fungal cells. In some further embodiments, the nucleic acid constructs comprise polynucleotide sequences containing codons optimized for expression in yeast cells.

In some embodiments, the nucleic acid constructs comprise polynucleotide sequences comprising at least one mutation and/or mutation set at position(s) selected from: 27/30/
42/51/54/60/63/69/72/75/78/114/126/129/133/135/138/147/
156/159/177/180/195/201/207/216/222/225/234/237/249/
252/255/261/271/273/274/275/306/307/309/318/321/324/
327/333/339/342/349/360/366/381/384/399/403/405/411/
420/426/429/432/435/438/453/456/466/467/468/471/477/
483/486/489/495/501/510/511/513/534/537/552/570/573/
576/579/580/583/600/601/603/607/625/627/642/645/648/
663/684/687/693/696/705/714/717/726/738/741/744/747/
751/753/756/765/766/771/792/804/807/810/811/816/822/
825/834/837/840/846/849/852/858/885/894/903/906/912/
915/921/924/927/936/954/960/963/966/969/975/987/993/
996/999/1011/1018/1020/1023/1029/1035/1038/1054/
1055/1083/1089/1098/1107/1108/1110/1113/1119/1125/
1131/1137/1146/1149/1155/1182/1185/1194/1200/1209/
1215/1218/1221/1233/129/1242/1245/1248/1254/1266/
1272/1275/1279/1281/1284/1287/1293/1308/1312/1314;
27/30/42/51/54/60/63/69/72/75/78/114/126/129/133/135/
138/147/156/159/177/180/195/201/207/216/222/225/234/
237/249/252/255/261/271/273/274/275/306/307/309/318/
321/324/327/333/339/342/349/360/366/381/384/399/403/
405/411/420/426/429/432/435/438/453/456/466/467/468/
471/477/483/486/489/495/501/510/511/513/534/537/552/
570/573/576/579/580/583/600/601/603/607/625/627/642/
645/648/663/684/687/693/696/705/741/744/747/751/753/
756/765/766/771/792/804/807/810/811/816/822/825/834/
837/840/846/849/852/858/885/894/903/906/912/915/921/
924/927/936/954/960/963/966/969/975/987/993/996/999/
1011/1018/1020/1023/1029/1035/1038/1054/1055/1083/
1089/1098/1107/1108/1110/1113/1119/1125/1131/1137/
1146/1149/1155/1182/1185/1194/1200/1209/1215/1218/
1221/1233/1239/1242/1245/1248/1254/1266/1272/1275/
1279/1281/1284/1287/1293/1308/1312/1314; 27/30/42/51/
54/60/63/69/72/75/78/114/126/129/133/135/138/147/156/
159/177/180/195/201/207/216/222/225/234/237/249/252/
255/261/271/273/274/275/306/307/309/318/321/324/327/
333/339/342/349/360/366/381/384/399/403/405/411/420/
426/429/432/435/438/453/456/466/467/468/471/477/483/
486/489/495/510/511/513/625/627/642/645/648/1047/

1054/1055/1095/1194/1200; 27/30/42/51/54/60/63/69/72/ 75/78/114/126/129/133/135/138/147/156/159/177/180/195/ 201/207/216/222/225/234/237/249/252/255/261/271/273/ 274/275/306/307/309/318/321/324/327/333/339/342/349/ 360/366/381/384/399/403/405/411/420/426/429/432/435/ 438/453/456/466/467/468/471/477/483/486/489/495/501/ 510/511/513/534/537/705/714/717/726/738/741/744/747/ 751/753/756/765/766/771/1185/1224; 27/30/42/51/54/60/ 63/69/72/75/78/114/126/129/133/135/138/147/156/159/ 177/180/195/201/207/216/222/225/234/237/249/252/255/ 261/271/273/274/275/306/307/309/318/321/324/327/333/ 339/342/349/360/366/381/384/399/403/405/411/420/426/ 429/432/435/438/453/456/466/467/468/471/477/483/486/ 489/495/501/510/511/513/552/601/924/1263/1269; 27/30/ 42/51/54/60/63/69/72/75/78/114/126/129/133/135/138/147/ 156/159/177/180/195/201/207/216/222/225/234/237/249/ 252/255/261/271/273/274/275/306/307/309/318/321/324/ 327/333/339/342/349/360/366/381/384/399/403/405/411/ 420/426/429/432/435/438/453/456/466/467/468/471/477/ 483/486/489/495/783/1185/1224; 27/30/42/51/54/60/63/69/ 72/75/78/114/126/129/133/135/138/147/156/159/177/180/ 195/201/207/216/222/225/234/237/249/252/255/261/271/ 273/274/275/306/307/309/318/321/324/327/333/339/342/ 349/360/366/381/384/399/403/405/411/420/426/429/432/ 435/438/453/456/466/467/468/471/477/483/486/489/495/ 501/510/511/513/534/537/1185/1224; 120/279/510/1185/ 1224; 138/150/783/1143/1146/1155/1263/1269; 171/279/ 510/1185/1224; 207/279/510/1152/1185/1224; 207/279/ 510/1185/1224; 219/279/510/607/771/1185/1224; 279/328/ 330/510/642/645/648; 279/483/510; 279/483/510/567/1029/ 1185/1224; 279/483/510/606/1185/1224; 279/483/510/771/ 783/1173/1185/1224; 279/483/510/1185/1224/1266; 279/510; 279/510/570/573/576/579/580/583/600/601/603/ 607/625/627/642/645/648/663/771/783/1170/185/1224; 279/510/511/1023/1029/1035/1038/1054/1055/1095; 279/ 510/552/570/573/576/579/580/583/600/601/603/607/1185/ 1224; 279/510/552/625/627/1185/1224; 279/510/552/735/ 1185/1224; 279/510/552/1185/1224; 279/510/558/1185/ 1224; 279/510/570/573/576/579/580/583/600/601/603/607/ 625/627/642/645/648/663/771/783/1170/1185/1224; 279/ 510/570/1185/1224; 279/510/580/1185/1224; 279/510/600/ 601/603/607/625/627/642/645/648/1194/1200; 279/510/ 625/627/642/645/648/783/1011/1018/1020/1023/1054/ 1055/1233/1239/1242; 279/510/625/627/696; 279/510/642/ 645/648/663/1185/1224; 279/510/657/783; 279/510/663/ 1054/1055/1194/1200; 279/510/675/1185/1224/1269; 279/ 510/684/687/978; 279/510/684/792/1185/1224; 279/510/ 705/1185/1224; 279/510/726; 279/510/753/1053/1185/ 1224; 279/510/783/1020/1185/1224; 279/510/783/1128/ 1185/1224; 279/510/783/1185/1224; 279/510/792; 279/510/ 873; 279/510/885/894/903/906/912/915/921/924/927/936/ 954/1035/1038; 279/510/906/1185/1224; 279/510/990/ 1185/1224; 279/510/1023/1185/1224; 279/510/1086; 279/ 510/1113/1185/1224; 279/510/1122/1185/1224; 279/510/ 1185/1224; 585/642/783/924/1263/1269; 783; 783/924/ 1263/1269; 924; 1185/1224; and/or 1255, wherein the positions are numbered by correspondence with the nucleotide sequence set forth in SEQ ID NO: 1.

In some additional embodiments, the nucleic acid constructs comprise polynucleotide sequences comprising at least one mutation and/or mutation set selected from: a27/ c30/t42/c51/a54/t60/g63/t69/a72/t75/t78/g114/a126/c129/ c133/a135/c138/c147/t156/c159/c177/a180/c195/c201/ t207/c216/g222/a225/g234/c237/t249/t252/c255/c271/ g273/a274/g275/c306/c307/t309/a318/t321/c324/c327/ a333/c339/t342/c349/t360/t366/g381/g384/g399/t403/a405/ c411/a420/t426/t429/c432/c435/g438/a453/a456/a466/ g467/t468/c471/t477/t483/t486/t489/g495/a501/a510/t511/ a513/c534/t537/t552/t570/c573/g576/c579/c580/c583/c600/ t601/a603/c607/c625/a627/a642/a645/c648/a663/c684/ g687/a693/c696/t705/c714/g717/c726/c738/a741/a744/ t747/t 751/a753/g756/g765/t766/t771/c792/c804/c807/ a810/c811/a816/c822/a825/t834/g837/a840/g846/t849/ g852/c858/c885/c894/a903/a906/c912/g915/a921/c924/ c927/t936/t954/t960/g963/c966/t969/c975/a987/c993/c996/ g999/g1011/c1018/t1020/g1023/a1029/g1035/t1038/ a1054g/g1083/g1089/a1098/a1107/t1108/g1110/t1113/ c1119/a1125/c131/t1137/c1146/g1149/c1155/t1182/t1185/ a1194/c1200/a1209/g1215/a1218/a1221/a1233/t1239/ a1242/t1245/c1248/a1254/t1266/a1272/g1275/c1279/ g1281/a1284/t1287/c1293/t1308/t1312/g1314; a27/c30/t42/ c51/a54/t60/g63/t69/a72/t75/t78/g114/a126/c129/c133/ a135/c138/c147/t156/c159/c177/a80/c195/c201/t207/c216/ g222/a225/g234/c237/t249/t252/c255/t261/c271/g273/ a274/g275/c306/c307/t309/a381/t321/c324/c327/a333/ c339/t342/c349/t360/t366/g381/g384/g399/t403/a405/c411/ a420/t426/t429/c432/c435/g438/a453/a456/a466/g467/ t468/c471/t477/t483/t486/t489/g495/a50/a510/t5111/a513/ c534/t537/t552/t570/c573/g576/c579/c580/c583/c600/t601/ a603/c607/c625/a627/a642/a645/c648/a663/c684/g687/ a693/c696/t705/a741/a744/t747/t751/a753/g756/g765/t766/ t771/c792/c804/c807/a810/c811/a816/c822/a825/t834/ g837/a840/g846/t849/g852/c858/c885/c894/a903/a906/ c912/g915/a921/c924/c927/t936/t954/t960/g963/c966/t969/ c975/a987/c993/c996/g999/g1011/c1018/t1020/g1023/ a1029/g1035/t1038/a1054/g1055/c183/g1089/a1098/ a1107/t11108/g1110/t1113/c1119/a11125/c1131/t1137/ c1146/g1149/c1155/t1182/t1185/a1194/c1200/a1209/ g1215/a1218/a1221/a1233/t1239/a1242/t1245/c1248/ a1254/t1266/a1272/g1275/c1279/g1281/a1284/t1287/ c1293/t1308/t1312/g1314; a27/c30/t42/c51/a54/t60/g63/ t69/a72/t75/t78/g114/a126/c129/c133/a135/c138/c147/ t156/c159/c177/a180/c195/c201/t207/c216/g222/a225/ g234/c237/t249/t252/c255/t261/c271/g273/a274/g275/ c306/c307/t309/a381/t321/c324/c327/a333/c339/t342/c349/ t360/t366/g381/g384/g399/t403/a405/c411/a420/t426/t429/ c432/c435/g38/a453/a456/a466/g467/t468/c471/t477/t483/ t486/t489/g495/a510/t511/a513/c625/a627/a642/a645/c648/ t1047/a1054/g1055/a1095/a1194/c1200; a27/c30/t42/c51/ a54/t60/g63/t69/a72/t75/t78/g114/a126/c129/c133/a135/ c138/c147/t156/c159/c177/a180/c195/c201/t207/c216/ g222/a225/g234/c237/t249/t252/c255/t261/c271/g273/ a274/g275/c306/c307/t309/a381/t321/c324/c327/a333/ c339/t342/c349/t360/t366/g381/g384/g399/t403/a405/c411/ a420/t426/t429/c432/c435/g438/a453/a456/a466/g467/ t468/c471/t477/t483/t486/t489/g495/a501/a510/t511/a513/ c534/t537/t705/c714/g717/c726/c738/a741/a744/t747/t751/ a753/g756/g765/t766/t771/t1185/t1224; a27/c30/t42/c51/ a54/t60/g63/t69/a72/t75/t78/g114/a126/c129/c133/a135/ c138/c147/t156/c159/c177/a180/c195/c201/t207/c216/ g222/a225/g234/c237/t249/t252/c255/t261/c271/g273/ a274/g275/c306/c307/t309/a381/t321/c324/c327/a 333/ c339/t342/c349/t360/t366/g381/g384/g399/t403/a405/c411/ a420/t426/t429/c432/c435/g438/a453/a456/a466/g467/ t468/c471/t477/t483/t486/t489/g495/a501/a510/t511/a513/ t552/t601/c924/t1263/a1269; a27/c30/t42/c51/a54/t60/g63/ t69/a72/t75/t78/g114/a126/c129/c133/a135/c138/c147/ t156/c159/c177/a180/c195/c201/t207/c216/g222/a225/ g234/c237/t249/t252/c255/t261/c271/g273/a274/g275/ c306/c307/t309/a381/t321/c324/c327/a333/c339/t342/c349/ t360/t366/g381/g384/g399/t403/a405/c411/a420/t426/t429/ c432/c435/g438/a453/a456/a466/g467/t468/c471/t477/ t483/t486/t489/g495/g783/t1185/t1224; a27/c30/t42/c511/ a54/t60/g63/t69/a72/t75/t78/g114/a126/c129/c133/a135/ c138/c147/t156/c159/c177/a180/c195/c201/t207/c216/ g222/a225/g234/c237/t249/t252/c255/t261/c271/g273/ a274/g275/c306/c307/t309/a381/t321/c324/c327/a 333/ c339/t342/c349/t360/t366/g381/g384/g399/t403/a405/c411/ a420/t426/t429/c432/c435/g438/a453/a456/a466/g467/ t468/c471/t477/t483/t486/t489/g495/a501/a510/t511/a513/ c534/t537/t1185/t1224; t120/t279/a510/t1185/t1224; c138/ t150/g783/t1143/c1146/c1155/t1263/a1269; t171/t279/ a510/t1185/t1224; t207/t279/a510/t1152/t1185/t1224; t207/ t279/a510/t1185/t1224; a219/t279/a510/c607/t771/t1185/ t1224; t279/t328/g330/a510/a642/a645/c648; t279/t483/ a510; t279/t483/a510/a567/a1029/t185/t1224; t279/t483/ a510/a606/t1185/t1224; t279/t483/a510/t771/g783/t1173/ t1185/t1224; t279/t483/a510/t1185/t1224/t1266; t279/a510; t279/a510/t570/c573/g576/c579/c580/c583/c600/t601/a603/ c607/c625/a627/a642/a645/c648/a663/t771/g783/t1170/ t1185/t1224; t279/a510/t511/g1023/a1029/g1035/t1038/ a1054/g1055/a1095; t279/a510/t552/t570/c573/g576/c579/ c580/c583/c600/t601/a603/c607/t1185/t1224; t279/a510/ t552/c625/a627/t1185/t1224; t279/a510/t552/t735/t1185/ t1224; t279/a510/t552/t1185/t1224; t279/a510/t558/t1185/ t1224; t279/a510/t570/c573/g576/c579/c580/c583/c600/ t601/a603/c607/c625/a627/a642/a645/c648/a663/t771/ g783/t1170/t1185/t1224; t279/a510/t570/t1185/t1224; t279/ a510/c580/t1185/t1224; t279/a510/t600/t601/a603/c607/ c625/a627/a642/a645/c648/a1194/c1200; t279/a510/c625/ a627/a642/a645/c648/g783/g1011/c1018/t1020/g1023/ a1054/g1055/a1233/t1239/a1242; t279/a510/c625/a627/ c696; t279/a510/a642/a645/c648/a663/t1185/t1224; t279/ a510/t657/g783; t279/a510/a663/a1054/g1055/a1194/ c1200; t279/a510/c675/t1185/t11224/a1269; t279/a510/ c684/g687/t978; t279/a510/c684/c792/t1185/t11224; t279/ a510/t705/t1185/t11224; t279/a510/c726; t279/a510/a753/ t1053/t1185/t11224; t279/a510/g783/t1020/t1185/t11224; t279/a510/g783/t1128/t1185/t11224; t279/a510/g783/t1185/ t11224; t279/a510/c792; t279/a510/t873; t279/a510/c885/ c894/a903/a906/c912/g915/a921/c924/c927/t936/t954/ g1035/t1038; t279/a510/a906/t1185/t1224; t279/a510/t990/ t1185/t11224; t279/a510/g1023/t1185/t11224; t279/a510/ a1086; t279/a510/t1113/t1185/t11224; t279/a510/t1122/ t11185/t11224; t279/a510/t1185/t1224; g585/a642/g783/ c924/t1263/a1269; g783; g783/c924/t1263/a1269; c924/ t1185/t1224; and/or t1255; wherein the positions are numbered by correspondence with the nucleotide sequence set forth in SEQ ID NO: 1.

In some still further embodiments, the nucleic acid constructs comprise polynucleotide sequences comprising at least one mutation and/or mutation set selected from: a27/ c30a/t42c/c51t/a54c/t60a/g63a/t69c/a72g/t75c/t78c/g114a/ a126g/c129t/c133t/a135g/c138t/c147t/t156a/c159t/c177t/ a180c/c195t/c201a/t207c/c216t/g222t/a225t/g234a/c237t/ t249c/t252a/c255t/t261c/c271t/g273a/a274t/g275c/c306t/ c307t/t309g/a318g/t321c/c324t/c327t/a333g/c339a/t342c/ c349t/t360c/t366c/g381a/g384a/g399a/t403c/a405t/c411t/ a420g/t426c/t429c/c432t/c435a/g438a/a453t/a456t/a466t/ g467c/t468a/c471t/t477t/t483a/t486c/t489a/g495t/a501c/ a510t/t511c/a513g/c534t/t537a/t552c/t570a/c573t/g576a/ c579g/c580t/c583t/c600a/t601c/a603t/c607t/c625t/a627 g/a642t/a645g/c648t/a663t/c684t/g687a/a693g/c696a/ t705a/t714t/g717a/c726t/c738a/a741c/a744g/t747c/t751c/ a753g/g756a/g765c/t766c/t771c/c792a/c804t/c807a/a810t/ c811t/a816g/c822t/a825c/t834c/g837a/a840g/g846c/t849c/ t852c/a858t/c885t/c894t/a903g/a906c/c912t/g915a/a921g/ c924t/c927t/t936c/t954c/t960c/g963a/c966t/t969c/c975t/ a987t/c993t/c996t/g999t/g1011t/c1018a/t1020a/g1023a/ a1029t/g1035t/t1038a/a1054t/g1055c/g1083t/g1089t/ a1098t/a1107g/t1108c/g1110a/t1113c/c1119t/a1125g/ c1131t/t1137c/c1146t/g1149a/c1155t/t1182c/t1185c/ a1194c/c1200t/a1209g/g1215a/a1218g/a1221g/a1233g/ t1239a/a1242g/t1245c/c1248t/a1254t/t1266a/a1272g/ g1275a/c1279t/g1281a/a1284g/t1287c/c1293t/t1308c/ t1312c/g1314a; a27g/c30a/t42c/c51t/a54c/t60a/g63a/t69c/ a72g/t75c/t78c/g114a/a126g/c129t/c133t/a135g/c138t/ c147t/t156a/c159t/c177t/a180c/c195t/c201a/t207c/c216t/ g222t/a225t/g234a/c237t/t249c/t252a/c255t/t261c/c271t/ g273a/a274t/g275c/c306t/c307t/t309g/a318g/t321c/c324t/ c327t/a333g/c339a/t342c/c349t/t360c/t366c/g381a/g384a/ g399a/t403c/a405t/c411t/a420g/t426c/t429c/c432t/c435a/ g438a/a453t/a456t/a466t/g467c/t468a/c471t/t477c/t483a/ t486c/t489a/g495t/a501c/a510t/t511c/a513g/c534t/t537a/ t552c/t570a/c573t/g576a/c579g/c580t/c583t/c600a/t601c/ a603t/c607t/c625t/a627g/a642t/a645g/c648t/a663t/c684t/ g687a/a693g/c696a/t705a/a741c/a744g/t747c/t751c/a753g/ g756a/g765c/t766c/t771c/c792a/c804t/c807a/a810t/c811t/ a816g/c822t/a825c/t834c/g837a/a840g/g846c/t849c/t852a/ c858t/c885t/c894t/a903g/a906c/c912t/g915a/a921g/c924t/ c927t/t936c/t954c/t960c/g963a/c966t/t969c/c975t/a987t/ c993t/c996t/g999t/g1011t/c1018a/t1020a/g1023a/a1029t/ g1035t/t1038a/a1054t/g1055c/g1083t/g1089t/a1098t/ a1107g/t1108c/g1110a/t1113c/c1119t/a1125g/c1311t/ t1137c/c1146t/g1149a/c1155t/t1182c/t1185c/a1194c/ c1200t/a1209g/g1215a/a1218g/a1221g/a1233g/t1239a/ a1242g/t1245c/c1248t/a1254t/t1266a/a1272g/g1275a/ c1279t/g1281a/a1284g/t1287c/c1293t/t1308c/t1312c/g1314a; a27g/c30a/t42c/c51t/a54c/t60a/g63a/t69c/a72g/t75c/t78c/ g114a/a126g/c129t/c133t/a135g/c138t/c147t/t156a/c159t/ c177t/a180c/c195t/c201a/t207c/c216t/g222t/a225t/g234a/ c237t/t249c/t252a/c255t/t261c/c271t/g273a/a274t/g275c/ c306t/c307t/t309g/a318g/t321c/c324t/c327t/a333g/c339a/ t342c/c349t/t360c/t366c/g381a/g384a/g399a/t403c/a405t/ c411t/a420g/t426c/t429c/c432t/c435a/g438a/a453t/a456t/ a466t/g467c/t468a/c471t/t477c/t483a/t486c/t489a/g495t/ a510t/t511c/a513g/c625t/a627g/a642t/a645g/c648t/t1047c/ a1054t/g1055c/a1095g/a1194c/c1200t; a27g/c30a/t42c/ c51t/a54c/t60a/g63a/t69c/a72g/t75c/t78c/g114a/a126g/ c129t/c133t/a135g/c138t/c147t/t156a/c159t/c177t/a180c/ c195t/c201a/t207c/c216t/g222t/a225t/g234a/c237t/t249c/ t252a/c255t/t261c/c271t/g273a/a274t/g275c/c306t/c307t/ t309g/a318g/t321c/c324t/c327t/a333g/c339a/t342c/c349t/ t360c/t366c/g381a/g384a/g399a/t403c/a405t/c411t/a420g/ t426c/t429c/c432t/c435a/g438a/a453t/a456t/a466t/g467c/ t468a/c471t/t477c/t483a/t486c/t489a/g495t/a501c/a510t/ t511c/a513g/c534t/t537a/t705a/t714t/g717a/c726t/c738a/ a741c/a744g/t747c/t751c/a753g/g756a/g765c/t766c/t771c/ t1185t/t1224c; a27g/c30a/t42c/c51t/a54c/t60a/g63a/t69c/ a72g/t75c/t78c/g114a/a126g/c129t/c133t/a135g/c138t/ c147t/t156a/c159t/c177t/a180c/c195t/c201a/t207c/c216t/ g222t/a225t/g234a/c237t/t249c/t252a/c255t/t261c/c271t/ g273a/a274t/g275c/c306t/c307t/t309g/a318g/t321c/c324t/ c327t/a333g/c339a/t342c/c349t/t360c/t366c/g381a/g384a/ g399a/t403c/a405t/c411t/a420g/t426c/t429c/c432t/c435a/ g438a/a453t/a456t/a466t/g467c/t468a/c471t/t477c/t483a/ t486c/t489a/g495t/a501c/a510t/t511c/a513g/t552c/t601c/ c924t/t1263c/a1269g; a27g/c30a/t42c/c51t/a54c/t60a/g63a/ t69c/a72g/t75c/t78c/g114a/a126g/c129t/c133t/a135g/c138t/ c147t/t156a/c159t/c177t/a180c/c195t/c201a/t207c/c216t/ g222t/a225t/g234a/c237t/t249c/t252a/c255t/t261c/c271t/ g273a/a274t/g275c/c306t/c307t/t309g/a318g/t321c/c324t/ c327t/a333g/c339a/t342c/c349t/t360c/t366c/g381a/g384a/ g399a/t403c/a405t/c411t/a420g/t426c/t429c/c432t/c435a/ g438a/a453t/a456t/a466t/g467c/t468a/c471t/t477c/t483a/ t486c/t489a/g495t/g783/t1185c/t1224c; a27g/c30a/t42c/ c51t/a54c/t60a/g63a/t69c/a72g/t75c/t78c/g114a/a126g/ c129t/c133t/a135g/c138t/c147t/t156a/c159t/c177t/a180c/ c195t/c201a/t207c/c216t/g222t/a225t/g234a/c237t/t249c/ t252a/c255t/t261c/c271t/g273a/a274t/g275c/c306t/c307t/ t309g/a318g/t321c/c324t/c327t/a333g/c339a/t342c/c349t/ t360c/t366c/g381a/g384c/g399a/t403c/a405t/c411t/a420g/ t426c/t429c/c432t/c435a/g438a/a453t/a456t/a466t/g467c/ t468a/c471g/t477c/t483a/t486c/t489a/g495t/a501c/a510t/ t511c/a513g/c534t/t537a/t11185c/t1224c; t120c/t279c/ a510t/t1185c/t1224c; c138a/t150a/g783a/t1143g/c1146t/ c1155a/t1263a/a1269g; t171c/t279c/a510t/t1185c/t1224c; t207c/t279c/a510t/t152c/t1185c/t1224c; t207c/t279c/a510t/ t1185c/t1224c; a219g/t279c/a510t/c607t/t771c/t1185c/ t1224c; t279c/t328c/g330c/a510t/a642t/a645g/c648t; t279c/ t483a/a510t; t279c/t483a/a510t/a567g/a1029t/t1185c/ t1224c; t279c/t483a/a510t/a606g/t1185c/t1224c; t279c/ t483a/a510t/t771c/g783a/t1173c/t1185c/t1224c; t279c/ t483a/a510t/t1185c/t1224c/t1266c; t279c/a510t; t279c/ a511t/t570a/c573t/g576a/c579g/c580t/c583t/c600a/t601c/ a603t/c607t/c625t/a627g/a642t/a645g/c648t/a663t/t771c/ g783a/t1170c/t1185c/t1224c; t279c/a510t/t511c/g1023a/ a1029t/g1035t/t1038a/a1054t/g1055c/a1095g; t279c/a510t/ t552c/t570a/c573t/g576a/c579g/c580t/c583t/c600a/t601c/ a603t/c607t/t1185c/t1224c; t279c/a510t/t552c/c625t/a627g/ t1185c/t1224c; t279c/a510t/t552c/t735c/t1185c/t1224c; t279c/a510t/t552c/t1185c/t1224c; t279c/a510t/t558c/ t1185c/t1224c; t279c/a51t/t570a/c573t/g576a/c579g/c580t/ c583t/c600a/t601c/a603t/c607t/c625t/a627g/a642t/a645g/ c648t/a663t/t 771c/g783a/t1170c/t1185c/t1224c; t279c/ a510t/t570c/t1185c/t1224c; t279c/a510t/c580t/t1185c/ t1224c; t279c/a510t/c600a/t601c/a603t/c607t/c625t/a627g/ a642t/a645g/c648t/a 194c/c1200t; t279c/a510t/c625t/a627g/ a642t/a645g/c648t/g783a/g1011t/c1018a/t11020a/g1023a/ a1054t/g1055c/a1233g/t1239a/a1242g; t279c/a510t/c625t/ a627g/c696a; t279c/a510t/a642t/a645g/c648t/a663t/t1185c/ t1224c; t279c/a510t/t657c/g783a; t279c/a510t/a663t/ a1054t/g1055c/a1194c/c1200t; t279c/a510t/c675t/t1185c/ t11224c/a1269g; t279c/a510t/c684t/g687a/t978c; t279c/ a510t/c684t/c792a/t1185c/t1224c; t279c/a510t/c705c/ t1185c/t11224c; t279c/a510t/c726t; t279c/a510t/a753g/ t11053c/t1185c/t1224c; t279c/a510t/g783a/t1020c/t1185c/ t1224c; t279c/a510t/g783a/t1128c/t1185c/t1224c; t279c/ a510t/g783a/t1185c/t1224c; t279c/a510t/c792a; t279c/ a510t/t873c; t279c/a510t/c885t/c894t/a903g/a906t/c912t/ g915a/a921g/c924t/c927t/t936c/t954c/g1035t/t1038a; t279c/a510t/a906g/t1185c/t1224c; t279c/a510t/t990c/ t1185c/t1224c; t279c/a510t/g1023a/t1185c/t1224c; t279c/ a510t/a1086g; t279c/a510t/t1113c/t1185c/t1224c; t279c/ a510t/t122g/t1185c/t1224c; t279c/a510t/t1185c/t1224c; g585a/a642g/g783a/c924t/t1263a/a1269g; g783a; g783a/ c924t/t1263a/a1269g; c924t; t1185c/t1224c; and/or t1255c, wherein the positions are numbered by correspondence with the polynucleotide sequence set forth in SEQ ID NO: 1.

The present invention also provides isolated xylose isomerase variants that are chimeras comprised of at least two xylose isomerase fragments obtained from *Ruminococcus, Clostridium, Abiotrophia*, and/or *Phytophthora*. In some embodiments, the isolated xylose isomerase variant is a chimera comprised of at least two xylose isomerase fragments obtained from *R. flavefaciens, C. phytofermentans, A. defectiva, Ruminococcus s.* 18P13, and *P. infestans*. In some further embodiments, the isolated xylose isomerase chimeric variants comprise xylose isomerase fragments comprising at least a portion of SEQ ID NOS:2, 4, 6, 8, and/or 10.

The present invention also provides isolated chimeric xylose isomerase variants, wherein the variants are mature forms having xylose isomerase activity and comprise at least one mutation and/or mutation set at position(s) selected from: 3/5/8/11/13/14/15/16/18/19/22/24/27/28/30/31/32/33/38/ 42/45/46/50/51/52/53/54/61/62/64/67/68/70/71/72/73/74/ 75/76/84/87/89/92/94/96/101/104/107/108/109/110/112/ 115/116/119/120/121/125/128/130/131/132/140/141/143/ 144/148/149/153/154/155/160/161/163/172/173/180/199/ 236/273/275/282/283/284/285/288/289/292/299/307/310/ 311/312/323/325/328/330/333/339/342/344/346/349/352/ 353/355/359; 5/8/11/13/15/16/19/22/29/33/36/39/40/41/64/ 70/71/89/96/112/115/119/126/129/130/131/132/180/219/ 220/266/269/273/275/277/281/282/285/288/292/306/311/ 312/313/314/315/317/318/320/323/345/346/347/350/352/ 359/364/365/366/368/369/370/372/377/381/387/388/393/ 394/396/397/399/400/401/402/403/404/407/409/411/412/ 413/415/416/417/418/419/420/423/426/429/437/438; 5/8/ 11/13/15/16/19/22/29/33/36/39/40/41/64/70/71/89/96/112/ 115/126/129/130/131/132/180/281/285/288/299/364/365/ 368/372/378/380/381/388/389/393/397/402/404/417/419/ 426/435/437; 2/3/5/7/8/9/10/11/13/16/19/21/22/27/28/29/ 30/32/33/38/41/42/51/52/53/54/56/58/61/62/64/66/68/70/ 71/74/75/76/84/87/89/92/94/95/96/101/103/104/107/108/ 109/110/111/112/113/114/115/116/118/119/120/121/128/ 129/130/131/132/134/140/141/143/152/155/156/162/163/ 166/169/172/173/175/180/219/220/223/249/257/273/311/ 312/313/314/315/317/318/320/323/339/345/346/347/350/ 364/365/366/368/369/370/372/377/381/387/388/393/394/ 396/397/399/400/401/402/403/404/407/409/411/412/413/ 415/416/417/418/419/420/426/429/434/437/438; 2/3/5/7/8/ 9/10/11/13/16/18/19/21/22/27/28/29/30/32/33/38/41/42/51/ 52/53/54/56/58/61/62/64/66/68/70/71/74/75/76/84/87/89/ 94/95/96/101/103/104/107/108/109/110/111/112/113/114/ 115/116/118/119/120/121/128/129/130/131/132/134/140/ 141/143/152/155/156/162/163/166/169/172/173/175/180/ 273/277/281/282/285/288/292/299/300/311/312/313/314/ 315/317/318/320/323/335/339/345/346/347/350/352/359/ 364/365/366/368/369/370/372/377/381/387/388/393/394/ 396/397/399/400/401/402/403/404/407/409/411/412/413/ 415/416/417/418/419/420/426/429/434/437/438; 2/3/5/7/8/ 9/10/11/13/16/19/21/22/27/28/29/30/32/33/38/41/42/51/52/ 53/54/56/58/61/62/64/66/68/70/71/74/75/76/84/87/89/92/ 94/95/96/101/103/104/107/108/109/110/111/112/113/114/ 115/116/118/119/120/121/128/129/130/131/132/134/140/ 141/143/152/155/156/162/163/166/169/172/173/175/180/ 198/199/206/219/220/223/249/257/273/277/281/282/292/ 299/300/311/312/313/314/315/317/318/320/323/339/345/ 346/347/350/352/359/364/365/366/368/369/370/372/377/ 381/387/388/393/394/396/397/399/400/401/402/403/404/ 407/409/411/412/413/415/416/417/418/419/420/426/429/ 434/437/438; 2/3/5/7/8/9/10/11/13/16/19/21/22/27/28/29/ 30/32/33/38/41/42/51/52/53/54/56/58/61/62/64/66/68/70/ 71/74/75/76/87/89/92/94/95/96/101/103/104/107/108/109/ 110/111/112/113/114/115/116/118/119/120/121/128/129/ 130/131/132/134/140/141/143/152/155/156/162/163/166/ 169/172/173/175/180/198/199/249/273/277/281/282/285/ 288/292/299/300/311/312/313/314/315/317/318/320/323/ 339/345/346/347/350/352/359/364/365/366/368/369/370/ 372/377/381/387/393/394/396/397/399/400/401/402/ 403/404/407/409/411/412/413/415/416/417/418/419/420/ 426/429/434/437/438; 3/5/8/11/13/15/16/18/19/22/24/27/ 28/30/31/32/33/38/42/45/46/50/51/52/53/54/61/62/64/67/ 68/70/71/72/73/74/75/76/84/87/89/92/94/96/101/104/107/ 108/109/110/112/113/115/116/119/120/121/125/128/130/ 131/132/140/141/143/144/148/149/153/154/155/160/161/ 163/172/173/180/198/199/200/201/203/204/206/208/236/ 244/247/248/253/262/273/275/282/283/284/285/288/289/ 292/299/307/310/311/312/323/325/328/330/333/339/342/ 344/346/349/352/353/355/359/364/365/366/368/373/375/ 376/378/380/381/382/385/387/388/389/390/393/394/396/ 397/398/399/401/402/403/404/406/407/410/412/414/415/

416/418/419/420/426/428/429/430/431/433/434/437/438; 2/3/5/7/8/9/10/11/13/16/19/21/22/27/28/29/30/32/33/38/41/ 42/51/52/53/54/56/58/61/62/64/66/68/70/71/74/75/76/84/ 87/89/92/94/95/96/101/103/104/107/108/109/110/111/112/ 113/114/115/116/118/119/120/121/128/129/130/131/132/ 134/140/141/143/152/155/156/162/163/166/169/172/173/ 175/180/244/247/248/253/262/273/275/282/283/284/285/ 288/289/292/299/300/311/312/313/314/315/317/318/320/ 323/339/345/346/347/350/352/364/365/366/368/369/370/ 372/377/381/387/388/393/394/396/397/399/400/401/402/ 403/404/407/409/411/412/413/415/416/417/418/419/420/ 426/429/434/437/438; 2/3/5/7/8/9/10/11/13/16/19/21/22/27/ 28/29/30/32/33/38/41/42/51/52/53/54/56/58/61/62/64/66/ 68/70/71/74/75/76/84/87/89/92/94/95/96/101/103/104/107/ 108/109/110/111/112/113/114/115/116/118/119/120/121/ 128/129/130/131/132/134/140/141/143/152/155/156/162/ 163/166/169/172/173/175/198/199/223/236/273/277/281/ 282/285/288/292/299/300/311/312/313/314/315/317/318/ 320/323/339/345/346/347/350/352/359/364/365/366/368/ 369/370/372/377/381/387/388/393/394/396/397/399/400/ 401/402/403/404/407/409/411/412/413/415/416/417/418/ 419/420/426/429/434/437/438; 2/3/5/7/8/9/10/11/13/16/19/ 21/22/27/28/29/30/32/33/38/41/42/51/52/53/54/56/58/61/ 62/64/66/68/70/71/74/75/76/84/87/89/92/94/95/96/101/103/ 104/107/108/109/110/111/112/113/114/115/116/118/119/ 120/121/128/129/130/131/132/134/140/141/143/152/155/ 156/162/163/166/169/172/173/175/180/198/199/219/220/ 223/249/257/273/277/281/282/285/288/292/299/300/311/ 312/313/314/315/317/318/320/323/339/345/346/347/350/ 352/359/364/365/366/368/369/370/372/377/381/387/388/ 393/394/396/397/399/400/401/402/403/404/407/409/411/ 412/413/415/416/417/418/419/420/426/429/434/437/438; 2/3/5/7/8/9/10/11/13/16/19/21/22/27/28/29/30/32/33/38/41/ 42/51/52/53/54/56/58/61/62/64/66/68/70/71/74/75/76/84/ 87/89/92/94/95/96/101/103/104/107/108/109/110/111/112/ 113/114/115/116/118/119/120/121/128/129/130/131/132/ 134/140/141/143/152/155/156/162/163/166/169/172/173/ 175/180/219/220/223/257/273/277/281/282/285/288/292/ 299/300/311/312/313/314/315/317/318/320/323/339/345/ 346/347/350/352/359/364/365/366/368/369/370/372/373/ 377/381/387/388/393/394/396/397/399/400/401/402/403/ 404/407/409/411/412/413/415/416/417/418/419/420/426/ 429/434/437/438; 2/3/5/6/7/8/10/11/13/16/19/21/22/27/28/ 29/30/32/33/38/41/42/51/52/53/54/56/58/61/62/64/66/68/ 70/71/74/75/76/84/87/89/92/94/95/96/101/103/104/107/ 108/109/110/111/112/113/114/115/116/118/119/120/121/ 128/129/130/131/132/134/140/141/143/152/155/156/162/ 163/166/169/172/173/175/180/198/199/219/257/292/311/ 312/313/314/315/317/318/320/323/339/345/346/347/350/ 352/359/364/365/366/368/369/370/372/377/381/387/388/ 393/394/396/397/399/400/401/402/403/404/407/409/411/ 412/413/415/416/417/418/419/420/426/429/434/437/438; 2/3/5/7/8/9/10/11/13/16/19/21/22/27/28/29/30/32/33/38/41/ 42/51/52/53/54/56/58/61/62/64/66/68/70/71/74/75/76/84/ 87/89/92/94/95/96/101/103/104/107/108/109/110/111/112/ 113/114/115/116/118/119/120/121/128/129/130/131/132/ 134/140/141/143/152/155/156/166/169/172/173/175/180/ 198/199/219/220/223/249/257/273/277/281/282/285/288/ 292/299/300/311/312/313/314/315/317/318/320/323/339/ 344/345/346/347/350/352/359/364/365/366/368/369/370/ 372/377/381/387/388/393/394/396/397/399/400/401/402/ 403/404/407/409/411/412/413/415/416/417/418/419/420/ 426/429/434/437/438; 2/3/5/7/8/9/10/11/13/16/19/21/22/27/ 28/29/30/32/33/38/41/42/51/52/53/54/56/58/61/62/64/66/ 68/70/71/74/75/76/84/87/89/92/94/95/96/101/103/104/107/ 108/109/110/111/112/113/114/115/116/118/119/120/121/ 128/129/130/131/132/134/140/141/143/152/155/156/162/ 163/166/169/172/173/175/180/219/220/223/236/244/247/ 248/257/273/277/281/282/285/288/292/299/300/311/312/ 313/314/315/317/318/320/323/339/345/346/347/350/352/ 359/364/365/366/368/369/370/372/377/381/387/388/393/ 394/396/39/399/400/401/402/403/404/407/409/411/412/ 413/415/416/417/418/419/420/426/429/434/437/438; 2/3/5/ 7/8/9/10/11/13/16/19/21/22/27/28/29/30/32/33/38/41/42/ 51/52/53/54/56/58/61/62/64/66/68/70/71/74/75/76/84/87/ 89/92/94/95/96/101/103/104/107/108/109/110/111/112/ 113/114/115/116/118/119/120/121/128/129/130/131/132/ 134/140/141/143/148/149/152/155/156/162/163/166/169/ 172/173/175/180/198/199/219/220/223/253/257/273/277/ 281/282/285/288/292/299/300/311/312/313/314/315/317/ 318/320/323/339/345/346/347/350/352/359/361/364/365/ 366/368/369/370/372/377/381/387/388/393/394/396/397/ 399/400/401/402/403/404/407/409/411/412/413/415/416/ 417/418/419/420/426/429/434/437/438; 2/3/5/7/8/9/10/11/ 13/16/19/21/22/27/28/29/30/32/33/38/41/42/51/52/53/54/ 56/58/61/62/64/66/68/70/71/74/75/76/84/87/89/92/94/95/ 96/101/103/104/107/108/109/110/111/112/113/114/115/ 116/118/119/120/121/128/129/130/131/132/134/140/141/ 143/155/156/162/163/166/169/172/173/175/180/273/275/ 416; 3/5/8/11/13/15/16/18/19/22/24/27/28/30/31/32/33/38/ 42/45/46/50/51/52/53/54/61/62/64/67/70/71/72/73/74/ 75/76/84/87/89/92/94/96/101/104/107/108/109/110/112/ 115/116/119/120/121/125/128/130/131/132/140/141/143/ 144/148/149/153/154/155/160/161/163/172/173/180/198/ 199/200/201/203/204/206/208/236/244/247/248/253/262/ 273/275/282/283/284/285/288/289/292/299/307/310/311/ 312/323/325/328/330/333/339/342/344/346/349/352/353/ 355/359/364/365/366/367/368/373/375/376/378/380/381/ 382/385/387/388/389/390/393/394/396/397/398/399/401/ 402/403/404/406/407/410/412/414/415/416/418/419/420/ 426/428/429/430/431/433/434/437/438; 3/5/8/11/13/15/16/ 18/19/22/24/27/28/30/31/32/33/38/42/45/46/50/51/52/53/ 54/61/62/64/67/70/71/72/73/74/75/76/84/87/89/92/94/ 96/101/104/107/108/109/110/112/115/116/119/120/121/ 125/128/130/131/132/140/141/143/144/148/149/153/154/ 155/160/161/163/172/173/180/198/199/200/201/203/204/ 206/208/236/244/247/248/253/262/273/275/282/A283/284/ 285/288/289/292/299/307/310/311/312/323/A325/328/330/ 333/A339/342/344/346/349/352/353/A355/A359/364/365/ A366/368/373/375/376/378/380/A381/382/A385/387/388/ 389/390/A393/394/396/A397/398/399/401/402/A403/404/ 406/407/410/412/414/415/416/418/419/420/426/428/429/ 430/431/433/434/437/438; 236/244/247/248/253/262/273/ 275/282/283/284/285/288/289/292; 2/3/5/7/8/9/10/11/13/ 16/19/21/22/27/28/29/30/32/33/38/41/42/51/52/53/54/56/ 58/61/62/64/66/68/70/71/74/75/76/84/87/89/92/94/95/96/ 101/103/104/107/108/109/110/111/112/113/114/115/116/ 118/119/120/121/128/129/130/131/132/134/140/141/143/ 152/155/156/162/163/166/169/172/173/175/180/208/219/ 220/223/273/277/281/282/285/288/292/299/300/311/312/ 313/314/315/317/318/320/323/334/339/345/346/347/350/ 352/359/364/365/366/368/369/370/372/374/377/381/387/ 391/393/394/396/397/399/400/401/402/403/404/407/409/ 411/412/413/415/416/417/418/419/420/425/426/429/434/ 437/438; 2/3/5/7/8/9/10/11/13/16/19/21/22/27/28/29/30/32/ 33/38/41/42/51/52/53/54/56/58/61/62/64/66/68/70/71/74/ 75/76/84/87/89/92/94/95/96/101/103/104/107/108/109/110/ 111/112/113/114/115/116/118/119/120/121/128/129/130/ 131/132/134/140/141/143/152/155/156/162/163/166/169/ 172/173/175/180/198/199/273/277/281/282/285/288/292/ 299/300; 2/3/5/7/8/9/10/11/13/16/19/21/22/27/28/29/30/32/ 33/38/41/42/51/52/53/54/56/58/61/62/64/66/68/70/71/74/ 75/76/84/87/89/92/94/95/96/101/103/104/107/108/109/110/ 111/112/113/114/115/116/118/119/120/121/128/129/130/

131/132/134/140/141/143/152/155/156/162/163/166/169/
172/173/175/180/223/273/275/282/283/284/285/288/289/
292/299; 2/3/5/7/8/9/10/11/13/15/16/19/21/22/27/28/29/30/
32/33/38/41/42/51/52/53/54/56/58/61/62/64/66/68/70/71/
74/75/76/84/87/89/92/94/95/96/101/103/104/107/108/109/
110/111/112/113/114/115/116/118/119/120/121/128/129/
130/131/132/134/140/141/143/152/155/156/162/163/166/
169/172/173/175/180/219/220/223/257/273/277/281/282/
285/288/292/299/300/311/312/313/314/315/317/318/320/
323/325/339/345/346/347/350/352/A359/364/365/A366/
368/369/370/372/377; 2/3/5/7/8/9/10/11/13/16/19/21/22/27/
28/29/30/32/33/38/41/42/51/52/53/54/56/58/61/62/64/66/
68/70/71/74/75/76/84/87/89/92/94/95/96/101/103/104/107/
108/109/110/111/112/113/114/115/116/118/119/120/121/
128/129/130/131/132/134/140/141/143/152/155/156/162/
163/166/169/172/173/175/180/223/273/275/282/283/284/
285/288/289/292/299; 5/8/11/13/15/16/19/22/29/33/36/39/
40/41/64/70/71/89/96/112/115/126/129/130/131/132/198/
199/219/220/223/247/248/253/262/269/285/288/311/312/
313/314/315/317/318/320/323/339/345/346/347/350/352/
359/364/365/366/368/369/370/372/377/381/387/388/393/
394/396/39/399/400/401/402/403/404/407/409/411/412/
413/415/416/417/418/419/420/426/429/434/437/438; 2/3/5/
7/8/9/10/11/13/16/19/21/22/27/28/29/30/32/33/38/41/42/
51/52/53/54/56/58/61/62/64/66/68/70/71/74/75/76/84/87/
89/92/94/95/96/101/103/104/107/108/109/110/111/112/
113/114/115/116/118/119/120/121/128/129/130/131/132/
134/140/141/143/152/155/156/162/163/166/169/172/173/
175/180/219/220/223/224/249/257/273/277/281/282/285/
288/292/299/300/311/312/313/314/315/317/318/320/323/
339/345/346/347/350/352/359/364/365/366/368/369/370/
372/377/381/387/388/393/394/396/397/399/400/401/402/
403/404/407/409/411/412/413/415/416/417/418/419/420/
426/429/434/437/438; 2/3/5/7/8/9/10/11/13/16/19/21/22/27/
28/29/30/32/33/38/41/42/51/52/53/54/56/58/61/62/64/66/
68/70/71/74/75/76/84/87/89/92/94/95/96/101/103/104/107/
108/109/110/111/112/113/114/115/116/118/119/120/121/
128/129/130/131/132/134/140/141/143/146/152/155/156/
162/163/166/169/172/173/175/180/219/220/223/249/257/
273/277/281/282/285/288/292/299/300/311/312/313/314/
315/317/318/320/323/339/345/346/347/350/352/359/364/
365/366/368/369/370/372/377/381/387/388/393/394/396/
397/399/400/401/402/403/404/407/409/411/412/413/415/
416/417/418/419/420/426/429/434/437/438; 2/3/5/7/8/9/10/
11/13/16/19/21/22/27/28/29/30/32/33/38/41/42/51/52/53/
54/56/58/61/62/64/66/68/70/71/74/75/76/84/87/89/92/94/
95/96/101/103/104/107/108/109/111/112/113/114/115/116/
118/119/120/121/128/129/130/131/132/134/140/141/143/
152/155/156/162/163/166/169/172/173/175/180/219/220/
223/273/275/282/283/284/285/288/289/292/299; 2/3/5/7/8/
9/10/11/13/16/19/21/22/27/28/29/30/32/33/38/41/42/51/52/
53/54/56/58/61/62/64/66/68/70/71/74/75/76/84/87/89/92/
94/95/96/101/103/104/107/108/109/110/111/112/113/114/
115/116/118/119/120/121/128/129/130/131/132/134/140/
141/143/152/155/156/162/163/166/169/172/173/175/180/
223/249/257/273/277/281/282/285/288/292/299/300/311/
312/313/314/315/317/318/320/323/345/346/347/350/352/
359/364/365/366/368/369/370/372/377/381/387/388/393/
394/396/397/399/400/401/402/403/404/407/409/411/412/
413/415/416/417/418/419/420/426/429/434/437/438; 2/3/5/
7/8/9/10/11/13/16/19/21/22/27/28/29/30/32/33/38/42/45/
46/50/51/52/53/54/61/62/64/67/68/70/71/72/73/74/75/76/
84/87/89/92/94/96/101/104/107/108/109/110/112/115/116/
119/120/121/125/128/130/131/132/140/141/143/144/148/
149/153/154/155/160/161/163/172/173/180/198/199/219/
236/244/247/248/253/262/273/275/282/283/284/285/288/
289/292/299/307/310/311/312/323/325/328/330/333/339/
342/344/346/349/352/353/355/359/364/365/366/368/373/
375/376/378/380/381/30/381/38293/3/385/394/396/37/388/
389/390/393/394/396/397/398/399/401/402/403/404/406/
407/410/412/414/415/416/418/419/420/426/428/429/430/
431/433/434/437/438; 2/3/5/7/8/9/10/11/13/16/19/21/22/27/
28/29/30/32/33/38/41/42/51/52/53/54/56/58/61/62/64/66/
68/70/71/74/75/76/84/87/89/92/94/95/96/101/103/104/107/
108/109/110/111/112/113/114/115/116/118/119/120/121/
128/129/130/131/132/134/140/141/143/152/155/156/162/
163/166/169/172/173/175/180/219/220/223/236/257/273/
277/281/282/285/288/292/299/300/311/312/313/314/315/
317/318/320/323/339/359/364/365/366/368/369/370/372/
377/381/387/388/393/394/396/397/399/400/401/402/403/
404/407/409/411/412/413/415/416/417/418/419/420/426/
429/434/437/438; 2/3/5/7/8/9/10/11/13/16/19/21/22/27/28/
29/30/32/33/38/41/42/51/52/53/54/56/58/61/62/64/66/68/
70/71/74/75/76/84/87/89/92/94/95/96/101/103/104/107/
108/109/110/111/112/113/114/115/116/118/119/120/121/
128/129/130/131/132/134/140/141/143/152/155/156/162/
163/166/169/172/173/175/180/198/199/236/244/247/248/
253/262/273/277/281/282/285/288/292/299/300/311/312/
313/314/315/317/318/320/323/339/345/346/347/349/350/
352/359/364/365/366/368/369/370/372/377/381; 2/3/5/7/8/
9/10/11/13/16/19/21/22/27/28/29/30/32/33/38/41/42/51/52/
53/54/56/58/61/62/64/66/68/70/71/74/75/76/84/87/89/92/
94/95/96/101/103/104/107/108/109/110/111/112/113/114/
115/116/118/119/120/121/128/129/130/131/132/134/140/
141/143/152/155/156/162/163/166/169/172/173/175/180/
219/220/223/249/299/300/311/312/313/314/315/317/318/
320/323/339/345/346/347/350/359/364/365/366/368/369/
370/372/377/381/387/388/393/394/396/397/399/400/401/
402/403/404/407/409/411/412/413/415/416/417/418/419/
420/426/429/434/437/438; 2/3/5/7/8/9/10/11/13/16/19/21/
22/27/28/29/30/32/33/35/36/38/41/42/51/52/53/54/56/58/
61/62/64/66/68/70/71/74/75/76/84/87/89/92/94/95/96/101/
103/104/107/108/109/110/111/112/113/114/115/116/118/
119/120/121/128/129/130/131/132/134/140/141/143/152/
155/156/162/163/166/169/172/173/175/180/236; 28/29/30/
32/33/38/41/42/51/52/53/54/56/58/61/62/64/66/68/70/71/
74/75/76/84/87/89/92/94/95/96/101/103/104/107/108/109/
110/111/112/113/114/115/116/118/119/120/121/128/129/
130/131/132/134/140/141/143/152/155/156/162/163/166/
169/172/173/175/180/219/220/249/299/300/339/345/346/
347/350/352/359/364/365/366/368/369/370/372/377; 2/3/5/
7/8/9/10/11/13/16/19/21/22/27/28/29/30/32/33/38/41/42/
51/52/53/54/56/58/61/62/64/66/68/70/71/74/75/76/84/87/
89/92/94/95/96/101/103/104/107/108/S109/110/111/112/
113/114/115/116/118/119/120/121/128/129/130/131/132/
134/140/141/143/152/155/156/162/163/166/169/172/173/
175/180/198/199/219/220/223/249/257/299/311/312/313/
314/315/317/318/320/323/339/345/346/347/350/352/359/
364/365/366/368/369/370/372/377/381/387/388/393/394/
396/397/399/400/401/402/403/404/407/409/411/412/413/
415/416/417/418/419/420/426/429/434/437/438; 2/3/5/7/8/
9/10/11/13/16/19/21/22/27/28/29/30/32/33/38/41/42/51/52/
53/54/56/58/61/62/64/66/68/70/71/74/75/76/84/87/89/92/
94/95/96/101/103/104/107/108/109/110/111/112/113/114/
115/116/118/119/120/121/128/129/130/131/132/134/140/
141/143/152/155/156/162/163/166/169/172/173/175/180/
219/220/223/249/311/312/313/314/315/317/318/320/323/
339/345/346/347/350/352/359/364/365/366/368/369/370/
372/377/378/381/387/388/393/394/396/397/399/400/401/
402/403/404/407/409/411/412/413/415/416/417/418/419/
420/426/429/434/437/438; 5/8/11/13/15/16/19/22/29/33/36/
39/40/41/64/70/71/89/96/112/115/126/129/130/131/132/
180/198/199/24/247/248/253/273/275/282/283/284/285/
288/289/292/311/312/313/314/315/317/318/320/323/387/

388; 2/3/5/7/8/9/10/11/13/16/19/21/22/27/28/29/30/32/33/ 38/41/42/51/52/53/54/56/58/61/62/64/66/68/70/71/74/75/ 76/84/87/89/92/94/95/96/101/103/104/107/108/109/110/ 111/112/113/114/115/116/118/119/120/121/128/129/130/ 131/132/134/140/141/143/152/155/156/162/163/166/169/ 172/173/175/180; 2/3/5/7/8/9/10/11/13/16/19/21/22/27/28/ 29/30/32/33/38/41/42/51/52/53/54/56/58/61/62/64/66/68/ 70/71/74/75/76/84/87/89/92/94/95/96/101/103/104/107/ 108/109/110/111/112/113/114/115/116/118/119/120/121/ 128/129/130/131/132/134/140/141/143/152/155/156/162/ 163/166/169/172/173/175/180/198/199/247/248/253/273/ 277/281/282/285/288/311/312/313/314/315/317/318/319/ 320/323/339/345/346/347/350/352/359/364/365/366/368/ 369/370/372/377/381/387/388/393/394/396/397/399/400/ 401/402/403/404/407/409/411/412/413/415/416/417/418/ 419/420/426/429/434/437/438; 2/3/5/7/8/9/10/11/13/16/19/ 21/22/27/28/29/30/32/33/38/41/42/51/52/53/54/56/58/61/ 62/64/66/68/70/71/74/75/76/84/87/89/92/94/95/96/101/103/ 104/107/108/109/110/111/112/113/114/115/116/118/119/ 120/121/128/129/130/131/132/134/140N/141/143/152/155/ 156/162/163/166/169/172/173/175/180/253/273/275; 2/3/5/ 7/8/9/10/11/13/16/19/21/22/27/28/29/30/32/33/38/41/42/ 51/52/53/54/56/58/61/62/64/66/68/70/71/74/75/76/84/87/ 89/92/94/95/96/101/103/104/106/107/108/109/110/111/ 112/113/114/115/116/118/119/120/121/123/128/129/130/ 131/132/134/140/141/143/152/155/156/162/163/166/169/ 172/173/175/180/249/257/273/277/281/282/285/288/292/ 299/300/311/312/313/314/315/317/318/320/323/339/345/ 346/347/350/352/359/364/365/366/368/369/370/372/377/ 381; 2/3/5/7/8/9/10/11/13/16/19/21/22/27/28/29/30/32/33/ 38/41/42/51/52/53/54/56/58/61/62/64/66/68/70/71/74/75/ 76/84/87/89/92/94/95/96/101/103/104/107/108/109/110/ 111/112/113/114/115/116/118/119/120/121/128/129/130/ 131/132/134/140/141/143/152/155/156/162/163/166/169/ 172/173/175/198/199/219/220/223/249/257/292/299/300/ 311/312/313/314/315/317/318/320/323/339/345/346/347/ 350/352/359/364/365/366/368/369/370/372/377/381/387/ 388/393/394/396/397/399/400/401/402/403/404/407/409/ 411/412/413/415/416/417/418/419/420/426/429/434/437/ 438; 2/3/5/7/8/9/10/11/13/16/19/21/22/27/28/29/30/32/33/ 38/41/42/51/52/53/54/56/58/61/62/64/66/68/70/71/74/75/ 76/84/87/89/92/94/95/96/101/103/104/107/108/109/110/ 111/112/113/114/115/116/118/119/120/121/128/129/130/ 131/132/134/140/141/143/152/155/162/163/166/169/172/ 173/175/180/198/199/299; 2/3/5/7/8/9/10/11/13/16/19/21/ 22/27/28/29/30/32/33/38/41/42/51/52/53/54/56/58/61/62/ 64/66/68/70/71/74/75/76/84/87/89/92/94/95/96/101/103/ 104/107/108/109/110/111/112/113/114/115/116/118/119/ 120/121/128/129/130/131/132/134/140/141/143/152/155/ 156/162/163/166/169/172/173/175/180/198/199/236/244/ 299/300/311/312/313/314/315/317/318/320/323/339/345/ 346/347/350/352/359/364/365/366/368/369/370/372/377/ 381/387/388/393/394/396/397/399/400/401/402/403/404/ 407/409/411/412/413/415/416/417/418/419/420/426/429/ 434/437/438; 2/3/5/7/8/9/10/11/13/16/19/21/22/27/28/29/ 30/32/33/38/41/42/51/52/53/54/56/58/61/62/64/66/68/70/ 71/74/75/76/84/87/89/92/94/95/96/101/103/104/107/108/ 109/110/111/112/113/114/115/116/118/119/120/121/128/ 129/130/131/132/134/140/141/143/152/155/156/162/163/ 166/169/172/173/175/180/183/198/199/219/220/257/311/ 312/313/314/315/317/318/320/323/339/345/346/347/350/ 352/359/364/365/366/368/369/370/372/377/381/387/388/ 393/394/396/397/399/400/401/402/403/404/407/409/411/ 412/413/415/416/417/418/419/420/426/429/434/437/438; 372; 5/8/11/13/15/16/19/22/29/33/36/39/40/41/64/70/71/89/ 96/112/115/126/129/130/131/132/180/198/199/219/220/ 236/249/257/273/277/281/282/285/288/292/311/312/313/ 314/315/317/318/320/323/339/345/346/347/350/352/359/ 364/365/366/368/369/370/372/377/381/387/388/393/394/ 396/397/399/400/401/402/403/404/407/409/411/412/413/ 415/416/417/418/419/420/426/429/434/437/438; 2/3/5/7/8/ 9/10/11/13/16/19/21/22/27/28/29/30/32/33/38/41/42/51/52/ 53/54/56/58/61/62/64/66/68/70/71/74/75/76/84/87/89/92/ 94/95/96/101/103/104/107/108/109/110/111/112/113/114/ 115/116/118/119/120/121/128/129/130/131/132/134/140/ 141/143/152/155/156/162/163/166/169/172/173/175/180/ 198/199/273/277/281/282/285/288/292/299/300/311/312/ 313/314/315/317/318/320/323/328/339/345/346/347/350/ 352/359/364/365/366/368/369/370/387/388/393/394/396/ 397/399/400/401/402/403/404/407/409/411/412/413/415/ 416/417/418/419/420/426/429/434/437/438; 2/3/5/7/8/9/10/ 11/13/16/19/21/22/27/28/29/30/32/33/38/41/42/51/52/53/ 54/56/58/61/62/64/66/68/70/71/74/75/76/84/87/89/92/94/ 95/96/101/103/104/107/108/109/110/111/112/113/114/115/ 116/118/119/120/121/128/129/130/131/132/134/140/141/ 143/152/155/156/162/163/166/169/172/173/175/180/288/ 289/292; and/or 2/3/5/7/8/9/10/11/13/16/19/21/22/27/28/29/ 30/32/33/38/41/42/51/52/53/54/56/58/61/62/64/66/68/70/ 71/74/75/76/84/87/89/92/94/95/96/101/103/104/107/108/ 109/110/111/112/113/114/115/116/118/119/120/121/128/ 129/130/131/132/134/140/141/143/152/155/156/162/163/ 166/169/172/173/175/180/253/273/275, wherein the positions are numbered by correspondence with the amino acid sequence set forth in SEQ ID NO:2.

The present invention also provides isolated chimeric xylose isomerase variants, wherein the variant are mature forms having xylose isomerase activity and comprise at least one mutation and/or one mutation set selected from F3/S5/ G8/Q 11/Q13/G14/P 15/K16/T 18/D 19/S22/K24/N27/P28/ E30/V31/I32/N33/R38/K42/L45/S46/T50/M51/G52/G53/ D54/C61/G62/T64/T67/W68/Q70/S571/D72/P73/A74/ A75/R76/A84/I87/D89/S92/D94/Y96/R101/S104/Y107/ G108/S109/L110/A112/D115/Q116/I119/V120/T121/ Q128/D130/K131/F132/K140/C141/D143/H144/M148/ H149/T 153/S154/P155/F160/A161/S163/E172/S173/ N180/M199/T236/Q273/T275/V282/A283/R284/D285/ V288/F289/I292/V299/Q307/T310/N311/I312/I323/A325/ F328/N330/L333/A339/G342/F344/P346/1349/5352/353/ A355/A359; S5/G8/Q11/Q13/P5/K16/D19/S22/E29/N33/ T36/E39/H40/L41/T64/Q70/S71/D89/Y96/A 12/D115/ I119/E126/G129/D130/K131/F132/N180/S219/I220/A266/ A269/Q273/T275/Q277/R281/V282/D285/V288/I292/ D306/N311/I312/Y313/D314/T315/M317/C318/Y320/ I323/T345/P346/E347/F350/S352/A359/F364/R365/A366/ L368/K369/L370/E372/D377/A381/W387/N388/A393/ D394/I396/A397/K399/A400/D401/F402/A403/I404/ K407/A409/E411/K412/G413/V415/T416/A417/S418/ L419/S420/R423/M426/S429/S437/L438; S5/G8/Q11/Q13/ P15/K16/D19/S22/E29/N33/T36/E39/H40/L41/T64/Q70/ S71/D89/Y96/A 12/D115/E126/G129/D130/K131/F132/ N180/R281/D285/V288/V299/F364/R365/L368/E372/ K378/V380/A381/N388/T389/A393/A397/F402/S404/ A417/L419/M426/L435/S437; E2/F3/S5/I7/G8/K9/I10/ Q11/Q13/K16/D19/L21/S22/N27/P28/E29/E30/I32/N33/ R38/L41/K42/M51/G52/G53/D54/T56/M58/C61/G62/T64/ K66/W68/Q70/S71/A74/A75/R76/A84/I87/D89/S92/D94/ Y95/Y96/R101/L103/S104/Y107/G108/S109/L110/K111/ A112/T113/N114/D115/Q116/D118/I119/V120/T121/ Q128/G129/D130/K131/F132/C134/K140/C141/D143/ G152/P155/S156/F162/S163/Q166/K169/E172/S173/ V175/N180/S219/I220/K223/G249/D257/Q273/N311/ I312/Y313/D314/T315/M317/C318/Y320/I323/A339/ T345/P346/E347/F350/F364/R365/A366/L368/K369/L370/ E372/D377/A381/W387/N388/A393/D394/I396/A397/

K399/A400/D401/F402/A403/S404/K407/A409/E411/
K412/G413/V415/T416/A417/S418/L419/S420/M426/
S429/V434/S437/L438; E2/F3/S5/I7/G8/K9/I10/Q11/Q13/
K16/T18/D19/L21/S22/N27/P28/E29/E30/I32/N33/R38/
L41/K42/M51/G52/G53/D54/T56/M58/C61/G62/T64/K66/
W68/Q70/S571/A74/A75/R76/A84/I87/D89/D94/Y95/
Y96/R101/L103/S104/Y107/G108/S109/L110/K111/A112/
T113/N114/D115/Q116/D118/I119/V120/T121/Q128/
G129/D130/K131/F132/C134/K140/C141/D143/G152/
P155/S156/F162/S163/Q166/K169/E172/S173/V175/
N180/Q273/Q277/R281/V282/D285/V288/I292/V299/
L300/N311/I312/Y313/D314/T315/M317/C318/Y320/
I323/F335/A339/T345/P346/E347/F350/S352/A359/F364/
R365/A366/L368/K369/L370/E372/D377/A381/W387/
N388/A393/D394/I396/A397/K399/A400/D401/F402/
A403/S404/K407/A409/E411/K412/G413/V415/T416/
A417/S418/L419/S420/M426/S429/V434/S437/L438;
E2/F3/S5/I7/G8/K9/I10/Q11/Q13/K16/D19/L21/S22/N27/
P28/E29/E30/I32/N33/R38/L41/K42/M51/G52/G53/D54/
T56/M58/C61/G62/T64/K66/W68/Q70/S71/A74/A75/R76/
A84/I87/D89/S92/D94/Y95/Y96/R10/L103/S104/Y107/
G108/S109/L110/K111/A112/T113/N114/D115/Q116/
D118/I119/V120/T121/Q128/G129/D130/K131/F132/
C134/K140/C141/D143/G152/P155/S156/F162/S163/
Q166/K169/E172/S173/V175/N180/N198/M199/M206/
S219/I220/K223/G249/D257/Q273/Q277/R281/V282/I292/
V299/L300/N311/I312/Y313/D314/T315/M317/C318/
Y320/I323/A339/T345/P346/E347/F350/S352/A359/F364/
R365/A366/L368/K369/L370/E372/D377/A381/W387/
N388/A393/D394/I396/A397/K399/A400/D401/F402/
A403/S404/K407/A409/E411/K412/G413/V415/T416/
A417/S418/L419/S420/M426/S429/V434/S437/L438;
E2/F3/S5/I7/G8/K9/I10/Q11/Q13/K16/D19/L21/S22/N27/
P28/E29/E30/I32/N33/R38/L41/K42/M51/G52/G53/D54/
T56/M58/C61/G62/T64/K66/W68/Q70/S71/A74/A75/R76/
I87/D89/S92/D94/Y95/Y96/R101/L103/S104/Y107/G108/
S109/L110/K111/A112/T113/N114/D115/Q116/D118/
I119/V120/T121/Q128/G129/D130/K131/F132/C134/
K140/C141/D143/G152/P155/S156/F162/S163/Q 66/K
69/E172/S173/V 75/N80/N198/M199/G249/Q273/Q277/
R281/V282/D285/V288/I292/V299/L300/N311/I312/
Y313/D314/T315/M317/C318/Y320/I323/A339/T345/
P346/E347/F350/S352/A359/F364/R365/A366/L368/
K369/L370/E372/D377/A381/W387/N388/A393/D394/
I396/A397/K399/A400/D401/F402/A403/S404/K407/
A409/E411/K412/G413/V415/T416/A417/S418/L419/
S420/M426/S429/V434/S437/L438; F3/S5/G8/Q11/Q13/
P15/K16/T18/D19/S22/K24/N27/P28/E30/V31/I32/N33/
R38/K42/L45/S46/T50/M51/G52/G53/D54/C61/G62/T64/
T67/W68/Q70/S71/D72/P73/A74/A75/R76/A84/I87/D89/
S92/D94/Y96/R101/S104/Y107/G108/S109/L110/A112/
T113/D115/Q116/I119/V120/T121/K125/Q128/D130/
K131/F132/K140/C141/D143/H144/M148/H149/T153/
S154/P155/F160/A161/S163/E172/S173/N180/N198/
M199/G200/L201/L203/D204/M206/R208/T236/T244/
V247/L248/K253/M262/Q273/T275/V282/A283/R284/
D285/V288/F229/S292/V299/Q307/T310/N311/I312/I323/
A325/F328/N330/L333/A339/G342/F344/P346/I349/S352/
Y353/A355/A359/F364/R365/A366/L368/D373/R375/
I376/K378/V380/A381/D382/A385/W387/N388/T389/
G390/A393/D394/I396/A397/G398/K399/D401/F402/
A403/S404/E406/K407/L410/K412/E414/V415/T416/
S418/L419/S420/M426/E428/S429/I430/V431/N433/
V434/S437/L438; E2/F3/S5/I7/G8/K9/I10/Q11/Q13/K16/
D19/L21/S22/N27/P28/E29/E30/I32/N33/R38/L41/K42/
M51/G52/G53/D54/T56/M58/C61/G62/T64/K66/W68/
Q70/S71/A74/A75/R76/A84/I87/D89/S92/D94/Y95/Y96/
R101/L103/S104/Y107/G108/S109/L110/K11/A112/T113/
N114/D115/Q116/D118/I119/V120/T121/Q128/G129/
D130/K131/F132/C134/K140/C141/D143/G152/P155/
S156/F162/S163/Q166/K169/E72/S173/V175/N180/T244/
V247/L248/K253/M262/Q273/T275/V282/A283/R284/
D285/V288/F289/I292/V299/L300/N311/I312/Y313/D314/
T315/M317/C318/Y320/I323/A339/T345/P346/E347/
F350/S352/F364/R365/A366/L368/K369/L370/E372/
D377/A381/W387/N388/A393/D 394/I396/A397/K399/
A400/D401/F402/A403/S404/K407/A409/E411/K412/
G413/V415/T416/A417/S418/L419/S420/M426/S429/
V434/S437/L438; E2/F3/S5/I7/G8/K9/I10/Q11/Q13/K16/
D19/L21/S22/N27/P28/E29/E30/I32/N33/R38/L41/K42/
M51/G52/G53/D54/T56/M58/C61/G62/T64/K66/W68/
Q70/S71/A74/A75/R76/A894I87/D89/S92/Y95/Y96/
R101/L103/S104/Y107/G108/S109/L110/K111/A112/
T113/N114/D115/Q116/D118/I119/V120/T121/Q128/
G129/D130/K131/F132/C134/K140/C141/D143/G152/
P155/S156/F162/S163/Q166/K 69/E172/S173/V175/N198/
M199/K223/T236/Q273/Q277/R281/V282/D285/V288/
I292/V299/L300/N311/I312/Y313/D314/T315/M317/
C318/Y320/I323/A339/T345/P346/E 347/F350/S352/A359/
F364/R365/A366/L368/K369/L370/E372/D377/A381/
W387/N388/A393/D394/I396/A397/K399/A400/D401/F402/A403/S404/K407/A409/E411/K412/G413/V415/T416/A417/S418/L419/S420/M426/S429/V434/S437/L438; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A89/I87/D89/S92/Y95/Y96/R101/L103/S104/Y107/G108/S109/L110/K111/A112/T113/N114/D115/Q116/D118/I119/V120/T121/Q128/G129/D130/K131/F132/C134/K140/C141/D143/G152/P155/S156/F162/S163/Q166/K169/E172/S173/V175/N180/N198/M199/S219/I220/K223/G249/D257/Q273/Q277/R281/V282/D285/V288/I292/V299/L300/N311/I312/Y313/D314/T315/M317/C318/Y320/I323/A339/T345/P346/E347/F350/S352/A359/F364/R365/A366/L368/K369/L370/E372/D377/A381/W387/N388/A393/D394/I396/A397/K399/A400/D401/F402/A403/S404/K407/A409/E411/K412/G413/V415/T416/A417/S418/L419/S420/M426/S429/V434/S437/L438; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A894187/D89/S92/Y95/Y96/R101/L103/S104/Y107/G108/S109/L110/K111/A112/T113/N114/D115/Q116/D118/I119/V120/T121/Q128/G129/D130/K131/F132/C134/K140/C141/D143/G152/P155/S156/F162/S163/Q166/K169/E172/S173/V175/N180/S219/I220/K223/D257/Q273/Q277/R281/V282/D285/V288/I292/V299/L300/N311/I312/Y313/D314/T315/M317/C318/Y320/I323/A339/T345/P346/E347/F350/S352/A359/F364/R365/A366/L368/K369/L370/E372/D373/D377/A381/W387/N388/A393/D394/I396/A397/K399/A400/D401/F402/A403/S404/K407/A409/E411/K412/G413/V415/T416/A417/I418/L419/S420/M426/S429/V434/S437/L438; E2/F3/S5/N6/I7/G8/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/S92/D94/Y95/Y96/R101/L103/S104/Y107/G108/S109/L110/K111/A112/T113/N114/D115/Q116/D118/I119/V120/T121/Q128/G129/D130/K131/F132/C134/K140/C141/D143/G152/P155/S156/F162/S163/Q166/K169/E172/S173/V175/N180/N198/M199/S219/D257/I292/N311/I312/Y313/D314/T315/M317/C318/Y320/I323/A339/T345/P346/E347/F350/S352/A359/F364/R365/A366/L368/K369/L370/E372/D377/A381/W387/

N388/A393/D394/I396/A397/K399/A400/D401/F402/
A403/A404/K407/A409/E411/K412/G413/V415/T416/
A417/S418/L419/S420/M426/S429/V434/S437/L438;
E2/F3/S5/I7/G8/K9/I10/Q11/Q13/K16/D19/L21/S22/N27/
P28/E29/E30/I32/N33/R38/L41/K42/M51/G52/G53/D54/
T56/M58/C61/G62/T64/K66/W68/Q70/S71/A74/A75/R76/
A84/I87/D89/S92/D94/Y95/Y96/R101/L103/S104/Y107/
G108/S109/L110/K111/A112/T113/N114/D115/Q116/
D118/I119/V120/T121/Q128/G129/D130/K131/F132/
C134/K140/C141/D143/G152/P155/S156/Q166/K169/
E172/S173/V175/N180/N198/M199/S219/I220/K223/
G249/D257/Q273/Q277/R281/V282/D285/V288/I292/
V299/L300/N311/I312/Y313/D314/T315/M317/C318/
Y320/I323/A339/F344/T345/P346/E347/F350/S352/A359/
F364/R365/A366/L368/K369/L370/E372/D377/A381/
W387/N388/A393/D 394/I396/A397/K399/A400/D401/
F402/A403/S404/K407/A409/E411/K412/G413/V415/
T416/A417/S418/L419/S420/M426/S429/V434/S437/
L438; E2/F3/S5/I7/G8/K9/I10/Q11/Q13/K16/D19/L21/
S22/N27/P28/E29/E30/I32/N33/R38/L41/K42/M51/G52/
G53/D54/T56/M58/C61/G62/T64/K66/W68/Q70/S71/A74/
A75/R76/A84/I87/D89/S92/D94/Y95/Y96/R101/L103/
S104/Y107/G108/S109/L110/K111/A112/T113/N114/
D115/Q116/D118/I119/V120/T121/Q128/G129/D130/
K131/F132/C134/K140/C141/D143/G152/P155/S156/
F162/S163/Q166/K69/E172/S173/V175/N180/S219/I220/
K223/T236/T244/V247/L248/D257/Q273/Q277/R281/
V282/D285/V288/I292/V299/L300/N311/I312/Y313/
D314/T315/M317/C318/Y320/I323/A339/T345/P346/
E347/F350/S352/A359/F364/R365/A366/L368/K369/
L370/E372/D377/A381/W387/N388/A393/D394/I396/
A397/K399/A400/D401/FA403/S404/K407/A409/E411/
K412/G413/V415/T416/A417/S418/L419/S420/M426/
S429/V434/S437/L438; E2/F3/S5/I7/G8/K9/I10/Q11/Q13/
K16/D19/L21/S22/N27/P28/E29/E30/I32/N33/R38/L41/
K42/M51/G52/G53/D54/T56/M58/C61/G62/T64/K66/
W68/Q70/S71/A74/A75/R76/A84/I87/D89/S92/D94/Y95/
Y96/R101/L103/S104/Y107/G108/S109/L110/K111/A112/
T113/N114/D115/Q116/D118/I119/V120/T121/Q128/
G129/D130/K131/F132/C134/K140/C141/D143/M148/
H149/G152/P155/S156/F162/S163/Q166/K169/E172/
S173/V175/N180/N198/M199/S219/I220/K223/K253/
D257/Q273/Q277/R281/V282/D285/V288/I292/V299/
L300/N311/I312/Y313/D314/T315/M317/C318/Y320/
I323/A339/T345/P346/E347/F350/S352/A359/A361/F364/
R365/A366/L368/K369/L370/E372/D377/A381/W387/
N388/A393/D394/I396/A397/K399/A400/D401/F402/
A403/S404/K407/A409/E411/K412/G413/V415/T416/
A417/S418/L419/S420/M426/S429/V434/S437/L438;
E2/F3/S5/I7/G8/K9/I10/Q11/Q13/K16/D19/L21/S22/N27/
P28/E29/E30/I32/N33/R38/L41/K42/M51/G52/G53/D54/
T56/M58/C61/G62/T64/K66/W68/Q70/S71/A74/A75/R76/
A84/I87/D89/S92/D94/Y95/Y96/R101/L103/S104/Y107/
G108/S109/L110/K111/A112/T113/N114/D115/Q116/
D118/I119/V120/T121/Q128/G129/D130/K131/F132/
C134/K140/C141/D143/P155/S156/F162/S163/Q166/K69/
E172/S173/V175/N180/Q273/T275/T416; F3/S5/G8/Q11/
Q13/P15/K16/T18/D19/S22/K24/N27/P28/E30/V31/I32/
N33/R38/K42/L45/S46/T50/M51/G52/G53/D54/C61/G62/
T64/T67/W68/Q70/S71/D72/P73/A74/A75/R76/A84/I87/
D89/S92/D94/Y96/R101/S104/Y107/G108/S109/L110/
A112/D115/Q116/I119/V120/T121/K125/Q128/D130/
K131/F132/K140/C141/D143/H144/M148/H149/T153/
S154/P155/F160/A161/S163/E172/S173/N180/N198/
M199/G200/L201/L203/D204/M206/R208/T236/T244/
V247/L248/K253/M262/Q273/T275/V282/A283/R284/
D285/V288/F289/I292/V299/Q307/T310/N311/I312/
I323/A 325/F328/N330/L333/A339/G342/F344/P346/I349/
S352/Y353/A355/A359/F364/R365/A366/L368/D373/
R375/I376/K378/V380/A381/D382/A385/W387/N388/
T389/G390/A393/D394/I396/A397/G398/K399/D401/
F402/A403/S404/E406/K407/L410/K412/E414/V415/
T416/S418/L419/S420/M426/E428/S429/I430/V431/N433/
V434/S437/L438; F3/S5/G8/Q11/Q13/P15/K16/T18/D19/
S22/K24/N27/P28/E30/V31/I32/N33/R38/K42/L45/S46/
T50/M51/G52/G53/D54/C61/G62/T64/T67/W68/Q70/S71/
D72/P73/A74/A75/R76/A84/I87/D89/S92/D94/Y96/R101/
S104/Y107/G108/S109/L110/A112/D115/Q116/I119/
V120/T121/K125/Q128/D130/K131/F132/K140/C141/
D143/H144/M148/H149/T153/S154/P155/F160/A161/
S163/E172/S173/N180/N198/M199/G200/L201/L203/
D204/M206/R208/T236/T244/V247/L248/K253/M262/
Q273/T275/V282/A283/R284/D285/V288/F289/I292/
V299/Q307/T310/N311/I312/I323/A325/F328/N330/L333/
A339/G342/F344/P346/I349/S352/Y353/A355/A359/
F364/R365/A366/L368/D373/R375/I376/K378/V380/
A381/D382/A385/W387/N388/T389/G390/A393/D394/
I396/A397/G398/K399/D401/F402/A403/S404/E406/
K407/L410/K412/E414/V415/T416/S418/L419/S420/
M426/E428/S429/I430/V431/N433/V434/S437/L438;
T236/T244/V247/L248/K253/M262/Q273/T275/V282/
A283/R284/D285/V288/F289/I292; E2/F3/S5/I7/G8/K9/
I10/Q11/Q13/K16/D19/L21/S22/N27/P28/E29/E30/I32/
N33/R38/L41/K42/M51/G52/G53/D54/T56/M58/C61/G62/
T64/K66/W68/Q70/S71/A74/A75/R76/A84/I87/D89/S92/
D94/Y95/Y96/R101/L103/S104/Y107/G108/S109/L110/
K111/A112/T113/N114/D115/Q116/D118/I119/V120/
T121/Q128/G129/D130/K131/F132/C134/K140/C141/
D143/G152/P155/S156/F162/S163/Q166/K169/E172/
S173/V175/N180/R208/I219/I220/K223/Q273/Q277/R281/
V282/D285/V288/I292/V299/L300/N311/I312/Y313/
D314/T315/M317/C318/Y320/I323/N334/A339/T345/
P346/E347/F350/S352/A359/F364/R365/A366/L368/
K369/L370/E372/G374/D377/A381/W387/N388/A393/
D394/I396/A397/K399/A400/D401/F402/A403/S404/
K407/A409/E411/K412/G413/V415/T416/A417/S418/
L419/S420/G422/M426/S429/V434/S437/L438; E2/F3/S5/
I7/G8/K9/I10/Q11/Q13/K16/D19/L21/S22/N27/P28/E29/
E30/I32/N33/R38/L41/K42/M51/G52/G53/D54/T56/M58/
C61/G62/T64/K66/W68/Q70/S71/A74/A75/R76/A84/I87/
D89/S92/D94/Y95/Y96/R101/L103/S104/Y107/G108/
S109/L110/K111/A112/T113/N114/D115/Q116/D118/
I119/V120/T121/Q128/G129/D130/K131/F132/C134/
K140/C141/D143/G152/P155/S156/F162/S163/Q166/
K169/E172/S173/V175/N180/N198/M199/Q273/Q277/
R281/V282/D285/V288/I292/V299/L300; E2/F3/S5/I7/G8/
K9/I10/Q11/Q13/K16/D19/L21/S22/N27/P28/E29/E30/
I32/N33/R38/L41/K42/M51/G52/G53/D54/T56/M58/C61/
G62/T64/K66/W68/Q70/S71/A74/A75/R76/A84/I87/D89/
S92/D94/Y95/Y96/R101/L103/S104/Y107/G108/S109/
L110/K111/A112/T113/N114/D115/Q116/D118/I119/
V120/T121/Q128/G129/D130/K1131/F132/C134/K140/
C141/D143/G152/P155/S156/F162/S163/Q166/K169/
E172/S173/V175/N180/K223/Q273/T275/V282/A283/
R284/D285/V288/F289/I292/V299; E2/F3/S5/I7/G8/K9/
I10/Q11/Q13/P15/K16/D19/L21/S22/N27/P28/E29/E30/
I32/N33/R38/L41/K42/M51/G52/G53/D54/T56/M58/C61/
G62/T64/K66/W68/Q70/S71/A74/A75/R76/A84/I87/D89/
S92/D94/Y95/Y96/R101/L103/S104/Y107/G108/S109/
L110/K111/A112/T113/N114/D115/Q116/D118/I119/
V120/T121/Q128/G129/D130/K131/F132/C134/K140/
C141/D143/G152/P155/S156/F162/S163/Q166/K169/
E172/S173/V175/N180/S219/I220/K223/D257/Q273/
Q277/R281/V282/D285/V288/I292/V299/L300/N311/

I312/Y313/D314/T315/M317/C318/Y320/I323/A325/A339/T345/P346/E347/F350/S352/A359/F364/R365/A366/L368/K369/L370/E372/D377; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/S92/D94/Y95/Y96/R101/L103/S104/Y107/G108/S109/L110/K111/A112/T113/N114/D115/Q116/D118/I119/V120/T121/Q128/G129/D130/K131/F132/C134/K140/C141/D143/G152/P155/S156/F62/S163/Q166/K69/E172/S173/V175/N180/K223/Q273/T275/V282/A283/R284/D285/V288/F289/I292/V299; S5/G8/Q11/Q13/P15/K16/D19/S22/E29/N33/T36/E39/H40/L41/T64/Q70/S71/D89/Y96/A112/D115/E126/G129/D130/K131/F132/N198/M199/S219/I220/K223/V247/L248/K253/M262/A269/D285/V288/N311/I312/Y313/D314/T 315/M317/C318/Y320/I323/A339/T345/P346/E347/F350/S352/A359/F364/R365/A366/L368/K369/L370/E372/D377/A381/W387/N388/A393/D394/I396/A397/K399/A400/D401/F402/A403/I404/K407/A409/E411/K412/G413/V 415/T416/A417/S418/L419/S420/M426/S429/V434/S437/L438; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/I92/D94/Y95/Y96/R101/L103/S104/Y107/G108/S109/L110/K111/A112/T113/N114/D115/Q116/D118/I119/V120/T121/Q128/G129/D130/K1131/F132/C134/K140/C141/D143/G152/P155/S156/F62/S163/Q166/K69/E172/S173/V175/N180/219/1220/K223/G224/G249/D257/Q273/Q277/R281/V282/D285/V288/I292/V299/L300/N311/I312/Y313/D314/T315/M317/C318/Y320/I323/A339/T345/P346/E347/F350/S352/A359/F364/R365/A366/L368/K369/L370/E372/D377/A381/W387/N388/A393/D394/I396/A397/K399/A400/D401/F402/A403/S404/K407/A409/E411/K412/G413/V415/T416/A417/S418/L419/S420/M426/S429/V434/S437/L438; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/I92/D94/Y95/Y96/R101/L103/S104/Y107/G108/S109/L110/K111/A112/T113/N114/D115/Q116/D118/I119/V120/T121/Q128/G129/D130/K131/F132/C134/K140/C141/D143/R146/G152/P55/S156/F162/S163/Q166/K69/E172/S173/V175/N180/S219/I220/K223/G249/D257/Q273/Q277/R281/V282/D285/V288/I292/V299/L300/N311/I312/Y313/D314/T315/M317/C318/Y320/I323/A339/T345/P346/E347/F350/S352/A359/F364/R365/A366/L368/K369/L370/E372/D377/A381/W387/N388/A393/D394/I396/A397/K399/A400/D401/F402/A403/S404/K407/A409/E411/K412/G413/V415/T416/A417/S418/L419/S420/M426/S429/V434/S437/L438; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/S92/D94/Y95/Y96/R101/L103/S104/Y107/G108/S109/K111/A 112/T113/N114/D115/Q116/D118/I119/V120/T121/Q128/G129/D130/K131/F132/C134/K140/C141/D143/G152/P155/S156/F162/S163/Q166/K 69/E172/S173/V175/N180/S219/I220/K223/Q273/T275/V282/A 283/R284/D285/V288/F289/I292/V299; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/S92/D94/Y95/Y96/R101/L103/S104/Y107/G108/S109/L110/K111/A112/T113/N114/D115/Q116/D118/I119/V120/T121/Q128/G129/D130/K1131/F132/C134/K140/C141/D143/G152/P155/S156/F162/S163/Q166/K169/E172/S173/V175/N180/K223/G249/D257/Q273/Q277/R281/V282/D285/V288/I292/V299/L300/N311/I312/Y313/D314/T315/M317/C318/Y320/I323/T345/P346/E347/F350/S352/A359/F364/R365/A366/L368/K369/L370/E372/D377/A381/W387/N388/A393/D394/I396/A397/K399/A400/D401/F402/A403/S404/K407/A409/E411/K412/G413/V415/T416/A417/S418/L419/S420/M426/S429/V434/S437/L438; E2/F3/S5/I7/G8/K9/I10/Q11/Q13/K16/D19/L21/S22/N27/P28/E29/E30/I32/N33/R38/K42/L45/S46/T50/M51/G52/G53/D54/C61/G62/T64/T67AV68/Q70/S71/D72/P73/A74/A75/R76/A84/I87/D89/S92/D94/Y96/R101/S104/Y107/G108/S109/L110/A112/D115/Q116/I119/V120/T121/K125/Q128/D130/K131/F132/K140/C141/D143/H144/M148/H149/T153/S154/P155/F160/A161/S163/E172/S173/N180/N198/M199/S219/T236/T244/V247/L248/K253/M262/Q273/T275/V282/A283/R284/D285/V288/F289/I292/V299/Q307/T310/N311/I312/I323/A325/F328/N330/L333/A 339/G342/F344/P346/I349/S352/Y353/A355/A359/F364/R365/A366/L368/D373/R375/S376/K378/V380/A381/D382/A385/W387/N388/T389/G390/A393/D394/I396/A397/G398/K399/D401/F402/A403/S404/E406/K407/L410/K412/E414/V415/T416/S418/L419/S420/M426/E428/S429/I430/V431/N433/V434/S437/L438; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/S92/D94/Y95/Y96/R101/L103/S104/Y107/G108/S109/I110/K111/A112/T113/N114/D115/Q116/D118/I119/V120/T121/Q128/G129/D130/K131/F132/C134/K140/C141/D143/G152/P155/S156/F162/S163/Q166/K169/E172/S173/V175/N180/219/1220/K223/T236/D257/Q273/Q277/R281/V282/D285/V288/I292/V299/L300/N311/I312/Y313/D314/T315/M317/C318/Y320/I323/A339/A359/F364/R365/A366/L368/K369/L370/E372/D377/A381/W387/N388/A393/D394/I396/A397/K399/A400/D401/F402/A403/S404/K407/A409/E411/K412/G413/V415/T416/A417/S418/L419/S420/M426/S429/V434/S437/L438; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/S92/D94/Y95/Y96/R101/L103/S104/Y107/G108/S109/L110/K111/A112/T113/N114/D115/Q116/D118/I119/V120/T121/Q128/G129/D130/K131/F132/C134/K140/C141/D143/G152/P155/S156/F162/S163/Q166/K169/E172/S173/V175/N180/N198/M199/T236/T244/V247/L248/K253/M262/Q273/Q277/R281/V282/D285/V288/I292/V299/I300/N311/I312/Y313/D314/T315/M317/C318/Y320/I323/A339/T345/P346/E347/I349/F350/S352/A359/F364/R365/A366/L368/K369/L370/E372/D377/A381; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/S92/D94/Y95/Y96/R101/L103/S104/Y107/G108/S109/I110/K111/A112/T113/N114/D115/Q116/D118/I119/V120/T121/Q128/G129/D130/K131/F132/C134/K140/C141/D143/G152/P155/S156/F162/S163/Q166/K169/E172/S173/V175/N180/I219/I220/K223/G249/V299/L300/N311/I312/Y313/D314/T315/M317/C318/Y320/I323/A339/T345/P346/E347/F350/A359/F364/R365/A366/L368/K369/L370/E372/D377/A381/W387/N388/A393/D394/I396/A397/K399/A400/D401/F402/A403/S404/K407/A409/E411/K412/G413/V415/T416/A417/S418/L419/S420/M426/S429/V434/I437/L438; E2/F3/S5/I7/G8/K9/I10/Q11/Q13/K16/D19/L21/S22/N27/P28/E29/E30/I32/N33/K35/T36/R38/L41/K42/M51/G52/G53/D54/T56/M58/C61/G62/T64/K66/

W68/Q70/S71/A74/A75/R76/A84/I87/D89/S92/D94/Y95/
Y96/R101/L103/S104/Y107/G108/S109/L110/K111/A112/
T113/N114/D115/Q116/D118/I119/V120/T121/Q128/
G129/D130/K131/F132/C134/K140/C141/D143/G152/
P155/S156/F162/S163/Q166/K169/E172/S173/V175/
N180/T236;   P28/E29/E30/I32/N33/R38/L41/K42/M51/
G52/G53/D54/T56/M58/C61/G62/T64/K66/W68/Q70/S71/
A74/A75/R76/A84/I87/D89/S92/D94/Y95/Y96/R101/
L103/S104/Y107/G108/S109/L110/K111/A112/T113/
N114/D115/Q116/D118/I119/V120/T121/Q128/G129/
D130/K131/F132/C134/K140/C141/D143/G152/P155/
S156/F162/S163/Q166/K169/E172/S173/V175/N180/
S219/I220/G249/V299/L300/A339/T345/P346/E347/F350/
S352/A359/F364/R365/A366/L368/K369/L370/E372/
D377;   E2/F3/S5/I7/G8/K9/I10/Q11/Q13/K16/D19/L21/
S22/N27/P28/E29/E30/I32/N33/R38/L41/K42/M51/G52/
G53/D54/T56/M58/C61/G62/T64/K66/W68/Q70/S71/A74/
A75/R76/A84/I87/D89/I92/D94/Y95/Y96/R101/L103/S104/Y107/G108/S109/L109/L110/K111/A112/T113/N114/D115/Q116/D118/I119/V120/T121/Q128/G129/D130/K131/F132/C134/K140/C141/D143/G152/P155/S156/F162/S163/Q166/K169/E172/S173/V175/N180/N198/M199/I219/I220/K223/G249/D257/V299/N311/I312/Y313/D314/T315/M317/C318/Y320/I323/A339/T345/P346/E347/F350/S352/A359/F364/R365/A366/L368/K369/L370/E372/D377/A381/W387/N388/A393/D394/I396/A397/K399/A400/D401/F402/A403/S404/K407/A409/E411/K412/G413/V415/T416/A417/S418/L419/S420/M426/S429/V434/S437/L438; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/I66/W68/Q70/S71/A74/A75/R76/A84/I87/D89/I92/D94/Y95/Y96/R101/L103/S104/Y107/G108/S109/L110/K111/A112/T113/N114/D115/Q116/D118/I119/V120/T121/Q128/G129/D130/K1131/F132/C134/K140/C141/D143/G152/P155/S156/F162/S163/Q166/I169/E172/S173/V175/N180/219/1220/K223/G249/N311/I312/Y313/D314/T315/M317/C318/Y320/I323/A339/T345/P346/E347/F350/S352/A359/F364/R365/A366/L368/K369/L370/E372/D377/K378/A381/W387/N388/A393/D394/I396/A397/K399/A400/D401/F402/A403/S404/I407/A409/E411/K412/G413/V415/T416/A417/S418/L419/S420/M426/S429/V434/S437/L438; S5/G8/Q11/Q13/P15/K16/D19/S22/E29/N33/T36/E39/H40/L41/T64/Q70/S71/D89/Y96/A112/D115/E126/G129/D130/K131/F132/N180/N198/M199/T244/V247/L248/K253/Q273/T275/V282/A283/R284/D285/V288/F289/I292/N311/I312/Y313/D314/T315/M317/C318/Y320/I323/W387/N388; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/S92/Y95/Y96/R101/L103/S104/Y107/G108/S109/L110/K111/A112/T113/N114/D115/Q116/D118/I119/V120/T121/Q128/G129/D130/K1131/F132/C134/K140/C141/D143/G152/P155/S156/F162/S163/Q166/K169/E172/S173/V175/N180; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/S92/Y95/Y96/R101/L103/S104/Y107/G108/S109/L110/K111/A112/T113/N114/D115/Q116/D118/I119/V120/T121/Q128/G129/D130/K1131/F132/C134/K140/C141/D143/G152/P155/S156/F162/S163/Q166/K169/E172/S173/V175/N180/N198/M199/V247/L248/K253/Q273/Q277/R281/I282/D285/V288/N311/I312/Y313/D314/T315/M317/C318/M319/Y320/I323/A339/T345/P346/E347/F350/S352/A359/F364/R365/A366/L368/K369/L370/E372/D377/A381/W387/N388/A393/D394/I396/A397/K399/A400/D401/F402/A403/S404/K407/A409/E411/K412/G413/V415/T416/A417/S418/L419/S420/M426/S429/V434/S437/L438; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/S92/Y95/Y96/R101/L103/S104/Y107/G108/S109/L110/K111/A112/T113/N114/D115/Q116/D118/I119/V120/T121/Q128/G129/D130/K1131/F132/C134/K140N/C141/D143/G152/P155/S156/F162/S163/Q166/K169/E172/S173/V175/N180/K253/Q273/T275; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/S92/D94/Y95/Y96/R101/L103/S104/E106/Y107/G108/S109/L110/K111/A112/T113/N114/D115/Q116/D118/I119/V120/T121/Y123/Q128/G129/D130/K131/F132/C134/K140/C141/D143/G152/P155/S156/F162/S163/Q166/K169/E172/S173/V175/N180/G249/D257/Q273/Q277/R281/V282/D285/V288/I292/V299/L300/N311/I312/Y313/D314/T315/M317/C318/Y320/I323/A339/T345/P346/E347/F350/S352/A359/F364/R365/A366/L368/K369/L370/E372/D377/A381; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/S92/D94/Y95/Y96/R101/L103/S104/Y107/G108/S109/L110/K11/A112/T113/N114/D115/Q116/D118/I119/V120/T121/Q128/G129/D130/K131/F132/C134/K140/C141/D143/G152/P55/S156/F162/S163/Q166/K169/E172/S173/V175/N198/M199/I219/I220/K223/G249/D257/I292/V299/L300/N311/I312/Y313/D314/T315/M317/C318/Y320/I323/A339/T345/P346/E347/F350/S352/A359/F364/R365/A336/L368/K369/L370/E372/D377/A338/W387/N388/A393/D394/I397/K399/A400/D40/F402/A403/S404/K407/A409/E411/K412/G413/V415/T416/A417/S418/L419/S420/M426/S429/V434/S437/L438; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/S92/D94/Y95/Y96/R101/L103/S104/Y107/G108/S109/L110/K111/A112/T113/N114/D115/Q116/D118/I119/V120/T121/Q128/G129/D130/K131/F132/C134/K140/C141/D143/G152/P155/F162/S163/Q166/K169/E172/S173/V175/N180/N198/M199/V299; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/S92/D94/Y95/Y96/R101/L103/S104/Y107/G108/S109/L110/K111/A112/T113/N114/D115/Q116/D118/I119/V120/T121/Q128/G129/D130/K131/F132/C134/K140/C141/D143/G152/P155/S156/F162/S162/S163/Q166/K169/E172/S173/V175/N180/N198/M199/T236/T244/V299/L300/N311/I312/Y313/D314/T315/M317/C318/Y320/I323/A339/T345/P346/E347/F350/S352/A359/F364/R365/A366/L368/K369/L370/E372/D377/A38/W387/N388/A393/D394/I396/A397/K399/A400/D401/F402/A403/S404/K407/A409/E411/K412/G413/V415/T416/A417/S418/L419/S420/M426/S429/V434/S437/L438; E2/F3/S5/I7/G8/K9/I10/Q11/Q13/K16/D19/L21/S22/N27/P28/E29/E30/I32/N33/R38/L41/K42/M51/G52/G53/D54/T56/M58/C61/G62/T64/K66/W68/Q70/S71/A74/A75/R76/A84/I87/D89/S92/D94/Y95/Y96/R101/L103/S104/Y107/G108/S109/L110/K111/A112/T113/N114/D115/Q116/D118/I119/V120/T121/Q128/G129/D130/K131/F132/C134/K140/C141/D143/G152/P155/S156/F162/S163/Q166/K169/E172/

S173/V175/N180/V183/N198/M199/S219/I220/D257/
N311/I312/Y313/D314/T315/M317/C318/Y320/I323/
A339/T345/P346/E347/F350/S352/A359/F364/R365/
A366/L368/K369/L370/E372/D377/A38/W387/N388/
A393/D394/I396/A397/K399/A400/D401/F402/A403/
S404/K407/A409/E411/K412/G413/V415/T416/A417/
S418/L419/S420/M426/S429/V434/S437/L438; E372G;
S5/G8/Q11/Q13/P15/K16/D19/S22/E29/N33/T36/E39/
H40/L41/T64/Q70/S71/D89/Y96/A 112/D115/E126/G129/
D130/K131/F132/N180/N198/M199/S219/I220/T236/
G249/D257/Q273/Q277/R281/V282/D285/V288/I292/
N311/I312/Y313/D314/T315/M317/C318/Y320/I323/
A339/T345/P346/E347/F350/S352/A359/F364/R365/
A366/L368/K369/L370/E372/D377/A381/W387/N388/
A393/D394/I396/A397/K399/A400/D401/F402/A403/
S404/K407/A409/E411/K412/G413/V415/T416/A417/
S418/L419/S420/M426/S429/V434/S437/L438; E2/F3/S5/
I7/G8/K9/I10/Q11/Q13/K16/D19/L21/S22/N27/P28/E29/
E30/I32/N33/R38/L41/K42/M51/G52/G53/D54/T56/M58/
C61/G62/T64/K66/W68/Q70/S71/A74/A75/R76/A84/I87/
D89/S92/D94/Y95/Y96/R101/L103/S104/Y107/G108/
S109/L110/K111/A112/T113/N114/D115/Q116/D118/
I119/V120/T121/Q128/G129/D130/K131/F132/C134/
K140/C141/D143/G152/P155/S156/F162/S163/Q166/
K169/E172/S173/V175/N180/N198/M199/Q273/Q277/
R281/V282/D285/V288/I292/V299/L300/N311/I312/
Y313/D314/T315/M317/C318/Y320/I323/F328/A339/
T345/P346/E347/F350/S352/A359/F364/R365/A366/L368/
K369/L370/W387/N388/A393/D394/I396/A397/K399/
A400/D401/F402/A403/S404/K407/A409/E411/K412/
G413/V415/T416/A417/S418/L419/S420/M426/S429/
V434/S437/L438; E2/F3/S5/I7/G8/K9/I10/Q11/Q13/K16/
D19/L21/S22/N27/P28/E29/E30/I32/N33/R38/L41/K42/
M51/G52/G53/D54/T56/M58/C61/G62/T64/K66/W68/
Q70/S71/A74/A75/R76/A84/I87/D89/I92/D94/Y95/Y96/
R101/L103/S104/Y107/G108/S109/L110/K111/A112/
T113/N114/D115/Q116/D118/I119/V120/T121/Q128/
G129/D130/K131/F132/C134/K140/C141/D143/G152/
P155/S156/F162/S163/Q166/K 69/E172/S173/V175/N180/
V288/F289/I292; and/or E2/F3/S5/I7/G8/K9/I10/Q11/Q13/
K16/D19/L21/S22/N27/P28/E29/E30/I32/N33/R38/L41/
K42/M51/G52/G53/D54/T56/M58/C61/G62/T64/K66/
W68/Q70/S71/A74/A75/R76/A84/I87/D89/S92/D94/Y95/
Y96/R101/L103/S104/Y107/G108/S109/L110/K111/A112/
T113/N114/D115/Q116/D118/I119/V120/T121/Q128/
G129/D130/K131/F132/C134/K140/C141/D143/G152/
P155/S156/F162/S163/Q166/K 69/E172/S173/V175/N180/
K253/Q273/T275, wherein the positions are numbered by
correspondence with the amino acid sequence set forth in
SEQ ID NO:2.

In some additional embodiments, the present invention provides isolated chimeric xylose isomerase variants, wherein the variants are mature forms having xylose isomerase activity and comprise at least one mutation and/or mutation set selected from: F3L/S5Q/G8P/Q11K/Q13E/ G14S/P15A/K16N/T18K/D19N/S22A/K24H/N27D/P28A/ E30K/V31I/I32V/N33L/R38K/K42P/L45M/S46A/T50N/ M51L/G52C/G53A/D54A/C61R/G62D/T64A/T67S/ W68L/Q70E/S71K/D72G/P73S/A 74M/A75E/R76H/ A84G/I87F/D89E/S92G/D94K/Y96F/R101V/S104V/ Y107A/G108C/S109D/L110I/A12E/D115 S/Q116R/I119E/ V120I/T121S/K125L/Q128K/D130T/K131D/F132I/ K140N/C141M/D143S/H144N/M148V/H149N/T153S/ S154T/P155N/F160Y/A161C/S163A/E172D/S173I/N18R/ M199V/T236A/Q273G/T275S/V282/A283S/R284S/ D285I/V288M/F289I/I292V/V299M/Q307E/T310F/ N311D/I312V/I323L/A325N/F328L/N330-/L333F/A339N/ G342P/F344Y/P346Y/I349M/S352G/Y353F/A355L/ A359S; S5K/G8S/Q11P/Q13E/P15K/K 6D/D19N/S22A/ E29D/N33D/T36K/E39D/H40I/L41M/T64A/Q70E/S71N/ D89Q/Y96F/A 112D/D115A/I19V/E126A/G129A/D130E/ K131T/F132L/N180T/S219A/I220N/A266P/A269T/ Q273G/T27S/Q277E/R281A/V282M/D285V/V288A/ I292V/D306G/N311D/I312V/Y313H/D314S/T315A/ M317L/C318A/Y320L/I323L/T345E/P346F/E347D/ F350A/S352G/A359T/F364L/R365I/A366K/L368A/ K369E/L370I/E372D/D377/A381D/W387Y/N388K/ A393K/D394A/I396V/A397D/K399T/A400T/D401S/ F402L/A403E/S404E/K407Q/A409V/E411T/K412H/ G413S/V415P/T416V/A417-/I418-/L419M/S420Q/R423G/ M426/S429T/S437R/L438-; S5K/G8S/Q11P/Q13E/ P15K/K 6D/D19N/S22A/E29D/N33D/T36K/E39D/H40I/ L41M/T64A/Q70E/S71N/D89Q/Y 96F/A 112D/D115A/ E126A/G129A/D130E/K131T/F132L/N18T/R281C/ D285T/V288A/V299P/F364Y/R365K/L368S/E372A/ K378S/V380I/A381S/N388S/T389E/A393L/A397S/F 402404A/A417D/L419I/M426L/L435I/I437N; E2K/F3Y/ S5P/I7V/G8P/K9E/I100V/Q11K/Q13E/K16N/D19N/L21F/ S22A/N27D/P28A/E29N/E30K/I32V/N33A/R38K/L41C/ K42R/M51L/G52C/G53A/D54G/T56A/M58P/C61V/ G62T/T64M/K66R/W68Y/Q70N/S71T/A74M/A75E/ R76L/A84G/I87L/D89T/S92G/D94E/Y95F/Y96F/R101A/ L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/ C134L/K140N/C141N/D143S/G152S/P55C/S156N/ F162Y/S163A/Q166K/K169N/E172D/S173A/V175I/ N180K/S219A/I220N/K223D/G249A/D257E/Q273G/ N311D/I312V/Y313H/D314S/T315A/M317L/C318A/ Y320L/I323L/A339V/T345E/P346F/E347D/F350A/ F364L/R365I/A366K/L368A/K369E/L370I/E372D/ D377A/A381D/W387Y/N388K/A393K/D394A/I396V/ A397D/K399T/A400T/D401S/F402L/A403E/S404E/ K407Q/A409V/E411T/K412H/G413S/V415P/T416V/ A417-/S418-/L419M/S420Q/M426V/S429T/V434I/S437R/ L438-; E2K/F3Y/S5P/I7V/G8P/K9E/I10V/Q11K/Q13E/ K16N/T18A/D19N/L21F/S22A/N27D/P28A/E29N/E30K/ I32V/N33A/R38K/L41C/K42R/M51L/G52C/G53A/D54G/ T56A/M58P/C61V/G62T/T64M/K66R/W68Y/Q70N/ S71T/A74M/A75E/R76L/A84G/I87L/D89T/D94E/Y95F/ Y96F/R101A/L103I/S104A/Y107G/G108D/S110F/K111E/ A112E/T113S/N114K/D115K/Q116N/D118F/I119E/ V120I/T121V/Q128M/G129D/D130Q/K131T/F132I/ C134L/K140N/C141N/D143S/G152S/P155C/S156N/ F162Y/S163A/Q166K/K169N/E172D/S173A/V175/ N180K/Q273G/Q277E/R281A/V282M/D285V/V288A/ I292V/V299P/L300N/N311D/I312V/Y313H/D314S/ T315A/M317L/C318A/Y320L/I323L/F335L/A339V/ T345E/P346F/E347D/F350A/S352G/A359F/F364L/R365I/ A366K/L368A/K369E/L370I/E372D/D377A/A381D/ W387Y/N388K/A393K/D394A/I396V/A397D/K399T/ A400T/D401S/F402L/A403E/S404E/K407Q/A409V/ E411T/K412H/G413S/V415P/T416V/A417-/S418-/ L419M/S420Q/M426V/S429T/V434I/S437R/L438-; E2K/ F3Y/S5P/I7V/G8P/K9E/I10V/Q11/Q13E/K16N/D19N/ L21F/S22A/N27D/P28A/E29N/E30K/I32V/N33A/R38K/ L41C/K42R/M51L/G52C/G53A/D54G/T56A/M58P/ C61V/G62T/T64M/K66R/W68Y/Q70N/S71A/A74M/ A75E/R76L/A84G/I87L/D89T/S92G/D94E/Y95F/Y96F/ R101A/L103I/S104A/Y107G/G108D/S109T/L110F/ K111E/A112E/T113S/N114K/D115K/Q116N/D118F/ I119E/V120I/T121V/Q128M/G129D/D130Q/K131T/ F132I/C134L/K140N/C14N/D143S/G152S/P155C/S156N/ F162Y/S163A/Q166K/K169N/E172D/S173A/V175I/

N180K/N198D/M199L/M206T/S219A/I220N/K223D/
G249A/D257E/Q273G/Q277E/R281A/V282M/I292V/
V299P/L300N/N311D/I312V/Y313H/D314S/T315A/
M317L/C318A/Y320L/I323L/A339V/T345E/P346F/
E347D/F350A/S352G/A359T/F364L/R365I/A366K/
L368A/K369E/L370I/E372D/D377A/A381D/W387Y/
N388K/A393K/D394A/I396V/A397D/K399T/A400T/
D401S/F402L/A403E/S404E/K407Q/A409V/E411T/
K412H/G413S/V415P/T416V/A417-/S418-/L419M/
S420Q/M426V/S429T/V434I/S437R/L438-;   E2K/F3Y/S5P/I7V/G8P/K9E/I10V/Q11/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/I87L/D89T/S92G/D94E/Y95F/Y96F/R101A/L103I/S104A/Y107G/G108D/S109T/L110F/K111E/A 12E/T113S/N114K/D115K/Q116N/D118F/I119E/V120I/T121V/Q128M/G129D/D130Q/K131T/F132I/C134L/K140N/C141N/D143S/G152S/P155C/S156N/F162Y/S163A/Q166K/K169N/E172D/S173A/V175I/N180R/N198D/M199L/G249A/Q273G/Q277E/R281A/V282M/D285V/V288A/I292V/V299P/L300N/N311D/I312V/Y313H/D314S/T315A/M317L/C318A/Y320L/I323L/A339V/T345E/P346F/E347D/F350A/S352G/A359T/F364L/R365I/A366K/L368A/K 369E/L370I/E372D/D377A/A381D/W387Y/N388K/A393K/D394A/I396V/A397D/K399T/A400T/D401S/F402L/A403E/S404E/K407Q/A409V/E411T/K412H/G413S/V415P/T416V/A417-/S418-/L419M/S420Q/M426V/S429T/V434I/S437R/L438-; F3L/S5Q/G8P/Q11K/Q13E/P15A/K16N/T18K/D19N/S22A/K24H/N27D/P28A/E30K/V31I/I32V/N33L/R38K/K42P/L45M/S46A/T50N/M51L/G52C/G53A/D54A/C61R/G62D/T64A/T67S/W68F/Q70E/S71K/D72G/P73S/A74M/A75E/R76H/A84G/I87F/D89E/S92G/D94K/Y96F/R101V/S104V/Y107A/G108C/S109D/L110I/A112E/T113I/D115S/Q116R/I119E/V120I/T121S/K125L/Q128K/D130T/K131D/F132I/K140N/C141M/D143S/H144N/M148V/H149 N/T153S/S154T/P155N/F160Y/A161C/S163A/E172D/S173I/N180R/N198D/M199V/G200K/L201F/L203Q/D204 E/M206I/R208N/T236M/T244A/V247A/L248I/K253Q/M262L/Q273G/T275S/V282I/A283S/R284S/D285I/V288 M/F289L/I292V/V299M/Q307E/T310F/N311D/I312V/I323L/A325N/F328L/N330-L333F/A339N/G342P/F344Y/P346Y/I349M/S352G/Y353F/A355L/A359S/F364L/R365I/A366K/L368A/D373E/R375T/I376L/K378N/V380I/A381K/D382E/A385K/W387F/N388E/T389S/G390E/A393K/D394K/I396R/A397S/G398K/K399S/D401S/F402L/A403Q/S404E/E406A/K407A/L410E/K412M/E414-/V415A/T416P/S418M/L419P/S420G/M426Y/E428Q/S429A/I430A/V431L/N433Q/V434N/S437E/L438V; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D15K/Q116N/D118F/I119E/V120I/T121V/Q128M/G129D/D130Q/K31T/F132I/C134L/K140N/C141N/D143S/G152S/P155C/S156N/F162Y/S163A/Q166K/K169N/E172G/S173A/V175/N18R/T244A/V247A/L248I/K253Q/M262L/Q273G/T275S/V282I/A283S/R284S/D285I/V288M/F289L/I292V/V299P/L300N/N311D/I312V/Y313H/D314S/T315A/M317L/C318A/Y320L/I323L/A339V/T345E/P346F/E347D/F350A/S352G/F364L/R365I/A366K/L368A/K369E/L370/E372D/D377A/A381D/W387Y/N388K/A393K/D394A/I396V/A397D/K399T/A400T/D401S/F402L/A403E/S404E/K407Q/A409V/E411T/K412H/G413S/V415P/T416V/A417-/S418-/L419M/S420Q/M426V/S429T/V434I/S437R/L438-; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K11E/A112E/T113S/N114K/D115K/Q116N/D118F/I119E/V120I/T121V/Q128M/G129D/D130Q/K131T/F132I/C134L/K140N/D143S/G152S/P155C/S156N/F162Y/S163A/Q166K/K169N/E172D/S173A/V175I/N198D/M199L/K223N/T236M/Q273G/Q277E/R281A/V282M/D285V/V288A/I292V/V299P/L300N/N311D/I312V/Y313H/D314S/T315A/M317L/C318A/Y320L/I323L/A339V/T345E/P346F/E347D/F350A/S352G/A359T/F364L/R365I/A366K/L368A/K369E/L370I/E372D/D377A/A381D/W387Y/N388K/A393K/D394A/I396V/A397D/K399T/A400T/D401S/F402L/A403E/S404E/K407Q/A409V/E411T/K412H/G413S/V415P/T416V/A417-/S418-/L419M/S420Q/M426V/S429T/V434I/S437R/L438-; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D15K/Q116N/D118F/I119E/V120I/T121V/Q128M/G129D/D130Q/K131T/F132I/C134L/K140N/C141N/D143S/G152S/P155C/S156N/F162Y/S163A/Q166K/K169N/E172D/S173A/V175I/N180K/N198D/M199L/S219A/I220N/K223D/G249A/D257E/Q273G/Q277E/R281A/V282M/D285V/V288A/I292V/V299P/L300N/N311D/I312V/Y313H/D314S/T315A/M317L/C318A/Y320L/I323L/A339V/T345E/P346F/E347D/F350A/S352G/A359T/F364L/R365I/A366K/L368A/K369E/L370I/E372D/D377A/A381D/W387Y/N388K/A393K/D394A/I396V/A397D/K399T/A400T/D401S/F402L/A403E/S404E/K407Q/A409V/E411T/K412H/G413S/V415P/T416V/A417-/S418-/L419M/S420Q/M426V/S429T/V434I/S437R/L438-; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D115K/Q116N/D118F/I119E/V120I/T121V/Q128M/G129D/D130Q/K131T/F132I/C134L/K140N/C141N/D143S/G152S/P155C/S156N/F 162Y/S163A/Q166K/K169N/E172D/S173A/V175/N180K/S219A/I220N/K223D/D257E/Q273G/Q277E/R281A/V282M/D285V/V288A/I292V/V299P/L300N/N311D/I312V/Y313H/D314S/T315A/M317L/C318A/Y320L/I323L/A339V/T345E/P346F/E347D/F350A/S352G/A359T/F364L/R365I/A366K/L368A/K369E/L370I/E372D/D373G/D377A/A381D/W387Y/N388K/A393K/D394A/I396V/A397D/K399T/A400T/D401S/F402L/A403E/S404E/K407Q/A409V/E411T/K412H/G413S/V415P/T416V/A417-/S418-/L419M/S420Q/M426V/S429T/V434I/S437R/L438-; E2K/F3D/S5P/N6Y/I7V/G8P/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/

S92G/D94E/Y95F/Y96F/R101A/L103I/S104A/Y107G/
G108D/S109T/L110F/K111E/A112E/T113S/N114K/
D115K/Q116N/D118F/I119E/V120I/T121V/Q128M/
G129D/D130Q/K31T/F132I/C134L/K140N/C141N/
D143S/G152S/P155C/S156N/F162Y/S163A/Q166K/
K69N/E172D/S173A/V175I/N180K/N198D/M199L/
S219A/D257E/I292V/N311D/I312V/Y313H/D314S/
T315A/M317L/C318AIY320L/I323L/A339V/T345E/
P346F/E347D/F350A/S352G/A359I/F364L/R365I/
A366K/L368A/K369E/L370/E372D/D377A/A381D/
W387Y/N388K/A393K/D394A/I396V/A397D/K399T/
A400T/D401S/F402L/A403E/S404E/K407Q/A409V/
E411T/K412H/G413S/V415P/T416V/A417-/S418-/
L419M/S420Q/M426V/S429T/V434I/S437R/L438-; E2K/
F3Y/S5P/I7V/G8P/K9E/I10V/Q11K/Q13E/K16N/D19N/
L21F/S22A/N27D/P28A/E29N/E30K/I32V/N33A/R 38K/
L41C/K42R/M51L/G52C/G53A/D54G/T56A/M58P/
C61V/G62T/T64M/K66R/W68Y/Q70N/S71T/A74M/
A75E/R76L/A84G/I87L/D89T/S92G/D94E/Y95F/Y96F/
R101A/L103I/S104A/Y107G/G108D/S109T/L110F/
K111E/A112E/T113S/N114K/D115K/Q116N/D118

A74M/A75E/R76L/A84G/I87L/D89T/S92G/D94E/Y95F/
Y96F/R101A/L103I/S104A/Y107G/G108D/S109T/L110F/
K111E/A112E/T113S/N114K/D115K/Q116N/D118F/
I119E/V120I/T121V/Q128M/G129D/D130Q/K131T/
F132I/C134L/K140N/C141N/D143S/G152S/P155C/
S156N/F162Y/S 163A/Q166K/K169N/E172D/S173A/
V175I/N180K/R208G/S219A/I220N/K223D/Q273G/
Q277E/R281A/V282M/D285V/V288A/I292V/V299P/
L300N/N311D/I312V/Y313R/D314S/T315A/M317L/
C318A/Y320L/I323L/N334D/A339V/T345E/P346F/
E347D/F350A/S352G/A359T/F364L/R365I/A366K/
L368A/K369E/L370I/E372D/G374S/D377A/A381D/
W387Y/N388K/A393K/D394A/I396V/A397D/K399T/
A400T/D401S/F402L/A403E/S404E/K407Q/A409V/
E411T/K412H/G413S/V415P/T416V/A417-/S418-/
L419M/S420Q/G422S/M426V/S429T/V434I/S437R/
L438-; E2K/F3Y/S5P/I7V/G8P/K9E/I10V/Q11K/Q13E/
K16N/D19N/L21F/S22A/N27D/P28A/E29N/E30K/I32V/
N33A/R 38K/L41C/K42R/M51L/G52C/G53A/D54G/
T56A/M58P/C61V/G62T/T64M/K66R/W68Y/Q70N/
S71T/A74M/A75E/R76L/A84G/I87L/D89T/S92G/D94E/
Y95F/Y96F/R101A/L103/S104A/Y107G/G108D/S109T/
L110F/K111E/A112E/T113S/N114K/D115K/Q116N/
D118F/I119E/V120I/T121V/Q128M/G129D/D130Q/
K131T/F132I/C134L/K140N/C141N/D143S/G152S/P155C/
S156N/F162Y/S163A/Q166K/K169N/E172D/S173A/
V175I/N180K/N198D/M199L/Q273G/Q277E/R281A/
V282M/D285V/V288A/I292V/V299P/L300N; E2K/F3Y/
S5P/I7V/G8P/K9E/I10V/Q11K/Q13E/K16N/D19N/L21F/
S22A/N27D/P28A/E29N/E30K/I32V/N33A/R38K/L41C/
K42R/M51L/G52C/G53A/D54G/T56A/M58P/C61V/
G62T/T64M/K66R/W68Y/Q70N/S71T/A74M/A75E/
R76H/A84G/I87L/D89T/S92G/D94E/Y95F/Y96F/R101A/
L103I/S104A/Y107G/G108D/S109T/L110F/K111E/
A112E/T113S/N114K/D115K/Q116N/D118F/I119E/
V120I/T121V/Q128M/G129D/D130Q/K131T/F132I/
C134L/K140N/C141N/D143S/G152S/P155C/S156N/
F162Y/S163A/Q166K/K169N/E172D/S173A/V175I/N8K/
K223D/Q273G/T275S/V282I/A283S/R284S/D285I/
V288M/F

A75E/R76L/A84G/I87L/D89T/S92G/D94E/Y95F/Y96F/
R101A/L103I/S104A/Y107G/G108D/S109T/L110F/
K111E/A112E/T113S/N114K/D115K/Q116N/D118F/
I119E/V120I/T121V/Q128M/G129D/D130T/K31T/F132I/
C134L/K140N/C141N/D143S/G152S/P155C/S156N/
F162Y/S163A/Q166K/K169N/E172D/S173A/V175I/
N180K/K223D/G249A/D257E/Q273G/Q277E/R281A/
V282M/D285V/V288A/I292V/V299P/L300N/N311D/
I312V/Y313H/D314S/T315A/M317L/C318A/Y320L/
I323L/T345E/P346F/E347F/F350A/S352G/A359T/F364L/
R365I/A366K/L368A/K369E/L370I/E372D/D377A/
A381D/W387Y/N388K/A393K/D394A/I396V/A397D/
K399T/A400T/D401S/F402L/A403E/S404E/K407Q/
A409V/E411T/K412H/G413S/V415P/T416V/A417-/
S418-/L419M/S420Q/M426V/S429T/V434I/S437R/L438-;
E2K/F3Y/S5P/I7V/G8P/K9E/I10V/Q11K/Q13E/K16N/
D19N/L21F/S22A/N27D/P28A/E29N/E30K/I32V/N33A/R
38K/K42P/L45M/S46A/T50N/M51L/G52C/G53A/D54A/
C61R/G62D/T64A/T67S/W68F/Q70E/S71K/D72G/P73S/
A74M/A75E/R76H/A84G/I87F/D89E/S92G/D94K/Y96F/
R101V/S104A/Y107A/G108C/S109D/L110I/A112E/
D115S/Q116R/I119E/V120I/T121S/K125L/Q128K/
D130T/K131D/F132I/K140N/C141M/D143S/H144N/
M148V/H149N/T153S/S154T/P155N/F160Y/A161C/
S163A/E172D/S173I/N18R/N198D/M199L/S219A/
T236A/T244A/V247A/L248I/K253Q/M262L/Q273G/
T275S/V282I/A283S/R284S/D285/V288M/F289L/I292V/
V299M/Q307E/T310F/N311D/I312V/I323L/A325N/
F328L/N330-/L333F/A339N/G342P/F344Y/P346Y/
I349M/S352G/Y353F/A355L/A359S/F364L/R365I/
A366K/L368A/D373E/R375T/I376L/K378N/V380I/
A381K/D382E/A385K/W387F/N388E/T389S/G390E/
A393K/D394K/I396R/A397S/G398K/K399S/D401S/
F402L/A403Q/S404E/E406A/K407A/L410E/K412M/
E414-/V415A/T416P/S418M/L419P/S420G/M426Y/
E428Q/S429A/I430A/V431L/N433Q/V434N/S437E/
L438V; E2K/F3Y/S5P/I7V/G8P/K9E/I10V/Q11K/Q13E/
K16N/D19N/L21F/S22A/N27D/P28A/E29N/E30K/I32V/
N33A/R 38K/L41C/K42R/M51L/G52C/G53A/D54G/
T56A/M58P/C61V/G62D/T64V/K66R/W68Y/Q70N/S71T/
A74M/A75E/R76L/A84G/I87L/D89T/S92G/D94E/Y95F/
Y96F/R101A/L103/S104A/Y107G/G108D/S109T/L110F/
K111E/A112E/T113S/N114K/D115K/Q116N/D118F/
I119E/V120I/T121V/Q128M/G129D/D130Q/K31T/F132I/
C134L/K140N/C141N/D143S/G152S/P155C/S156N/
F162Y/S163A/Q166K/K169N/E172D/I173A/V175/
N180K/S219A/I122N/K223D/T236M/D257E/Q273G/
Q277E/R281A/V282M/D285V/V288A/I292V/V299P/
L300N/N311D/I312V/Y313H/D314S/T315A/M317L/
C318A/Y320L/I323L/A339V/A359T/F364L/R365I/
A366K/L368A/K369E/L370I/E372D/D377A/A

C61V/G62T/T64M/K66R/W68Y/Q70N/S71T/A74M/
A75E/R76L/A84G/I87L/D89T/S92G/D94E/Y95F/Y96F/
R101A/L103I/S104A/Y107G/G108D/S109T/L110F/
K111E/A112E/T113S/N114K/D115K/Q116N/D118F/
I119E/V120I/T121V/Q128M/G129D/D130Q/K31T/F132I/
C134L/K140N/C1416NS/G152S/F162Y/S163A/Q166K/
K169N/E172D/S173A/V175I/N180K/S219A/I220N/
K223D/G249A/N311D/I312V/Y313H/D314S/T315A/
M317L/C318A/Y320L/I323L/A339V/T345E/P346F/
E347D/F350A/S352G/A359T/F364L/R365/A366K/
L368A/K369E/L370I/E372D/D377A/K378E/A381D/
W387Y/N388K/A393K/D394A/I396V/A397D/K399T/
A400T/D401S/F402L/A403E/S404E/K407Q/A409V/
E411T/K412H/G413S/V415P/T416V/A417-/S418-/
L419M/S420Q/M426V/S429T/V434I/S437R/L438-; S5K/
G8S/Q11P/Q13E/P15K/K 6D/D19N/S22A/E29D/N33D/
T36K/E39D/H40I/L41M/T64A/Q70E/S71N/D89Q/
Y96F/A 12D/D115A/E126A/G129D/D130E/K131T/
F132L/N180K/N198D/M199V/T244A/V247A/L248I/
K253Q/Q273G/T275S/V282I/A283S/R D285I/V288M/
F289L/I292V/N311D/I312V/Y313H/D314S/T315A/
M317L/C318A/Y320L/I323L/W387Y/N388K; E2K/F3Y/
S5P/I7V/G8P/K9E/I10V/Q11K/Q13E/K16N/D19N/L21F/
S22A/N27D/P28A/E29N/E30K/I32V/N33A/R38K/L41C/
K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103/S104A/Y107G/G108D/S109T/L110F/K111E/A112E/T113S/N114K/D115K/Q116N/D118F/I119E/V120I/T121V/Q128M/G129D/D130Q/K131T/F132I/C134L/K140N/D143S/G152S/P155C/S156N/F162Y/S163A/Q166K/K169N/E172D/S173A/V175I/N80K; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103/S104A/Y107G/G108D/S109T/L110F/K111E/A112E/T113S/N114K/D115K/Q116N/D118F/I119E/V120I/T121V/Q128M/G129D/D130Q/K131T/F132I/C134L/K140N/C141N/D143S/G152S/P155C/S156N/F162Y/S163A/Q166K/K69N/E172D/S173A/V 175/N180K/N198D/M199L/V247A/L248I/K253Q/Q273G/Q277E/R281A/V282M/D285V/V288A/N311D/I312V/Y313H/D314S/T315A/M317L/C318A/M319T/Y320L/I323L/A339V/T345E/P346F/E347D/F350A/S352G/A359T/F364L/R365I/A366K/L368A/K369E/L370I/E372D/D377A/A381D/W387Y/N388K/A393K/D394A/I396V/A397D/K399T/A400T/D401S/F402L/A403E/S404E/K407Q/A409V/E411T/K412H/G413S/V415P/T416V/A417-/S418-/L419M/S420Q/M426V/S429T/V434I/S437R/L438-; E2K/F3Y/S5P/I7V/G8P/K9E/I10V/Q11K/Q13E/K16N/D19N/L21F/S22A/N27D/P28A/E29N/E30K/I32V/N33A/R 38K/L41C/K42R/M51L/G52C/G53A/D54G/T56A/M58P/C61V/G62T/T64V/K66R/W68Y/Q70N/S71T/A74M/A75E/R76L/A84G/I87L/D89T/S92G/D94E/Y95F/Y96F/R101A/L103/S104A/Y107G/G108D/S109T/L110F/K111E/A112E/T113S/N114K/D115K/Q116N/D118F/I119E/V120I/T121V/Q128M/G129D/D130Q/K131T/F132I/C134L/K140N/C141N/D143S/G152S/P55C/S156N/F162Y/S163A/Q166K/K169N/E172D/S173A/V175/N180K/K253Q/Q273G/T275S; E2K/F3Y/S5P/I7V/G8P/K9E/I10V/Q11K/Q13E/K16N/D19N/L21F/S22A/N27D/P28A/E29N/E30K/I32V/N33A/R 38K/L41C/K42R/M51L/G52C/G53T/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103/S104A/E106G/Y107G/G108D/S109T/L110F/K 111E/A112E/T113S/N114K/D115K/Q116N/D118F/I119E/V120I/T121V/Y123H/Q128M/G129D/D130Q/K131T/F 132I/C134L/K14N/C141N/D143S/G152S/P155C/S156N/F162Y/S163A/Q166K/K169N/E172D/S173A/V175I/N180K/G249A/D257E/Q273G/Q277E/R281A/V282M/D285V/V288A/I292V/V299P/L300N/N311D/I312V/Y313H/D 314S/T315A/M317L/C318A/Y320L/I323L/A339V/T345E/P346F/E347D/F350A/S352G/A359T/F364L/R365I/A366K/L368A/K369E/L370I/E372D/D377A/A381D; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D115K/Q116N/D118F/I119E/V120I/T121V/Q128M/G129D/D130Q/K31T/F132I/C134L/K140N/C141N/D143S/G152S/P55C/S56N/F162Y/S163A/Q166K/K169N/E167D/S173A/V175I/N198D/M199L/S219A/I220N/K223D/G249A/D257E/I292V/V299P/L300N/N311D/I312V/Y313H/D314S/T315A/M317L/C318A/Y320L/I323L/A339V/T345E/P346F/E347D/F350A/S352G/A359T/F364L/R365I/A366K/L368A/K369E/L370I/E372D/D377A/A381D/W387Y/N388K/A393K/D394A/I396V/A397D/K399T/A400T/D401S/F402L/A403E/S404E/K407Q/A409V/E411T/K412H/G413S/V415P/T416V/A417-/S418-/L419M/S420Q/M426V/S429T/V434I/S437R/L438-; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D115K/Q116N/D118F/I119E/V120I/T121V/Q128M/G129D/D130Q/K31T/F132I/C134L/K140N/C141N/D143S/G152S/P155C/F162Y/S163A/Q166K/K69N/E172D/S173A/V175/N180K/N198D/M199L/V299P; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D115K/Q116N/D118F/I119E/V120I/T121V/Q128M/G129D/D130Q/K131T/F132I/C134L/K140N/D143S/G152S/P155C/S156N/F162Y/S163A/Q166R/K169N/E172D/S173A/V175/N180K/N198D/M199L/T236M/I244A/V299P/L300N/N311D/I312V/Y313H/D314S/T315A/M317L/C318A/Y320L/I323L/A339V/T345E/P346F/E347D/F350A/S352G/A359T/F364L/R365I/A366K/L368A/K369E/L370I/E372D/D377A/A381D/W387Y/N388K/A393K/D394A/I396V/A397D/K399T/A400T/D401S/F402L/A403E/S404E/K407Q/A409V/E411T/K412H/G413S/V415P/T416V/A417-/S418-/L419M/S420Q/M426V/S429T/V434I/S437R/L438-; E2K/F3Y/S5P/I7V/G8P/K9E/I10V/Q11K/Q13E/K16N/D19N/L21F/S22A/N27D/P28A/E29N/E30K/I32V/N33A/R38K/L41C/K42R/M51L/G52C/G53A/D54G/T56A/M58P/C61V/G62T/T64M/K66R/W68Y/Q70N/S71T/A74M/A75E/R76L/A84G/I87L/D89T/S92G/D94E/Y95F/Y96F/R101A/L103I/S104A/Y107G/G108D/S109T/L110F/K111E/A112E/T113S/N114K/D115K/Q116N/D118F/I119E/V120I/T121V/Q128M/G129D/D130Q/K131T/F132I/C134L/K140N/C141N/D143S/G152S/P155C/

S156N/F162Y/S163A/Q166K/K69N/E172D/S173A/V175/
N180K/V183A/N198D/M199L/S219A/I220N/D257E/
N311D/I312V/Y313H/D314S/T315A/M317L/C318A/
Y320L/I323L/A339V/T345E/P346F/E347D/F350A/
S352G/A359T/F364L/R365I/A366K/L368A/K369E/
L370I/E372D/D377A/A381D/W387Y/N388K/A393K/
D394A/I396V/A397D/K399T/A400T/D401S/F402L/
A403E/S404E/K407Q/A409V/E411T/K412H/G413S/
V415P/T416V/A417-/S418-/L419M/S420Q/M426V/
S429T/V434I/S437R/L438-;  E372G;  S5K/G8S/Q11P/
Q13E/P15K/K16D/D19N/S22A/E29D/N33D/T36K/E39D/
H40I/L41M/T64A/Q70E/S71N/D89Q/Y96F/A  112D/
D115A/E126A/G129A/D130E/K131T/F132L/N180T/
N198D/M199L/S219A/I220N/T236M/G249A/D257E/
Q273G/Q277E/R281A/V282M/D285V/V288A/I292V/
N311D/I312V/Y313H/D314S/T315A/M317L/C318A/
Y320L/I323L/A339V/T345E/P346F/E347D/F350A/
S352G/A359T/F364L/R365I/A366K/L368A/K369E/
L370I/E372D/D377A/A381D/W387Y/N388K/A393K/
D394A/I396V/A397D/K399T/A400T/D401S/F402L/
A403E/S404E/K407Q/A409V/E411T/K412H/G413S/
V415P/T416V/A417-/S418-/L419M/S420Q/M426V/
S429T/V434I/S437R/L438-;  E2K/F3Y/S5P/I7V/G8P/K9E/
I10V/Q11K/Q13E/K16N/D19N/L21F/S22A/N27D/P28A/
E29N/E30K/I32V/N33A/R 38K/L41C/K42R/M51L/G52C/
G53A/D54G/T56A/M58P/C61V/G62T/T64M/K66R/
W68Y/Q70N/S71T/A74M/A75E/R76L/A84G/I87L/D89T/
S92G/D94E/Y95F/Y96F/R101A/L103I/S104A/Y107G/
G108D/S109T/L110F/K111E/A112E/T113S/N114K/
D115K/Q116N/D118F/I119E/V120I/T121V/Q128M/
G129D/D130Q/K131T/F132I/C134L/K140N/C141N/
D143S/G152S/P155C/S156N/F162Y/S163A/Q166K/
K69N/E172D/S173A/V175/N180K/N98D/M199L/Q273G/
Q277E/R281A/V282M/D285V/V288A/I292V/V299P/
L300N/N311D/I312V/Y313H/D314S/T315A/M317L/
C318A/Y320L/I323L/F328L/A339V/T345E/P346F/
E347D/F350A/S352G/A359T/F364L/R365I/A366E/
L368A/K369E/L370I/W387Y/N388K/A393K/D394A/
I396V/A397D/K399T/A400T/D401S/F402L/A403E/
S404E/K407Q/A409V/E411T/K412H/G413S/V415P/
T416V/A417-/S418-/L419M/S420Q/M426V/S429T/
V434I/S437R/L438-;  E2K/F3Y/S5P/I7V/G8P/K9E/I10V/
Q11K/Q13E/K16N/D19N/L21F/S22A/N27D/P28A/E29N/
E30K/I32V/N33A/R38K/L41C/K42R/M51L/G52C/G53A/
D54G/T56A/M58P/C61V/G62T/T64M/K66R/W68Y/
Q70N/S71T/A74M/A75E/R76H/A84G/I87L/D89T/S92G/
D94E/Y95F/Y96F/R101A/L103/S104A/Y107G/G108D/
S109T/L110F/K111E/A112E/T113S/N114K/D115K/
Q116N/D118F/I119E/V120I/T121V/Q128M/G129D/
D130Q/K31T/F132I/C134L/K140N/C141N/D143S/
G152S/P55C/S156N/F162Y/S163A/Q166K/K69N/E172D/
S173A/V175/N180K/V288M/F289L/I292V; and/or E2K/
F3Y/S5P/I7V/G8P/K9E/I10V/Q11K/Q13E/K16N/D19N/
L21F/S22A/N27D/P28A/E29N/E30K/I32V/N33A/R38K/
L41C/K42R/M51L/G52C/G53A/D54G/T56A/M58P/
C61V/G62T/T64V/K66R/W68Y/Q70N/S71T/A74M/
A75E/R76L/A84G/I87L/D89T/S92G/D94E/Y95F/Y96F/
R101A/L103/S04A/Y107G/G108D/S109T/L110F/K111E/
A112E/T113S/N114K/D115K/Q116N/D118F/I119E/
V120I/T121V/Q128M/G129D/D130Q/K131T/F132I/
C134L/K140N/C141N/D143S/G152S/P55C/S156N/
F162Y/S163A/Q166K/K169N/E172D/S173A/V175/N8K/
K253Q/Q273G/T275S, wherein the positions are numbered by correspondence with the amino acid sequence set forth in SEQ ID NO:2.

The present invention also provides isolated chimeric xylose variants, wherein the variants are mature forms having xylose isomerase activity and comprise at least one insertion set selected from: 131G132/436G437; 1S2/69L70/127M128/436G437; 2N3/69L70/127M128/436G437; 2S3/70I71/131G132; and/or 2Y3/70I71/131G132, wherein the positions are numbered by correspondence with the amino acid sequence set forth in SEQ ID NO:2.

The present invention further provides isolated chimeric xylose isomerase variants, wherein the variants are mature forms having xylose isomerase activity and comprise about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% sequence identity to SEQ ID NO:2.

In some embodiments, the isolated chimeric xylose isomerase variants provided herein are mature forms having xylose isomerase activity and comprise at least one mutation and/or mutation set in the polynucleotide sequence encoding the variants, wherein the at least one mutation and/or mutation set comprises positions selected from 27/30/42/51/54/
60/63/69/72/75/78/114/126/129/133/135/138/147/156/159/
177/180/195/201/207/216/222/225/234/237/249/252/255/
261/271/273/274/275/306/307/309/318/321/324/327/333/
339/342/349/360/366/381/384/399/403/405/411/420/426/
429/432/435/438/453/456/466/467/468/471/477/483/486/
489/495/501/510/511/513/534/537/552/570/573/576/579/
580/583/600/601/603/607/625/627/642/645/648/663/684/
687/693/696/705/714/717/726/738/741/744/747/751/753/
756/765/766/771/792/804/807/810/811/816/822/825/834/
837/840/846/849/852/858/885/894/903/906/912/915/921/
924/927/936/954/960/963/966/969/975/987/993/996/999/
1011/1018/1020/1023/1029/1035/1038/1054/1055/1083/
1089/1098/1107/1108/1110/1113/1119/1125/1131/1137/
1146/1149/1155/1182/1185/1194/1200/1209/1215/1218/
1221/1233/1239/1242/1245/1248/1254/1266/1272/1275/
1279/1281/1284/1287/1293/1308/1312/1314;  27/30/42/51/
54/60/63/69/72/75/78/114/126/129/133/135/138/147/156/
159/177/180/195/201/207/216/222/225/234/237/249/252/
255/261/271/273/274/275/306/307/309/318/321/324/327/
333/339/342/349/360/366/381/384/399/403/405/411/420/
426/429/432/435/438/453/456/466/467/468/471/477/483/
486/489/495/501/510/511/513/534/537/552/570/573/576/
579/580/583/600/601/603/607/625/627/642/645/648/663/
684/687/693/696/705/741/744/747/751/753/756/765/766/
771/792/804/807/810/811/816/822/825/834/837/840/846/
849/852/858/885/894/903/906/912/915/921/924/927/936/
954/960/963/966/969/975/987/993/996/999/1011/1018/
1020/1023/1029/1035/1038/1054/1055/1083/1089/1098/
1107/1108/1110/1113/1119/1125/1131/1137/1146/1149/
1155/1182/1185/1194/1200/1209/1215/1218/1221/1233/
1239/1242/1245/1248/1254/1266/1272/1275/1279/1281/
1284/1287/1293/1308/1312/1314;  27/30/42/51/54/60/63/
69/72/75/78/114/126/129/133/135/138/147/156/159/177/
180/195/201/207/216/222/225/234/237/249/252/255/261/
271/273/274/275/306/307/309/318/321/324/327/333/339/
342/349/360/366/381/384/399/403/405/411/420/426/429/
432/435/438/453/456/466/467/468/471/477/483/486/489/
495/510/511/513/625/627/642/645/648/1047/1054/1055/
1095/1194/1200;  27/30/42/51/54/60/63/69/72/75/78/114/
126/129/133/135/138/147/156/159/177/180/195/201/207/
216/222/225/234/237/249/252/255/261/271/273/274/275/
306/307/309/318/321/324/327/333/339/342/349/360/366/
381/384/399/403/405/411/420/426/429/432/435/438/453/

456/466/467/468/471/477/483/486/489/495/501/510/511/ 513/534/537/705/714/717/726/738/741/744/747/751/753/ 756/765/766/771/1185/1224; 27/30/42/51/54/60/63/69/72/ 75/78/114/126/129/133/135/138/147/156/159/177/180/195/ 201/207/216/222/225/234/237/249/252/255/261/271/273/ 274/275/306/307/309/318/321/324/327/333/339/342/349/ 360/366/381/384/399/403/405/411/420/426/429/432/435/ 438/453/456/466/467/468/471/477/483/486/489/495/501/ 510/511/513/552/601/924/1263/1269; 27/30/42/51/54/60/ 63/69/72/75/78/114/126/129/133/135/138/147/156/159/ 177/180/195/201/207/216/222/225/234/237/249/252/255/ 261/271/273/274/275/306/307/309/318/321/324/327/333/ 339/342/349/360/366/381/384/399/403/405/411/420/426/ 429/432/435/438/453/456/466/467/468/471/477/483/486/ 489/495/783/1185/1224; 27/30/42/51/54/60/63/69/72/75/ 78/114/126/129/133/135/138/147/156/159/177/180/195/ 201/207/216/222/225/234/237/249/252/255/261/271/273/ 274/275/306/307/309/318/321/324/327/333/339/342/349/ 360/366/381/384/399/403/405/411/420/426/429/432/435/ 438/453/456/466/467/468/471/477/483/486/489/495/501/ 510/511/513/534/537/1185/1224; 120/279/510/1185/1224; 138/150/783/1143/1146/1155/1263/1269; 171/279/510/ 1185/1224; 207/279/510/1152/1185/1224; 207/279/510/ 1185/1224; 219/279/510/607/771/1185/1224; 279/328/330/ 510/642/645/648; 279/483/510; 279/483/510/567/1029/ 1185/1224; 279/483/510/606/1185/1224; 279/483/510/771/ 783/1173/1185/1224; 279/483/510/1185/1224/1266; 279/510; 279/510/570/573/576/579/580/583/600/601/603/ 607/625/627/642/645/648/663/771/783/1170/185/1224; 279/510/511/1023/1029/1035/1038/1054/1055/1095; 279/ 510/552/570/573/576/579/580/583/600/601/603/607/1185/ 1224; 279/510/552/625/627/1185/1224; 279/510/552/735/ 1185/1224; 279/510/552/1185/1224; 279/510/558/1185/ 1224; 279/510/570/573/576/579/580/583/600/601/603/607/ 625/627/642/645/648/663/771/783/1170/1185/1224; 279/ 510/570/1185/1224; 279/510/580/1185/1224; 279/510/600/ 601/603/607/625/627/642/645/648/1194/1200; 279/510/ 625/627/642/645/648/783/1011/1018/1020/1023/1054/ 1055/1233/1239/1242; 279/510/625/627/696; 279/510/642/ 645/648/663/1185/1224; 279/510/657/783; 279/510/663/ 1054/1055/1194/1200; 279/510/675/1185/1224/1269; 279/ 510/684/687/978; 279/510/684/792/1185/1224; 279/510/ 705/1185/1224; 279/510/726; 279/510/783/1053/1185/ 1224; 279/510/783/1020/1185/1224; 279/510/783/1128/ 1185/1224; 279/510/783/1185/1224; 279/510/792; 279/510/ 873; 279/510/885/894/903/906/912/915/921/924/927/936/ 954/1035/1038; 279/510/906/1185/1224; 279/510/990/ 1185/1224; 279/510/1023/1185/1224; 279/510/1086; 279/ 510/1113/1185/1224; 279/510/1122/1185/1224; 279/510/ 1185/1224; 585/642/783/924/1263/1269; 783; 783/924/ 1263/1269; 924; 1185/1224; and/or 1255, wherein the positions are numbered by correspondence with the nucleotide sequence set forth in SEQ ID NO: 1.

In some embodiments, the isolated chimeric xylose isomerase variants provided herein are mature forms having xylose isomerase activity and comprise at least one mutation and/or mutation set in the polynucleotide sequences encoding the variants, wherein the at least one mutation and/or mutation set comprises mutation(s) and/or mutation sets selected from:

a27/c30/t42/c51/a54/t60/g63/t69/a72/t75/t78/g114/a126/ c129/c133/a135/c138/c147/t156/c159/c177/a180/c195/ c201/t207/c216/g222/a225/g234/c237/t249/t252/c255/t261/ c271/g273/a274/g275/c306/c307/t309/a318/t321/c324/ c327/a333/c339/t342/c349/t360/t366/g381/g384/t403/ a405/c411/a420/t426/t429/c432/c435/g438/a453/a456/ a466/g467/t468/c471/t477/t483/t486/t489/g495/a501/a510/ t511/a513/c534/t537/t552/t570/c573/g576/c579/c580/c583/ c600/t601/a603/c607/c625/a627/a642/a645/c648/a663/ c684/g687/a693/c696/t705/c714/g717/c726/c738/a741/ a744/t747/t751/a753/g756/g765/t766/t771/c792/c804/c807/ a810/c811/a816/c822/a825/t834/g837/a840/g846/t849/ g852/c858/c885/c894/a903/a906/c912/g915/a921/c924/ c927/t936/t954/t960/g963/c966/t969/c975/a987/c993/c996/ g999/g1011/c1118/t1020/g1023/a1029/g1035/t0358/a1054/ g1055/g1083/g1089/a1098/a1107/t1108/g1110/t1113/ c1119/a1125/c1131/t1137/c1146/g1149/c1155/t1182/ t1185/a1194/c1200/a1209/g1215/a1218/a1221/a1233/ t1239/a1242/t1245/c1248/a1254/t1266/a1272/g1275/ c1279/g1281/a1284/t1287/c1293/t1308/t1312/g1314; a27/ c30/t42/c51/a54/t60/g63/t69/a72/t75/t78/g114/a126/c129/ c133/a135/c138/c147/t156/c159/c177/a180/c195/c201/ t207/c216/g222/a225/g234/c237/t249/t252/c255/t261/c271/ g273/a274/g275/c306/c307/t309/a318/t321/c324/c327/ a333/c339/t342/c349/t360/t366/g381/g384/g399/t403/a405/ c411/a420/t426/t429/c432/c435/g438/a453/a456/a466/ g467/t468/c471/t477/t483/t486/t489/g495/a501/a510/t511/ a513/c534/t537/t552/t570/c573/g576/c579/c580/c583/c600/ t601/a603/c607/c625/a627/a642/a645/c648/a663/c684/ g687/a693/c696/t705/a741/a744/t747/t751/a753/g756/ g765/t766/t771/c792/c804/c807/a810/c811/a816/c822/ a825/t834/g837/a840/g846/t849/g852/c858/c885/c894/ a903/a906/c912/g915/a921/c924/c927/t936/t954/t960/ g963/c966/t969/c975/a987/c993/c996/g999/g1011/c1018/ t1020/g1023/a1029/g1035/t1038/a1054/g1055/g1083/ g1089/a098/a1107/t11108/g1110/t1113/c1119/a1125/ c1131/t1137/c1146/g1149/c1155/t1182/t1185/a1194/ c1200/a1209/g1215/a1218/a1221/a1233/t1239/a1242/ t1245/c1248/a1254/t1266/a1272/g1275/c1279/g1281/ a1284/t1287/c1293/t1308/t1312/g1314; a27/c30/t42/c51/ a54/t60/g63/t69/a72/t75/t78/g114/a126/c129/c133/a135/ c138/c147/t156/c159/c177/a180/c195/c201/t207/c216/ g222/a225/g234/c237/t249/t252/c255/t261/c271/g273/ a274/g275/c306/c307/t309/a381/t321/c324/c327/a333/ c339/t342/c349/t360/t366/g381/g384/g399/t403/a405/c411/ a420/t426/t429/c432/c435/g438/a453/a456/a466/g467/ t468/c471/t477/t483/t489/g495/a510/t5111/a513/c625/ a627/a642/a645/c648/t1047/a1054/g1055/a1095/a1194/ c1200; a27/c30/t42/c51/a54/t60/g63/t69/a72/t75/t78/g114/ a126/c129/c133/a135/c138/c147/t156/c159/c177/a180/ c195/c201/t207/c216/g222/a225/g234/c237/t249/t252/ c255/t261/c271/g273/a274/g275/c306/c307/t309/a381/ t321/c324/c327/a333/c339/t342/c349/t360/t366/g381/g384/ g399/t403/a405/c411/a420/t426/t429/c432/c435/g438/ a453/a456/a466/g467/t468/c471/t477/t483/t486/t489/g495/ a501/a510/t511/a513/c534/t537/t705/c714/g717/c726/c738/ a741/a744/t747/t751/a753/g756/g765/t766/t771/t1185/ t1224; a27/c30/t42/c51/a54/t60/g63/t69/a72/t75/t78/g114/ a126/c129/c133/a135/c138/c147/t156/c159/c177/a180/ c195/c201/t207/c216/g222/a225/g234/c237/t249/t252/ c255/t261/c271/g273/a274/g275/c306/c307/t309/a381/ t321/c324/c327/a333/c339/t342/c349/t360/t366/g381/g384/ g399/t403/a405/c411/a420/t426/t429/c432/c435/g438/ a453/a456/a466/g467/t468/c471/t477/t483/t4836/t489/ g495/a501/a510/t511/a513/t552/t601/c924/t1263/a1269; a27/c30/t42/c51/a54/t60/g63/t69/a72/t75/t78/g114/a126/ c129/c133/a135/c138/c147/t156/c159/c177/a180/c195/ c201/t207/c216/g222/a225/g234/c237/t249/t252/c255/t261/ c271/g273/a274/g275/c306/c307/t309/a381/t321/c324/ c327/a333/c339/t342/c349/t360/t366/g381/g384/g399/t403/ a405/c411/a420/t426/t429/c432/c435/g438/a453/a456/ a466/g467/t468/c471/t477/t483/t486/t489/g495/g783/ t1185/t1224; a27/c30/t42/c51/a54/t60/g63/t69/a72/t75/t78/ g114/a126/c129/c133/a135/c138/c147/t156/c159/c177/ a180/c195/c201/t207/c216/g222/a225/g234/c237/t249/
t252/c255/t261/c271/g273/a274/g275/c306/c307/t309/
a381/t321/c324/c327/a333/c339/t342/c349/t360/t366/g381/
g384/g399/t403/a405/c411/a420/t426/t429/c432/c435/
g438/a453/t456/a466/g467/t468/c471/t477/t483/t486/t489/
g495/a501/a510/t511/a513/c534/t537/t1185/t11224;  t120/
t279/a510/t1185/t1224;  c138/t150/g783/t1143/c1146/
c11155/t1263/a1269;  t171/t279/a510/t1185/t1224;  t207/
t279/a510/t1152/t1185/t1224;    t207/t279/a510/t1185/
t11224; a219/t279/a510/c607/t771/t1185/t1224; t279/t328/
g330/a510/a642/a645/c648;   t279/t483/a510;   t279/t483/
a510/a567/a1029 c51t/a54c/t60a/g63a/t69c/a72g/t75c/t78c/g114a/a126g/ c129t/c133t/a135g/c138t/c147t/t156a/c159t/c177t/a180c/ c195t/c201a/t207c/c216t/g222t/a225t/g234a/c237t/t249c/ t252a/c255t/t261c/c271t/g273a/a274t/g275c/c306t/c307t/ t309g/a318g/t321c/c324t/c327t/a333g/c339a/t342c/c349t/ t360c/t366c/g381a/g384a/g399a/t403c/a405t/c411t/a420g/ t426c/t429c/c432t/c435a/g438a/a453t/a456t/a466t/g467c/ t468a/c470g/t477c/t483a/t486c/t489a/g495t/a501c/a510t/ t511c/a513g/c534t/t537a/t11185c/t1224c; t120c/t279c/a510t/t1185c/t1224c; c138a/t150a/g783a/t1143g/c1146t/c1155a/t1263a/a1269g; t171c/t279c/a510t/t1185c/t1224c; t207c/t279c/a510t/t1152c/t1185c/t1224c; t207c/t279c/a510t/t1185c/t1224c; a219g/t279c/a510t/c607t/t771c/t1185c/t1224c; t279c/t328c/g330c/a510t/a642t/a645g/c648t; t279c/t483a/a510t; t279c/t483c/a510t/a567g/a1029t/t1185c/t1224c; t279c/t483c/a510t/a606g/t1185c/t1224c; t279c/t483a/a510t/t771c/g783a/t1173c/t1185c/t1224c; t279c/t483c/a510t/t1185c/t1224c/t1266c; t279c/a510t; t279c/a510t/t570a/c573t/g576a/c579g/c580t/c583t/c600a/t601c/a603t/c607t/c625t/a627g/a642t/a645g/c648t/a663t/t771c/g783a/t11170c/t1185c/t1224c; t279c/a510t/t511c/g1023a/a1029t/g1035t/t1038a/a1054t/g1055c/a1095g; t279c/a510t/t552c/t570a/c573t/g576a/c579g/c580t/c583t/c600a/t601c/a603t/c607t/t1185c/t1224c; t279c/a510t/t552c/c625t/a627g/t1185c/t1224c; t279c/a510t/t552c/t735c/t1185c/t1224c; t279c/a510t/t552c/t1185c/t11224c; t279c/a510t/t558c/t1185c/t1224c; t279c/a510t/t570a/c573t/g576a/c579g/c580t/c583t/c600a/t601c/a603t/c607t/c625t/a627g/a642t/a645g/c648t/a663t/t771c/g783a/t1170c/t1185c/t1224c; t279c/a510t/t570c/t1185c/t1224c; t279c/a510t/c580t/t1185c/t1224c; t279c/a510t/c600a/t601c/a603t/c607t/c625t/a627g/a642t/a645g/c648t/a 1194c/c1200t; t279c/a510t/c625t/a627g/a642t/a645g/c648t/g783a/g1011t/c1018a/t120a/g1023a/a1054t/g1055c/a1233g/t1239a/a1242g; t279c/a510t/c625t/a627g/c696a; t279c/a510t/a642t/a645g/c648t/a663t/t1185c/t1224c; t279c/a510t/t657c/g783a; t279c/a510t/a663t/a1054t/g1055c/a1194c/c1200t; t279c/a510t/c675t/t1185c/t1224c/a1269g; t279c/a510t/c684t/g687a/t978c; t279c/a510t/c684t/c792a/t1185c/t1224c; t279c/a510t/t705c/t1185c/t1224c; t279c/a510t/c726t; t279c/a510t/a753g/t1053c/t1185c/t1224c; t279c/a510t/g783a/t1020c/t1185c/t1224c; t279c/a510t/g783a/t1128c/t1185c/t1224c; t279c/a510t/g783a/t1185c/t1224c; t279c/a510t/c792a; t279c/a510t/t873c; t279c/a510t/c885t/c894t/a903g/a906t/c912t/g915a/a921g/c924t/c927t/t936c/t954c/g1035t/t1038a; t279c/a510t/a906g/t1185c/t1224c; t279c/a510t/t990c/t11185c/t1224c; t279c/a510t/g1023a/t1185c/t1224c; t279c/a510t/a1086g; t279c/a501t/t1113c/t1185c/t1224c; t279c/a510t/t1122g/t11185c/t1224c; t279c/a510t/t1185c/t1224c; g585a/a642g/g783a/c924t/t1263a/a1269g; g783a; g783a/c924t/t1263a/a1269g; c924t; t1185c/t1224c; and/or t1255c, wherein the positions are numbered by correspondence with the polynucleotide sequence set forth in SEQ ID NO:1.

The present invention also provides recombinant fungal host cells comprising polynucleotide sequences that encode a polypeptide that is capable of catalyzing the isomerization of D-xylose directly to D-xylulose, wherein the polynucleotide is a polynucleotide encoding a polypeptide comprising an amino acid sequence having at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to SEQ ID NO:23; 25, 27, 29, 31, and/or 33, or a polynucleotide that hybridizes under stringent hybridization conditions to the complement of a polynucleotide that encodes a polypeptide having the amino acid sequence of SEQ ID NO: 23; 25, 27, 29, 31, and/or 33. In some embodiments, the host cell comprises a polynucleotide sequence encoding a chimeric xylose isomerase variant as provided herein. In some embodiments, the host cell comprises at least one chimeric xylose isomerase variant as provided in Table 3-1. In some embodiments, the host cell comprises at least one chimeric xylose isomerase variant comprising at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% identity to at least one chimeric xylose isomerase variant provided in Table 3-1. In some embodiments, the host cell comprises a polynucleotide sequence comprising a recombinant nucleic acid construct as provided herein. In some embodiments, the polynucleotide is integrated into the host cell genome. In some embodiments, the host cell is a yeast cell. In some further embodiments, the host cell has had one or more native genes deleted from its genome. In some additional embodiments, the deletion results in one or more phenotypes including increased transport of xylose into the host cell, increased xylulose kinase activity, increased flux through the pentose phosphate pathway, decreased sensitivity to catabolite repression, increased tolerance to ethanol, increased tolerance to acetate, increased tolerance to increased osmolarity, increased tolerance to low pH, and/or reduced production of by-products, wherein comparison is made with respect to the corresponding host cell without the deletion(s). In yet some additional embodiments, the host cell is altered to overexpress one or more polynucleotides. In some further embodiments, the overexpression results in one or more phenotypes, including increased transport of xylose into the host cell, increased xylulose kinase activity, increased flux through the pentose phosphate pathway, decreased sensitivity to catabolite repression, increased tolerance to ethanol, increased tolerance to acetate, increased tolerance to increased osmolarity, increased tolerance to low pH, and/or reduced product of by products, wherein comparison is made to the corresponding unaltered host cell. In still additional embodiments, the host cell is capable of growth in a xylose-based culture medium. In some further embodiments, the host cell is capable of fermentation in a xylose-based culture medium. In some additional embodiments, the host cell is capable of faster growth in a xylose-based culture medium as compared to wild-type *Saccharomyces cerevisiae*. In still some further embodiments, the xylose-based culture medium is a product from a cellulosic saccharification process and/or a hemicellulosic feedstock.

The present invention also provides methods for producing a fermentation product, wherein the methods comprise: providing the recombinant host cell provided herein; providing a fermentation medium comprising xylose; and contacting the fermentation medium with the recombinant fungal host cell under conditions suitable for generating the fermentation product. In some embodiments, the methods further comprise the step of recovering the fermentation product. In some embodiments, the fermenting step is carried out under microaerobic or aerobic conditions, while in some alternative embodiments, the fermenting step is carried out under anaerobic conditions. In some embodiments, the fermentation product is at least one alcohol, fatty alcohol, fatty acid, lactic acid, acetic acid, 3-hydroxypropionic acid, acrylic acid, succinic acid, citric acid, malic acid, fumaric acid, succinic acid, amino acid, 1,3-propanediol, ethylene, glycerol, and/or a β-lactam. In some embodiments, the alcohol is ethanol, butanol, and/or a fatty alcohol. In some additional embodiments, the fermentation product is ethanol. In some further embodiments, the fermentation product is a fatty alcohol that is a C8-C20 fatty alcohol. In some embodiments, the fermentation medium comprises product from a saccharification process.

DESCRIPTION OF THE FIGURES

FIG. 2A depicts the pentose phosphate pathway (PPP). The substrates and products are shown. The enzymes are represented by numbers as follows: 6. Ribulose-5-phosphate 3-epimerase; 7. Transketolase (TKL1); 8. Transaldolase (TAL1); 9. Ribose-5-phosphate ketoisomerase (RKI1); 10. 6-phosphogluconate dehydrogenase (GND1); 11. 6-phosphogluconalactonase (SOL3); and 12. Glucose-6-phosphate-1-dehydrogenase (ZWF).

FIG. 2B depicts the pathway of glycolysis. The substrates and products are shown. The enzymes are represented by numbers as follows: 13. Hexokinase; 14. Phosphoglucose isomerase; 15. Phosphofructokinase; 16. Aldolase; 17. Triose phosphate isomerase; 18. Glyceraldehyde 3-phosphate dehydrogenase; 19. 3-Phosphoglycerate kinase; 20. Phosphoglyceromutase; 21. Enolase; and 22. Pyruvate kinase.

FIG. 2C depicts the metabolic pathway for converting pyruvate to ethanol. The substrates and products are shown. The enzymes are represented by numbers as follows: 23. Pyruvate decarboxylase; 24. Aldehyde dehydrogenase; and 25. Alcohol dehydrogenase.

DESCRIPTION OF THE INVENTION

Figure 1:
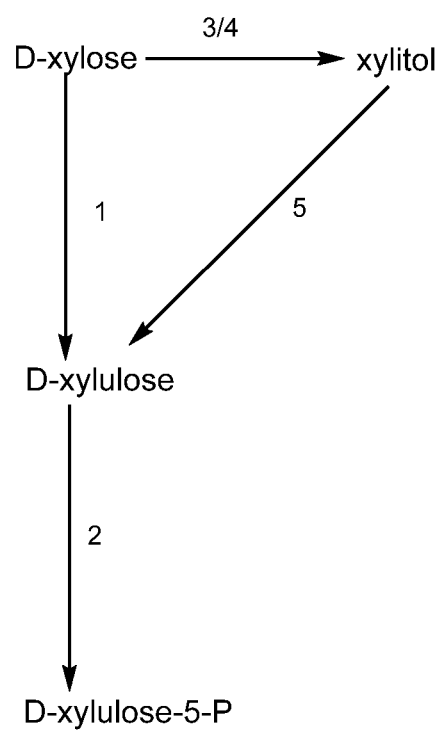
FIG. 1 depicts the two pathways for converting D-xylose to D-xylulose. In one pathway, the D-xylose can be converted to xylitol by xylose reductase (3) or aldoreductase (4). The xylitol can be further converted to D-xylulose with a xylulose reductase (5). In the second pathway, D-xylose is converted directly to D-xylulose with a xylose isomerase (1). The D-xylulose produced from either pathway—can be further converted to D-xylulose-5-P with a xylulokinase (2). The numbers in the figure correspond to the numbers in this description.

The present invention provides methods and compositions suitable for use in the isomerization of xylose to xylulose.

All patents and publications, including all sequences disclosed within such patents and publications, referred to herein are expressly incorporated by reference. Unless otherwise indicated, the practice of the present invention involves conventional techniques commonly used in molecular biology, fermentation, microbiology, and related fields, which are known to those of skill in the art. Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. Indeed, it is intended that the present invention not be limited to the particular methodology, protocols, and reagents described herein, as these may vary, depending upon the context in which they are used. The headings provided herein are not limitations of the various aspects or embodiments of the present invention.

Nonetheless, in order to facilitate understanding of the present invention, a number of terms are defined below. Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

As used herein, the term "comprising" and its cognates are used in their inclusive sense (i.e., equivalent to the term "including" and its corresponding cognates).

As used herein and in the appended claims, the singular "a", "an" and "the" include the plural reference unless the context clearly dictates otherwise. Thus, for example, reference to a "host cell" includes a plurality of such host cells.

Unless otherwise indicated, nucleic acids are written left to right in 5' to 3' orientation; amino acid sequences are written left to right in amino to carboxy orientation, respectively. The headings provided herein are not limitations of the various aspects or embodiments of the invention that can be had by reference to the specification as a whole. Accordingly, the terms defined below are more fully defined by reference to the specification as a whole.

As used herein, the terms "isolated" and "purified" are used to refer to a molecule (e.g., an isolated nucleic acid, polypeptide, etc.) or other component that is removed from at least one other component with which it is naturally associated.

As used herein, the term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide.

As used herein, the term "overexpress" is intended to encompass increasing the production (i.e., expression) of a protein to a level greater than the cell normally produces. It is intended that the term encompass overexpression of endogenous, as well as heterologous proteins.

For clarity, reference to a cell of a particular strain refers to a parental cell of the strain as well as progeny and genetically modified derivatives of the same. Genetically modified derivatives of a parental cell include progeny cells that contain a modified genome or episomal plasmids that confer for example, antibiotic resistance, improved fermentation capability, the ability to utilize xylose as a carbon source, etc.

As used herein "parent" refers to a starting cell, gene or protein. In some embodiments, "parental strains" are used as the starting point to develop additional strains (e.g., derivatives). In some additional embodiments, "parental molecules" (e.g., "parental enzymes") are used as starting points for evolution/modification to produce variant molecules (e.g., "variant enzymes," including "variant xylose isomerases").

As used herein, in reference to a specific sequence, the term "modification" encompasses any alteration in a parent amino acid sequence, including but not limited to at least one substitution, deletion, and/or insertion, as well as any change to any component of the sequence. The terms also encompasses any alteration in a parent nucleotide sequence, including but not limited to at least one substitution, deletion, insertion, and/or point mutation, etc., (e.g., any change to any component of the sequence). Thus, the term "modification" encompasses the term "mutation," in which a parent nucleotide sequence is altered through any means of mutagenesis.

A nucleic acid construct, nucleic acid (e.g., a polynucleotide), polypeptide, or host cell is referred to herein as "recombinant" when it is non-naturally occurring, artificial and/or engineered.

The terms "xylose isomerase" and "xylose isomerase polypeptide" are used interchangeably herein to refer to an enzyme that is capable of catalyzing the isomerization of D-xylose directly to D-xylulose. The ability to catalyze the isomerization of D-xylose directly to D-xylulose is referred to herein as "xylose isomerase activity". An exemplary assay for detecting xylose isomerase activity is provided in Example 2.

The terms "protein" and "polypeptide" are used interchangeably herein to refer to a polymer of amino acid residues. The term "xylose isomerase polynucleotide" refers to a polynucleotide that encodes a xylose isomerase polypeptide.

As used hereint, the term "xylose isomerase variant" refers to a xylose isomerase that has been modified from an original starting xylose isomerase. In some embodiments, the term is used in reference to a xylose isomerase polypeptide or polynucleotide encoding a xylose isomerase polypeptide comprising one or more modifications relative to wild-type xylose isomerase or the wild-type polynucleotide encoding xylose isomerase (such as substitutions, insertions, deletions, and/or truncations of one or more amino acid residues or of one or more specific nucleotides or codons in the polypeptide or polynucleotide, respectively), and biologically active fragments thereof. In some embodiments, the xylose isomerase variants are xylose isomerase chimeras.

The terms "xylose isomerase chimera," "xylose isomerase chimeric variant," and "chimeric xylose isomerase" refer to xylose isomerases that comprise sequences from at least two different xylose isomerase parent molecules. In some embodiments, the chimeras are hybrid proteins encoded by nucleotide sequences that have been spliced together from at least two genes. It is not intended that the present invention be limited to any specific number of starting (i.e., "parental" sequences). In some embodiments, the term "chimeric" refers to a nucleic acid, nucleotide sequence and/or encoded product thereof, that contains sequences from two or more different sources. It is contemplated that any suitable source will find use in the present invention, including but not limited to nucleic acid, nucleotide sequence, ribosomal nucleic acid, RNA, DNA, regulatory nucleotide sequences (e.g., promoter, URL, enhancer, repressor, etc.), coding nucleic acid, gene, nucleic acid linker, nucleic acid tag, amino acid sequence, peptide, polypeptide, protein, chromosome, and/or organism. In some embodiments, "chimeric" molecules include sequences of contiguous nucleotides or amino acids from any suitable source, including but not limited to viruses, prokaryotes, and/or eukaryotes, etc. In some embodiments, chimeras are generated by placing fragments of related and/or unrelated nucleic acids, nucleotide sequences, and/or DNA segments in juxtaposition. In some embodiments, the nucleic acids, nucleotide sequences and/or DNA segments are native (e.g., wild-type) sequences, while in other embodiments, they are mutant and/or engineered (e.g., recombinant) sequences. It is not intended that the present invention be limited to any particular starting component. In some embodiments, the chimera comprises sequences (e.g., 1, 2, 3, 4, 5, 6, 7, 8, 9, or 10 sequences) from one organism and sequences (e.g., 1, 2, 3, 4, 5, 6, 7, 8, 9, or 10 sequences) from another organism (e.g., as contiguous nucleotides or contiguous amino acids). In some embodiments, the organisms are microorganisms, including but not limited to bacteria, yeast, filamentous fungi, etc. In some embodiments, the sequences are obtained from at least two organisms of the same genus and/or species, but of different strains. In some other embodiments, the sequences are obtained from at least two organisms of the same species, while in some other embodiments, the sequence are obtained from at least two organisms of the same genus (i.e., different species). In some embodiments, the chimeras comprise a portion of a xylose isomerase from one bacterial species and at least one additional portion of a xylose isomerase from at least one additional bacterial species. In some embodiments, the chimeras comprise a portion of a xylose isomerase from one fungal species and at least one additional portion of a xylose isomerase from at least one additional fungal species. In some embodiments, the chimeras are comprised of sequences obtained from various types of organisms, for example combinations of bacterial and fungal species, as well as combinations of bacterial, fungal, viral, and/or plant species. Some embodiments of the present invention comprise one portion of a xylose isomerase from a plant, another portion of a xylose isomerase from a bacterium, and another portion of a xylose isomerase from a fungus. Indeed, it is intended that any combination of parental organisms will find use in the present invention. In some embodiments, the chimeric molecule comprises up to about 99% of sequence(s) from one organism (e.g., about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, or about 99%) and the balance percentage from one or more other organisms. In some embodiments, the chimeric molecules comprise altered codons (e.g., a chimeric nucleic acid) and one or more mutations (e.g., point mutations, nucleotide substitutions, insertions, deletions, etc.).

In some embodiments, the chimeras are produced by recombination of two or more nucleotide sequences. Any suitable method for recombination finds use in producing the chimeras of the present invention, including, but not limited to the methods described in more detail herein. In some embodiments, fragments used to generate chimeras are juxtaposed as units (e.g., nucleotide sequences from the various sources are combined end-to-end and are not interspersed). In some embodiments in which the chimeras include one stretch of contiguous nucleotides per each source organism, nucleotide sequence combinations can be noted as DNA source 1 (1DNA), DNA source 2 (2DNA), etc. (e.g., 1DNA/2DNA etc.), including combinations thereof. In some other embodiments, fragments used to generate the chimeras are interspersed (e.g., 1DNA/2DNA/4DNA/3DNA, etc.). In some embodiments, the nucleotide sequence length of the fragments used to generate chimeras is in the range of from about 5 base pairs to about 1300 base pairs (e.g., about 5 base pairs, about 10 base pairs, about 15 base pairs, about 20 base pairs, about base pairs, about 30 base pairs, about 35 base pairs, about 40 base pairs, about 45 base pairs, about 50 base pairs, about 55 base pairs, about 60 base pairs, about 65 base pairs, about 70 base pairs, about 75 base pairs, about 80 base pairs, about 85 base pairs, about 90 base pairs, about 95 base pairs, about 100 base pairs, about 105 base pairs, about 110 base pairs, about 115 base pairs, about 120 base pairs, about 125 base pairs, about 150 base pairs, about 175 base pairs, about 200 base pairs, about 225 base pairs, about 250 base pairs, about 300 base pairs, about 350 base pairs, about 400 base pairs, about 450 base pairs, about 500 base pairs, about 550 base pairs, about 600 base pairs, about 650 base pairs, about 700 base pairs, about 750 base pairs, about 800 base pairs, about 850 base pairs, about 900 base pairs, about 950 base pairs, about 1000 base pairs, about 1200 base pairs, about 1250 base pairs, or about 1300 basepairs. In some embodiments, the chimeric nucleotide sequence encodes the same activity as the activity encoded by the source nucleotide sequences. In some embodiments, the chimeric nucleotide sequence encodes activity higher than any of the source nucleotide sequences. In some alternative embodiments, the chimeric nucleotide sequences have similar or same activity as the source nucleotide sequences, but the amount of the activity or kinetics of the activity (e.g., increased or decreased activity), specific activity, and/or other aspects of the activity are altered. In some additional embodiments, the chimeric nucleotide sequences encode different activities and in some further embodiments, the chimeric nucleotide sequences encode chimeric activities (e.g., a combination of two or more activities).

In some embodiments, xylose isomerase polynucleotides employed in the practice of the present invention encode a polypeptide comprising an amino acid sequence that is at least about 30%, at least about 35%, at least about 40%, at least about 45%, at least about 50%, at least about 55%, at least about 60%, at least about 65%, at least about 70%, at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO: 2, 4, 6, 8, 10, 23, 25, 27, 29, 31, and/or 33, and/or a fragment of any of these sequences.

In some embodiments, xylose isomerase polynucleotides employed in the practice of the present invention comprise a polynucleotide sequence that is at least about 30%, at least about 35%, at least about 40%, at least about 45%, at least about 50%, at least about 55%, at least about 60%, at least about 65%, at least about 70% identical, at least about 71% identical, at least about 72% identical, at least about 73% identical, at least about 74% identical, at least about 75% identical, at least about 76% identical, at least about 77% identical, at least about 78% identical, at least about 79% identical, at least about 80% identical, at least about 81% identical, at least about 82% identical, at least about 83% identical, at least about 84% identical, at least about 85% identical, at least about 86% identical, at last about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO: 1, 3, 5, 7, 9, 22, 24, 26, 28, 30, and/or 32, and/or a fragment of any of these sequences.

The terms "percent identity," "% identity", "percent identical," and "% identical," are used interchangeably herein to refer to the percent amino acid or polynucleotide sequence identity that is obtained by ClustalW analysis (version W1.8 available from European Bioinformatics Institute, Cambridge, UK), counting the number of identical matches in the alignment and dividing such number of identical matches by the length of the reference sequence, and using the following ClustalW parameters to achieve slow/accurate pairwise optimal alignments—DNA/Protein Gap Open Penalty: 15/10; DNA/Protein Gap Extension Penalty:6.66/0.1; Protein weight matrix: Gonnet series; DNA weight matrix: Identity; Toggle Slow/Fast pairwise alignments=SLOW or FULL Alignment; DNA/Protein Number of K-tuple matches:2/1; DNA/Protein number of best diagonals: 4/5; DNA/Protein Window size:4/5.

Two sequences are "aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well known in the art (See, e.g., Dayhoff et al., in Dayhoff [ed.], *Atlas of Protein Sequence and Structure*," Vol. 5, Suppl. 3, Natl. Biomed. Res. Round., Washington D.C. [1978]; pp. 345-352; and Henikoff et al., Proc. Natl. Acad. Sci. USA, 89:10915-10919 [1992], both of which are incorporated herein by reference). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acid position of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm (e.g., gapped BLAST 2.0; See, Altschul et al., Nucleic Acids Res., 25:3389-3402 [1997], which is incorporated herein by reference), and made available to the public at the National Center for Biotechnology Information Website). Optimal alignments, including multiple alignments can be prepared using readily available programs such as PSI-BLAST (See e.g., Altschul et al., supra).

The present invention also provides a recombinant nucleic acid construct comprising a xylose isomerase polynucleotide sequence that hybridizes under stringent hybridization conditions to the complement of a polynucleotide which encodes a polypeptide having the amino acid sequence of SEQ ID NOS:2, 4, 6, 8, 10, 23, 25, 27, 29, 31, and/or 33, wherein the polypeptide is capable of catalyzing the isomerization of D-xylose directly to D-xylulose. An exemplary polynucleotide sequence that encodes a polypeptide having the amino acid sequence of SEQ ID NOS: 2, 4, 6, 8, 10, 23, 25, 27, 29, 31, or 33 is selected from SEQ ID NOS:1, 3, 5, 7, 9, 14, 15, 16, 17, 18, 19, 20, 21, 22, 24, 26, 28, 30, and/or 32.

In some embodiments, the polynucleotide that hybridizes to the complement of a polynucleotide which encodes a polypeptide having the amino acid sequence of SEQ ID NOS: 2, 4, 6, 8, 10, 23, 25, 27, 29, 31, and/or 33, does so under high or very high stringency conditions to the complement of a reference sequence encoding a polypeptide having the sequence of SEQ ID NOS: 2, 4, 6, 8, 10, 23, 25, 27, 29, 31, and/or 33 (e.g., over substantially the entire length of the reference sequence).

Nucleic acids "hybridize" when they associate, typically in solution. There are numerous texts and other reference materials that provide details regarding hybridization methods for nucleic acids (See e.g., Tijssen, *Laboratory Techniques in Biochemistry and Molecular Biology-Hybridization with Nucleic Acid Probes*," Part1, Chapter 2, Elsevier, N.Y., [1993], incorporated herein by reference). For polynucleotides of at least 100 nucleotides in length, low to very high stringency conditions are defined as follows: prehybridization and hybridization at 42° C. in 5×SSPE, 0.3% SDS, 200 µg/ml sheared and denatured salmon sperm DNA, and either 25% formamide for low stringencies, 35% formamide for medium and medium-high stringencies, or 50% formamide for high and very high stringencies, following standard Southern blotting procedures. For polynucleotides of at least 200 nucleotides in length, the carrier material is finally washed three times each for 15 minutes using 2×SSC, 0.2% SDS at least at 50° C. (low stringency), at least at 55° C. (medium stringency), at least at 60° C. (medium-high stringency), at least at 65° C. (high stringency), and at least at 70° C. (very high stringency).

The terms "corresponding to", "with reference to," and "relative to" when used in the context of the numbering of a given amino acid or polynucleotide sequence refers to the numbering of the residues of a specified reference sequence when the given amino acid or polynucleotide sequence is compared to the reference sequence.

The "position" is denoted by a number that sequentially identifies each amino acid in the reference sequence based on its position relative to the N-terminus. Owing to deletions, insertions, truncations, fusions, and the like that must be taken into account when determining an optimal alignment, in general the amino acid residue number in a test sequence determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence. As used herein, in referring to variants (e.g., variants with substitutions, insertions, and/or deletions), a hyphen indicates a deletion in a sequence and an asterisk indicates a mutation in a stop codon.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

A "conservative substitution," as used with respect to amino acids, refers to the substitution of an amino acid with a chemically similar amino acid. Amino acid substitutions which often preserve the structural and/or functional properties of the polypeptide in which the substitution is made are well known in the art. The most commonly occurring exchanges are isoleucine/valine, tyrosine/phenylalanine, aspartic acid/glutamic acid, lysine/arginine, methionine/leucine, aspartic acid/asparagine, glutamic acid/glutamine, leucine/isoleucine, methionine/isoleucine, threonine/serine, tryptophan/phenylalanine, tyrosine/histidine, tyrosine/tryptophan, glutamine/arginine, histidine/asparagine, histidine/glutamine, lysine/asparagine, lysine/glutamine, lysine/glutamic acid, phenylalanine/leucine, phenylalanine/methionine, serine/alanine, serine/asparagine, valine/leucine, and valine/methionine.

The following nomenclature finds use in describing substitutions in a reference sequence relative to a reference sequence or a variant polypeptide or nucleic acid sequence: "R-#-V," where "#" refers to the position in the reference sequence, "R" refers to the amino acid (or base) at that position in the reference sequence, and "V" refers to the amino acid (or base) at that position in the variant sequence. In some embodiments, an amino acid (or base) may be called "X," by which is meant any amino acid (or base). As a non-limiting example, for a variant polypeptide described with reference to SEQ ID NO:2, "E372G" indicates that in the variant polypeptide, the glutamic acid at position 372 of the reference sequence is replaced by glycine, with amino acid position being determined by optimal alignment of the variant sequence with SEQ ID NO:2. Similarly, "E372G/D" describes two variants: a variant in which the glutamic acid at position 372 of the reference sequence is replaced by glycine; and a variant in which the glutamic acid at position 372 of the reference sequence is replaced by aspartic acid.

As used herein, the terms "amino acid substitution set" and "substitution set" when used in the context of amino acid sequences (e.g., polypeptides) refer to a group of amino acid substitutions. In some embodiments, substitution set refers to the amino acid substitution sets present in some of the variant chimeric xylose isomerase variants provided in Table 3-1.

As used herein, the terms "amino acid mutation set" and "mutation set" when used in the context of amino acid sequences (e.g., polypeptides) refer to a group of amino acid substitutions, insertions, and/or deletions. In some embodiments, mutation set refers to the nucleic acid mutation sets present in some of the chimeric xylose isomerase variants provided in Table 3-1.

As used herein, the terms "nucleic acid substitution set" and "substitution set" when used in the context of nucleotide sequences (e.g., polynucleotides) refer to a group of nucleic acid substitutions. In some embodiments, mutation set refers to the nucleic acid substitution sets present in some of the variant chimeric xylose isomerase variants provided in Table 3-1.

As used herein, the terms "nucleic acid mutation set" and "mutation set" when used in the context of nucleotide sequences (e.g., polynucleotides) refer to a group of nucleic acid substitutions, insertions, and/or deletions. In some embodiments, mutation set refers to the amino acid mutation sets present in some of the chimeric xylose isomerase variants provided in Table 3-1.

As used herein, the term "by-product" refers to an organic molecule that is an undesired product of a particular fermentation process.

As used herein, the term "transformed" or "transformation" used in reference to a cell means that the cell has a non-native nucleic acid sequence integrated into its genome or has an episomal plasmid that is maintained through multiple generations.

DETAILED DESCRIPTION OF THE INVENTION

The present invention provides methods and compositions suitable for use in the isomerization of xylose to xylulose.

The initial metabolic pathways for xylose utilization in fungi and bacteria differ. In most fungi, including xylose-fermenting yeasts (e.g., *Pichia stipitis, Pachysolen tannophilus*, and *Candida shehatae*), D-xylose is converted to D-xylulose by two oxidoreductases involving cofactors NAD(P)H and NAD(P)$^+$. (See, Matsushika et al., Appl. Microbiol. Biotechnol., 84:37-53 [2009]). In these organisms, D-xylose is initially reduced to xylitol by NAD(P)H-dependent xylose reductase (XR) (EC 1.1.1.21). Xylitol is subsequently oxidized to D-xylulose by NAD+-dependent xylitol dehydrogenase (XDH) (EC 1.1.1.9). Xylulokinase (XK) (EC 2.7.1.17) subsequently phosphorylates D-xylulose to produce D-xylulose 5-phosphate (X5P), which is then further metabolized through the pentose phosphate pathway (PPP).

However, most strains of *S. cerevisiae* cannot utilize xylose even though the genes encoding XR, XDH, and XK are present in its genome, as the expression levels of these enzymes are too low to allow xylose utilization (See, Matsushika et al., supra). Some strains have been shown to natively utilize xylose but at very low rates and fermentation to ethanol has not been detected (See, Wenger et al., PLoS Genet., 6(5):e1000942 [2010]). Even when the endogenous genes are overexpressed in *S. cerevisiae*, only slow growth on xylose has been observed (See, Matsushika et al., supra).

In contrast, most bacteria (e.g., *Escherichia coli* and *Streptomyces* species) can isomerize D-xylose directly to D-xylulose by using a xylose isomerase (XI) (EC 5.3.1.5) (See, Matsushika et al., supra). In bacteria, as in fungi, the D-xylulose is phosphorylated to D-xylulose 5-phosphate by XK, which is then further metabolized through the pentose phosphate pathway.

Efforts to express a functional heterologous xylose isomerase gene (xylA) in *S. cerevisiae* and grow the yeast on xylose has met with very limited success (See e.g., Matsushika et al. supra). It has been reported that xylose isomerase genes from the fungi *Piromyces* (Kuyper et al. FEMS Yeast Res., 4:69-78 [2003]) and *Orpinomyces* (Madhaven et al., Appl. Microbiol. Biotechnol., 82:1067-1078 [2009a]) have been functionally expressed in *S. cerevisiae*, but that growth on xylose was very slow. In addition, the functional expression of the *Thermus thermophilus* xylose isomerase (Accession No. 1BXB) in *S. cerevisiae* has been reported (See, Walfridsson et al., Appl. Environ. Microbiol., 62:4648-4651 [1996]). The success in producing an active xylose isomerase by expressing the *T. thermophilus* xylA gene in *S. cerevisiae* may have been due to the relatedness between the two organisms, as *T. thermophilus* diverged from the domain of eubacteria and may, in many respects, be more closely related to *S. cerevisiae* than are the eubacteria (Id., at 4651).

Heterologous expression of xylose isomerase genes from *Actinoplanes missouriensis* and *Clostridium thermosulfurogenes* in *S. cerevisiae* generated inactive proteins, even though their messenger RNA could be detected (See, Amore et al., Appl. Microbiol. Biotechnol., 30:351-357 [1989]; and Moes et al., Biotech. Lett., 18:269-274 [1996]; and Matsushika et al., supra). Other studies report the heterologous expression of the xylA from *E. coli* (See e.g., Sarthy et al., Appl. Environ. Microbiol., 53:1996-2000 [1987]), *Bacillus subtilis* (Amore et al., Appl. Microbiol. Biotechnol., 30:351-357 [1989]), and *Streptomyces rubiginosus* (Girdonyi et al., Enzyme Microb. Technol., 32:252-259 [2003]) in *S. cerevisiae* resulted in mainly insoluble proteins which were catalytically inactive (See, Matsushika et al., supra). In addition, some reports indicate that attempts to produce xylose isomerase from recombinant *S. cerevisiae* transformed with the xylA genes from *Bacillus subtilis* and *Lactobacillus pentosus* resulted in inactive protein (See, Walfridsson et al., supra).

In further studies, the results of screening for xylose isomerase activity in *S. cerevisiae* transformed with the xylose isomerase genes from various organisms have been reported (See e.g., Brat et al., Appl. Environ. Microbiol. Doi: 10.1128/AEM.02522-9 [13 Feb. 2009]). The xylose isomerases have been reported to share from 17% to 60% sequence identity to the xylose isomerase from *Piromyces*. While transformants expressing the xylose isomerase from *Clostridium phytofermentans* (DSM 18823) could grow on xylose medium, *S. cerevisiae* transformed with the xylose isomerase gene from the following organisms could not: *Bacillus licheniformis* (DSM 13), *Burkholderia xenovaorans* (DSM 17367), *Lactobacillus pentosus* (DSM 20314), Leifsonia xyli subsp. *cynodontis* (DSM 46306), *Pseudomonas savastanoi* pvar. *Phaseolicola* (DSM 50282), *Robiginitalea biformata* (DSM 15991), *Saccharophagus degradans* (DSM 17024), *Staphylococcus xylosus* (DSM 20266), *Streptomyces diastaticus* subsp. *diastaticus* (DSM 40496), *Xanthomonas campestris* pvar. *campestris* (DSM 3586), *Salmonella typhimurium* (71-098L), *Agrobacterium tumefaciens*, and *Arabidopsis thaliana* (See, Brat et al., supra).

The present invention provides sequences that are capable of conferring the property of xylose-utilization in a non-mammalian, eukaryotic host cell, such as, for example, a fungal host cell. These sequences and variants thereof, encode xylose isomerases, which catalyze the isomerization of D-xylose directly to D-xylulose, as depicted in FIG. 1. Xylose isomerase is distinguished from xylose reductase (XD), which catalyzes the conversion of xylose to xylitol. Xylose isomerase is also distinguished from xylitol dehydrogenase (XD), which catalyzes the conversion of xylitol to D-xylulose (See, FIG. 1).

Figure 2A:
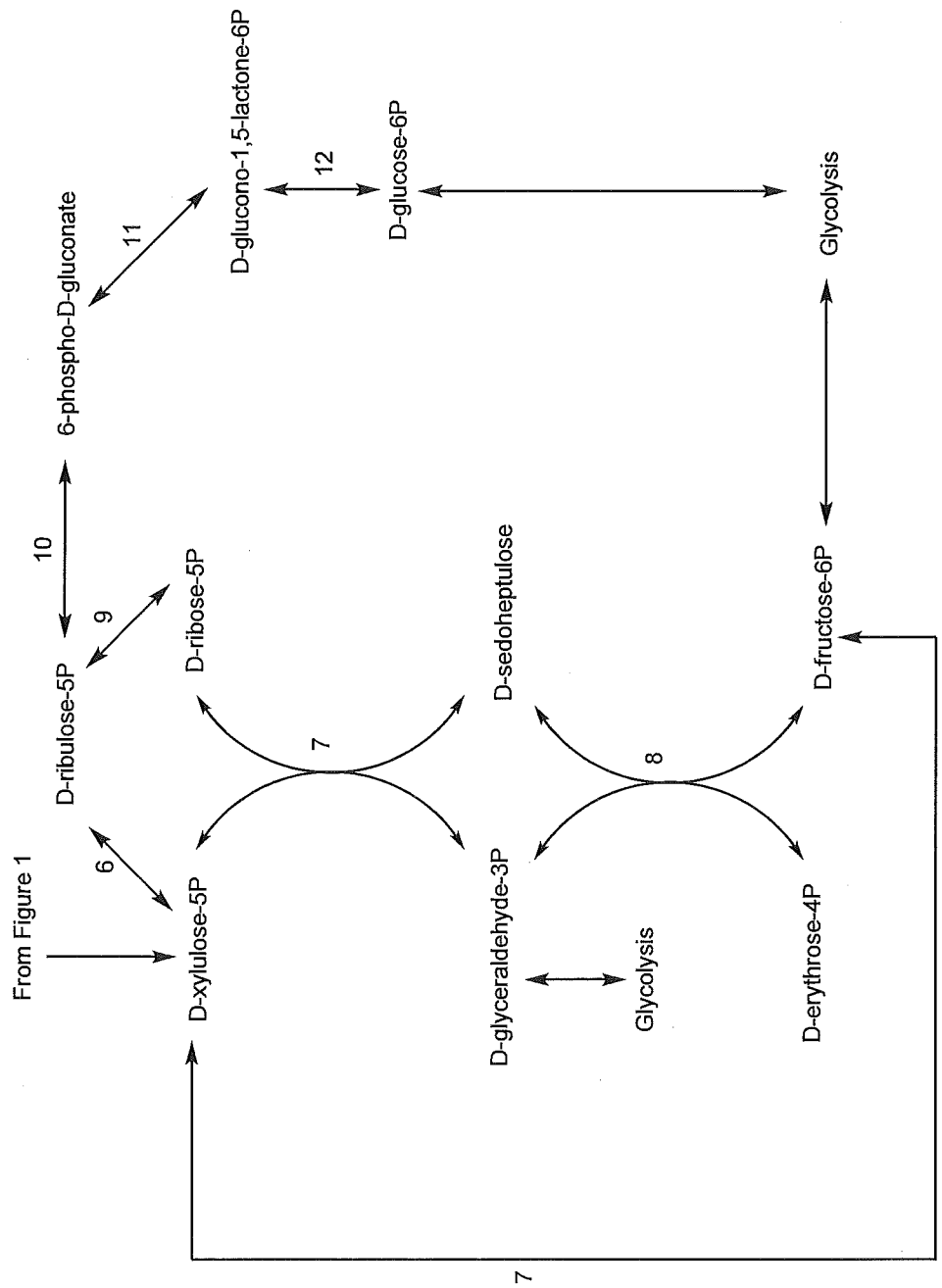
FIGS. 2A-C depict the metabolic pathways for converting D-xylulose-5-P to ethanol.

Xylose utilization by these host cells results in useful products that are produced metabolically by the host cell. In these host cells, D-xylulose may be phosphorylated by a native or recombinant xylulokinase to xylulose-5-P, as depicted in FIG. 1. The xylulose-5-P may be further metabolized by enzymes in the pentose phosphate pathway to products such as glucose-6-P, fructose-6-P, glyceraldehydes-3-P, and the like. The pentose phosphate pathway and relevant enzymes and products are depicted in FIG. 2A. As used herein, the terms "enzyme from the pentose phosphate pathway" and "pentose phosphate pathway enzyme" are used interchangeably to refer to an enzyme from the group of enzymes involved in the pentose phosphate pathway, (i.e., 6. Ribulose-5-phosphate ketoisomerase (RK11); 7. Transketolase (TKL1); 8. Transaldolase (TAL1); 9. Ribose-5-phosphate ketoisomerase (RK11); 10. 6-phosphogluconate dehydrogenase (GND1); 11. 6-phosphogluconalactonase (SOL3); and/or 12. Glucose-6-phosphate-1-dehydrogenase (ZWF); the reference numbers are depicted in FIG. 2A).

Figure 2B:
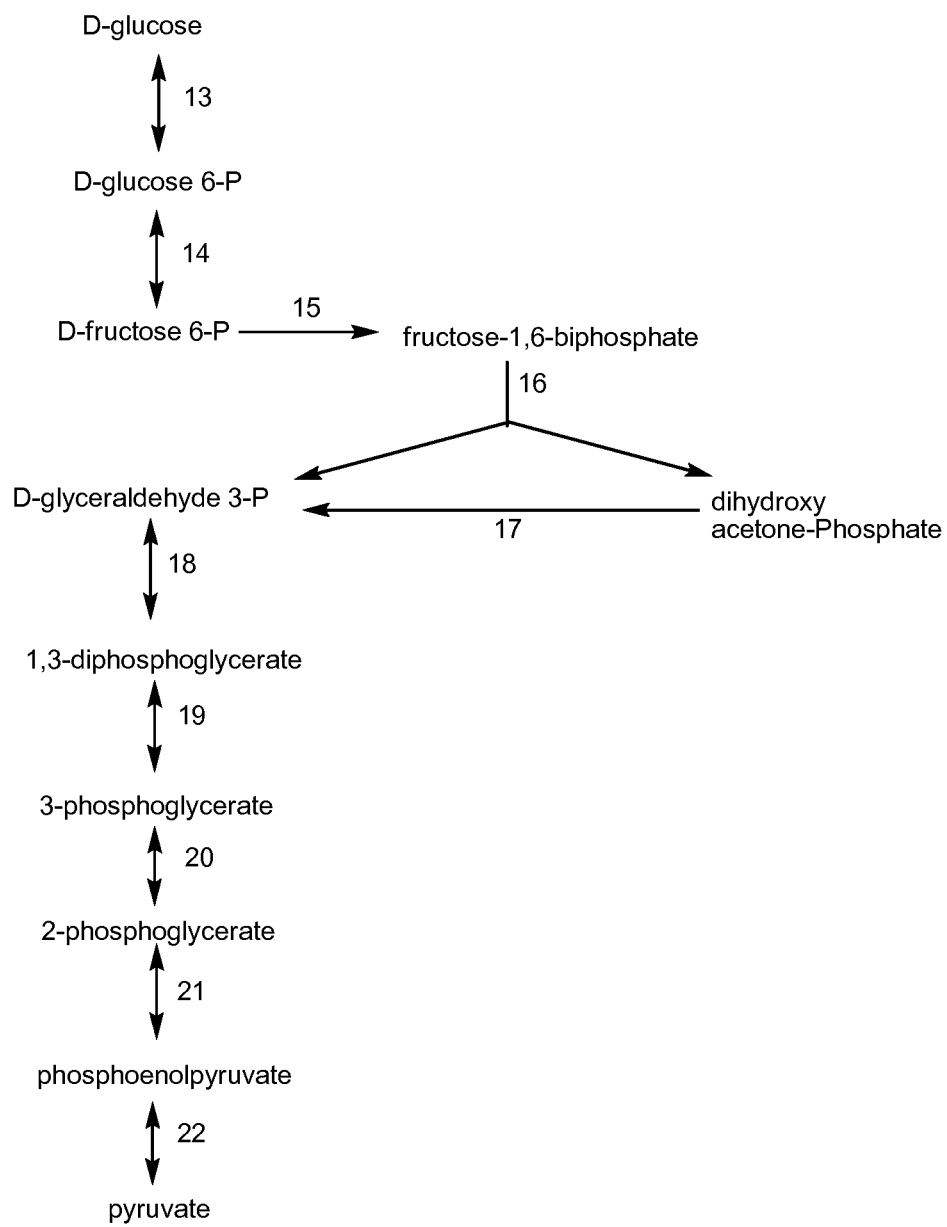

Products of the pentose phosphate pathway may be further metabolized through the process of glycolysis. The metabolic process of glycolysis is depicted in FIG. 2B. As used herein, the term "glycolytic enzyme" refers to an enzyme from the group of enzymes involved in glycolysis (i.e.: 13. Hexokinase; 14. Phosphoglucose isomerase; 15. Phosphofructokinase; 16. Aldolase; 17. Triose phosphate isomerase; 18. Glyceraldehyde phosphate dehydrogenase; 19. Phosphoglycerate kinase; 20. Phosphoglyceromutase; 21. Enolase; and/or 22. Pyruvate kinase; the reference numbers are depicted in FIG. 2B).

Figure 2C:
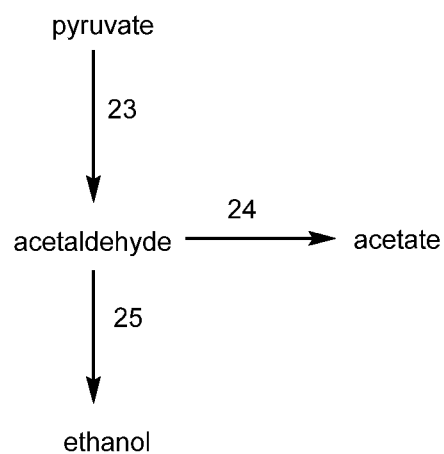

Pyruvate from the glycolytic pathway (i.e., glycolysis) may be further metabolized to ethanol as shown in FIG. 2C by ethanologenic enzymes. As used herein, the term "ethanologenic enzyme" refers to an enzyme involved in the conversion of pyruvate to ethanol, (e.g., a pyruvate decarboxylase, an aldehyde dehydrogenase, and/or an alcohol dehydrogenase). The term "ethanologenic pathway" refers to the pathway depicted in FIG. 2C.

Therefore, the polynucleotide sequences described herein are useful for creating recombinant fungal host cells, particularly yeast host cells, that are capable of isomerizing D-xylose directly to D-xylulose, which can lead to the production of desirable fermentation products (e.g., an alcohol, such as ethanol, butanol, and the like, including a fatty alcohol [such as a C8-C20 fatty alcohol], a fatty acid [e.g., a C8-C20 fatty acid], lactic acid, 3-hydroxpropionic acid, acrylic acid, acetic acid, succinic acid, citric acid, malic acid, fumaric acid, an amino acid, 1,3-propanediol, ethylene, glycerol, a β-lactam, and other products of interest).

Recombinant Nucleic Acid Constructs

The present invention provides a recombinant nucleic acid construct comprising a polynucleotide sequence that encodes a polypeptide comprising an amino acid sequence having at least 70% identity to SEQ ID NO:2, 4, 6, 8, 10, 23, 25, 27, 39, 31, and/or 33, wherein the polypeptide is capable of catalyzing the isomerization of D-xylose directly to D-xylulose. SEQ ID NO:2 corresponds to the amino acid sequence of a putative xylose isomerase from the bacteria, *Ruminococcus flavefaciens*. SEQ ID NO: 1 corresponds to the native *R. flavefaciens* polynucleotide sequence that encodes the putative *R. flavefaciens* xylose isomerase (SEQ ID NO: 2), both of which are provided below.

```
                                              (SEQ ID NO: 1)
ATGGAATTTTTCAGCAATATCGGTAAAATTCAGTATCAGGGACCAAAAA

GTACTGATCCTCTCTCATTTAAGTACTATAACCCTGAAGAAGTCATCAA

CGGAAAGACAATGCGCGAGCATCTGAAGTTCGCTCTTTCATGGTGGCAC

ACAATGGGCGGCGACGGAACAGATATGTTCGGCTGCGGCACAACAGACA

AGACCTGGGGACAGTCCGATCCCGCTGCAAGAGCAAAGGCTAAGGTTGA

CGCAGCATTCGAGATCATGGATAAGCTCTCCATTGACTACTATTGTTTC

CACGATCGCGATCTTTCTCCCGAGTATGGCAGCCTCAAGGCTACCAACG

ATCAGCTTGACATAGTTACAGACTATATCAAGGAGAAGCAGGGCGACAA

GTTCAAGTGCCTCTGGGGTACAGCAAAGTGCTTCGATCATCCAAGATTC

ATGCACGGTGCAGGTACATCTCCTTCTGCTGATGTATTCGCTTTCTCAG

CTGCTCAGATCAAGAAGGCTCTCGAGTCAACAGTAAAGCTCGGCGGTAA

CGGTTACGTTTTCTGGGGCGGACGTGAAGGCTATGAGACACTTCTTAAT

ACAAATATGGGACTCGAACTCGACAATATGGCTCGTCTTATGAAGATGG

CTGTTGAGTATGGACGTTCGATCGGCTTCAAGGGCGACTTCTATATCGA

GCCCAAGCCCAAGGAGCCCACAAAGCATCAGTACGATTTCGATACAGCT

ACTGTTCTGGGATTCCTCAGAAAGTACGGTCTCGATAAGGATTTCAAGA
```

```
                                               -continued
TGAATATCGAAGCTAACCACGCTACACTTGCTCAGCATACATTCCAGCA

TGAGCTCCGTGTTGCAAGAGACAATGGTGTGTTCGGTTCTATCGACGCA

AACCAGGGCGACGTTCTTCTTGGATGGGATACAGACCAGTTCCCCACAA

ATATCTACGATACAACAATGTGTATGTATGAAGTTATCAAGGCAGGCGG

CTTCACAAACGGCGGTCTCAACTTCGACGCTAAGGCACGCAGAGGGAGC

TTCACTCCCGAGGATATCTTCTACAGCTATATCGCAGGTATGGATGCAT

TTGCTCTGGGCTTCAGAGCTGCTCTCAAGCTTATCGAAGACGGACGTAT

CGACAAGTTCGTTGCTGACAGATACGCTTCATGGAATACCGGTATCGGT

GCAGACATAATCGCAGGTAAGGCAGATTTCGCATCTCTTGAAAAGTATG

CTCTTGAAAAGGGCGAGGTTACAGCTTCACTCTCAAGCGGCAGACAGGA

AATGCTGGAGTCTATCGTAAATAACGTTCTTTTCAGTCTGTAA (SEQ ID NO: 2)
MEFFSNIGKIQYQGPKSTDPLSFKYYNPEEVINGKTMREHLKFALSWWH

TMGGDGTDMFGCGTTDKTWGQSDPAARAKAKVDAAFEIMDKLSIDYYCF

HDRDLSPEYGSLKATNDQLDIVTDYIKEKQGDKFKCLWGTAKCFDHPRF

MHGAGTSPSADVFAFSAAQIKKALESTVKLGGNGYVFWGGREGYETLLN

TNMGLELDNMARLMKMAVEYGRSIGFKGDFYIEPKPKEPTKHQYDFDTA

TVLGFLRKYGLDKDFKMNIEANHATLAQHTFQHELRVARDNGVFGSIDA

NQGDVLLGWDTDQFPTNIYDTTMCMYEVIKAGGFTNGGLNFDAKARRGS

FTPEDIFYSYIAGMDAFALGFRAALKLIEDGRIDKFVADRYASWNTGIG

ADIIAGKADFASLEKYALEKGEVTASLSSGRQEMLESIVNNVLFSL
```

SEQ ID NO:3 corresponds to the native *Clostridium phytofermentans* polynucleotide sequence that encodes the putative *C. fermentans* xylose isomerase (SEQ ID NO:4), both of which are provided below.

```
                                              (SEQ ID NO: 3)
ATGAAGAACTATTTCCCCAACGTCCCAGAAGTCAAATACGAAGGTCCAA

ACTCCACAAATCCTTTCGCTTTTAAATATTATGATGCTAATAAAGTAGT

CGCCGGTAAGACCATGAAGGAGCATTGTAGATTCGCTCTATCCTGGTGG

CACACTTTGTGTGCCGGTGGTGCTGATCCATTCGGAGTAACTACTATGG

ACAGGACCTACGGTAACATTACCGACCCAATGGAACTAGCTAAGGCCAA

AGTTGATGCTGGTTTCGAACTGATGACTAAGCTGGGCATCGAGTTCTTC

TGCTTCCATGATGCCGACATTGCTCCAGAAGGTGACACCTTCGAAGAGT

CCAAGAAGAATCTGTTCGAGATTGTTGATTACATCAAGGAGAAGATGGA

CCAAACCGGCATCAAGTTGTTATGGGCACTGCTAACAACTTTAGTCAC

CCCAGGTTCATGCACGGTGCATCAACTTCTTGTAATGCCGATGTTTTCG

CTTATGCTGCTGCGAAAATAAAGAACGCTTTAGATGCGACCATCAAGTT

GGGCGGTAAGGGTTATGTCTTTTGGGTGGTAGAGAAGGTTACGAGACC

CTGCTGAATACTGACCTGGGCTTAGAACTGGACAACATGGCTAGGCTAA

TGAAGATGGCCGTAGAATACGGTAGGGCTAATGGATTCGACGGTGACTT

CTACATCGAGCCTAAACCCAAGGAACCTACTAAGCACCAGTACGACTTC

GACACTGCTACCGTATTAGCTTTTTTAAGGAAGTACGGGTTGGAAAAAG
```

-continued
ACTTCAAGATGAACATCGAAGCCAATCACGCCACACTAGCAGGCCACAC

ATTCGAGCATGAGTTAGCTATGGCTAGGGTAAACGGTGCATTCGGTTCT

GTTGATGCTAACCAAGGTGACCCAAACTTAGGATGGGACACGGATCAAT

TCCCCACAGACGTTCATTCTGCTACTCTTGCTATGCTGGAGGTCTTGAA

AGCCGGTGGTTTCACAAATGGCGGCCTGAACTTTGATGCGAAAGTTCGT

AGGGGTTCATTCGAGTTTGACGATATTGCCTATGGTTACATTGCTGGTA

TGGATACTTTCGCGTTAGGGTTAATTAAAGCTGCTGAAATCATTGATGA

CGGTAGAATTGCCAAGTTTGTGGATGACAGGTATGCCTCTTACAAGACC

GGTATTGGTAAAGCGATCGTTGACGGAACTACCTCTTTGGAAGAATTGG

AACAATACGTGTTGACTCATTCTGAACCTGTCATGCAATCTGGTAGACA

AGAGGTTCTGGAAACTATTGTCAACAACATATTGTTTAGATAA (SEQ ID NO: 4)
MKNYFPNVPEVKYEGPNSTNPFAFKYYDANKVVAGKTMKEHCRFALSWW

HTLCAGGADPFGVTTMDRTYGNITDPMELAKAKVDAGFELMTKLGIEFF

CFHDADIAPEGDTFEESKKNLFEIVDYIKEKMDQTGIKLLWGTANNFSH

PRFMHGASTSCNADVFAYAAAKIKNALDATIKLGGKGYVFWGGREGYET

LLNTDLGLELDNMARLMKMAVEYGRANGFDGDFYIEPKPKEPTKHQYDF

DTATVLAFLRKYGLEKDFKMNIEANHATLAGHTFEHELAMARVNGAFGS

VDANQGDPNLGWDTDQFPTDVHSATLAMLEVLKAGGFTNGGLNFDAKVR

RGSFEFDDIAYGYIAGMDTFALGLIKAAEIIDDGRIAKFVDDRYASYKT

GIGKAIVDGTTSLEELEQYVLTHSEPVMQSGRQEVLETIVNNILFR

SEQ ID NO:5 corresponds to the native *Abiotrophia defectiva* polynucleotide sequence that encodes the putative *A. defectiva* xylose isomerase (SEQ ID NO:6), both of which are provided below.

(SEQ ID NO: 5)
ATGAGTGAATTGTTCCAAAACATCCCAAAAATCAAATACGAAGGTGCAA

ATTCCAAAAATCCTTTGGCTTTTCATTATTATGATGCTGAAAAAATAGT

CCTCGGTAAGACCATGAAGGAGCATTTGCCATTCGCTATGGCATGGTGG

CACAATTTTGTGTGCCGCTGGTACTGATATGTTCGGACGTGATACTGCGG

ACAAGTCCTTTGGTTTGGAAAAAGGCTCAATGGAACATGCTAAGGCCAA

AGTTGATGCTGGTTTCGAATTTATGGAAAAGCTGGGCATTAAATACTTC

TGCTTCCATGATGTAGACCTTGTTCCAGAAGCTTGCGACATTAAAGAGA

CCAATTCTCGACTGGACGAAATTTCTGATTACATCTTGGAGAAGATGAA

GGGCACTGATATTAAGTGTTTATGGGCACTGCTAATATGTTTTCTAAC

CCCAGGTTCGTGAACGGTGCAGGATCTACTAATAGTGCCGATGTTTACT

GTTTTGCTGCTGCGCAAATAAAGAAAGCATTAGATATTACCGTCAAGTT

GGGCGGTAGAGGTTATGTCTTTTGGGGTGGTAGAGAAGGTTACGAGACC

CTGCTGAATACTGACGTGAAATTTGAACAGGAAAACATTGCTAATCTAA

TGAAGATGGCCGTAGAATACGGTAGGTCTATTGGATTCAAAGGTGACTT

CTACATCGAGCCTAAACCCAAGGAACCTATGAAGCACCAGTACGACTTC

-continued
GACGCTGCTACCGCAATAGGTTTTTTAAGGCAGTACGGGTTGGATAAAG

ACTTCAAATTGAACATCGAAGCCAATCACGCCACACTAGCAGGACACTC

ATTCCAGCATGAGTTACGTATTTCTAGTATTAACGGTATGTTGGGTTCT

GTTGATGCTAACCAAGGTGACATGTTGTTAGGATGGGACACGGATGAAT

TTCCCTTTGACGTTTATGATACTACTATGTGTATGTATGAGGTCCTTAA

AAACGGTGGTTTGACAGGCGGCTTTAACTTTGATGCGAAAAATCGTAGG

CCTTCATACACGTATGAAGATATGTTCTATGGTTTCATTCTTGGTATGG

ATTCTTTCGCGTTAGGGTTGATAAAAGCTGCTAAATTGATTGAAGAAGG

TACACTTGACAATTTTATTAAGGAAAGGTATAAATCTTTTGAATCCGAA

ATTGGTAAAAAAATTAGATCCAAATCAGCCTCTTTGCAAGAATTGGCAG

CTTATGCTGAGGAAATGGGTGCTCCCGCGATGCCGGGTTCAGGTAGGCA

AGAGTATCTGCAAGCTGCTCTCAACCAAAATTTGTTTGGTGAAGTGTAA

TAA (SEQ ID NO: 6)
MSELFQNIPKIKYEGANSKNPLAFHYYDAEKIVLGKTMKEHLPFAMAWW

HNLCAAGTDMFGRDTADKSFGLEKGSMEHAKAKVDAGFEFMEKLGIKYF

CFHDVDLVPEACDIKETNSRLDEISDYILEKMKGTDIKCLWGTANMFSN

PRFVNGAGSTNSADVYCFAAAQIKKALDITVKLGGRGYVFWGGREGYET

LLNTDVKFEQENIANLMKMAVEYGRSIGFKGDFYIEPKPKEPMKHQYDF

DAATAIGFLRQYGLDKDFKLNIEANHATLAGHSFQHELRISSINGMLGS

VDANQGDMLLGWDTDEFPFDVYDTTMCMYEVLKNGGLTGGFNFDAKNRR

PSYTYEDMFYGFILGMDSFALGLIKAAKLIEEGTLDNFIKERYKSFESE

IGKKIRSKSASLQELAAYAEEMGAPAMPGSGRQEYLQAALNQNLFGEV

SEQ ID NO:7 corresponds to the native *Ruminococcus* sp. 18p13 polynucleotide sequence that encodes the putative *Ruminococcus* sp. 18p13 xylose isomerase (SEQ ID NO:8), both of which are provided below.

(SEQ ID NO: 7)
ATGGAATTTTTCAAGAACATCTCTAAGATACCATACGAAGGCAAAGACT

CTACCAATCCATTAGCATTCAAGTACTACAATCCTGACGAAGTAATCGA

CGGTAAGAAGATGAGAGACATCATGAAGTTTGCTTTGTCTTGGTGGCAT

ACTATGGGAGGTGATGGTACTGATATGTTTGGCTGTGGTACTGCTGATA

AGACATGGGCGAGAATGATCCAGCTGCTAGAGCTAAAGCTAAAGTTGA

TGCCGCATTTGAAATCATGCAGAAGTTATCCATTGATTACTTCTGCTTC

CATGATAGAGATTTGTCTCCAGAGTACGGTTCTTTGAAGGACACAAACG

CTCAATTGGACATTGTCACTGACTACATCAAGGCTAAACAAGCTGAAAC

CGGTTTGAAATGTCTTTGGGGTACTGCTAAGTGCTTCGACCATCCAAGA

TTCATGCACGGTGCTGGTACTTCTCCTTCAGCGGATGTCTTCGCATTCT

CAGCTGCTCAAATCAAGAAAGCTCTGGAATCTACCGTCAAGTTGGGTGG

AACTGGTTATGTCTTCTGGGGTGGTAGAGAAGGATATGAAACGTTGTTG

AATACTAACATGGGACTTGAATTGGACAACATGGCTAGGTTGATGAAGA

TGGCCGTTGAGTATGGTAGGTCTATTGGTTTCAAAGGTGACTTCTACAT

```
TGAACCTAAGCCAAAGGAACCAACTAAGCATCAATACGACTTTGACACT

GCTACAGTCTTGGGCTTTCTGAGAAAGTACGGCCTGGACAAAGACTTCA

AGATGAACATAGAAGCCAATCATGCAACTTTAGCGCAACATACCTTCCA

GCACGAATTGTGTCGCCAGAACTAATGGTGCTTTCGGTTCTATTGAT

GCTAATCAAGGTGATCCCTTGTTGGGTTGGGATACAGATCAGTTTCCTA

CAAACATCTATGATACTACTATGTGCATGTACGAAGTTATCAAAGCTGG

TGGTTTCACTAATGGTGGTCTTAACTTTGATGCTAAAGCTAGAAGAGGT

TCTTTCACTCCAGAAGATATTTTCTATTCTTACATTGCTGGTATGGATG

CTTTCGCTTTAGGTTACAAAGCTGCTTCTAAGCTAATCGCTGATGGTAG

GATTGATAGCTTCATTAGCGATAGATATGCTTCTTGGTCTGAAGGTATT

GGTTTGGACATCATTTCCGGCAAAGCTGATATGGCGGCTTTAGAGAAGT

ATGCTTTGGAGAAAGGAGAGGTCACTGATTCTATCTCTTCTGGAAGACA

GGAACTGTTAGAGTCCATTGTTAACAACGTAATCTTCAACCTATAATAA (SEQ ID NO: 8)
MEFFKNISKIPYEGKDSTNPLAFKYYNPDEVIDGKKMRDIMKFALSWWH

TMGGDGTDMFGCGTADKTWGENDPAARAKAKVDAAFEIMQKLSIDYFCF

HDRDLSPEYGSLKDTNAQLDIVTDYIKAKQAETGLKCLWGTAKCFDHPR

FMHGAGTSPSADVFAFSAAQIKKALESTVKLGGTGYVFWGGREGYETLL

NTNMGLELDNMARLMKMAVEYGRSIGFKGDFYIEPKPKEPTKHQYDFDT

ATVLGFLRKYGLDKDFKMNIEANHATLAQHTFQHELCVARTNGAFGSID

ANQGDPLLGWDTDQFPTNIYDTTMCMYEVIKAGGFTNGGLNFDAKARRG

SFTPEDIFYSYIAGMDAFALGYKAASKLIADGRIDSFISDRYASWSEGI

GLDIISGKADMAALEKYALEKGEVTDSISSGRQELLESIVNNVIFNL
```

SEQ ID NO:9 corresponds to the native Phytophora infestans polynucleotide sequence that encodes the putative *P. infestans* xylose isomerase (SEQ ID NO:10), both of which are provided below.

(SEQ ID NO: 9)

```
ATGCAACATCAAGTGAAAGAATATTTCCCAAACGTCCCAAAAATCACAT
TCGAAGGTCAAAATGCCAAAAGTGTTTTGGCTTATCGTGAATATAATGC
TTCAGAAGTAATCATGGGTAAGACCATGGAGGAGTGGTGTAGATTCGCT
GTGTGTTATTGGCACACTTTTGGTAACTCTGGTTCTGATCCGTTCGGAG
GTGAAACTTATACCAATAGATTGTGGAATGAATCATTGGAAAGAGCTAA
TATTTCTTCTAGGGAAAGATTGTTGGAAGCTGCTAAGTGCAAAGCTGAT
GCTGCTTTCGAAACTTTTACAAAGCTGGGCGTTAAATACTACACCTTCC
ATGATGTAGACCTTATTTCAGAAGGTGCCAACCTTGAAGAGTCCCAATC
TCTACTGGACGAAATTTCTGATTACTTGTTGGATAAGCAGAATCAAACT
GGTGTTAGGTGTTTATGGGGCACTACTAATTTGTTTGGTCACAGAAGGT
TCATGAACGGTGCATCAACTAATCCTGATATGAAAGTTTTCGCTCATGC
TGCTGCGAGAGTAAAGAAAGCAATGGAAATTACCTTGAAGTTGGGCGGT
CAAAATTTTGTCTTTTGGGGTGGTAGAGAAGGTTTCCAGTCCATTCTGA
```

-continued

```
ATACTGACATGAAAACTGAACTGGATCACATGGCTGCTTTTTTTAAGTT
GGTCGTAGCATACAAAAAGGAACTTGGAGCCACATTTCAATTCTTGGTC
GAGCCTAAACCCAGGGAACCTATGAAGCACCAGTACGACTACGACGCTG
CTACCGTAGTAGCTTTTTTACATACGTACGGGTTGCAAAATGACTTCAA
ATTGAACATCGAACCCAATCACACCACACTAGCAGGACACGATTACGAG
CATGATATATATTATGCTGCTAGTTACAAAATGTTGGGTTCTGTTGATT
GTAACACAGGTGACCCGTTGGTAGGATGGGACACGGATCAATTTTTGAT
GGACGAAAAAAAAGCTGTTTTGGTTATGAAAAAGATCGTTGAAATCGGT
GGTTTGGCACCAGGCGGCTTGAACTTTGATGCGAAAGTTCGTAGGGAAT
CAACCGATTTGGAAGATATTTTCATTGCTCACATTGGTAGTATGGATTG
TTTCGCGAGAGGGTTGAGACAAGCTGCTAAATTGCTTGAAAAAAATGAA
CTTGGCGAATTGGTTAAGCAAAGGTATGCATCTTGGAAATCCACACTTG
GTGAAAGAATTGAACAAGGACAAGCCACTTTGGAAGAAGTGGCAGCTTA
TGCTAAGGAAAGTGGTGAACCCGATCATGTGTCAGGTAAGCAAGAGTTG
GCGGAACTTATGTGGAGCACAGTTGCGTTGGCTACAGGGATTTGGCAAG
ATCATGTTACTTGTTCTTTGACTAAAAATTGGTGTTAA
```

(SEQ ID NO: 10)

```
MQHQVKEYFPNVPKITFEGQNAKSVLAYREYNASEVIMGKTMEEWCRFA
VCYWHTFGNSGSDPFGGETYTNRLWNESLERANISSRERLLEAAKCKAD
AAFETFTKLGVKYYTFHDVDLISEGANLEESQSLLDEISDYLLDKQNQT
GVRCLWGTTNLFGHRRFMNGASTNPDMKVFAHAAARVKKAMEITLKLGG
QNFVFWGGREGFQSILNTDMKTELDHMAAFFKLVVAYKKELGATFQFLV
EPKPREPMKHQYDYDAATVVAFLHTYGLQNDFKLNIEPNHTTLAGHDYE
HDIYYAASYKMLGSVDCNTGDPLVGWDTDQFLMDEKKAVLVMKKIVEIG
GLAPGGLNFDAKVRRESTDLEDIFIAHIGSMDCFARGLRQAAKLLEKNE
LGELVKQRYASWKSTLGERIEQGQATLEEVAAYAKESGEPDHVSGKQEL
AELMWSTVALATGIWQDHVTCSLTKNWC
```

In some embodiments, recombinant nucleic acid constructs of the present invention further comprise a polynucleotide sequence (genetic) element that facilitates integration into a fungal host cell genome, by homologous or non-homologous recombination. In some embodiments, the nucleic acid construct of the present invention further comprises an origin of replication that is functional in a fungal cell (e.g., a yeast origin of replication). Typically, the fungal host cell is a yeast or filamentous fungal cell, more typically, a yeast cell. In some embodiments, nucleic acid constructs of the present invention comprise a transcriptional regulatory element that is functional in a fungal cell. For example, in some embodiments the recombinant nucleic acid construct comprises a promoter sequence and/or transcription terminator sequence that is functional in a fungal cell such that the xylose isomerase polynucleotide is operatively linked to the promoter sequence and/or transcription terminator sequences.

Xylose isomerase polynucleotides that are suitable for use in the practice of the present invention include those encoding the chimeric variants of SEQ ID NOS:2, 4, 6, 8, 10, 23, 25, 27, 29, 31, 33, and/or any of the variants set forth in Table 3-1. In some embodiments, the chimeric xylose isomerase variants comprise portions of at least two starting xylose isomerases (e.g., SEQ ID NOS:2, 4, 6, 8, 10, 14, 15, 16, 17, 18, 19, 20, and/or 21).

As used herein, the term "conservative substitution" refers to the substitution of a residue for another residue that does not generally alter the specific activity of the encoded polypeptide. An exemplary conservative substitution is a substitution that is within the same group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine, proline, cysteine and methionine). Amino acid substitutions that do not generally alter the specific activity are known in the art (See e.g., Neurath and Hill, *The Proteins*, Academic Press, New York [1979], which is incorporated herein by reference). The most commonly occurring exchanges are Ala/Ser, Val/Ile, Asp/Glu, Thr/Ser, Ala/Gly, Ala/Thr. Ser/Asn, Ala/Val, Ser/Gly, Tyr/Phe, Ala/Pro, Lys/Arg, Asp/Asn, Leu/Ile, Leu/Val, Ala/Glu, and Asp/Gly, as well as these in reverse.

Other xylose isomerase polynucleotides suitable for use in the practice of the present invention include those encoding xylose isomerase variants generated by mutagenesis, recombination, and/or any other protein engineering method. In some embodiments, the variants are screened for xylose utilization using any suitable method, including but not limited to those described in the Examples. In some embodiments, the resulting variants comprise one or more substitutions (conservative or non-conservative), deletions, and/or insertions.

The present invention thus provides methods for making chimeric xylose isomerase polynucleotide variants. In some embodiments, the methods comprise shuffling one or more polynucleotide sequences encoding at least one xylose isomerase to produce a modified polynucleotide; transforming a host cell with the modified polynucleotide; and screening the transformed host cell for an improvement in a desired phenotype relative to the corresponding untransformed host cell. Exemplary phenotypes include improved utilization of a pentose sugar (e.g., xylose, arabinose, etc.), stability, specific activity, lower Ki for xylitol, ethanol/acetate tolerance and/or tolerance to low pH, decreased by-product formation, and/or increased ethanol yield. Exemplary desirable xylose utilization phenotypes include the ability to ferment xylose to ethanol, the ability to ferment xylose to other metabolic intermediates/products, the ability to undergo aerobic or anaerobic growth on xylose, and the like.

Methods for generating variant libraries of polynucleotides encoding modified polypeptides are well known in the art. For example, mutagenesis and directed evolution methods can be readily applied to polynucleotides encoding the xylose isomerase polypeptides to generate variant libraries that can be expressed, screened, and assayed using the methods described herein. Mutagenesis and directed evolution methods are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811,238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 603,344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391: 288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; and WO 2009/152336, all of which are incorporated herein by reference).

In some embodiments, the present invention provides chimeric xylose isomerase polypeptide variants that comprise at least one modification that is a substitution, insertion, and/or deletion relative to SEQ ID NO:2. In some embodiments, the polypeptide variant has from about 1 to about 2, about 1 to about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 75, about 100, about 110, about 115, about 120, about 125, about 130, about 135, about 140, about 145, about 150, about 155, about 160, about 165, about 170, about 175, about 200, about 225, about 250, about 275, about 300, about 325, about 350, about 375, about 400, about 410, about 420, about 430, about 440 modifications.

In some embodiments, the chimeric xylose isomerase variants of the present invention comprise SEQ ID NOS:23, 25, 27, 29, 31, and/or 33, as well as any of the variants set forth in Table 3-1.

Also suitable for use in the practice of the present invention are polynucleotides encoding a truncated xylose isomerase or sequence variant thereof that is capable of catalyzing the isomerization of D-xylose directly to D-xylulose. These truncation variants may be truncated at the carboxy (C)-terminus and/or the amino (N)-terminus. Typically, the truncation is from about 1 to about 50 amino acid residues. However, it not intended that the present invention be limited to any specific number of truncated amino acid residues.

Those having ordinary skill in the art will understand that due to the degeneracy of the genetic code, a multitude of nucleotide sequences that encode the xylose isomerase polypeptides described herein exist. Table 1 provides the standard triplet genetic code for each amino acid. For example, the codons AGA, AGG, CGA, CGC, CGG, and CGU all encode the amino acid arginine. Thus, at every position in the nucleic acids referred to herein, where an arginine is specified by a codon, the codon can be altered to any of the corresponding codons described above without altering the encoded polypeptide. It is understood that U in an RNA sequence corresponds to T in a DNA sequence. The invention contemplates and provides each and every possible variation of nucleic acid sequence encoding a polypeptide of the invention that could be made by selecting combinations based on possible codon choices.

TABLE 1

Genetic Code

| Amino Acid | 3 Letter Code | Single Letter Code | Codon(s) |
|---|---|---|---|
| Alanine | Ala | A | GCA, GCC, GCG, GCU |
| Cysteine | Cys | C | UGC, UGU |
| Aspartic acid | Asp | D | GAC, GAU |
| Glutamic acid | Glu | E | GAA, GAG |
| Phenylalanine | Phe | F | UUC, UUU |
| Glycine | Gly | G | GGA, GGC, GGG, GGU |
| Histidine | His | H | CAC, CAU |
| Isoleucine | Ile | I | AUA, AUC, AUU |
| Lysine | Lys | K | AAA, AAG |
| Leucine | Leu | L | UUA, UUG, CUA, CUC, CUG, CUU |
| Methionine | Met | M | AUG |
| Asparagine | Asn | N | AAC, AAU |
| Proline | Pro | P | CCA, CCC, CCG, CCU |
| Glutamine | Gln | Q | CAA, CAG |
| Arginine | Arg | R | AGA, AGG, CGA, CGC, CGG, CGU |
| Serine | Ser | S | AGC, AGU, UCA, UCC, UCG, UCU |
| Threonine | Thr | T | ACA, ACC, ACG, ACU |
| Valine | Val | V | GUA, GUC, GUG, GUU |
| Tryptophan | Trp | W | UGG |
| Tyrosine | Tyr | Y | UAC, UAU |

In some embodiments, DNA sequences are designed for high codon usage bias (i.e., codons that are used at higher frequency in the protein coding regions than other codons that code for the same amino acid). The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. Codons whose frequency increases with the level of gene expression are typically optimal codons for expression. In particular, a DNA sequence can be optimized for expression in a particular host organism. References providing preference information for a wide range of organisms are readily available and known in the art (See e.g., Henaut and Danchin in Neidhardt et al. [eds.], *Escherichia coli* and *Salmonella*, ASM Press, Washington D.C., [1987], p. 2047-2066, which is incorporated herein by reference).

A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (See, GCG CodonPreference, Genetics Computer Group Wisconsin Package; Peden, *CodonW*, University of Nottingham; McInerney, Bioinform., 14:372-73 [1998]; Stenico et al., Nucl. Acids Res. 222437-46 [1994]; Wright, Gene 87:23-29 [1990]; Wada et al., Nucl. Acids Res., 20:2111-2118 [1992]; Nakamura et al., Nucl. Acids Res., 28:292 [2000]; and Henaut and Danchin, supra; all of which are incorporated herein by reference). The data source for obtaining codon usage may rely on any available nucleotide sequence capable of coding for a protein. These data sets include nucleic acid sequences actually known to express proteins (e.g., complete protein coding sequences-CDS), expressed sequence tags (ESTs), or predicted coding regions of genomic sequences (See e.g., Mount, *Bioinformatics: Sequence and Genome Analysis*, Chapter 8, Cold Spring Harbor Laboratory Press, Cold Spring Harbor, N.Y., [2001]; Uberbacher, Methods Enzymol., 266:259-281 [1996]; and Tiwari et al., Comput. Appl. Biosci. 13:263-270 [1997]; all of which are incorporated herein by reference). It is not intended that the present invention be limited to any particular method, data source and/or data set.

In some embodiments, the xylose isomerase polynucleotide contains codons optimized for expression in a fungal cell, particularly a yeast cell. Some silent mutations (i.e., DNA mutations that do not affect the amino acid sequence of the protein) have been identified in the chimeric xylose isomerase polynucleotide variants provided herein. These silent mutations include those set forth in Table 3-1.

In some embodiments, the xylose isomerase polynucleotides are employed in recombinant nucleic acid constructs that comprise a vector (e.g., a plasmid, a cosmid, a phage, a virus, a yeast artificial chromosome [YAC], and the like), into which a xylose isomerase polynucleotide sequence has been inserted. The xylose isomerase polynucleotides provided herein find use incorporated into any one of a variety of vectors. Suitable vectors include, but are not limited to chromosomal, nonchromosomal and synthetic DNA sequences, yeast plasmids, vectors derived from combinations of plasmids and phage DNA, and many others. Indeed, any suitable vector that transduces genetic material into a cell, and, if replication is desired, that is replicable and viable in the relevant host find use in the present invention.

Nucleic acid constructs of the present invention find use in transforming a host cell to permit the host to express the xylose isomerase polypeptide. Methods for recombinant expression of proteins in fungi are well known in the art, and a number of vectors are available or can be constructed using routine methods (See e.g., Zhu et al., Plasmid 6:128-33 [2009], incorporated herein by reference; and the many standard references in this field).

In some embodiments, recombinant nucleic acid constructs of the present invention further comprise a transcriptional regulatory element that is functional in a fungal cell. In some embodiments, the nucleic acid construct comprises the xylose isomerase polynucleotide operatively linked to a transcriptional regulatory sequence (e.g., a promoter, transcription termination sequence, and the like), that is functional in a fungal cell. Examples of promoters that are functional in a fungal host cell include, but are not limited to promoters from yeast and filamentous fungi. Promoters that are suitable for use in the practice of the present invention include endogenous or heterologous promoters and include both constitutive and inducible promoters that are natural or modified. Particularly useful promoters are those that are insensitive to catabolite (glucose) repression and/or do not require xylose for induction. Such promoters are well known in the art. In some embodiments, a promoter sequence is operably linked to the 5' region of the xylose isomerase coding sequence using routine methods that are well known in the art.

Promoters that are suitable for use in the practice of the present invention include, but are not limited to yeast promoters from glycolytic genes (e.g., yeast phosphofructokinase (PFK), triose phosphate isomerase (TPI), glyceraldehyde-3-phosphate dehydrogenase (GPD, TDH3 or GAPDH), pyruvate kinase (PYK), phosphoglycerate kinase (PGK) promoters, and the like; See e.g., WO 93/03159, incorporated herein by reference); promoters of glucose transporters; ribosomal protein encoding gene promoters; alcohol dehydrogenase promoters (e.g., ADH1, ADH4, and the like), and the enolase promoter (ENO).

Exemplary promoters useful for directing the transcription of the nucleic acid constructs of the present invention in yeast host cells include, but are not limited to those from the genes for *Saccharomyces cerevisiae* enolase (eno-1), *Saccharomyces cerevisiae* galactokinase (gall), *Saccharomyces cerevisiae* alcohol dehydrogenase/glyceraldehyde-3-phosphate dehydrogenase (ADH1/ADH2/GAP), and *Saccharomyces cerevisiae* 3-phosphoglycerate kinase, *Saccharomyces cerevisiae* transcription elongation factor (TEF), *Saccharomyces cerevisiae* fructose 1,6-bisphosphate aldolase (FBA1), and *Saccharomyces cerevisiae* 3-phosphate glycerate kinase (PGK1). Other useful promoters for yeast host cells are well known in the art (See e.g., Romanos et al., Yeast 8:423-488 [1992], incorporated herein by reference).

Suitable filamentous fungal promoters useful in the practice of the present invention include, but are not limited to promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787, which is incorporated herein by reference), as well as the NA2-tpi promoter (a hybrid of the promoters from the genes for *Aspergillus niger* neutral alpha-amylase and *Aspergillus oryzae* triose phosphate isomerase), promoters such as cbh1, cbh2, egl1, egl2, pepA, hfb1, hfb2, xynl, amy, and glaA (See, Nunberg et al., Mol. Cell. Biol., 4:2306-2315 [1984]; Boel et al., EMBO J. 3:1581-85 [1984]; and EP 0 137 280A, all of which are incorporated herein by reference), and mutant, truncated, and hybrid promoters thereof. Promoters associated with chitinase production in fungi also find use in some embodiments (See e.g., Blaiseau and Lafay, Gene 120: 243-248 [1992][filamentous fungus Aphanocladium album]; and Limon et al., Curr. Genet., 28:478-83 [1995][*Trichoderma harzianum*]; both of which are incorporated herein by reference).

Any other suitable promoter sequence that drives expression in a fungal host cell, particularly a yeast host cell finds use in the present invention. Suitable promoter sequences can be identified using well known methods. In one approach, a putative promoter sequence is linked 5' to a sequence encoding a reporter protein, the construct is transfected into the host cell and the level of expression of the reporter is measured. Expression of the reporter can be determined by measuring, for example, mRNA levels of the reporter sequence, an enzymatic activity of the reporter protein, or the amount of reporter protein produced. For example, promoter activity may be determined by using the green fluorescent protein as coding sequence (See e.g., Henriksen et al., Microbiol., 145: 729-34 [1999], which is incorporated herein by reference) or a lacZ reporter gene (See e.g., Punt et al., Gene, 197:189-93 [1997], which is incorporated herein by reference). In some embodiments, functional promoters are derived from naturally occurring promoter sequences by directed evolution methods (See e.g., Wright et al., Hum. Gene Ther., 16:881-892 [2005], which is incorporated herein by reference).

In some embodiments, heterologous and/or recombinant transcription termination sequences find use in the present invention. There are various exemplary transcription termination sequences (terminators) functional in fungal host cells, include transcription termination sequences from yeast and filamentous fungi well known in the art. In some embodiments, the transcription termination sequence is a yeast sequence. Exemplary yeast transcription termination sequences include, but are not limited to CYC1, ADHlt, ADH2t, etc. In some embodiments, the nucleic acid constructs of the present invention contain a ribosome binding site for translation initiation. In some embodiments, the construct includes appropriate sequences for amplifying expression (e.g., an enhancer). Such elements are well known in the art and any suitable enhancers and/or transcription termination sequences, and/or ribosome binding sites find use in the present invention.

In some additional embodiments, nucleic acid constructs of the present invention contain one or more selectable marker genes to provide a phenotypic trait for selection of transformed host cells. Suitable marker genes include, but are not limited to those coding for antimicrobial resistance such as, ampicillin (ampR), kanamycin, chloramphenicol, tetracycline, streptomycin or spectinomycin (e.g., the aada gene); including but not limited to the streptomycin phosphotransferase (spt) gene coding for streptomycin resistance, the neomycin phosphotransferase (nptII) gene encoding kanamycin or geneticin resistance, the nourseothricin acetyltransferase (natl) gene coding for nourseothricin resistance, the hygromycin phosphotransferase (hpt) gene coding for hygromycin resistance, genes encoding dihydrofolate reductase, phleomycin, or neomycin resistance for eukaryotic cell culture, and tetracycline or ampicillin resistance in *E. coli*, as well as other marker genes that are well known in the art. Indeed, any suitable marker gene finds use in the present invention.

In some embodiments, nucleic acid constructs of the present invention typically comprise a fungal origin of replication (e.g., a filamentous fungal or yeast origin of replication). In some embodiments, the recombinant nucleic acid constructs of the present invention comprise a yeast origin of replication. Examples include, but are not limited to constructs containing autonomous replicating sequences, constructs containing 2 micron DNA including the autonomous replicating sequence and rep genes, constructs containing centromeres like the CEN6, CEN4, CEN11, CDN3 and autonomous replicating sequences, and other like sequences that are well known in the art. Exemplary nucleic acid constructs include constructs suitable for transforming yeast. These include, but are not limited to episomal constructs based on the yeast 2µ or CEN origin based plasmids like pYES2/CT, pYES3/CT, pESC/His, pESC/Ura, pESC/Trp, pES/Leu, p427TEF, pRS405, pRS406, pRS413, and other yeast-based constructs that are known in the art. Indeed, any suitable origin of replication finds use in the present invention.

In some embodiments, the nucleic acid constructs of the present invention comprise elements to facilitate integration of the xylose isomerase polynucleotide into a fungal host chromosome (i.e., the genome), by either homologous or non-homologous recombination and/or either site-directed and/or random mutagenesis. In some embodiments, the nucleic acid constructs comprise elements that facilitate homologous integration. In some embodiments, the xylose isomerase polynucleotide is integrated at one or more sites and is present in one or more copies. In some embodiments, the nucleic acid construct comprises the xylose isomerase polynucleotide and no promoter that is operatively linked to the xylose isomerase polynucleotide. This type of construct typically comprises genetic elements to facilitate integration into the fungal host chromosome at a location that is downstream of a native promoter (i.e., in the host chromosome). In some embodiments, a second nucleic acid comprising a promoter and genetic elements to facilitate integration into the fungal host chromosome in a location upstream of the targeted integration site of the xylose isomerase polynucleotide finds use. In some embodiments, the nucleic acid construct comprises the xylose isomerase polynucleotide operatively linked to a promoter or promoter and terminator sequences such that all are integrated into the host chromosome (genome). It is contemplated that any suitable element that facilitates integration will find use in the present invention.

Genetic elements that facilitate integration by homologous recombination include those having sequence homology to targeted integration sites in the fungal host chromosome (genome). Suitable sites that find use as targets for integration include, but are not limited to the TY1 loci, the RDN loci, the ura3 locus, the GPD locus, aldose reductase (GRE3) locus, etc. Those having ordinary skill in the art will appreciate that additional sites for integration can be readily identified using methods known in the art, including but not limited to microarray analysis, metabolic flux analysis, comparative genome hybridization analysis, etc.

Genetic elements or techniques that facilitate integration by non-homologous recombination include, but are not limited to restriction enzyme-mediated integration (REMI) (See e.g., Manivasakam et al., Mol. Cell. Biol., 18(3):1736-1745 [1998], incorporated herein by reference), transposon-mediated integration, and other elements and methods that are well known in the art. Indeed, any suitable method that facilitates homologous and/or non-homologous recombination finds use in the present invention.

In some embodiments, the nucleic acid constructs of the present invention comprise at least one further recombinant polynucleotide that is capable of conferring a desired phenotype to a fungal host cell, particularly in the context of xylose fermentation. In some embodiments, the recombinant polynucleotide that is capable of conferring an improved phenotype to the fungal host cell is a non-coding polynucleotide (e.g., a regulatory polynucleotide), a coding polynucleotide, or combination thereof.

Exemplary further desired phenotypes include, but are not limited to increased transport of xylose into the host cell, increased xylulose kinase activity, increased flux through the pentose phosphate pathway, decreased sensitivity to catabolite repression, increased tolerance to ethanol, increased tolerance to increased osmolarity, increased tolerance to organic acids, reduced production of by-products, and other similar properties related to increasing flux through the pentose phosphate and glycolysis pathways to produce a desired metabolic product/intermediate at higher levels as compared to the corresponding wild-type host cell. In some embodiments, the desired metabolic product is an alcohol (e.g., ethanol).

In some embodiments, nucleic acid constructs comprising at least one further polynucleotide that is capable of conferring a desired phenotype to a fungal host cell comprise a polynucleotide encoding a protein known to impact the desired phenotype, wherein the polynucleotide is either native or heterologous to the fungal host cell. In some embodiments, this polynucleotide is operatively linked to its native promoter, or to a heterologous promoter (i.e., a promoter that is not associated with the polynucleotide in the corresponding native gene). In some embodiments, at least one further polynucleotide is overexpressed. In some additional embodiments, the nucleic acid constructs comprise multiple copies of a least one polynucleotide. Suitable polynucleotides include, but are not limited to those that facilitate overexpression of proteins known to have an impact on the desired phenotype.

Exemplary recombinant polynucleotides that are capable of conferring a desired phenotype to a fungal host cell include, but are not limited to recombinant polynucleotides (either wild-type or mutated forms) that encode a xylose and/or hexose transporter, xylulose kinase (XKS), at least one enzyme from the pentose phosphate pathway (See e.g., FIG. 2A), at least one glycolytic enzyme (i.e., from the glycolytic metabolic pathway; See e.g., FIG. 2B), at least one ethanologenic enzyme (See e.g., FIG. 2C), regulatory sequences that enhance expression of these sequences, and/or combinations thereof. Additional recombinant polynucleotides (either wild-type or mutated forms) that find use in the present invention include, but are not limited to those that encode additional proteins involved in the pentose phosphate, glycolysis, and ethanologenic pathways (See e.g., FIGS. 2A-C), used alone or in combination in various embodiments of the present invention.

In some embodiments, transporter proteins find use in the present invention. Exemplary transporters include, but are not limited to GXF1, SUT1 and At6g59250 from *Candida intermedia, Pichia stipitis* and *Arabidopsis thaliana*, respectively (See e.g., Runquist et al., Biotechnol. Biofuels, 3:5 [2010], incorporated herein by reference), as well as HXT4, HXT5, HXT7, GAL2, AGT1, GXF2 (See e.g., Matsushika et al., Appl. Microbiol. Biotechnol., 84:37-53 [2009], incorporated herein by reference). In some embodiments, overexpression of native *S. cerevisiae* transporters is desirable, particularly HXT5 and HXT7.

In some embodiments, additional recombinant polynucleotides find use, including but not limited to those that encode: xylulose kinase (XK); an enzyme from the pentose phosphate pathway (e.g., a ribulose-5-phosphate 3-epimerase (RPE1), ribose-5-phosphate ketol-isomerase (RKI1), transketolase (TKL1), transaldolase (TAL1), etc.); glycolytic enzyme(s) (e.g., a hexokinase (HXK1/HXK2), glyceraldehyde-3-phosphate dehydrogenase (GAPDH), pyruvate kinase (PVK2), etc.); and/or at least one ethanologenic enzyme (e.g., pyruvate decarboxylase, alcohol dehydrogenase, etc.).

In some embodiments of the present invention, regulatory polynucleotides find use. Exemplary regulatory polynucleotides include promoters, enhancers, terminators, and any other suitable regulatory element that functions to improve the expression of polynucleotides in a fungal host cell, particularly, a yeast host cell. These polynucleotides include, but are not limited to the regulatory elements described hereinabove.

The nucleic acid constructs described herein are useful for transforming fungal host cells to confer to these cells the property of xylose utilization.

Recombinant Fungal Host Cells

The present invention provides a recombinant fungal host cell comprising at least one xylose isomerase polynucleotide provided herein. In some embodiments, the recombinant fungal host cell comprises at least one polynucleotide sequence that encodes a polypeptide capable of catalyzing the isomerization of D-xylose directly to D-xylulose. In some embodiments, the polynucleotide is selected from: (a) a polynucleotide that encodes a polypeptide comprising an amino acid sequence that is at least about 70% identical to SEQ ID NO:2, 4, 6, 8, 10, 23, 25, 27, 29, 31, 33, and/or any of the variants set forth in Table 3-1; and (b) a polynucleotide that hybridizes under stringent hybridization conditions to the complement of a polynucleotide encoding a polypeptide having the amino acid sequence of SEQ ID NO: 2, 4, 6, 8, 10, 23, 25, 27, 29, 31, 33, and/or any of the variants set forth in Table 3-1.

In some embodiments, the present invention provides a recombinant fungal host cell comprising and/or transformed with a nucleic acid construct of the present invention. In some embodiments, the xylose isomerase polynucleotide is integrated into the host cell genome. Typically, the recombinant fungal host cell is a filamentous fungal or yeast host cell. More typically, the recombinant fungal host cell is a yeast host cell.

The present invention also provides methods for producing a recombinant fungal host cell, wherein the method comprises: (a) providing at least one nucleic acid construct of the present invention, wherein the nucleic acid construct comprises at least one xylose isomerase polynucleotide provided herein; and (b) transforming a fungal host cell with the nucleic acid construct to produce a recombinant fungal host cell. In some embodiments, the xylose isomerase polynucleotide sequence is integrated into the host cell genome.

Introduction of the expression construct of the present invention into the host cell can be accomplished using any suitable method, including but not limited to calcium phosphate transfection, DEAE-dextran mediated transfection, electroporation, or any other suitable technique. Indeed, there are numerous methods known in the art and described in various standard reference texts.

In some embodiments of the present invention, the fungal host cells include yeast and filamentous fungal host cells. In some additional embodiments, the fungal host cell is a yeast cell. Exemplary yeast host cells useful in the present invention include, but are not limited to Candida, Hansenula, Saccharomyces, Schizosaccharomyces, Pichia, Kluyveromyces, and Yarrowia. In some embodiments of the invention, the yeast cell is Hansenula polymorpha, Saccharomyces cerevisiae, Saccharomyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans, or Yarrowia lipolytica. In some embodiments, the yeast host cell is Saccharomyces species. In some additional embodiments, the yeast host cell is Saccharomyces cerevisiae. However, it is not intended that the present invention be limited to any particular genus and/or species of yeast cells.

Yeast strains that find use in the present invention include, but are not limited to those available from various yeast collections, such as Lallemand 6469, Lallemand LYCC 6391, Lallemand LYCC 6939, Lallemand LYCC 6469, Lallemand LYCC 6469 (all from Lallemand, Inc., Montreal, Canada); NRRL YB-1952 (ARS(NRRL) Collection, U.S. Department of Agriculture); and BY4741 (available from the ATCC and other sources).

Suitable fungal host cells include, but are not limited to, Ascomycota, Basidiomycota, Deuteromycota, Zygomycota, and Fungi imperfecti. The filamentous fungal host cells of the present invention include, but are not limited to all filamentous forms of the subdivision Eumycotina and Oomycota. Filamentous fungi are characterized by a vegetative mycelium with a cell wall composed of chitin, cellulose and other complex polysaccharides. In some embodiments, the filamentous fungal host cells of the present invention are morphologically distinct from yeast.

In some embodiments, the filamentous fungal host cell is a cell of a species of Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothia, Fusarium, Gibberella, Gliocladium, Humicola, Hypocrea, Myceliophthora, Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Trametes, Tolypocladium, Trichoderma, Verticillium, Volvariella, or teleomorphs, or anamorphs, and synonyms, basonyms, and/or taxonomic equivalents thereof. However, it is not intended that the present invention be limited to any particular genus and/or species of filamentous fungal cells.

In some embodiments of the invention, the filamentous fungal host cell is of the Aspergillus species, Ceriporiopsis species, Chrysosporium species, Corynascus species, Fusarium species, Humicola species, Neurospora species, Penicillium species, Tolypocladium species, Tramates species, or Trichoderma species. However, it is not intended that the present invention be limited to any particular genus and/or species of filamentous fungal cells.

Additionally, exemplary filamentous fungal host cells that find use in the present invention include, but are not limited to a filamentous fungal host cell of Trichoderma (e.g., T. longibrachiatum, T. viride [e.g., ATCC 32098 and 32086], T. reesei [NRRL 15709, ATTC 13631, 56764, 56765, 56466, 56767, and RL-P37 and derivatives thereof; See e.g., Sheir-Neiss et al., Appl. Microbiol. Biotechnol., 20:46-53 [1984], incorporated herein by reference), T. koningii, and T. harzianum), as well as Hypocreajecorina. The term "Trichoderma" refers to any fungal strain that was previously classified as Trichoderma or is currently classified as Trichoderma.

In some embodiments of the present invention, the filamentous fungal host cell is an Aspergillus species (e.g., A. awamori, A. funigatus, A. japonicas, A. nidulans, A. niger, A. aculeatus, A. foetidus, A. oryzae, A. sojae, or A. kawachi (See e.g., Kelly and Hynes, EMBO J., 4:475479 [1985]; NRRL 3112, ATCC 11490, 22342, 44733, and 14331; Yelton et al., Proc. Natl. Acad. Sci. USA, 81, 1480-1474 [1984]; Tilburn et al., Gene 26, 205-221 [1982]; and Johnston et al., EMBO J., 4:1307-1311 [1985], all of which are incorporated herein by reference). In some embodiments of the invention, the filamentous fungal host cell is a Fusarium species (e.g., F. bacterioides, F. cerealis, F. crookwellense, F. culmorum, F. graminaearum, F. graminum, F. oxysporum, F. rosium, or F. venenatum). In some embodiments of the invention, the filamentous fungal host cell is of a Neurospora species (e.g., N. crassa; See e.g., Case, et al., Proc. Natl. Acad. Sci. USA, 76:5259-5263 [1979]; U.S. Pat. No. 4,486,553; and Kinsey and Rambosek, Mol. Cell. Biol., 4:117-122 [1984], all of which are incorporated herein by reference). In some embodiments of the invention, the filamentous fungal host cell is of a Humicola species (e.g., *H. insolens. H. grisea*, or *H. lanuginose*). In some embodiments of the invention, the filamentous fungal host cell is a *Mucor* species (e.g., *M. miehei* or *M. circinelloides*). In some embodiments of the invention, the filamentous fungal host cell is a *Rhizopus* species (e.g., *R. oryzae* or *R. niveus*). In some embodiments of the invention, the filamentous fungal host cell is of a *Penicillium* species (e.g., *P. purpurogenum, P. chrysogenum*, or *P. verruculosum*). In some embodiments of the invention, the filamentous fungal host cell is a *Thielavia* species (e.g., *T. terrestris*). In some embodiments of the invention, the filamentous fungal host cell is a *Tolypocladium* species (e.g., *T. inflatum* or *T. geodes*). In some embodiments of the invention, the filamentous fungal host cell is a *Trametes* species (e.g., *T. villosa* or *T. versicolor*). In some embodiments of the invention, the filamentous fungal host cell is a *Chrysosporium* species, (e.g., *C. lucknowense, C. keratinophilum, C. tropicum, C. merdarium, C. inops, C. pannicola*, or *C. zonatum*). In some embodiments of the invention, the filamentous fungal host cell is of the *Myceliophthora* species, e.g., *M. thermophila*.

Strains that find use in the present invention include those that are readily accessible to the public from a number of culture collections, including but not limited to the American Type Culture Collection (ATCC), Deutsche Sammlung von Mikroorganismen und Zellkutlturen GmbH (DSM), Centraalbureau Voor Schimmelcultures (CBS), and Agricultural Research Service Patent Culture Collection, Northern Regional Research Center (NRRL). Strains that find use in the present invention include those that are readily accessible to the public from any commercial source.

Recombinant fungal host cells of the present invention are capable of growth in a xylose-based culture medium (i.e., a culture medium where xylose is the primary carbon source). In these xylose-based culture media, the carbon source comprises xylose. In some xylose-based culture media, the carbon source consists of xylose. In some embodiments, the recombinant fungal host cell is capable of faster growth in a xylose-based culture medium as compared to the corresponding wild-type fungal host cell. In some embodiments, the recombinant fungal host cell is capable of faster growth in a xylose-based culture medium as compared to wild-type *Saccharomyces cerevisiae*. In some embodiments, the recombinant fungal host cell is capable of growth at a rate of at least about 0.2 per hour ($h^{-1}$) in a xylose-based culture medium, while in some other embodiments, the growth rate is at least about 0.3 or 0.4 per hour ($h^{-1}$). Growth rate can be determined using any suitable method, including optical density, cell counting methods, etc. Indeed, there are various well known methods for determining cell growth that find use in the present invention. Exemplary xylose-based culture media include culture media that have been formulated to contain xylose (See e.g., Example 2 herein), as well as feedstock obtained from a cellulosic saccharification process and/or feedstock from a hemicellulose pre-treatment process (i.e., a "hemicellulosic feedstock").

In some embodiments, recombinant fungal host cells of the present invention are also capable of fermenting xylose when provided with a xylose based culture medium. Typically, the recombinant fungal host cells described herein are capable of fermenting xylose at a faster rate compared to the corresponding wild-type fungal host cell. In some embodiments, the recombinant fungal host cells are capable of fermenting xylose at a rate of at least about 1g/L/h, while in some additional embodiments, the recombinant fungal host cells are capable of fermenting xylose at a rate of at least about 2 g/L/h. In some embodiments the recombinant fungal host cells are capable of fermenting xylose at a rate of at least 0.5 g/g CDW/h, while in some additional embodiments, the fungal host cells are capable of fermenting xylose at a rate of 0.25 g/g CDW/h, and in some further embodiments, the fungal host cells are capable of fermenting xylose at a rate of 0.1g/g CDW/h. Exemplary xylose-based culture media include, but are not limited to culture media that have been formulated to contain xylose, as well as feedstock from cellulosic saccharification processes and/or feedstock from a hemicellulose pre-treatment process (i.e., a "hemicellulosic feedstock").

In some embodiments, the fungal host cell is a wild-type fungal cell, while in some other embodiments, it is a mutated or otherwise altered or engineered form of a wild-type fungal cell (i.e., a recombinant cell). In some embodiments, the fungal host cell (either wild-type or otherwise altered or engineered) comprises polynucleotides encoding a xylulokinase and one or more enzymes in the pentose phosphate, glycolytic, and/or ethanologenic pathways. In some embodiments, the fungal host cell comprises polynucleotides encoding at least one xylulokinase and all or some of the enzymes in the pentose phosphate, glycolytic, and ethanologenic pathways. In some embodiments, the fungal host cell comprises recombinant polynucleotides encoding enzymes that are heterologous to the fungal host cell (i.e., not native to the fungal host cell). In some additional embodiments, the fungal host cell is engineered to comprise other metabolic pathways that utilize products/intermediates from the pentose phosphate, glycolytic, and/or ethanologenic pathways to produce other desirable products. For example, in some embodiments, the fungal host cell is engineered to comprise at least one metabolic pathway for the biosynthesis of a fatty alcohol or fatty acid (See e.g., WO 2007/136762, incorporated herein by reference). In some embodiments, the fatty alcohol or fatty acid is a C8-C20 fatty acid or fatty alcohol. In some embodiments, the fungal host cell is altered or engineered to overexpress any one or more of the polynucleotides encoding the enzymes in one or more of these metabolic pathways.

In some embodiments, the recombinant fungal host cell of the present invention further comprises genetic modifications in addition to the xylose isomerase polynucleotide. In some embodiments, in addition to having a xylose isomerase polynucleotide described herein, the recombinant host cell comprises at least one different recombinant polynucleotide that is capable of conferring a further desired phenotype to the fungal host cell. In some embodiments, the present invention provides a recombinant fungal host cell comprising at least one chimeric xylose isomerase polynucleotide and/or variant thereof as described herein, and at least one recombinant polynucleotide that encodes a polypeptide that differs from the chimeric xylose isomerase or variant thereof, wherein the recombinant polynucleotide imparts a desired phenotype to the fungal host cell. It is contemplated that in some embodiments, the recombinant polynucleotide that is capable of conferring a desired phenotype to the fungal host cell is introduced to the fungal host cell in the same nucleic construct as the xylose isomerase polynucleotide, while in some other embodiments, the recombinant polynucleotide that is capable of conferring a desired phenotype to the fungal host cell is introduced to the fungal host cell in a different nucleic construct as the xylose isomerase polynucleotide. Nucleic acid constructs of the present invention comprising both a xylose isomerase polynucleotide and at least one further recombinant polynucleotide capable of conferring a desired phenotype to the fungal host cell are described above.

In some embodiments, the recombinant polynucleotide that is capable of conferring a desired phenotype to the fungal host cell is a non-coding polynucleotide (e.g., a regulatory polynucleotide), a coding polynucleotide, or a combination thereof. As described above, exemplary further desired phenotypes include, but are not limited to increased transport of xylose into the host cell, increased xylulose kinase activity, increased flux through the pentose phosphate pathway, decreased sensitivity to catabolite repression, increased tolerance to ethanol, increased tolerance to increased osmolarity, increased tolerance to organic acids, reduced production of by-products, and other like properties related to increasing flux through the pentose phosphate, glycolysis, and/or ethanologenic pathways to produce the desired metabolic product/intermediate at higher levels as compared to the corresponding wild-type host cell. In some embodiments, the desired metabolic product is an alcohol (e.g., ethanol).

In some embodiments, recombinant fungal host cells comprising at least one further polynucleotide capable of conferring a desired phenotype to the fungal host cell comprise at least one polynucleotide encoding a protein known to impact the desired phenotype, wherein the polynucleotide is either native or heterologous to the fungal host cell. In some embodiments, the polynucleotide(s) is/are operatively linked to the native promoter(s), while in some other embodiments, the polynucleotide is operatively linked to a heterologous promoter (i.e., one not associated with the polynucleotide in the corresponding native gene). In some embodiments, the polynucleotide is overexpressed. In some embodiments, the recombinant fungal host cell comprises multiple copies of the polynucleotide. Suitable polynucleotides include, but are not limited to those that facilitate overexpression of proteins known to have an impact on the desired phenotype. Therefore, in some embodiments, the fungal host cell is altered or engineered to overexpress one or more polynucleotides.

In some embodiments, recombinant polynucleotides that are capable of imparting a desired phenotype to a fungal host cell find use in the present invention include, but are not limited to recombinant polynucleotides that encode a xylose or hexose transporter, xylulose kinase (XKS), at least one enzyme from the pentose phosphate pathway (See e.g., FIG. 2A), at least one glycolytic enzyme (i.e., from the metabolic pathway of glycolysis; See e.g., FIG. 2B), ethanologenic enzyme(s) (See e.g., FIG. 2C), regulatory sequences associated with any of these sequences, and any combination thereof.

As indicated above, exemplary transporters that find use in the present invention include, but are not limited to GXF1, SUT1 and At6g59250 from *Candida intermedia*, *Pichia stipitis*, and *Arabidopsis thaliana*, respectively (See e.g., Runquist et al., 84:37-53 [2010], incorporated herein by reference), HXT4, HXT5, HXT7, GAL2, AGT1, and GXF2, (See e.g., Matsushika et al., Appl. Microbiol. Biotechnol., 84:37-53 [2009]). In some embodiments, overexpression of native *S. cerevisiae* transporters is desirable, particularly HXT5 and HXT7.

Also as indicated, above, recombinant polynucleotides suitable for use in the present invention include, but are not limited to those that encode: xylulose kinase (XK); at least one enzyme from the pentose phosphate pathway (e.g., a ribulose-5-phosphate 3-epimerase (RPE1), ribose-5-phosphate ketol-isomerase (RKI1), transketolase (TKL1), transaldolase (TAL1), etc.); at least one glycolytic enzyme (e.g., hexokinase (HXK1/HXK2), glyceraldehyde-3-phosphate dehydrogenase (GAPDH), pyruvate kinase (PVK2), etc.; and at least one ethanologenic enzyme (e.g., pyruvate decarboxylase, alcohol dehydrogenase, etc.).

As indicated above, exemplary regulatory polynucleotides that find use in the present invention include promoters, enhancer, terminator, and other regulatory elements that function to improve the expression of polynucleotides in a fungal host cell, particularly, a yeast host cell, as described above.

In some embodiments, recombinant host cells of the present invention comprise one or more native genes deleted from its genome. In some embodiments, the deletion(s) cause removal or diminishment of a biological activity that is otherwise exhibited by the fungal host cell. In some embodiments, the cumulative effect of the deletion(s) also leads to an improvement in a phenotype of the fungal host cell. Any suitable method for deleting gene finds use in the present invention. There are numerous methods well known in the art. For example, in some embodiments, recombinant host cells of the present invention have certain native genes deleted from the host genome in order to improve the utilization of pentose sugars (e.g., xylose), increase transport of xylose into the host cell, increase xylulose kinase activity, increase flux through the pentose phosphate pathway, decrease sensitivity to catabolite repression, increase tolerance to ethanol/acetate, increase tolerance to increased osmolarity, increase tolerance to organic acids (low pH), reduce production of by-products, and other like properties related to increasing flux through the relevant pathways to produce ethanol and other desired metabolic products at higher levels, where comparison is made with respect to the corresponding host cell without the deletion(s). Genes targeted for deletion include, but are not limited to genes encoding enzymes in the pentose phosphate pathway, a glycolytic enzyme, and/or an ethanologenic enzyme, as well as any other gene, the deletion of which provides an advantage.

In some embodiments, other genes are targeted for deletion, including but not limited to those encoding aldose reductase (GRE3) (See e.g., Matsushika et al., Appl. Microbiol. Biotechnol., 84:37-53 [2009]), sorbitol dehydrogenases (SOR1/SOR2), glutamate dehydrogenase (GDH1), 6-phosphogluconate dehydrogenase (GND), glucose-5-phosphate dehydrogenase (ZWF1), and any enzyme for which its deletion is known in the art to improve the utilization of a pentose sugar, decrease by-product formation, and/or increase the ethanol yield of a fungal host cell. The genes encoding these enzymes in many fungi are known in the art. Those having ordinary skill in the art appreciate that additional genes encoding these and other enzymes of interest can be readily identified using various suitable techniques, such as by microarray analysis (See e.g., Sedlak et al., Yeast 21:671-684 [2004]), metabolic flux analysis (See e.g., Sonderegger et al., Appl. Environ. Microbiol., 70(4):2307-2317 [2004]), in silico modeling (See e.g., Hjersted et al., Biotechnol. Bioengineer. 97(5):1190-1204 [2007]), chemogenomics (See e.g., Teixeira et al., Appl. Environ. Microbiol., 75(18):5761-5772 [2009]), and other well known methods. Indeed, any suitable method finds use in the present invention.

In some embodiments, the host cells employed in the practice of the present invention are mutagenized and/or evolved to exhibit further desired phenotypes, for example, further improvement in the utilization of pentose sugars (e.g., xylose, arabinose, etc.), increased transport of xylose into the host cell, increased xylulose kinase activity, increased flux through the pentose phosphate pathway, decreased sensitivity to catabolite repression, increased tolerance to ethanol/acetate, increased tolerance to increased osmolarity, increased tolerance to organic acids (low pH), reduced production of by-products, and other like properties related to increasing flux through the pentose phosphate and glycolysis pathways to produce a desired metabolic product/intermediate at higher levels. In some embodiments, the desired metabolic product is an alcohol (e.g., ethanol). In some embodiments, the host cells are mutagenized and/or evolved using known methods either prior to or after transformation with one or at least one xylose isomerase polynucleotide. These methods include, but are not limited to classical mutagenesis, whole genome shuffling, evolutionary engineering methods, methods that employ screening and/or selection methods, and/or any combination of such well known methods.

Classical mutagenesis methods that find use in the present invention include, but are not limited to treatment of the host cell with a mutagen such as a chemical mutagen or irradiation exposure (e.g., ultraviolet or gamma-irradiation). Whole genome shuffling methods involving, for example, recombination of genomic DNA between native genomic DNA sequences and/or variants thereof, can be facilitated by sexual mating, protoplast fusion methods and other methods well known in the art (See e.g., WO 98/31837 and WO 2000/04190, incorporated herein by reference) aslso find use. In some embodiments, these methods are coupled with screening and/or selection methods to identify altered fungal host cells that exhibit the desired phenotype. For example, such methods find use in altering or engineering a fungal host cell to overexpress one or more desired polynucleotides. Indeed, any suitable method finds use in the present invention.

In some embodiments, evolutionary engineering is accomplished by prolonged cultivation and selection of strains under desired conditions through chemostat, turbidostat and/or batch cultures. Evolutionary engineering methods can be practiced under aerobic, microaerophilic or anaerobic conditions. Selection strategies can be optimized by varying culture conditions, for example, carbon source, nitrogen source, aeration, pH and temperature. Methods for evolutionary engineering are well known in the art (See e.g., Wisselink et al., Appl. Environ. Microbiol., 75(4):907-914 [2009]; Kuyper et al., FEMS Yeast Res., 5:399-409 [2005]; and Sauer, Adv. Biochem. Engineer. Biotechnol., 73:129-169 [2001], all of which are incorporated herein by reference). Indeed, any suitable method finds use in the present invention.

In some embodiments of the present inventon, the recombinant fungal host cell comprising a xylose isomerase polynucleotide exhibits an improved phenotype relative to the corresponding fungal host cell without the xylose isomerase polynucleotide. In some embodiments, the improved phenotype comprises further improvement in the utilization of pentose sugars (e.g., xylose, arabinose, etc.), increased transport of xylose into the host cell, increased xylulose kinase activity, increased flux through the pentose phosphate pathway, decreased sensitivity to catabolite repression, increased tolerance to ethanol/acetate, increased tolerance to increased osmolarity, increased tolerance to organic acids (low pH), and reduced production of by products, and/or other properties.

Enzyme Mixtures

In some embodiments, the present invention provides an enzyme mixture that comprises at least one xylose isomerase variant polypeptide as provided herein. In some embodiments, the enzyme mixture is cell-free (i.e., an enzyme mixture comprising enzymes that have been separated from cells), while in some alternative embodiments, the enzymes are not separated from the host cells that secrete at least one enzyme mixture component. Cell-free enzyme mixtures can be prepared by any of a variety of methodologies known in the ar (e.g., filtration and/or centrifugation methodologies). In some embodiments, the enzyme mixtures are partially cell-free, substantially cell-free, or entirely cell-free.

In some embodiments, at least one chimeric xylose isomerase and any additional enzymes present in the enzyme mixture are secreted from a single genetically modified cell (e.g., a fungal host cell), while in some additional embodiments, at least one chimeric xylose isomerase and any additional enzymes present in the enzyme mixture are sectreted from different microbes in combined or separate fermentations. Similarly, in some additional embodiments, at least one chimeric xylose isomerase and any additional enzymes present in the enzyme mixture are expressed individually or in sub-groups from different strains of different organisms and the enzymes are combined in vitro to make the enzyme mixture. It is also contemplated that the xylose isomerases and any additional enzymes in the enzyme mixture are expressed individually or in sub-groups from different strains of a single organism, and the enzymes combined to make the enzyme mixture. In some embodiments, all of the enzymes are expressed from a single host organism, such as a genetically modified fungal cell. In some embodiments, the enzymes described in WO 2011/041594, WO 2011/066457, WO 2011/14363, WO 2011/150318, WO 2012/024698, WO 2012/027282, WO 2010/148148, WO 2012/024662, WO 2012/044868, WO 2012/061432, US Pat. Appln. Publ. No. 2012/0003703, US Pat. Appln. Publ. No. 2012/0083019, US Pat. Appln. Publ. No. 2012/0077216, US Pat. Appln. Publ. No. 2012/0045793, US Pat. Appln. Publ. No. 2012/0088271, US Pat. Appln. Publ. No. 2012/0107881, and/or U.S. Pat. No. 8,143,050 (all of which are incorporated herein by reference), find use in the present invention.

In some embodiments, the enzyme mixture comprises at least one cellulase, selected from cellobiohydrolase (CBH), endoglucanase (EG), and/or beta-glucosidase (BG1) cellulase. Cellulase enzymes of the cellulase mixture work together in decrystallizing and hydrolyzing the cellulose from a biomass substrate to yield soluble sugars, such as but not limited to glucose (See e.g., Brigham et al. in Wyman ([ed.], *Handbook on Bioethanol*, Taylor and Francis, Washington D.C. [1995], pp 119-141, incorporated herein by reference). In some embodiments, the cellobiohydrolase is *T. reesei* cellobiohydrolase II. In some embodiments, the endoglucanase comprises a catalytic domain derived from the catalytic domain of a *Streptomyces avermitilis* endoglucanase. In some embodiments, at least one cellulase is *Acidothermus cellulolyticus, Thermobifidafusca, Humicola grisea*, and/or a *Chrysosporium* sp. cellulase. It is intended that the present invention encompass enzyme mixtures comprising any suitable cellulase obtained from any suitable source. It is not intended that the present invention be limited to any particular cellulase and/or cellulase source.

Cellulase mixtures for efficient enzymatic hydrolysis of cellulose are known (See e.g., Viikari et al., Adv. Biochem. Eng. Biotechnol., 108:121-45 [2007]; and US Pat. Publns. 2009/0061484; US 2008/0057541; and US 2009/0209009, each of which is incorporated herein by reference). In some embodiments, mixtures of purified naturally occurring or recombinant enzymes are combined with cellulosic feedstock or a product of cellulose hydrolysis. In some embodiments, one or more cell populations, each producing one or more naturally occurring or recombinant cellulases, are combined with cellulosic feedstock or a product of cellulose hydrolysis.

In some embodiments, at least one chimeric xylose isomerase polypeptide of the present invention is present in mixtures comprising at least one additional enzyme other than cellulases that degrade cellulose, hemicellulose, pectin, and/or lignocellulose. In some embodiments, the enzyme mixtures comprise at least one chimeric xylose isomerase of the present invention, at least one cellulase, and at least one additional enzyme. In some embodiments, the enzymes comprise at least one xylanase, xylosidase, furanosidase, glucoronidase, esterase, acetylxylanesterase, feruloyl esterase, coumaroyl esterase, galactosidases, mannanases, mannosidases, pectinase, lyase, polygalacturonate lyase, galacturonase, pectin methyl esterase, galactanase, pectin acetyl esterase, pectin lyase, pectate lyase, rhamnosidase, polygalacturonate lyase, rhamnogalacturonanase, rhamnogalacturonan lyase, galacturonohydrolase, arabinase, lignin-degrading enzyme, laccase, peroxidase, lipase, protease, amylase, expansin, expansin-like protein, cellulose integrating protein, scaffoldin, scaffoldin-like protein, cellulose-induced protein or modulating protein, and/or any additional enzyme of interest.

A "hemicellulase" as used herein, refers to a polypeptide that can catalyze hydrolysis of hemicellulose into small polysaccharides such as oligosaccharides, or monomeric saccharides. Hemicellulloses include xylan, glucuonoxylan, arabinoxylan, glucomannan and xyloglucan. Hemicellulases include, for example, the following: endoxylanases, b-xylosidases, a-L-arabinofuranosidases, a-D-glucuronidases, feruloyl esterases, coumarolyl esterases, a-galactosidases, b-galactosidases, b-mannanases, and b-mannosidases. In some embodiments, the present invention provides enzyme mixtures that comprise at least one xylose isomerase variant of the present invention and one or more hemicellulases.

In some additional embodiments, the present invention provides at least one chimeric xylose isomerase and at least one endoxylanase. Endoxylanases (EC 3.2.1.8) catalyze the endohydrolysis of 1,4-β-D-xylosidic linkages in xylans. This enzyme may also be referred to as endo-1,4-β-xylanase or 1,4-β-D-xylan xylanohydrolase. In some embodiments, an alternative is EC 3.2.1.136, a glucuronoarabinoxylan endoxylanase, an enzyme that is able to hydrolyze 1,4 xylosidic linkages in glucuronoarabinoxylans.

In some additional embodiments, the present invention provides at least one chimeric xylose isomerase and at least one 3-xylosidase. P-xylosidases (EC 3.2.1.37) catalyze the hydrolysis of 1,4-β-D-xylans, to remove successive D-xylose residues from the non-reducing termini. This enzyme may also be referred to as xylan 1,4-β-xylosidase, 1,4-β-D-xylan xylohydrolase, exo-1,4-β-xylosidase or xylobiase.

In some additional embodiments, the present invention provides at least one chimeric xylose isomerase and at least one α-L-arabinofuranosidase. α-L-arabinofuranosidases (EC 3.2.1.55) catalyze the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, arabinofuranosidase, polysaccharide alpha-L-arabinofuranosidase, alpha-L-arabinofuranoside hydrolase, L-arabinosidase and alpha-L-arabinanase.

In some additional embodiments, the present invention provides at least one chimeric xylose isomerase and at least one alpha-glucuronidase. Alpha-glucuronidases (EC 3.2.1.139) catalyze the hydrolysis of an alpha-D-glucuronoside to D-glucuronate and an alcohol.

In some additional embodiments, the present invention provides at least chimeric xylose isomerase and at least one acetylxylanesterase. Acetylxylanesterases (EC 3.1.1.72) catalyze the hydrolysis of acetyl groups from polymeric xylan, acetylated xylose, acetylated glucose, alpha-napthyl acetate, and p-nitrophenyl acetate.

In some additional embodiments, the present invention provides at least one chimeric xylose isomerase and at least one feruloyl esterase. Feruloyl esterases (EC 3.1.1.73) have 4-hydroxy-3-methoxycinnamoyl-sugar hydrolase activity (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II.

In some additional embodiments, the present invention provides at least one chimeric xylose isomerase and at least one coumaroyl esterase. Coumaroyl esterases (EC 3.1.1.73) catalyze a reaction of the form: coumaroyl-saccharide+ $H_2O$=coumarate+saccharide. In some embodiments, the saccharide is an oligosaccharide or a polysaccharide. This enzyme may also be referred to as trans-4-coumaroyl esterase, trans-p-coumaroyl esterase, p-coumaroyl esterase or p-coumaric acid esterase. The enzyme also falls within EC 3.1.1.73 so may also be referred to as a feruloyl esterase.

In some additional embodiments, the present invention provides at least one chimeric xylose isomerase and at least one alpha-galactosidase. Alpha-galactosidases (EC 3.2.1.22) catalyze the hydrolysis of terminal, non-reducing β-D-galactose residues in β-D-galactosides, including galactose oligosaccharides, galactomannans, galactans and arabinogalactans. This enzyme may also be referred to as melibiase.

In some additional embodiments, the present invention provides at least one chimeric xylose isomerase and at least one beta-galactosidase. Beta-galactosidases (EC 3.2.1.23) catalyze the hydrolysis of terminal non-reducing β-D-galactose residues in β-D-galactosides. In some embodiments, the polypeptide is also capable of hydrolyzing α-L-arabinosides. This enzyme may also be referred to as exo-(1-4)-β-D-galactanase or lactase.

In some additional embodiments, the present invention provides at least one chimeric xylose isomerase and at least one beta-mannanase. Beta-mannanases (EC 3.2.1.78) catalyze the random hydrolysis of 1,4-β-D-mannosidic linkages in mannans, galactomannans and glucomannans. This enzyme may also be referred to as mannan endo-1,4-β-mannosidase or endo-1,4-mannanase.

In some additional embodiments, the present invention provides at least one chimeric xylose isomerase and at least one beta-mannosidase. Beta-mannosidases (EC 3.2.1.25) catalyze the hydrolysis of terminal, non-reducing β-D-mannose residues in β-D-mannosides. This enzyme may also be referred to as mannanase or mannase.

In some embodiments one or more enzymes that degrade pectin are included in enzyme mixtures that comprise at least one chimeric xylose isomerase of the present invention. A pectinase catalyzes the hydrolysis of pectin into smaller units such as oligosaccharide or monomeric saccharides. In some embodiments, the enzyme mixtures comprise any pectinase, for example an endo-polygalacturonase, a pectin methyl esterase, an endo-galactanase, a pectin acetyl esterase, an endo-pectin lyase, pectate lyase, alpha rhamnosidase, an exo-galacturonase, an exo-polygalacturonate lyase, a rhamnogalacturonan hydrolase, a rhamnogalacturonan lyase, a rhamnogalacturonan acetyl esterase, a rhamnogalacturonan galacturonohydrolase and/or a xylogalacturonase.

In some additional embodiments, the present invention provides at least one chimeric xylose isomerase and at least one endo-polygalacturonase. Endo-polygalacturonases (EC 3.2.1.15) catalyze the random hydrolysis of 1,4-α-D-galactosiduronic linkages in pectate and other galacturonans. This enzyme may also be referred to as polygalacturonase pectin depolymerase, pectinase, endopolygalacturonase, pectolase, pectin hydrolase, pectin polygalacturonase, poly-α-1,4-galacturonide glycanohydrolase, endogalacturonase; endo-D-galacturonase or poly(1,4-α-D-galacturonide) glycanohydrolase.

In some additional embodiments, the present invention provides at least one chimeric xylose isomerase variant and at least one pectin methyl esterase. Pectin methyl esterases (EC 3.1.1.11) catalyze the reaction: pectin+n $H_2O$=n methanol+ pectate. The enzyme may also been known as pectinesterase, pectin demethoxylase, pectin methoxylase, pectin methylesterase, pectase, pectinoesterase or pectin pectylhydrolase.

In some additional embodiments, the present invention provides at least one chimeric xylose isomerase variant and at least one endo-galactanase. Endo-galactanases (EC 3.2.1.89) catalyze the endohydrolysis of 1,4-β-D-galactosidic linkages in arabinogalactans. The enzyme may also be known as arabinogalactan endo-1,4-β-galactosidase, endo-1,4-β-galactanase, galactanase, arabinogalactanase or arabinogalactan 4-β-D-galactanohydrolase.

In some additional embodiments, the present invention provides at least one chimeric xylose isomerase variant and at least one pectin acetyl esterase. Pectin acetyl esterases catalyze the deacetylation of the acetyl groups at the hydroxyl groups of GalUA residues of pectin.

In some additional embodiments, the present invention provides at least one chimeric xylose isomerase variant and at least one endo-pectin lyase. Endo-pectin lyases (EC 4.2.2.10) catalyze the eliminative cleavage of (1→4)-α-D-galacturonan methyl ester to give oligosaccharides with 4-deoxy-6-O-methyl-α-D-galact-4-enuronosyl groups at their non-reducing ends. The enzyme may also be known as pectin lyase, pectin trans-eliminase; endo-pectin lyase, polymethylgalacturonic transeliminase, pectin methyltranseliminase, pectolyase, PL, PNL or PMGL or (1→4)-6-O-methyl-α-D-galacturonan lyase.

In some additional embodiments, the present invention provides at least one chimeric xyloseisomerase variant and at least one pectate lyase. Pectate lyases (EC 4.2.2.2) catalyze the eliminative cleavage of (1→4)-α-D-galacturonan to give oligosaccharides with 4-deoxy-α-D-galact-4-enuronosyl groups at their non-reducing ends. The enzyme may also be known polygalacturonic transeliminase, pectic acid transeliminase, polygalacturonate lyase, endopectin methyltranseliminase, pectate transeliminase, endogalacturonate transeliminase, pectic acid lyase, pectic lyase, α-1,4-D-endopolygalacturonic acid lyase, PGA lyase, PPase-N, endo-α-1,4-polygalacturonic acid lyase, polygalacturonic acid lyase, pectin trans-eliminase, polygalacturonic acid transeliminase or (1→4)-α-D-galacturonan lyase.

In some additional embodiments, the present invention provides at least one chimeric xylose isomerase variant and at least one alpha-rhamnosidase. Alpha-rhamnosidases (EC 3.2.1.40) catalyze the hydrolysis of terminal non-reducing α-L-rhamnose residues in α-L-rhamnosides or alternatively in rhamnogalacturonan. This enzyme may also be known as α-L-rhamnosidase T, α-L-rhamnosidase N or α-L-rhamnoside rhamnohydrolase.

In some additional embodiments, the present invention provides at least one chimeric xylose isomerase variant and at least one exo-galacturonase. Exo-galacturonases (EC 3.2.1.82) hydrolyze pectic acid from the non-reducing end, releasing digalacturonate. The enzyme may also be known as exo-poly-α-galacturonosidase, exopolygalacturonosidase or exopolygalacturanosidase.

In some additional embodiments, the present invention provides at least one chimeric xylose isomerase variant and at least one exo-galacturonase. Exo-galacturonases (EC 3.2.1.67) catalyze a reaction of the following type: (1,4-α-D-galacturonide)n+H2O=(1,4-α-D-galacturonide)n-i+D-galacturonate. The enzyme may also be known as galacturan 1,4-α-galacturonidase, exopolygalacturonase, poly(galacturonate) hydrolase, exo-D-galacturonase, exo-D-galacturonanase, exopoly-D-galacturonase or poly(1,4-α-D-galacturonide) galacturonohydrolase.

In some additional embodiments, the present invention provides at least one chimeric xylose isomerase variant and at least one exopolygalacturonate lyase. Exopolygalacturonate lyases (EC 4.2.2.9) catalyze eliminative cleavage of 4-(4-deoxy-α-D-galact-4-enuronosyl)-D-galacturonate from the reducing end of pectate (i.e. de-esterified pectin). This enzyme may be known as pectate disaccharide-lyase, pectate exo-lyase, exopectic acid transeliminase, exopectate lyase, exopolygalacturonic acid-trans-eliminase, PATE, exo-PATE, exo-PGL or (1→4)-α-D-galacturonan reducing-end-disaccharide-lyase.

In some additional embodiments, the present invention provides at least one chimeric xylose isomerase variant and at least one rhamnogalacturonanase. Rhamnogalacturonanases hydrolyze the linkage between galactosyluronic acid and rhamnopyranosyl in an endo-fashion in strictly alternating rhamnogalacturonan structures, consisting of the disaccharide [(1,2-alpha-L-rhamnoyl-(1,4)-alpha-galactosyluronic acid].

In some additional embodiments, the present invention provides at least one chimeric xylose isomerase variant and at least one rhamnogalacturonan lyase. Rhamnogalacturonan lyases cleave α-L-Rhap-(1→4)-α-D-GalpA linkages in an endo-fashion in rhamnogalacturonan by beta-elimination.

In some additional embodiments, the present invention provides at least one chimeric xylose isomerase variant and at least one rhamnogalacturonan acetyl esterase. Rhamnogalacturonan acetyl esterases catalyze the deacetylation of the backbone of alternating rhamnose and galacturonic acid residues in rhamnogalacturonan.

In some additional embodiments, the present invention provides at least one chimeric xylose isomerase variant and at least one rhamnogalacturonan galacturonohydrolase. Rhamnogalacturonan galacturonohydrolases hydrolyze galacturonic acid from the non-reducing end of strictly alternating rhamnogalacturonan structures in an exo-fashion. This enzyme may also be known as xylogalacturonan hydrolase.

In some additional embodiments, the present invention provides at least one chimeric xylose isomerase variant and at least one endo-arabinase. Endo-arabinanases (EC 3.2.1.99) catalyze endohydrolysis of 1,5-α-arabinofuranosidic linkages in 1,5-arabinans. The enzyme may also be known as endo-arabinase, arabinan endo-1,5-α-L-arabinosidase, endo-1,5-α-L-arabinanase, endo-α-1,5-arabanase; endo-arabanase or 1,5-α-L-arabinan 1,5-α-L-arabinanohydrolase.

In some additional embodiments, the present invention provides at least one chimeric xylose isomerase variant and at least one enzyme that participates in lignin degradation in an enzyme mixture. Enzymatic lignin depolymerization can be accomplished by lignin peroxidases, manganese peroxidases, laccases and cellobiose dehydrogenases (CDH), often working in synergy. These extracellular enzymes are often referred to as "lignin-modifying enzymes" or "LMEs." Three of these enzymes comprise two glycosylated heme-containing peroxidases: lignin peroxidase (LIP); Mn-dependent peroxidase (MNP); and, a copper-containing phenoloxidase laccase (LCC).

In some additional embodiments, the present invention provides at least one chimeric xylose isomerase variant and at least one laccase. Laccases are copper containing oxidase enzymes that are found in many plants, fungi and microorganisms. Laccases are enzymatically active on phenols and similar molecules and perform a one electron oxidation. Laccases can be polymeric and the enzymatically active form can be a dimer or trimer.

In some additional embodiments, the present invention provides at least one chimeric xylose isomerase variant and at least one Mn-dependent peroxidase. The enzymatic activity of Mn-dependent peroxidase (MnP) in is dependent on $Mn^{2+}$. Without being bound by theory, it has been suggested that the main role of this enzyme is to oxidize Mn2+ to Mn3+ (See e.g., Glenn et al., Arch. Biochem. Biophys., 251:688-696 [1986]). Subsequently, phenolic substrates are oxidized by the Mn3+ generated.

In some additional embodiments, the present invention provides at least one chimeric xylose isomerase variant and at least one lignin peroxidase. Lignin peroxidase is an extracellular heme that catalyses the oxidative depolymerization of dilute solutions of polymeric lignin in vitro. Some of the substrates of LiP, most notably 3,4-dimethoxybenzyl alcohol (veratryl alcohol, VA), are active redox compounds that have been shown to act as redox mediators. VA is a secondary metabolite produced at the same time as LiP by ligninolytic cultures of *P. chrysosporium* and without being bound by theory, has been proposed to function as a physiological redox mediator in the LiP-catalyzed oxidation of lignin in vivo (See e.g., Harvey, et al., FEBS Lett., 195:242-246 [1986]).

In some additional embodiments, the present invention provides at least one chimeric xylose isomerase variant and at least one protease and/or a lipase that participates in cellulose degradation.

As used herein, "protease" includes enzymes that hydrolyze peptide bonds (peptidases), as well as enzymes that hydrolyze bonds between peptides and other moieties, such as sugars (glycopeptidases). Many proteases are characterized under EC 3.4, and are suitable for use in the present invention. Some specific types of proteases include, cysteine proteases including pepsin, papain and serine proteases including chymotrypsins, carboxypeptidases and metalloendopeptidases.

As used herein, "lipase" includes enzymes that hydrolyze lipids, fatty acids, and acylglycerides, including phosphoglycerides, lipoproteins, diacylglycerols, and the like. In plants, lipids are used as structural components to limit water loss and pathogen infection. These lipids include waxes derived from fatty acids, as well as cutin and suberin.

In some additional embodiments, the present invention provides at least one chimeric xylose isomerase variant and at least one expansin or expansin-like protein, such as a swollenin (See e.g., Salheimo et al., Eur. J. Biochem., 269:4202-4211 [2002]) or a swollenin-like protein. Expansins are implicated in loosening of the cell wall structure during plant cell growth. Expansins have been proposed to disrupt hydrogen bonding between cellulose and other cell wall polysaccharides without having hydrolytic activity. In this way, they are thought to allow the sliding of cellulose fibers and enlargement of the cell wall. Swollenin, an expansin-like protein contains an N-terminal Carbohydrate Binding Module Family 1 domain (CBD) and a C-terminal expansin-like domain. In some embodiments, an expansin-like protein or swollenin-like protein comprises one or both of such domains and/or disrupts the structure of cell walls (such as disrupting cellulose structure), optionally without producing detectable amounts of reducing sugars.

In some additional embodiments, the present invention provides at least one chimeric xylose isomerase variant and at least one polypeptide product of a cellulose integrating protein, scaffoldin or a scaffoldin-like protein, for example CipA or CipC from *Clostridium thermocellum* or *Clostridium cellulolyticum* respectively. Scaffoldins and cellulose integrating proteins are multi-functional integrating subunits which may organize cellulolytic subunits into a multi-enzyme complex. This is accomplished by the interaction of two complementary classes of domain (i.e. a cohesion domain on scaffoldin and a dockerin domain on each enzymatic unit). The scaffoldin subunit also bears a cellulose-binding module that mediates attachment of the cellulosome to its substrate. A scaffoldin or cellulose integrating protein for the purposes of this invention may comprise one or both of such domains.

In some additional embodiments, the present invention provides at least one chimeric xylose isomerase variant and at least one cellulose induced protein or modulating protein, for example as encoded by cip1 or cip2 gene or similar genes from *Trichoderma reesei* (See e.g., Foreman et al., J. Biol. Chem., 278:31988-31997 [2003]).

In some additional embodiments, the present invention provides at least one chimeric xylose isomerase variant and at least one member of each of the classes of the polypeptides described above, several members of one polypeptide class, or any combination of these polypeptide classes to provide enzyme mixtures suitable for various uses.

Other Components of Xylose Isomerase Compositions

In some embodiments, xylose isomerase polypeptides of the present invention (e.g., xylose isomerase chimeras) are used in combination with other optional ingredients such as at least one buffer, surfactant, and/or scouring agent. In some embodiments, at least one buffer is used with at least one xylose isomerase polypeptide (e.g., xylose isomerase chimera) of the present invention (optionally combined with other enzymes) to maintain a desired pH within the solution in which the xylose isomerase is employed. The exact concentration of buffer employed will depend on several factors which the skilled artisan can determine. Suitable buffers are well known in the art and any suitable buffer finds use in the present invention.

In some embodiments, at least one surfactant is used with at least one xylose isomerase variant of the present invention. Suitable surfactants include any surfactant compatible with the xylose isomerase(s) and, optionally, with any other enzymes being used in the mixture. Exemplary surfactants include, but are not limited to anionic, non-ionic, and ampholytic surfactants. Suitable anionic surfactants include, but are not limited to, linear or branched alkylbenzenesulfonates; alkyl or alkenyl ether sulfates having linear or branched alkyl groups or alkenyl groups; alkyl or alkenyl sulfates; olefinsulfonates; alkanesulfonates, and the like. Suitable counter-ions for anionic surfactants include, but are not limited to alkali metal ions, such as sodium and potassium; alkaline earth metal ions, such as calcium and magnesium; ammonium ion; and alkanolamines having from 1 to 3 alkanol groups of carbon number 2 or 3. Ampholytic surfactants suitable for use in the practice of the present invention include, but are not limited to surfactants such as quaternary ammonium salt sulfonates, betaine-type ampholytic surfactants, and the like. Suitable nonionic surfactants include, but are not limited to polyoxalkylene ethers, as well as higher fatty acid alkanolamides or alkylene oxide adduct thereof, fatty acid glycerine monoesters, and the like. Mixtures of surfactants also find use in the present invention, as known in the art. Indeed, any suitable mixture of surfactants finds use in the present invention.

Fermentation

The present invention provides processes for producing fermentation products, wherein the method comprises: (a) providing the recombinant fungal cell of the present invention; (b) providing a fermentation medium comprising xylose; (c) contacting the fermentation medium with the recombinant fungal cell under conditions suitable for generating the fermentation product; and optionally (d) recovering the fermentation product. In some embodiments, the fermentation product is an alcohol (e.g., ethanol, butanol, etc.), a fatty alcohol (e.g., a C8-C20 fatty alcohol), a fatty acid (e.g., a C8-C20 fatty acid), lactic acid, 3-hydroxypropionic acid, acrylic acid, acetic acid, succinic acid, citric acid, malic acid, fumaric acid, an amino acid, 1,3-propanediol, ethylene, glycerol, and/or a β-lactam (e.g., cephalosporin). However, it is contemplated that other fermentation products will be produced using the methods of the present invention.

In some embodiments, the fermentation medium is feedstock from a cellulosic saccharification process and/or feedstock from a hemicellulose pre-treatment process. Such feedstocks include, but are not limited to carbohydrates (e.g., lignocellulose, xylans, cellulose, starch, etc.), other sugars (e.g., glucose, xylose, arabinose, etc.), and other compositions. Compositions of fermentation media suitable for the growth of yeast and filamentous fungi are well known in the art and there are various reference texts that provide recipes for these media. Any suitable medium finds use in the present invention.

Fermentation conditions suitable for generating desired fermentation products are well known in the art and any suitable method finds use in the present invention. In some embodiments, the fermentation process is carried out under aerobic or microaerophilic (i.e., where the concentration of oxygen is less than that in air), or anaerobic conditions. In some embodiments, fermentation is conducted under anaerobic conditions (i.e., no detectable oxygen), or less than about 5, about 2.5, or about 1 mmol/L/h oxygen. In the absence of oxygen, the NADH produced in glycolysis cannot be oxidized by oxidative phosphorylation. Under anaerobic conditions, pyruvate or a derivative thereof may be utilized by the host cell as an electron and hydrogen acceptor in order to generated NAD+. In some embodiments of the present invention, when the fermentation process is carried out under anaerobic conditions, pyruvate is reduced to a fermentation product such as ethanol, butanol, lactic acid, 3-hydroxypropionic acid, acrylic acid, acetic acid, succinic acid, citric acid, malic acid, fumaric acid, an amino acid, 1,3-propanediol, ethylene, glycerol, and/or a β-lactam (e.g., a cephalosporin).

In some embodiments, the fermentation process is run at a temperature that is optimal for the recombinant fungal cell. For example, in some embodiments, the fermentation process is performed at a temperature in the range of from about 20° C. to about 42° C. In some embodiments, the process is carried out a temperature that is less than about 38° C., less than about 35° C., less than about 33° C., or less than about 38° C., but at least about 20° C., 22° C., or 25° C. However, in some embodiments, the temperature is much higher (e.g., up to 100° C. or greater). In some embodiments, recombinant host cells of the present invention are grown under batch or continuous fermentation conditions. Classical batch fermentation is a closed system, wherein the composition of the medium is set at the beginning of the fermentation and is not subject to artificial alterations during the fermentation. A variation of the batch system is a fed-batch fermentation, which also finds use in the present invention. In this variation, the substrate is added in increments as the fermentation progresses. Fed-batch systems are useful when catabolite repression is likely to inhibit the metabolism of the cells and/or where it is desirable to have limited amounts of substrate in the medium. Batch and fed-batch fermentations are common and well known in the art. Continuous fermentation is an open system where a defined fermentation generally maintains the culture at a constant high density where cells are primarily in log phase growth. Continuous fermentation systems strive to maintain steady state growth conditions. Methods for modulating nutrients and growth factors for continuous fermentation processes, as well as techniques for modulating nutrients and growth factors for continuous fermentation processes as well as techniques for maximizing the rate of product formation are well known in the art of industrial microbiology. It is intended that any suitable fermentation method method will find use in the present invention.

The foregoing and other aspects of the invention may be better understood in connection with the following non-limiting examples.

EXPERIMENTAL

The present invention is described in further detail in the following Examples, which are not in any way intended to limit the scope of the invention as claimed.

In the experimental disclosure below, the following abbreviations apply: wrt (with regard to); pm (parts per million); M (molar); mM (millimolar), uM and μM (micromolar); nM (nanomolar); mol (moles); gm and g (gram); mg (milligrams); ug and μg (micrograms); L and l (liter); ml and mL (milliliter); cm (centimeters); mm (millimeters); um and jm (micrometers); sec. (seconds); min(s) (minute(s)); h(s) and hr(s) (hour(s)); U (units); MW (molecular weight); rpm (rotations per minute); ° C. (degrees Centigrade); DNA (deoxyribonucleic acid); RNA (ribonucleic acid); CDW (cell dry weight); HPLC (high pressure liquid chromatography); HMF (hydroxymethylfurfural); YPD (10 g/L yeast extract, 20 g/L peptone 20 g/L dextrose); YPD agar (10 g/L yeast extract, 20 g/L peptone, 20 g/L dextrose, 15 g/L agar, 200 ug/ml G418); propagation medium (160 g/l glucose, 40 g/l xylose, 4.5 g/l arabinose, 20 g/l yeast extract, 6 g/l acetic acid, 0.6 g/l furfural, 0.9 g/l hydroxymethylfurfural with a vitamin solution added to final concentrations of 0.05 mg/l biotin, 1 mg/l calcium pantothenate, 1 mg/l nicotinic acid, 1 mg/l myoinositol, 1 mg/l thiamine chloride hydrochloride, 1 mg/l pyridoxal hydrochloride potassium iodide and a trace element solution added to final concentrations of 0.403 M EDTA, 15.6 M $ZnSO_4$, 5 M $MnCl_2$, 1.3 M $CoCl_2$, 1.2 μM $CuSO_4$, 1.6 M disodium molybdate, 30.6 M $CaCl_2$, 10.8 M $FeSO_4$, 16.2 M boric acid, 0.6 M potassium iodide, 5g/l $NH_4SO_4$, 3g/l $K_2PO_4$, 0.5 g/l $MgSO_4$ and pH adjusted to 5.0 with NaOH); ARS (ARS Culture Collection or NRRL Culture Collection, Peoria, Ill.); Lallemand (Lallemand Ethanol Technology, Milwaukee, Wis.); Dualsystems (Dualsystems Biotech AG, Basel, Switzerland); Megazyme (Megazyme International Ireland, Ltd., Wicklow, Ireland); Dasgip (Dasgip Biotools, LLC, Shrewsbury, Mass.); Difco (Difco Laboratories, BD Diagnostic Systems, Detroit, Mich.); PCRdiagnostics (PCRdiagnostics, *E. coli* SRO, Slovak Republic); Agilent (Agilent Technologies, Inc., Santa Clara, Calif.); and Bio-Rad (Bio-Rad Laboratories, Hercules, Calif.).

Example 1

Cloning of Xylose Isomerase Genes

Xylose isomerase genes from *Ruminococcus flavefaciens* (RF_XI; SEQ ID NO:1), *Clostridium phytofermentans* (CP_XI; SEQ ID NO:3), *Abiotrophia defectiva* (AD_XI; SEQ ID NO:5), *Rumninococcus* sp. 18P13 (RFFD_XI; SEQ ID NO:7) and *Phytophthora infestans* (PI_XI; SEQ ID NO:9) were synthesized with codons optimized for expression in yeast with the following 5' and 3' flanks (5'GGATCCCAAA-CAAA [SEQ ID NO: 11]; 3'-TAACATATG [SEQ ID NO:12]) to introduce 5'-BamH1 and 3'-NdeI restriction sites flanking the gene.

The yeast vector p427TEF (Dualsystems) was used for gene expression. This vector contains a kanamycin resistance gene that allows for selection in yeast, an ampicillin resistance gene that allows for selection in E. coli, and a 2 micron origin of replication that allows for propagation of plasmids in high copy numbers in yeast cells. For cloning the isomerase gene, p427TEF was digested with SacI and XhoI restriction enzymes. The larger fragment (6235 bp) was ligated with an oligomer of the following sequence, 5'GAGCTCACGGATC-CGTCATATGCTAGATCTCTGAATTCT-TACTAGTTCGACGTCTACCTAGGCAGTCG ACACGCGGCCGCTTCTCGAG 3' (SEQ ID NO: 13) to introduce a new multiple cloning site (MCS) with desired restriction sites. Using the new MCS, the TEF1 promoter of S. cerevisiae was re-introduced in the vector using SacI/BamHI restriction sites resulting in vector PLS1567. Additional promoters (Adh1p, GPDp) and terminators (Adh2t, Adh1t) were cloned into PLS1567 using yeast recombination cloning using methods commonly used in the art. For yeast recombinational cloning, PLS1567 was digested with BamHI/XhoI, and a 3:1 mass ratio of each insert to digested PLS1567 was used. The transformants were selected on culture plates containing G418. The resulting plasmid (PLS1448) with 3 promoters and terminators was confirmed by sequencing.

The codon optimized xylose isomerase genes were cloned in PLS1448 downstream of the TEF1 promoter using BamHI/NdeI restriction sites resulting in the following plasmids: PLS8965 (RF_XI), PLS1569 (CP_XI), PLS10096 (AD_XI), PLS12980 (PI_XI), and PLS12982 (RFFD_XI).

Plasmids PLS8965 (RFXI), PLS1569 (CPXI), PLS10096 (AD_XI), PLS12980 (PI_XI), PLS12982 (RFFD_XI) and PLS1448 (vector control) were used to transform S. cerevisiae BY4741 (MATa; his3Δ1 leu2Δ0 met15Δ0 ura3Δ0) using methods known in the art. Transformants were selected on YPD agar plates. Positive transformants were confirmed using PCR diagnostics.

Example 2

Directed Evolution of Xylose Isomerase Using Family Shuffling

Xylose isomerase genes from *Ruminococcus flavefaciens* (RF_XI; SEQ ID NO: 1), *Clostridium phytofermentans* (CP_XI; SEQ ID NO:3), *Abiotrophia defectiva* (AD_XI; SEQ ID NO:5), *Ruminococcus* sp. 18P13 (RFFD_XI; SEQ ID NO:7) and *Phytophthora infestans* (PI_XI; SEQ ID NO:9) were recombined to generate libraries of gene variants using methods as described in U.S. Pat. No. 6,277,638, incorporated herein by reference. The truncated sequences used in the library construction are provided below.

```
RF.XI-5':
                                                                  (SEQ ID NO: 14)
atggaatattctccaacatcggaaaaatccaataccaaggtccaaaatccacagatcctttgtcttttaaatattataatcctgaagaagtaatcaacggtaa gaccatgagggagcatttgaaattcgctctatcctggtggcacactatgggtggcgatggtactgatatgttcggatgtggtactacggacaagacctggggt caatccgacccagcggcaagagctaaggccaaagttgatgctgctacgaaattatggataagctgagcattgattactactgcttccatgatagagacctact ccagaatatggctccttgaaagcgaccaatgatcaactggacattgttactgattacatcaaggagaagcagggcgataaattcaagtgtttatgggcactg ctaaatgctttgatcaccccaggttcatgcacggtgcaggaacttctcctagtgccgatgtatcgcttttctgctgcgcaaataaagaaagcattagaatcta ccgtcaagttgggcggtaatggttatgtcttttggggtggtagagaaggttacgagaccctgctgaatactaacatgggcttagaactggacaacatggctag gctaatgaagatggccgtagaatacggtaggtctattggattcaaaggtgacttctacatcgagcctaaacccaaggaacctactaagcaccagtacgacttc gacactgctaccgtattaggttttttaaggaagtacgggttggataaagacttcaagatgaacatcgaagccaatcacgccacactagcacaacacacattcc agcatgagttacgtgtggctagggataacggtgtattcggttctattgatgctaaccaaggtgacgtattgttaggatgggacacggatcaattccccacaaa catttatgatactactatgtgtatgtatgaggtcattaaagccggtggtttcacaaatggcggcctgaactttgatgcgaaagctcgtagggggttcattcacg cctgaagatattactatagttacattgctggtatggatgcttcgc RF.XI-3':
                                                                  (SEQ ID NO: 15)
ttacgagaccctgctgaatactaacatgggcttagaactggacaacatggctaggctaatgaagatggccgtagaatacggtaggtctattggattcaaaggt gacttctacatcgagcctaaacccaaggaacctactaagcaccagtacgacttcgacactgctaccgtattaggttttttaaggaagtacgggttggataaag acttcaagatgaacatcgaagccaatcacgccacactagcacaacacacattccagcatgagttacgtgtggctagggataacggtgtattcggttctattga tgctaaccaaggtgacgtattgttaggatgggacacggatcaattccccacaaacatttatgatactactatgtgtatgtatgaggtcattaaagccggtggt ttcacaaatggcggcctgaactttgatgcgaaagctcgtagggggttcattcacgcctgaagatattttctatagttacattgctggtatggatgctttcgcgt tagggtttagagcagctcttaaattgattgaagacggtagaattgacaagtagtggctgacaggtatgcctatggaataccggtattggtgcagatattattg ccggaaaagccgattttgcatcattggaaaaatatgctaggaaaaaggtgaagttaccgcgtcattgtatctggtagacaagagatgctggaatctattgtca acaacgtattgtttagtagtaa
```

-continued

CP.XI-5':

(SEQ ID NO: 16)
atgaagaactatttccccaacgtcccagaagtcaaatacgaaggtccaaactccacaaatcctacgctataaatattatgatgctaataaagtagtcgccggt aagaccatgaaggagcattgtagattcgctctatcctggtggcacactttgtgtgccggtggtgctgatccattcggagtaactactatggacaggacctacg gtaacattaccgacccaatggaactagctaaggccaaagttgatgctggtttcgaactgatgactaagctgggcatcgagttcttctgcttccatgatgccga cattgctccagaaggtgacaccttcgaagagtccaagaagaatctgttcgagattgttgattacatcaaggagaagatggaccaaaccggcatcaagttgtta tgggcactgctaacaactttagtcaccccaggttcatgcacggtgcatcaacttatgtaatgccgatgttttcgcttatgctgctgcgaaaataaagaacgc tttagatgcgaccatcaagttgggcggtaagggttatgtcttttggggtggtagagaaggttacgagaccctgctgaatactgacctgggcttagaactggac aacatggctaggctaatgaagatggccgtagaatacggtagggctaatggattcgacggtgacttctacatcgagcctaaacccaaggaacctactaagcacc agtacga

CP.XI-3':

(SEQ ID NO: 17)
Ttatgtatagggtggtagagaaggttacgagaccctgctgaatactgacctgggcttagaactggacaacatggctaggctaatgaagatggccgtagaata cggtagggctaatggattcgacggtgacttctacatcgagcctaaacccaaggaacctactaagcaccagtacgacttcgacactgctaccgtattagatttt taaggaagtacgggttggaaaaagacttcaagatgaacatcgaagccaatcacgccacactagcaggccacacattcgagcatgagttagctatggctagggt aaacggtgcattcggttctgttgatgctaaccaaggtgacccaaacttaggatgggacacggatcaattccccacagacgttcattctgctactcttgctatg ctggaggtcttgaaagccggtggtttcacaaatggcggcctgaactttgatgcgaaagttcgtaggggttcattcgagtttgacgatattgcctatggttaca ttgctggtatggatactttcgcgttagggttaattaaagctgctgaaatcattgatgacggtagaattgccaagtttgtggatgacaggtatgcctatacaag taccggtattggtaaagcgatcgttgacggaactacctatggaagaattggaacaatacgtgttgactcattctgaacctgtcatgcaatctggtagacaaga ggttctggaaactattgtcaacaacatattgtttagataa

AD.XI-5':

(SEQ ID NO: 18)
Atgagtgaattgttccaaaacatcccaaaaatcaaatacgaaggtgcaaattccaaaaatcattggatttcattattatgatgctgaaaaaatagtcctcggt aagaccatgaaggagcatttgccattcgctatggcatggtggcacaatttgtgtgccgctggtactgatatgttcggacgtgatactgcggacaagtcctttg gtttggaaaaaggctcaatggaacatgctaaggccaaagttgatgctggtttcgaatttatggaaaagctgggcattaaatacttctgcttccatgatgtaga ccttgttccagaagcttgcgacattaaagagaccaattctcgactggacgaaatactgattacatatggagaagatgaagggcactgatattaagtgtttatg gggcactgctaatatgtatctaaccccaggttcgtgaacggtgcaggatctactaatagtgccgatgttactgttttgctgctgcgcaaataaagaaagcat tagatattaccgtcaagttgggcggtagaggttatgtcttttggggtggtagagaaggttacgagaccagctgaatactgacgtgaaatttgaacaggaaaac attgctaatctaatgaagatggccgtagaatacggtaggtctattggattcaaaggtgacttctacatcgagcctaaacccaaggaacctatgaagcaccagt acgacttcgacgctgctaccgcaataggttttttaaggcagtacgggttggataaagacttcaaattgaacatcgaagccaatcacgccacactagcaggaca ctcattccagcatgagttacgtatttctagtattaacggtatgttgggttctgttgatgctaaccaaggtgacatgttgttaggatgggacacggatgaattt ccctttgacgtttatgatactactatgtgtatgtatgaggtccttaaaaacggtggtttgacaggcggctttaactttgatgcgaaaaatcgtaggccttcat acacgtatgaagatatgttctatggtttcattcttggtatggattctttcgc

AD.XI-3':

(SEQ ID NO: 19)
ttatgtcttttggggtggtagagaaggttacgagaccctgctgaatactgacgtgaaatttgaacaggaaaacattgctaatctaatgaagatggccgtagaa tacggtaggtctattggattcaaaggtgacttctacatcgagcctaaacccaaggaacctatgaagcaccagtacgacttcgacgctgctaccgcaataggtt ttttaaggcagtacgggttggataaagacttcaaattgaacatcgaagccaatcacgccacactagcaggacactcattccagcatgagttacgtatttctag tattaacggtatgttgggttctgttgatgctaaccaaggtgacatgttgttaggatgggacacggatgaatttccctttgacgtttatgatactactatgtgt atgtatgaggtccttaaaaacggtggtttgacaggcggctttaactttgatgcgaaaaatcgtaggccttcatacacgtatgaagatatgttctatggtttca ttcttggtatggattctttcgcgttagggttgataaaagctgctaaattgattgaagaaggtacacttgacaattttattaaggaaaggtataaatcttttga atccgaaattggtaaaaaaattagatccaaatcagcctctttgcaagaattggcagcttatgctgaggaaatgggtgctcccgcgatgccgggttcaggtagg caagagtatctgcaagctgctctcaaccaaaatttgtttggtgaagtgtaataa -continued

RFFD.XI2-5':

(SEQ ID NO: 20)

Atggaattttctcaagaacatctctaagataccatacgaaggcaaagactctaccaatccattagcattcaagtactacaatcctgacgaagtaatcgacggta agaagatgagagacatcatgaagtttgctttgtcttggtggcatactatgggaggtgatggtactgatatgtttggctgtggtactgctgataagacatgggg cgagaatgatccagctgctagagctaaagctaaagttgatgccgcatttgaaatcatgcagaagttatccattgattacttctgatccatgatagagatttgt accagagtacggttattgaaggacacaaacgctcaattggacattgtcactgactacatcaaggctaaacaagctgaaaccggtttgaaatgtattggggtac tgctaagtgcttcgaccatccaagattcatgcacggtgctggtacttctccttcagcggatgtatcgcattctcagctgctcaaatcaagaaagctctggaat ctaccgtcaagttgggtggaactggttatgtatctggggtggtagagaaggatatgaaacgttgttgaatactaacatgggacttgaattggacaacatggct aggttgatgaagatggccgttgagtatggtaggtctattggtttcaaaggtgacttctacattgaacctaagccaaaggaaccaactaagcatcaatacgact ttgacactgctacagtatgggattctgagaaagtacggcctggacaaagacttcaagatgaacatagaagccaatcatgcaactttagcgcaacataccttcc agcacgaattgtgtgtcgccagaactaatggtgattcggttctattgatgctaatcaaggtgatcccttgttgggttgggatacagatcagtttcctacaaac atctatgatactactatgtgcatgtacgaagttatcaaagctggtggtttcactaatggtggtcttaactttgatgctaaagctagaagaggttattcactcc agaagatattactattatacattgctggtatggatgattcgc

RFFD.XI2-3':

(SEQ ID NO: 21)

Tgtcttctggggtggtagagaaggatatgaaacgttgttgaatactaacatgggacttgaattggacaacatggctaggttgatgaagatggccgttgagta tggtaggtctattggtttcaaaggtgacttctacattgaacctaagccaaaggaaccaactaagcatcaatacgactttgacactgctacagtcttgggctt tctgagaaagtacggcctggacaaagacttcaagatgaacatagaagccaatcatgcaactttagcgcaacataccttccagcacgaattgtgtgtcgccag aactaatggtgattcggttctattgatgctaatcaaggtgatcccttgttgggttgggatacagatcagtttcctacaaacatctatgatactactatgtgc atgtacgaagttatcaaagctggtggtttcactaatggtggtcttaactttgatgctaaagctagaagaggttctttcactccagaagatattttctattct tacattgctggtatggatgctttcgctttaggttacaaagctgcttctaagctaatcgctgatggtaggattgatagcttcattagcgatagatatgcttct tggtctgaaggtattggtttggacatcatttccggcaaagctgatatggcggctttagagaagtatgctaggagaaaggagaggtcactgattctatctctt ctggaagacaggaactgttagagtccattgttaacaacgtaatcttcaaccta The parent sequences used for each constructed library are summarized in Table 2-1. In some cases, truncated variants of each parent gene were used to promote crossover events in defined gene regions.

TABLE 2-1

Parent Nucleotide Sequences for Each Library Constructed

| Library | Parent Genes |
|---|---|
| 1.06a | AD_XI (SEQ ID NO: 5), RF_XI (SEQ ID NO: 1) |
| 1.06b | AD_XI (SEQ ID NO: 5), RF_XI (SEQ ID NO: 1) |
| 1.07 | RF_XI (SEQ ID NO: 1), CP_XI (SEQ ID NO: 3) |
| 1.09 | RF_XI (SEQ ID NO: 1), CP_XI (SEQ ID NO: 3), AD_XI (SEQ ID NO: 5), RFFD_XI (SEQ ID NO: 7) |
| 1.10a | AD_XI_5'(SEQ ID NO: 5), CP_XI_5' (SEQ ID NO: 16), RF_XI_3'(SEQ ID NO: 15), RFFD_XI_3' (SEQ ID NO: 21) |
| 1.10b | AD_XI_5'(SEQ ID NO: 18), CP_XI_5' (SEQ ID NO: 16), RF_XI_3'(SEQ ID NO: 15), RFFD_XI_3'(SEQ ID NO: 21) |
| 1.11a | RF_XI_5'(SEQ ID NO: 14), RFFD_XI_5' (SEQ ID NO: 20), AD_XI_3'(SEQ ID NO: 19), CP_XI_3'(SEQ ID NO: 17) |
| 1.11b | RF_XI_5'(SEQ ID NO: 14), RFFD_XI_5'(SEQ ID NO: 20), AD_XI_3' (SEQ ID NO: 19), CP_XI_3'(SEQ ID NO: 17) |

Example 3

Screening of Xylose Isomerase Variants for Activity Improvements

Libraries of xylose isomerase variants were transformed into S. cerevisiae BY4741 and selected on YPD agar plates. Single colonies were used to inoculate 400 ul of YPD supplemented with 200 ug/ml G418. Cells were grown at 30° C. for 24 h at 250 rpm. This culture was used to inoculate YP (10 g/L yeast extract, 20 g/L peptone) media containing 0.5% glucose and 4% xylose. Cultures were incubated at 30° C. and 250 rpm. Growth was monitored by measuring the optical density at 600 nm. After 120h, the residual xylose was measured using a spectrophotometric assay (Megazyme xylose assay; Cat no. K-XYLOSE) performed according to the manufacturer's protocol. Variants with activity equivalent to or improved relative to parent genes used for library synthesis were isolated and sequenced. These variants were also retested at n≥3 using the same assay procedure outlined above to confirm activity improvements. Improved variants are listed in Table 3-1. In this Table, fold improvement ("Fold Improve.") results are provided as values ≥1 (i.e., 1-1.4), ≥1.5 (i.e., 1.5-1.9), ≥2 (i.e., 2-2.4), ≥2.5 (i.e., 2.5-2.9), ≥3 (i.e., 3-3.4), ≥3.5 ((i.e., 3.5-3.9), ≥5.0 (i.e., 5.0-5.4) or >6.5 (i.e., 6.5-7.0). In Table 3-1, the fold improvement is relative to RF_XI (i.e., SEQ ID NO:2). Variant 1 is RF.XI. In the following Table, the hyphens indicate deletions in the sequence and the asterisks indicate mutations in stop codons. In the following Table, "FI" refers to the "fold improvement" observed for the variants relative to RF_XI (SEQ ID NO:2).

TABLE 3-1

Improved Xylose Isomerase Variants

| Var. No. | FI | Active Mutations | Silent Mutations | Insertions wrt RF.XI.4 |
|---|---|---|---|---|
| 1 | | | | |
| 2 | ≥6.5 | F3L/S5Q/G8P/Q11K/Q13E/G14S/P15A/K16N/T18K/D19N/ S22A/K24H/N27D/P28A/E30K/V31I/I32V/N33L/R38K/ K42P/L45M/S46A/T50N/M51L/G52C/G53A/D54A/ C61R/G62D/T64A/T67S/W68L/Q70E/S71K/D72G/P73S/ A74M/A75E/R76H/A84G/I87F/D89E/S92G/D94K/Y96F/ R101V/S104V/Y107A/G108C/S109D/L110I/A112E/ D115S/Q116R/I119E/V120I/T121S/K125L/Q128K/D130T/ K131D/F132I/K140N/C141M/D143S/H144N/M148V/ H149N/T153S/S154T/P155N/F160Y/A161C/S163A/E172D/ S173I/N180R/M199V/T236A/Q273G/T275S/V282I/ A283S/R284S/D285I/V288M/F289L/I292V/V299M/ Q307E/T310F/N311D/I312V/I323L/A325N/F328L/N330-/ L333F/A339N/G342P/F344Y/P346Y/I349M/S352G/Y353F/ A355L/A359S | c924t | 1S2/69L70/127M128 |
| 3 | ≥5 | S5K/G8S//Q11P/Q13E/P15K/K16D/D19N/S22A/E29D/ N33D/T36K/E39D/H40I/L41M/T64A/Q70E/S71N/D89Q/ Y96F/A112D/D115A/I119V/E126A/G129A/D130E/K131T/ F132L/N180T/S219A/I220N/A266P/A269T/Q273G/ T275S/Q277E/R281A/V282M/D285V/V288A/I292V/ D306G/N311D/I312V/Y313H/D314S/T315A/M317L/C318A/ Y320L/I323L/T345E/P346F/E347D/F350A/S352G/ A359T/F364L/R365I/A366K/L368A/K369E/L370I/E372D/ D377A/A381D/W387Y/N388K/A393K/D394A/I396V/ A397D/K399T/A400T/D401S/F402L/A403E/S404E/K407Q/ A409V/E411T/K412H/G413S/V415P/T416V/A417-/ S418-/ L419M/S420Q/R423G/M426V/S429T/S437R/L438- | a27g/c30a/t42c/c51t/ a54c/t60a/g63a/ t69c/a72g/t75c/ t78c/g114a/a126g/ c129t/c133t/a135g/ c138t/c147t/ t156a/c159t/c177t/ a180c/c195t/c201a/ t207c/c216t/ g222t/a225t/g234a/ c237t/t249c/t252a/ c255t/t261c/ c271t/g273a/a274t/ g275c/c306t/c307t/ t309g/a318g/ t321c/c324t/c327t/ a333g/c339a/ t342c/c349t/t360c/ t366c/g381a/g384a/ g399a/t403c/ a405t/c411t/a420g/ t426c/t429c/c432t/ c435a/g438a/ a453t/a456t/a466t/ g467c/t468a/c471g/ t477c/t483a/ t486c/t489a/g495t/ a501c/a510t/t511c/ a513g/c534t/t537a/ t705a/c714t/ g717a/c726t/c738a/ a741c/a744g/t747c/ t751c/a753g/ g756a/g765c/t766c/ t771c/t1185c/ t1224c | 131G132 |
| 4 | ≥3.5 | S5K/G8S/Q11P/Q13E/P15K/K16D/D19N/S22A/E29D/N33D/ T36K/E39D/H40I/L41M/T64A/Q70E/S71N/D89Q/ Y96F/A112D/D115A/E126A/G129A/D130E/K131T/F132L/ N180T/R281C/D285T/V288A/V299P/F364Y/R365K/ L368S/E372A/K378S/V380I/A381S/N388S/T389E/A393L/ A397S/F402M/S404A/A417D/L419I/M426L/L435I/ S437N | a27g/c30a/t42c/c51t/ a54c/t60a/g63a/ t69c/a72g/t75c/ t78c/g114a/a126g/ c129t/c133t/a135g/ c138t/c147t/ t156a/c159t/c177t/ a180c/c195t/c201a/ t207c/c216t/ g222t/a225t/g234a/ c237t/t249c/t252a/ c255t/t261c/ c271t/g273a/a274t/ g275c/c306t/c307t/ t309g/a318g/ t321c/c324t/c327t/ a333g/c339a/ t342c/c349t/t360c/ t366c/g381a/g384a/ g399a/t403c/ a405t/c411t/a420g/ t426c/t429c/c432t/ c435a/g438a/ a453t/a456t/a466t/ | 131G132 |

TABLE 3-1-continued

Improved Xylose Isomerase Variants

| Var. No. | FI | Active Mutations | Silent Mutations | Insertions wrt RF.XI.4 |
|---|---|---|---|---|
| | | | g467c/t468a/c471g/ t477c/t483a/ t486c/t489a/g495t/ a501c/a510t/t511c/ a513g/c534t/t537a/ t552c/t570a/ c573t/g576a/c579g/ c580t/c583t/c600a/ t601c/a603t/ c607t/c625t/a627g/ a642t/a645g/c648t/ a663t/c684t/ g687a/a693g/c696a/ t705a/c714t/ g717a/c726t/c738a/ a741c/a744g/t747c/ t751c/a753g/ g756a/g765c/t766c/ t771c/c792a/ c804t/c807a/a810t/ c811t/a816g/c822t/ a825c/t834c/ g837a/a840g/g846c/ t849c/g852a/ c858t/c885t/c894t/ a903g/a906t/c912t/ g915a/a921g/ c924t/c927t/t936c/ t954c/t960c/g963a/ c966t/t969c/ c975t/a987t/c993t/ c996t/g999t/g1011t/ c1018a/t1020a/ g1023a/a1029t/ g1035t/t1038a/ a1054t/g1055c/g1083t/ g1089t/a1098t/ a1107g/t1108c/ g1110a/t1113c/ c1119t/a1125g/ c1131t/t1137c/ c1146t/g1149a/c1155t/ t1182c/t1185c/ a1194c/c1200t/ a1209g/g1215a/ a1218g/a1221g/ a1233g/t1239a/a1242g/ t1245c/c1248t/ a1254t/t1266a/ a1272g/g1275a/ c1279t/g1281a/ a1284g/t1287c/c1293t/ t1308c/t1312c/ g1314a | |
| 5 | ≥3.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/K223D/G249A/D257E/Q273G/ Q277E/R281A/V282M/D285V/V288A/I292V/V299P/ L300N/N311D/I312V/Y313H/D314S/T315A/M317L/ C318A/Y320L/I323L/A339V/T345E/P346F/E347D/F350A/ A359T/F364L/R365I/A366K/L368A/K369E/L370I/E372D/ D377A/A381D/W387Y/N388K/A393K/D394A/I396V/ A397D/K399T/A400T/D401S/F402L/A403E/S404E/ K407Q/A409V/E411T/K412H/G413S/V415P/T416V/ A417-/S418-/ L419M/S420Q/M426V/S429T/V434I/S437R/L438- | t279c/t483c/a510t/ t1185c/t1224c/t1266c | 2N3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
| 6 | ≥3.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/K223D/G249A/D257E/Q273G/ Q277E/R281A/V282M/D285V/V288A/I292V/V299P/ L300N/N311D/I312V/Y313H/D314S/T315A/M317L/ C318A/Y320L/I323L/A339V/T345E/P346F/E347D/F350A/ S352G/A359T/F364L/R365I/A366K/L368A/K369E/ L370I/E372D/D377A/A381D/W387Y/N388K/A393K/D394A/ I396V/A397D/K399T/A400T/D401S/F402L/A403E/ S404E/K407Q/A409V/E411T/K412H/G413S/V415P/ T416V/A417-/S418-/ L419M/S420Q/M426V/S429T/V434I/S437R/L438- | t279c/a510t/t1185c/ t1224c | 2N3/70I71/131G132 |
| 7 | ≥3.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/K223D/G249A/D257E/Q273G/ Q277E/R281A/V282M/D285V/V288A/I292V/V299P/ L300N/N311D/I312V/Y313H/D314S/T315A/M317L/ C318A/Y320L/I323L/A339V/T345E/P346F/E347D/F350A/ S352G/A359T/F364L/R365I/A366K/L368A/K369E/ L370I/E372D/D377A/A381D/W387Y/N388K/A393K/D394A/ I396V/A397D/K399T/A400T/D401S/F402L/A403E/ S404E/K407Q/A409V/E411T/K412H/G413S/V415P/ T416V/A417-/S418-/ L419M/S420Q/M426V/S429T/S437R/L438* | t279c/a510t/a753g/ t1053c/t1185c/ t1224c | 2N3/70I71/131G132 |
| 8 | ≥3.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/K223D/G249A/D257E/Q273G/ Q277E/R281A/V282M/D285V/V288A/I292V/V299P/ L300N/N311D/I312V/Y313H/D314S/T315A/M317L/ C318A/Y320L/I323L/A339V/T345E/P346F/E347D/F350A/ S352G/A359T/F364L/R365I/A366K/L368A/K369E/ L370I/E372D/D377A/A381D/W387Y/N388K/A393K/D394A/ I396V/A397D/K399T/A400T/D401S/F402L/A403E/ S404E/K407Q/A409V/E411T/K412H/G413S/V415P/ T416V/A417-/S418-/L419M/S420Q | t279c/a510t/t1185c/ t1224c | 2N3/70I71/131G132/ 438*439 |
| 9 | ≥3.0 | E2K/F3Y/S5P/I7V/G8P/K9E/I10V/Q11K/Q13E/K16N/D19N 19N/L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76H/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/T236M/T244A/V247A/L248I/K253Q/M262L/ Q273G/Q277E/R281A/V282M/D285V/V288A/I292V/ V299P/L300N/N311D/I312V/Y313H/D314S/T315A/ M317L/C318A/Y320L/I323L/A339V/T345E/P346F/E347D/ F350A/S352G/F364L/R365I/A366K/L368A/K369G/ L370I/E372D/D377A/A381D/W387Y/N388K/A393K/D394A/ | t279c/a510t/g783a/ t1020c/t1185c/t1224c | 2N3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
| | | I396V/A397D/K399T/A400T/D401S/F402L/A403E/ S404E/K407Q/A409V/E411T/K412H/G413S/V415P/ T416V/A417-/S418-/ L419M/S420Q/M426V/S429T/V434I/S437R/L438- | | |
| 10 | ≥3.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/K223D/G249A/D257E/Q273G/ Q277E/R281A/V282M/D285V/V288A/I292V/V299P/ L300N/N311D/I312V/Y313H/D314S/T315A/M317L/ C318A/Y320L/I323L/A339V/T345E/P346F/E347D/F350A/ S352G/A359T/F364L/R365I/A366K/L368A/K369E/ L370I/E372D/D377A/A381D/W387Y/N388K/A393K/D394A/ I396V/A397D/K399T/A400T/D401S/F402L/A403E/ S404E/K407Q/A409V/E411T/K412H/G413S/V415P/ T416V/A417-/S418-/ L419M/S420Q/M426V/S429T/V434I/S437R/L438-/ | t279c/a510t/t1185c/ t1224c | 2N3/70I71/131G132 |
| 11 | ≥3.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/T236M/V247A/L248I/K253Q/ M262L/Q273G/Q277E/R281A/V282M/D285V/V288A/ I292V/V299P/L300N/N311D/I312V/Y313H/D314S/ T315A/M317L/C318A/Y320L/I323L/A339V/T345E/P346F/ E347D/F350A/S352G/A359T/F364L/R365I/A366K/ L368A/K369E/L370I/E372D/D377A/W387Y/N388K/A393K/ D394A/I396V/A397D/K399T/A400T/D401S/F402L/ A403E/S404E/K407Q/A409V/E411T/K412H/G413S/ V415P/T416V/A417-/S418-/ L419M/S420Q/M426V/S429T/V434I/S437R/L438- | t279c/t483a/a510t/ t771c/g783a/t1173c/ t1185c/t1224c | 2N3/70I71/131G132 |
| 12 | ≥3.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76H/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/T236M/T244A/V247A/L248I/K253Q/M262L/ Q273G/Q277E/R281A/V282M/D285V/V288A/I292V/ V299P/L300N/N311D/I312V/Y313H/D314S/T315A/ M317L/C318A/Y320L/I323L/A339V/T345E/P346F/E347D/ F350A/S352G/F364L/R365I/A366K/L368A/K369G/ L370I/E372D/D377A/A381D/W387Y/N388K/A393K/D394A/ I396V/A397D/K399T/A400T/D401S/F402L/A403E/ S404E/K407Q/A409V/E411T/K412H/G413S/V415P/ T416V/A417-/S418-/ L419M/S420Q/M426V/S429T/V434I/S437R/L438- | t279c/a510t/g783a/ t1020c/t1185c/t1224c | 2N3/70I71/131G132 |
| 13 | ≥3.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/N198D/M199L/ S219A/I220N/K223D/T236M/M262L/Q273G/Q277E/R281A/ | t279c/a510t/g783a/ t1128c/t1185c/t1224c | 2N3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
| | | V282M/D285V/V288A/I292V/V299P/L300N/N311D/ I312V/Y313H/D314S/T315A/M317L/C318A/Y320L/I323L/ A339V/T345E/P346F/E347D/F350A/S352G/A359T/ F364L/R365I/A366K/L368A/K369E/L370I/E372D/D377A/ A381D/W387Y/N388K/A393K/D394A/I396V/A397D/ K399T/A400T/D401S/F402L/A403E/S404E/K407Q/ A409V/E411T/K412H/G413S/V415P/T416V/A417-/ S418-/ L419M/S420Q/M426V/S429T/V434I/S437R/L438- | | |
| 14 | ≥3.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75V/R76H/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/F162Y/S163A/Q166K/K169N/ E172D/S173A/V175I/N180K/G249A/K253R/D257E/ Q273G/Q277E/R281A/V282M/D285V/V288A/I292V/V299P/ L300N/N311D/I312V/Y313H/D314S/T315A/M317L/ C318A/Y320L/I323L/A339V/T345P/E347D/F350A/ S352G/A359T/F364L/R365I/A366K/L368A/K369E/ L370I/E372D/D377A/A381D/W387Y/N388K/A393K/ D394A/I396V/A397D/K399T/A400T/D401S/F402L/A403E/ S404E/K407Q/A409V/E411T/K412H/G413S/V415P/ T416V/A417-/S418-/ L419M/S420Q/M426V/S429T/V434I/S437R/L438- | t279c/a510t/t1185c/ t1224c | 2N3/70I71/131G132 |
| 15 | ≥3.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/K211R/G249A/D257E/M262V/Q273G/ Q277E/R281A/V282M/D285V/V288A/I292V/V299P/L300N/ N311D/I312V/Y313H/D314S/T315A/M317L/C318A/ Y320L/I323L/A339V/T345E/P346F/E347D/F350A/S352G/ A359T/F364L/R365I/A366K/L368A/K369E/L370I/ E372D/D377A/A381D/W387Y/N388K/A393K/D394A/I396V/ A397D/K399T/A400T/D401S/F402L/A403E/S404E/ K407Q/A409V/E411T/K412H/G413S/V415P/T416V/ A417-/S418-/ L419M/S420Q/M426V/S429T/V434I/S437R/L438- | t207c/t279c/a510t/ t1185c/t1224c | 2N3/70I71/131G132 |
| 16 | ≥3.0 | E2K/F3Y/S5P/I7V/G8P/K9E/I10V/Q11K/Y12F/Q13E/K16N/ D19N/L21F/S22A/N27D/P28A/E29N/E30K/I32V/ N33A/R38K/L41C/K42R/M51L/G52C/G53A/D54G/T56A/ M58P/C61V/G62T/T64M/K66R/W68Y/Q70N/S71T/ A74M/A75E/R76L/A84G/I87L/D89T/S92G/D94E/Y95F/ Y96F/R101A/L103I/S104A/Y107G/G108D/S109T/L110F/ K111E/A112E/T113S/N114K/D115K/Q116N/D118F/ I119E/V120I/T121V/Q128M/G129D/D130Q/K131T/F132I/ C134L/K140N/C141N/D143S/G152S/P155C/S156N/ F162Y/S163A/Q166K/K169N/E172D/S173A/V175I/N180K/ N198D/M199L/S219A/I220N/K223D/D257E/Q273G/ Q277E/R281A/V282M/D285V/V288A/I292V/N311D/ I312V/Y313H/D314S/T315A/M317L/C318A/Y320L/I323L/ A339V/T345E/P346F/E347D/F350A/S352G/A359T/ F364L/R365I/A366K/L368A/K369E/L370I/E372D/D377A/ A381D/W387Y/N388K/A393K/D394A/I396V/A397D/ K399T/A400T/D401S/F402L/A403E/S404E/K407Q/ A409V/E411T/K412H/G413S/V415P/T416V/A417-/ S418-/ L419M/S420Q/M426V/S429T/V434I/S437R/L438- | t279c/a510t/t1122g/ t1185c/t1224c | 2N3/70I71/131G132 |
| 17 | ≥2.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ | t279c/a510t/t570c/ t1185c/t1224c | 2N3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
|  |  | V120I/T121V/Q128M/G129D/D130Q/K131T/F132I/C134L/ K140N/C141N/D143S/G152S/P155C/S156N/F162Y/ S163A/Q166K/K169N/E172D/S173A/N198D/M199L/ Q273G/Q277E/R281A/V282M/D285V/V288A/I292V/V299P/ L300N/N311D/I312V/Y313H/D314S/T315A/M317L/ C318A/Y320L/I323L/T345E/P346F/E347D/F350A/S352G/ A359T/F364L/R365I/A366K/L368A/K369E/L370I/ E372D/D377A/A381D/W387Y/N388K/A393K/D394A/ I396V/A397D/K399T/A400T/D401S/F402L/A403E/S404E/ K407Q/A409V/E411T/K412H/G413S/V415P/T416V/ A417-/S418-/ L419M/S420Q/M426Y/S429T/V434I/S437R/L438- |  |  |
| 18 | ≥2.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/K223D/G249A/D257E/Q273G/ Q277E/R281A/V282M/D285V/V288A/I292V/V299P/ L300N/N311D/I312V/Y313H/D314S/T315A/M317L/ C318A/Y320L/I323L/A339V/T345E/P346F/E347D/F350A/ S352G/A359T | t279c/t483a/a510t | 2N3/70I71/131G132/ 438*439 |
| 19 | ≥2.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/K223D/G249A/D257E/Q273G/ Q277E/R281A/V282M/D285V/V288A/I292V/V299P/ L300N/N311D/I312V/Y313H/D314S/T315A/M317L/ C318A/Y320L/I323L/A339V/T345E/P346F/E347D/F350A/ S352G/A359T/F364L/R365I/A366K/L368A/K369E/ L370I/E372D/D377A/A381D/W387Y/N388K/A393K/D394A/ I396V/A397D/K399T/A400T/D401S/F402L/A403E/ S404E/K407Q/A409V/E411T/K412H/G413S/V415P/ T416V/A417-/S418-/L419M/S420Q/M426V | t279c/a510t/t705c/ t1185c/t1224c | 2N3/70I71/131G132 |
| 20 | ≥2.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/S219A/I220N/ K223D/G249A/D257E/Q273G/Q277E/R281A/V282M/ D285V/V288A/I292V/V299P/L300N/N311D/I312V/ Y313H/D314S/T315A/M317L/C318A/Y320L/I323L/ A339V/T345E/P346F/E347D/F350A/S352G/A359T/F364L/ R365I/A366K/L368A/K369E/L370I/E372D/D377A/ A381D/W387Y/N388K/A393K/D394A/I396V/A397D/K399T/ A400T/D401S/F402L/A403E/S404E/K407Q/A409V/ E411T/K412H/G413S/V415P/T416V/A417-/S418-/ L419M/S420Q/M426V/S429T/V434I/S437R/L438- | t120c/t279c/a510t/ t1185c/t1224c | 2N3/70I71/131G132 |
| 21 | ≥2.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172G/S173A/V175I/N180R/ | t279c/a510t/t570a/ c573t/g576a/c579g/ c580t/c583t/ c600a/t601c/a603t/ c607t/c625t/a627g/ a642t/a645g/ c648t/a663t/t771c/ g783a/t1170c/t1185c/ t1224c | 2N3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
| | | T244A/V247A/L248I/K253Q/M262L/Q273G/T275S/V282I/ A283S/R284S/D285I/V288M/F289L/I292V/V299P/ L300N/N311D/I312V/Y313H/D314S/T315A/M317L/C318A/ Y320L/I323L/A339V/T345E/P346F/E347D/F350A/ S352G/F364L/R365I/A366K/L368A/K369E/L370I/E372D/ D377A/A381D/W387Y/N388K/A393K/D394A/I396V/ A397D/K399T/A400T/D401S/F402L/A403E/S404E/K407Q/ A409V/E411T/K412H/G413S/V415P/T416V/A417-/ S418-/ L419M/S420Q/M426V/S429T/V434I/S437R/L438- | | |
| 22 | ≥2.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/K223D/I228V/D257E/Q273G/ Q277E/R281A/V282M/D285V/V288A/I292V/V299P/ L300N/N311D/I312V/Y313H/D314S/T315A/M317L/ C318A/Y320L/I323L/A339V/T345E/P346F/E347D/F350A/ A359T/F364L/R365I/A366K/L368A/K369E/L370I/E372D/ D377A/A381D/W387Y/N388K/A393K/D394A/I396V/ A397D/K399T/A400T/D401S/F402L/A403E/S404E/ K407Q/A409V/E411T/K412H/G413S/V415P/T416V/ A417-/S418-/ L419M/S420Q/M426V/S429T/S437R/L438* | t171c/t279c/a510t/ t1185c/t1224c | 2N3/70I71/131G132 |
| 23 | ≥2.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/N198D/M199L/ T236M/D257E/Q273G/Q277E/R281A/V282M/D285V/ V288A/I292V/N311D/I312V/Y313H/D314S/T315A/M317L/ C318A/Y320L/I323L/A339V/T345E/P346F/E347D/ F350A/S352G/A359T/F364L/R365I/A366K/L368A/K369E/ L370T/E372D/D377A/A381D/W387Y/N388K/A393K/ D394A/I396V/A397D/K399T/A400T/D401S/F402L/ A403E/S404E/K407Q/A409V/E411T/K412H/G413S/V415P/ T416V/A417-/S418-/ L419M/S420Q/M426V/S429T/V434I/S437R/L438- | t279c/a510t/t1185c/ t1224c | 2N3/70I71/131G132 |
| 24 | ≥2.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/K223D/G249A/D257E/Q273G/ Q277E/R281A/V282M/D285V/V288A/I292V/V299P/ L300N/N311D/I312V/Y313H/D314S/T315A/M317L/ C318A/Y320L/I323L/A339V/T345E/P346F/E347D/F350A/ S352G/A359T | t279c/t483a/a510t | 2N3/70I71/131G132 |
| 25 | ≥2.5 | S5K/G8S/Q11P/Q13E/P15K/K16D/D19N/S22A/E29D/N33D/ T36K/E39D/H40I/L41M/T64A/Q70E/S71N/D89Q/ Y96F/A112D/D115A/E126A/G129A/D130E/K131T/F132L/ N198D/M199L/S219A/I220N/K223E/K253Q/Q273G/ T275S/V282I/A283S/R284S/D285I/V288M/F289L/I292V/ V299M/Q307E/T310F/N311D/I312V/I323L/A325N/F328L/ N330-/ L333F/A339N/G342P/F344Y/P346Y/I349M/S352G/Y353F/ A355L/A359S/F364L/R365I/A366K/L368A/D373E/ R375T/I376L/K378N/V380I/A381D/D382E/A385K/W387F/ N388E/T389S/G390E/A393K/D394K/I396R/A397S/ | a27g/c30a/t42c/c51t/ a54c/t60a/g63a/ t69c/a72g/t75c/ t78c/g114a/a126g/ c129t/c133t/a135g/ c138t/c147t/ t156a/c159t/c177t/ a180c/c195t/c201a/ t207c/c216t/ g222t/a225t/g234a/ c237t/t249c/t252a/ | 131G132/436G437 |

TABLE 3-1-continued

Improved Xylose Isomerase Variants

| Var. No. | FI | Active Mutations | Silent Mutations | Insertions wrt RF.XI.4 |
|---|---|---|---|---|
| | | G398K/K399S/D401S/F402L/A403Q/S404E/E406A/K407A/ L410E/K412M/E414-/ V415A/T416P/S418M/L419P/S420G/M426Y/E428Q/S429A/ I430A/V431L/N433Q/V434N/S437E/L438V | c255t/t261c/ c271t/g273a/a274t/ g275c/c306t/c307t/ t309g/a318g/ t321c/c324t/c327t/ a333g/c339a/ t342c/c349t/t360c/ t366c/g381a/g384a/ g399a/t403c/ a405t/c411t/a420g/ t426c/t429c/c432t/ c435a/g438a/ a453t/a456t/a466t/ g467c/t468a/c471g/ t477c/t483a/ t486c/t489a/g495t/ a501c/a510t/t511c/ a513g/t552c/t601c/ c924t/t1263a/ a1269g | |
| 26 | ≥2.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/K78R/A84G/I87L/D89T/S92G/D94E/Y95F/ Y96F/R101A/L103I/S104A/Y107G/G108D/S109T/L110F/ K111E/A112E/T113S/N114K/D115K/Q116N/D118F/I119E/ V120I/T121V/Q128M/G129D/D130Q/K131T/F132I/ C134L/K140N/C141N/D143S/G152S/P155C/S156N/ F162Y/S163A/Q166K/K169N/E172D/S173A/V175I/N180K/ N198D/M199L/S219A/I220N/K223D/G249A/D257E/ Q273G/Q277E/R281A/V282M/D285V/V288A/I292V/ V299P/L300N/N311D/I312V/Y313H/D314S/T315A/M317L/ C318A/Y320L/I323L/A339V/T345E/P346F/E347D/ F350A/S352G/A359T/F364L/R365I/A366K/L368A/K369E/ L370I/E372D/D377A/A381D/W387Y/N388K/A393K/ D394A/I396V/A397D/K399T/A400T/D401S/F402L/ A403E/S404E/K407Q/A409V/E411T/K412H/G413V/V415P/ T416V/A417-/S418-/ L419M/S420Q/M426V/S429T/V434I/S437R/L438* | t279c/a510t/t1185c/ t1224c | 2N3/70I71/131G132 |
| 27 | ≥2.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/G249A/D257E/Q273G/Q277E/R281A/V282M/ D285V/V288A/I292V/V299P/L300N/N311D/I312V/ Y313H/D314S/T315A/M317L/C318A/Y320L/I323L/ A339V/T345E/P346F/E347D/F350A/S352G/A359T/F364L/ R365I/A366K/L368A/K369E/L370I/E372D/D377A/ A381D | t279c/a510t/a1086g | 2N3/70I71/131G132 |
| 28 | ≥2.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/K223D/G249A/D257E/Q273G/ Q277E/R281A/V282M/D285V/V288A/I292V/V299P/ L300N/N311D/I312V/Y313H/D314S/T315A/M317L/ C318A/Y320L/I323L/A339V/T345E/P346F/E347D/F350A/ S352G/A359T | t279c/t483a/a510t | 2N3/70I71/131G132 |
| 29 | ≥2.5 | S5K/G8S/Q11P/Q13E/P15K/K16D/D19N/S22A/E29N/N33D/ T36K/E39D/H40I/L41M/T64A/Q70E/S71N/D89Q/ Y96F/A112D/D115A/E126A/G129D/D130E/K131T/F132L/ N180T/R281C/D285T/V288A/V299P/F364Y/R365K/ | a27g/c30a/t42c/c51t/ a54c/t60a/g63a/ t69c/a72g/t75c/ t78c/g114a/a126g/ | 131G132 |

TABLE 3-1-continued

Improved Xylose Isomerase Variants

| Var. No. | FI | Active Mutations | Silent Mutations | Insertions wrt RF.XI.4 |
|---|---|---|---|---|
| | | L368S/E372A/K378S/V380I/A381S/N388S/T389E/A393L/ A397S/F402M/S404A/A417D/L419I/M426L/L435I/ S437N | c129t/c133t/a135g/ c138t/c147t/ t156a/c159t/c177t/ a180c/c195t/c201a/ t207c/c216t/ g222t/a225t/g234a/ c237t/t249c/t252a/ c255t/t261c/ c271t/g273a/a274t/ g275c/c306t/c307t/ t309g/a318g/ t321c/c324t/c327t/ a333g/c339a/ t342c/c349t/t360c/ t366c/g381a/g384a/ g399a/t403c/ a405t/c411t/a420g/ t426c/t429c/c432t/ c435a/g438a/ a453t/a456t/a466t/ g467c/t468a/c471g/ t477c/t483a/ t486c/t489a/g495t/ a501c/a510t/t511c/ a513g/c534t/t537a/ t552c/t570a/ c573t/g576a/c579g/ c580t/c583t/c600a/ t601c/a603t/ c607t/c625t/a627g/ a642t/a645g/c648t/ a663t/c684t/ g687a/a693g/c696a/ t705a/a741c/ a744g/t747c/t751c/ a753g/g756a/g765c/ t766c/t771c/ c792a/c804t/c807a/ a810t/c811t/a816g/ c822t/a825c/ t834c/g837a/a840g/ g846c/t849c/ g852a/c858t/c885t/ c894t/a903g/a906t/ c912t/g915a/ a921g/c924t/c927t/ t936c/t954c/t960c/ g963a/c966t/ t969c/c975t/a987t/ c993t/c996t/g999t/ g1011t/c1018a/ t1020a/g1023a/ a1029t/g1035t/ t1038a/a1054t/g1055c/ g1083t/g1089t/ a1098t/a1107g/ t1108c/g1110a/ t1113c/c1119t/a1125g/ c1131t/t1137c/ c1146t/g1149a/ c1155t/t1182c/ t1185c/a1194c/c1200t/ a1209g/g1215a/ a1218g/a1221g/ a1233g/t1239a/ a1242g/t1245c/ c1248t/a1254t/t1266a/ a1272g/a1275a/ c1279t/g1281a/ a1284g/t1287c/ c1293t/t1308c/ t1312c/g1314a | |
| 30 | ≥2.5 | E2K/F3Y/S5P/I7V/G8P/I10V/Q11K/Q13E/K16N/D19N/ L21F/S22A/N27D/P28A/E29N/E30K/I32V/N33A/R38K/ L41C/K42R/M51L/G52C/G53A/D54G/T56A/M58P/C61V/ | t279c/a510t/t705c/ t1185c/t1224c | 2N3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
| | | G62T/T64M/K66R/W68Y/Q70N/S71T/A74M/A75E/ R76L/A84G/I87L/D89T/S92G/D94E/Y95F/Y96F/R101A/ L103I/S104A/Y107G/G108D/S109T/L110F/K111E/A112E/ T113S/N114K/D115K/Q116N/D118F/I119E/V120I/ T121V/Q128M/G129D/D130Q/K131T/F132I/C134L/K140N/ C141N/D143S/G152S/P155C/S156N/F162Y/S163A/ Q166K/K169N/E172D/S173A/V175I/N180K/L194P/ Q273G/Q277E/R281A/V282M/D285V/V288A/I292V/V299P/ L300N/N311D/I312V/Y313H/D314S/T315A/M317L/ C318A/Y320L/I323L/A339V/T345E/P346F/E347D/F350A/ S352G/A359T/F364L/R365I/A366K/L368A/K369E/ L370I/E372D/D377A/A381D/W387Y/N388K/A393K/ D394A/I396V/A397D/K399T/A400T/D401S/F402L/A403E/ S404E/K407Q/A409V/E411T/K412H/G413S/V415P/ T416V/A417-/S418-/ L419M/S420Q/M426V/S429T/V434I/S437R/L438- | | |
| 31 | ≥2.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/K223D/G249A/D257E/Q273G/ Q277E/R281A/V282M/D285V/V288A/I292V/V299P/ L300N/N311D/I312V/Y313H/D314S/T315A/M317L/ C318A/Y320L/I323L/A339V/T345E/P346F/E347D/F350A/ S352G/A359T | t279c/t483a/a510t | 2N3/70I71/131G132 |
| 32 | ≥2.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ F184L/N198D/M199L/S219A/I220N/K223D/D257E/Q273G/ Q277E/R281A/V282M/D285V/V288A/I292V/V299P/ L300N/N311D/I312V/Y313H/D314S/T315A/M317L/ C318A/Y320L/I323L/A339V/T345E/P346F/E347D/F350A/ S352G/A359T/F364L/R365I/A366K/L368A/K369E/ L370I/E372D/D377A/A381D/W387Y/N388K/A393K/D394A/ I396V/A397D/K399T/A400T/D401S/F402L/A403E/ S404E/K407Q/A409V/E411T/K412H/G413S/V415P/ T416V/A417-/S418-/ L419M/S420R/M426V/S429T/V434I/S437R/L438- | t279c/a510t/t1185c/ t1224c | 2N3/70I71/131G132 |
| 33 | ≥2.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/T244A/Q273G/Q277E/R281A/V282M/ D285V/V288A/I292V/V299P/L300N/N311D/I312V/Y313H/ D314S/T315A/M317L/C318A/Y320L/I323L/T345E/ P346F/E347D/F350A/S352G/F364L/R365I/A366K/L368A/ K369E/L370I/E372D/D377A/A381D/W387Y/N388K/ A393K/D394A/I396V/A397D/K399T/A400T/D401S/ F402L/A403E/S404E/K407Q/A409V/E411T/K412H/G413S/ V415P/T416V/A417-/S418-/ L419M/S420Q/M426V/S429T/V434I/S437R/L438- | t279c/a510t/c684t/ c792a/t1185c/t1224c | 2N3/70I71/131G132 |
| 34 | ≥2.0 | F3L/S5Q/G8P/Q11K/Q13E/P15A/K16N/T18K/D19N/S22A/ K24H/N27D/P28A/E30K/V31I/I32V/N33L/R38K/K42P/ L45M/S46A/T50N/M51L/G52C/G53A/D54A/C61R/ G62D/T64A/T67S/W68F/Q70E/S71K/D72G/P73S/A74M/ A75E/R76H/A84G/I87F/D89E/S92G/D94K/Y96F/R101V/ | g783a/c924t/t1263a/ a1269g | 1S2/69L70/127M128/ 436G437 |

TABLE 3-1-continued

Improved Xylose Isomerase Variants

| Var. No. | FI | Active Mutations | Silent Mutations | Insertions wrt RF.XI.4 |
|---|---|---|---|---|
| | | S104V/Y107A/G108C/S109D/L110I/A112E/D115S/ Q116R/I119E/V120I/T121S/K125L/Q128K/D130T/K131D/ F132I/K140N/C141M/D143S/H144N/M148V/H149N/ T153S/S154T/P155N/F160Y/A161C/S163A/E172D/S173I/ N180R/N198D/M199V/G200K/L201F/L203Q/D204E/ M206I/R208N/A213V/T236M/T244A/V247A/L248I/ K253Q/M262L/Q273G/T275S/V282I/A283S/R284S/D285I/ V288M/F289L/I292V/V299M/Q307E/T310F/N311D/ I312V/I323L/A325N/F328L/N330-/ L333F/A339N/G342P/F344Y/P346Y/I349M/S352G/Y353F/ A355L/A359S/F364L/R365I/A366K/L368A/D373E/ R375T/I376L/K378N/V380I/A381K/D382E/A385K/W387F/ N388E/T389S/G390E/A393K/D394K/I396R/A397S/ G398K/K399S/D401S/F402L/A403Q/S404E/E406A/K407A/ L410E/K412M/E414-/ V415A/T416P/S418M/L419P/S420G/M426Y/E428Q/S429A/ I430A/V431N/L433Q/V434N/S437E/L438V | | |
| 35 | ≥2.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/K223D/D285V/V288A/I292V/ V299P/L300N/N311D/I312V/Y313H/D314S/T315A/ M317L/C318A/Y320L/I323L/A339V/T345E/P346F/E347D/ F350A/S352G/A359T/F364L/R365I/A366K/L368A/ K369E/L370I/E372D/D377A/A381D/W387Y/N388K/ A393K/D394A/I396V/A397D/K399T/A400T/D401S/F402L/ A403E/S404E/K407Q/A409V/E411T/K412H/G413S/ V415P/T416V/A417-/S418-/ L419M/S420Q/M426V/S429T/V434I/S437R/L438* | t279c/a510t/t1185c/ t1224c | 2N3/70I71/131G132 |
| 36 | ≥2.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/K223D/D257E/Q273G/Q277E/ R281A/V282M/D285V/V288A/I292V/V299P/L300N/ N311D/I312V/Y313H/D314S/T315A/M317L/C318A/ Y320L/I323L/T345E/P346F/E347D/F350A/S352G/A359T/ F364L/R365I/A366K/L368A/K369E/L370I/E372D/D377A/ A381D/W387Y/N388K/A393K/D394A/I396V/A397D/ K399T/A400T/D401S/F402L/A403E/S404E/K407Q/ A409V/E411T/K412H/G413S/V415P/T416V/A417-/ S418-/ L419M/S420Q/M426V/S429T/V434I/S437R/L438- | t279c/a510t/t1185c/ t1224c | 2N3/70I71/131G132 |
| 37 | ≥2.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/K223D/G249A/D257E/Q273G/ Q277E/R281A/V282M/D285V/V288A/I292V/V299P/ L300N/N311D/I312V/Y313H/D314S/T315A/M317L/ C318A/Y320L/I323L/A339V/T345E/P346F/E347D/F350A/ S352G/A359T | t279c/t483a/a510t | 2N3/70I71/131G132 |
| 38 | ≥2.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ | t207c/t279c/a510t/ t1152c/t1185c/t1224c | 2N3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
| | | A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ S219A/I220N/K223D/D257E/Q273G/I292V/V299P/L300N/ N311D/I312V/Y313H/D314S/T315A/M317L/C318A/ Y320L/I323L/A339V/T345E/P346F/E347D/F350A/S352G/ A359T/F364L/R365I/A366K/L368A/K369E/L370I/E372D/ D377A/A381D/W387Y/N388K/A393K/D394A/I396V/ A397D/K399T/A400T/D401S/F402L/A403E/S404E/ K407Q/A409V/E411T/K412H/G413S/V415P/T416V/ A417-/S418-/ L419M/S420Q/M426V/S429T/V434I/S437R/L438- | | |
| 39 | ≥2.0 | F3L/S5Q/G8P/Q11K/Q13E/P15A/K16N/T18K/D19N/S22A/ K24H/N27D/P28A/E30K/V31I/I32V/N33L/R38K/K42P/ L45M/S46A/T50N/M51L/G52C/G53A/D54A/C61R/ G62D/T64A/T67S/W68F/Q70E/S71K/D72G/P73S/A74M/ A75E/R76H/A84G/I87F/D89E/S92G/D94G/Y96F/R101V/ S104V/Y107A/G108C/S109D/L110I/A112E/D115S/ Q116R/I119E/V120I/T121S/K125L/Q128K/D130T/K131D/ F132I/K140N/C141M/D143S/H144N/M148V/H149N/ T153S/S154T/P155N/F160Y/A161C/S163A/E172D/S173I/ N180R/N198D/M199V/G200K/L201F/L203Q/D204E/ M206I/R208N/T236M/T244A/V247A/L248I/K253Q/ M262L/Q273G/T275S/V282I/A283S/R284S/D285I/V288M/ F289L/I292V/V299M/Q307E/T310F/N311D/I312V/ I323L/A325N/F328L/N330-/ L333F/A339N/G342P/F344Y/P346Y/I349M/S352G/Y353F/ A355L/A359S/F364L/R365I/A366K/L368A/D373E/ R375T/I376L/K378N/V380I/A381K/D382E/A385K/W387F/ N388E/T389S/G390E/A393K/D394K/I396R/A397S/ G398K/K399S/D401S/F402L/A403Q/S404E/E406A/K407A/ L410E/K412M/E414-/ V415A/T416P/S418M/L419P/S420G/M426Y/E428Q/S429A/ I430A/V431L/N433Q/V434N/S437E/L438V/ | g783a/c924t/t1263a/ a1269g | 1S2/69L70/127M128/ 436G437 |
| 40 | ≥2.0 | F3L/S5Q/G8P/Q11K/Q13E/P15A/K16N/T18K/D19N/S22A/ K24H/N27D/P28A/E30K/V31I/I32V/N33L/R38K/K42P/ L45M/S46A/T50N/M51L/G52C/G53A/D54A/C61R/ G62D/T64A/T67S/W68F/Q70E/S71K/D72G/P73S/A74M/ A75E/R76H/A84G/I87F/D89E/S92G/D94G/Y96F/R101V/ S104V/Y107A/G108C/S109D/L110I/A112E/D115S/ Q116R/I119E/V120I/T121S/K125L/Q128K/D130T/K131D/ F132I/K140N/C141M/D143S/H144N/M148V/H149N/ T153S/S154T/P155N/F160Y/A161C/S163A/E172D/S173I/ N180R/N198D/M199V/G200K/L201F/L203Q/D204E/ M206I/R208N/T236M/T244A/V247A/L248I/K253Q/ M262L/Q273G/T275S/V282I/A283S/R284S/D285I/V288M/ F289L/I292V/V299M/Q307E/T310F/N311D/I312V/ I323L/A325N/F328L/N330-/ L333F/A339N/G342P/F344Y/P346Y/I349M/S352G/Y353F/ A355L/A359S/F364L/R365I/A366K/L368A/D373E/ R375T/I376L/K378N/V380I/A381K/D382E/A385K/W387F/ N388E/T389S/G390E/A393K/D394K/I396R/A397S/ G398K/K399S/D401S/F402L/A403Q/S404E/E406A/K407A/ L410E/K412M/E414-/ V415A/T416P/S418M/L419P/S420G/M426Y/E428Q/S429A/ I430A/V431L/N433Q/V434N/S437E/L438V | g783a/c924t/t1263a/ a1269g | 1S2/69L70/127M128/ 436G437 |
| 41 | ≥2.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70E/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ M212I/S219A/I220N/K223D/Q249A/D257E/Q273G/Q277E/ V282I/A283S/R284S/D285I/V288M/F289L/I292V/ V299P/L300N/N311D/I312V/Y313H/D314S/T315A/M317L/ C318A/Y320L/A339V/T345E/P346F/E347D/F350A/ S352G/A359T/F364L/R365I/A366K/L368A/K369E/L370I/ E372D/D377A/A381D/W387Y/N388K/A393K/D394A/ | t279c/a510t/t1185c/ t1224c | 2N3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
| | | I396V/A397D/K399T/A400T/D401S/F402L/A403E/ S404E/K407Q/A409V/E411T/K412H/G413S/V415P/T416V/ A417-/S418-/ L419M/S420Q/M426V/S429T/V434I/S437R/L438- | | |
| 42 (RN. XI) | ≥2.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/F162Y/S163A/Q166K/K169N/ E172D/S173A/V175I/N180R/T236M/K253Q/M262L/ Q273G/T275S/V282I/A283S/R284S/D285I/V288M/F289L/ I292V | t279c/a510t/c625t/ a627g/a642t/a645g/ c648t/g783a/ g1011t/c1018a/t1020a/ g1023a/a1054t/ g1055c/a1233g/ t1239a/a1242g | 2N3/70I71/131G132 |
| 43 | ≥2.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ S219A/I220N/K223D/G249A/D257E/Q273G/N311D/I312V/ Y313H/D314S/T315A/M317L/C318A/Y320L/I323L/ A339V/T345E/P346F/E347D/F350A/F364L/R365I/A366K/ L368A/K369E/L370I/E372D/D377A/A381D/W387Y/ N388K/A393K/D394A/I396V/A397D/K399T/A400T/ D401S/F402L/A403E/S404E/K407Q/A409V/E411T/K412H/ G413S/V415P/T416V/A417-/S418-/ L419M/S420Q/M426V/S429T/V434I/S437R/L438- | t279c/a510t/t1185c/ t1224c | 2N3/70I71/131G132 |
| 44 | ≥2.0 | E2K/F3Y/S5P/I7V/G8P/K9E/I10V/Q11K/Q13E/K16N/T18A/ D19N/L21F/S22A/N27D/P28A/E29N/E30K/I32V/ N33A/R38K/L41C/K42R/M51L/G52C/G53A/D54G/T56A/ M58P/C61V/G62T/T64M/K66R/W68Y/Q70N/S71T/ A74M/A75E/R76L/A84G/I87L/D89T/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ Q273G/Q277E/R281A/V282M/D285V/V288A/I292V/V299P/ L300N/N311D/I312V/Y313H/D314S/T315A/M317L/ C318A/Y320L/I323L/F335L/A339V/T345E/P346F/E347D/ F350A/S352G/A359T/F364L/R365I/A366K/L368A/ K369E/L370I/E372D/D377A/A381D/W387Y/N388K/ A393K/D394A/I396V/A397D/K399T/A400T/D401S/F402L/ A403E/S404E/K407Q/A409V/E411T/K412H/G413S/ V415P/T416V/A417-/S418-/ L419M/S420Q/M426V/S429T/V434I/S437R/L438- | t279c/a510t/a642t/ a645g/c648t/a663t/ t1185c/t1224c | 2N3/70I71/131G132 |
| 45 | ≥2.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71A/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/M206T/S219A/I220N/K223D/G249A/D257E/ Q273G/Q277E/R281A/V282M/I292V/V299P/L300N/ N311D/I312V/Y313H/D314S/T315A/M317L/C318A/ Y320L/I323L/A339V/T345E/P346F/E347D/F350A/S352G/ A359T/F364L/R365I/A366K/L368A/K369E/L370I/E372D/ D377A/A381D/W387Y/N388K/A393K/D394A/I396V/ A397D/K399T/A400T/D401S/F402L/A403E/S404E/ K407Q/A409V/E411T/K412H/G413S/V415P/T416V/ A417-/S418-/ L419M/S420Q/M426V/S429T/V434I/S437R/L438- | t279c/a510t/t1185c/ t1224c | 2N3/70I71/131G132 |
| 46 | ≥2.0 | E2K/F3Y/S5P/I7V/G8P/K9E/I10V/Q11K/Q13E/K16N/D19N/ L21F/S22A/N27D/P28A/E29N/E30K/I32V/N33A/ | t279c/a510t/a906g/ t1185c/t1224c | 2N3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
| | | R38K/L41C/K42R/M51L/G52C/G53A/D54G/T56A/M58P/ C61V/G62T/T64M/K66R/W68Y/Q70N/S71T/A74M/ A75E/R76L/I87L/D89T/S92G/D94E/Y95F/Y96F/R101A/ L103I/S104A/Y107G/G108D/S109T/L110F/K111E/A112E/ T113S/N114K/D115K/Q116N/D118F/I119E/V120I/ T121V/Q128M/G129D/D130Q/K131T/F132I/C134L/K140N/ C141N/D143S/G152S/P155C/S156N/F162Y/S163A/ Q166K/K169N/E172D/S173A/V175I/N180R/N198D/M199L/ G249A/Q273G/Q277E/R281A/V282M/D285V/V288A/ I292V/V299P/L300N/N311D/I312V/Y313H/D314S/ T315A/M317L/C318A/Y320L/I323L/A339V/T345E/P346F/ E347D/F350A/S352G/A359T/F364L/R365I/A366K/ L368A/K369E/L370I/E372D/D377A/A381D/W387Y/N388K/ A393K/D394A/I396V/A397D/K399T/A400T/D401S/ F402L/A403E/S404E/K407Q/A409V/E411T/K412H/ G413S/V415P/T416V/A417-/S418-/ L419M/S420Q/M426V/S429T/V434I/S437R/L438- | | |
| 47 | ≥2.0 | F3L/S5Q/G8P/Q11K/Q13E/P15A/K16N/T18K/D19N/S22A/ K24H/N27D/P28A/E30K/V31I/I32V/N33L/R38K/K42P/ L45M/S46A/T50N/M51L/G52C/G53A/D54A/C61R/ G62D/T64A/T67S/W68F/Q70E/S71K/D72G/P73S/A74M/ A75E/R76H/A84G/I87F/D89E/S92G/D94K/Y96F/R101V/ S104V/Y107A/G108C/S109D/L110I/A112E/T113I/ D115S/Q116R/I119E/V120I/T121S/K125L/Q128K/D130T/ K131D/F132I/K140N/C141M/D143S/H144N/M148V/ H149N/T153S/S154T/P155N/F160Y/A161C/S163A/E172D/ S173I/N180R/N198D/M199V/G200K/L201F/L203Q/ D204E/M206I/R208N/T236M/T244A/V247A/L248I/ K253Q/M262L/Q273G/T275S/V282I/A283S/R284S/D285I/ V288M/F289L/I292V/V299M/Q307E/T310F/N311D/ I312V/I323L/A325N/F328L/N330-/ L333F/A339N/G342P/F344Y/P346Y/I349M/S352G/Y353F/ A355L/A359S/F364L/R365I/A366K/L368A/D373E/ R375T/I376L/K378N/V380I/A381K/D382E/A385K/W387F/ N388E/T389S/G390E/A393K/D394K/I396R/A397S/ G398K/K399S/D401S/F402L/A403Q/S404E/E406A/K407A/ L410E/K412M/E414-/ V415A/T416P/S418M/L419P/S420G/M426Y/E428Q/S429A/ I430A/V431N/L433Q/V434N/S437E/L438V | g783a/c924t/t1263a/ a1269g | 1S2/69L70/127M128/ 436G437 |
| 48 | ≥1.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180R/ T244A/V247A/L248I/K253Q/M262L/Q273G/T275S/V282I/ A283S/R284S/D285I/V288M/F289L/I292V/V299P/ L300N/N311D/I312V/Y313H/D314S/T315A/M317L/C318A/ Y320L/I323L/A339V/T345E/P346F/E347D/F350A/ S352G/F364L/R365I/A366K/L368A/K369E/L370I/E372D/ D377A/A381D/W387Y/N388K/A393K/D394A/I396V/ A397D/K399T/A400T/D401S/F402L/A403E/S404E/K407Q/ A409V/E411T/K412H/G413S/V415P/T416V/A417-/ S418-/ L419M/S420Q/M426V/S429T/V434I/S437R/L438- | t279c/a510t/t570a/ c573t/g576a/c579g/ c580t/c583t/ c600a/t601c/a603t/ c607t/c625t/a627g/ a642t/a645g/ c648t/a663t/t771c/ g783a/t1170c/t1185c/ t1224c | 2N3/70I71/131G132 |
| 49 | ≥1.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N198D/ M199L/K223N/T236M/Q273G/Q277E/R281A/V282M/ D285V/V288A/I292V/V299P/L300N/N311D/I312V/Y313H/ D314S/T315A/M317L/C318A/Y320L/I323L/A339V/ T345E/P346F/E347D/F350A/S352G/A359T/F364L/R365I/ A366K/L368A/K369E/L370I/E372D/D377A/A381D/ W387Y/N388K/A393K/D394A/I396V/A397D/K399T/ | t279c/a510t/t552c/ c625t/a627g/t1185c/ t1224c | 2N3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
| 50 | ≥1.5 | A400T/D401S/F402L/A403E/S404E/K407Q/A409V/E411T/ K412H/G413S/V415P/T416V/A417-/S418-/ L419M/S420Q/M426V/S429T/V434I/S437R/L438- E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/K223D/G249A/D257E/Q273G/ Q277E/R281A/V282M/D285V/V288A/I292V/V299P/ L300N/N311D/I312V/Y313H/D314S/T315A/M317L/ C318A/Y320L/I323L/A339V/T345E/P346F/E347D/F350A/ S352G/A359T/F364L/R365I/A366K/L368A/K369E/ L370I/E372D/D377A/A381D/W387Y/N388K/A393K/D394A/ I396V/A397D/K399T/A400T/D401S/F402L/A403E/ S404E/K407Q/A409V/E411T/K412H/G413S/V415P/ T416V/A417-/S418-/ L419M/S420Q/M426V/S429T/V434I/S437R/L438- | t279c/a510t/t1185c/ t1224c | 2N3/70I71/131G132 |
| 51 | ≥1.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ S219A/I220N/K223D/D257E/Q273G/Q277E/R281A/V282M/ D285V/V288A/I292V/V299P/L300N/N311D/I312V/ Y313H/D314S/T315A/M317L/C318A/Y320L/I323L/ A339V/T345E/P346F/E347D/F350A/S352G/A359T/F364L/ R365I/A366K/L368A/K369E/L370I/E372D/D373G/ D377A/A381D/W387Y/N388K/A393K/D394A/I396V/A397D/ K399T/A400T/D401S/F402L/A403E/S404E/K407Q/ A409V/E411T/K412H/G413S/V415P/T416V/A417-/ S418-/ L419M/S420Q/M426V/S429T/V434I/S437R/L438- | t279c/a510t/t552c/ t570a/c573t/g576a/ c579g/c580t/ c583t/c600a/t601c/ a603t/c607t/t1185c/ t1224c | 2N3/70I71/131G132 |
| 52 | ≥1.5 | E2K/F3D/S5P/N6Y/I7V/G8P/I10V/Q11K/Q13E/K16N/ D19N/L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/D257E/I292V/N311D/I312V/Y313H/ D314S/T315A/M317L/C318A/Y320L/I323L/A339V/ T345E/P346F/E347D/F350A/S352G/A359T/F364L/R365I/ A366K/L368A/K369E/L370I/E372D/D377A/A381D/ W387Y/N388K/A393K/D394A/I396V/A397D/K399T/ A400T/D401S/F402L/A403E/S404E/K407Q/A409V/E411T/ K412H/G413S/V415P/T416V/A417-/S418-/ L419M/S420Q/M426V/S429T/V434I/S437K/L438* | t279c/a510t/t558c/ t588c/t1185c/t1224c | 2N3/70I71/131G132 |
| 53 | ≥1.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/Q166K/ K169N/E172D/S173A/V175I/N180K/N198D/M199L/ S219A/I220N/K223D/G249A/D257E/Q273G/Q277E/R281A/ V282M/D285V/V288A/I292V/V299P/L300N/N311D/ I312V/Y313H/D314S/T315A/M317L/C318A/Y320L/I323L/ A339V/F344L/T345E/P346F/E347D/F350A/S352G/ | t279c/a510t/c675t/ t1185c/t1224c/a1269g | 2N3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
| | | A359T/F364L/R365I/A366K/L368A/K369E/L370I/E372D/ D377A/A381D/W387Y/N388K/A393K/D394A/I396V/ A397D/K399T/A400T/D401S/F402L/A403E/S404E/ K407Q/A409V/E411T/K412H/G413S/V415P/T416V/A417-/ S418-/ L419M/S420Q/M426V/S429T/V434I/S437R/L438* | | |
| 54 | ≥1.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ S219A/I220N/K223D/T236M/T244A/V247A/L248I/D257E/ Q273G/Q277E/R281A/V282M/D285V/V288A/I292V/ V299P/L300N/N311D/I312V/Y313H/D314S/T315A/ M317L/C318A/Y320L/I323L/A339V/T345E/P346F/E347D/ F350A/S352G/A359I/F364L/R365I/A366K/L368A/ K369E/L370I/E372D/D377A/A381D/W387Y/N388K/A393E/ D394A/I396V/A397D/K399T/A400T/D401S/F402L/ A403E/S404E/K407Q/A409V/E411T/K412H/G413S/ V415P/T416V/A417-/S418-/ L419M/S420Q/M426V/S429T/V434I/S437R/L438- | t279c/a510t/c580t/ t1185c/t1224c | 2N3/70I71/131G132 |
| 55 | ≥1.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/M148V/H149N/G152S/P155C/ S156N/F162Y/S163A/Q166K/K169N/E172D/S173A/ V175I/N180K/N198D/M199L/S219A/I220N/K223D/K253Q/ D257E/Q273G/Q277E/R281A/V282M/D285V/V288A/ I292V/V299P/L300N/N311D/I312V/Y313H/D314S/ T315A/M317L/C318A/Y320L/I323L/A339V/T345E/P346F/ E347D/F350A/S352G/A359T/A361G/F364L/R365I/ A366K/L368A/K369E/L370I/E372D/D377A/A381D/W387Y/ N388K/A393K/D394A/I396V/A397D/K399T/A400T/ D401S/F402L/A403E/S404E/K407Q/A409V/E411T/K412H/ G413S/V415P/T416V/A417-/S418-/ L419M/S420Q/M426V/S429T/V434I/S437R/L438- | t279c/a510t/t552c/ t1185c/t1224c | 2N3/70I71/131G132 |
| 56 | ≥1.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/P155C/S156N/F162Y/S163A/ Q166K/K169N/E172D/S173A/V175I/N180R/Q273G/ T275S/T416A | t279c/a510t/c684t/ g687a/t978c | 2N3/70I71/131G132 |
| 57 | ≥1.5 | F3L/S5Q/G8P/Q11K/Q13E/P15A/K16N/T18K/D19N/S22A/ K24H/N27D/P28A/E30K/V31I/I32V/N33A/R38K/K42P/ L45M/S46A/T50N/M51L/G52C/G53A/D54A/C61R/ G62D/T64A/T67S/W68F/Q70E/S71K/D72G/P73S/A74M/ A75E/R76H/A84G/I87F/D89E/S92G/D94K/Y96F/R101V/ S104V/Y107A/G108C/S109D/L110I/A112E/D115S/ Q116R/I119E/V120I/T121S/K125L/Q128K/D130T/K131D/ F132I/K140N/C141M/D143S/H144N/M148V/H149N/ T153S/S154T/P155N/F160Y/A161C/S163A/E172D/S173I/ N180R/N198D/M199V/G200K/L201F/L203Q/D204E/ M206I/R208N/T236M/T244A/V247A/L248I/K253Q/ M262L/Q273G/T275S/V282I/A283S/R284S/D285I/V288M/ F289L/I292V/V299M/Q307E/T310F/N311D/I312V/ I323L/A325N/F328L/N330-/ L333F/A339N/G342P/F344Y/P346Y/I349M/S352G/Y353F/ A355L/A359S/F364L/R365I/A366K/L368A/D373E/ R375T/I376L/K378N/V380I/A381D/D382E/A385K/W387F/ N388E/T389S/G390E/A393K/D394K/I396R/A397S/ | g783a/c924t/t1263a/ a1269g | 1S2/69L70/127M128/ 436G437 |

TABLE 3-1-continued

Improved Xylose Isomerase Variants

| Var. No. | FI | Active Mutations | Silent Mutations | Insertions wrt RF.XI.4 |
|---|---|---|---|---|
| | | G398K/K399S/D401S/F402L/A403Q/S404E/E406A/K407A/ L410E/K412M/E414-/ V415A/T416P/S418M/L419P/S420G/M426Y/E428Q/S429A/ I430A/V431L/N433Q/V434N/S437E/L438V | | |
| 58 | ≥1.5 | F3L/S5Q/G8P/Q11K/Q13E/P15A/K16N/T18K/D19N/S22A/ K24H/N27D/P28A/E30K/V31I/I32V/N33L/R38K/K42P/ L45M/S46A/T50N/M51L/G52C/G53A/D54A/C61R/ G62D/T64A/T67S/W68F/Q70E/S71K/D72G/P73S/A74M/ A75E/R76H/A84G/I87F/D89E/S92G/D94K/Y96F/R101V/ S104V/Y107A/G108C/S109D/L110I/A112E/D115S/ Q116R/I119E/V120I/T121S/K125L/Q128K/D130T/K131D/ F132I/K140N/C141M/D143S/H144N/M148V/H149N/ T153S/S154T/P155N/F160Y/A161C/S163A/E172D/S173I/ N180R/N198D/M199V/G200K/L201F/L203Q/D204E/ M206I/R208N/T236M/T244A/V247A/L248I/K253Q/ M262L/Q273G/T275S/V282I/A283S/R284S/D285I/V288M/ F289L/I292V/V299M/Q307E/T310F/N311D/I312V/ I323L/A325N/F328L/N330-/ L333F/A339N/G342P/F344Y/P346Y/I349M/S352G/Y353F/ A355L/A359S/F364L/R365I/A366K/L368A/D373E/ R375T/I376L/K378N/V380I/A381K/D382E/A385K/W387F/ N388E/T389G/V390E/A393K/D394K/I396R/A397S/ G398K/K399S/D401S/F402L/A403Q/S404E/E406A/K407A/ L410E/K412M/E414-/ V415A/T416P/S418M/L419P/S420G/M426Y/E428Q/S429A/ I430A/V431L/N433Q/V434N/S437E/L438V | g783a/c924t/t1263a/ a1269g | 1S2/69L70/127M128/ 436G437 |
| 59 | ≥1.5 | T236M/T244A/V247A/L248I/K253Q/M262L/Q273G/T275S/ V282I/A283S/R284S/D285I/V288M/F289L/I292V | g783a | |
| 60 | ≥1.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ R208G/S219A/I220N/K223D/Q273G/Q277E/R281A/V282M/ D285V/V288A/I292V/V299P/L300N/N311D/I312V/ Y313R/D314S/T315A/M317L/C318A/Y320L/I323L/ N334D/A339V/T345E/P346F/E347D/F350A/S352G/A359T/ F364L/R365I/A366K/L368A/K369E/L370I/E372D/ G374S/D377A/A381D/W387Y/N388K/A393K/D394A/I396V/ A397D/K399T/A400T/D401S/F402L/A403E/S404E/ K407Q/A409V/E411T/K412H/G413S/V415P/T416V/ A417-/S418-/ L419M/S420Q/G422S/M426V/S429T/V434I/S437R/L438- | t279c/a510t/g783a/ t1185c/t1224c | 2N3/70I71/131G132 |
| 61 | ≥1.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76H/A84G/I87T/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/Q273G/Q277E/R281A/V282M/D285V/ V288M/I292V/V299P/L300N | t279c/a510t/c625t/ a627g/c696a | 2N3/70I71/131G132 |
| 62 | ≥1.5 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76H/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ K223D/Q273G/T275S/V282I/A283S/R284S/D285I/V288M/ F289L/I292V/V299M | t279c/a510t/t511c/ g1023a/a1029t/ g1035t/t1038a/a1054t/ g1055c/a1095g | 2N3/70I71/131G132 |
| 63 | ≥1.0 | | t1255c | |
| 64 | ≥1.0 | E2K/F3Y/S5P/I7V/G8P/K9E/I10V/Q11K/Q13E/P15A/K16N/ D19N/L21F/S22A/N27D/P28A/E29N/E30K/I32V/ | t279c/a510t/c792a | 2N3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
| | | N33A/R38K/L41C/K42R/M51L/G52C/G53A/D54G/T56A/ M58P/C61V/G62T/T64M/K66R/W68Y/Q70D/S71T/ A74M/A75E/R76L/A84G/I87L/D89T/S92G/D94E/Y95F/ Y96F/R101A/L103I/S104A/Y107G/G108D/S109T/L110F/ K111E/A112E/T113S/N114K/D115K/Q116N/D118F/ I119E/V120I/T121A/Q128M/G129D/D130Q/K131T/F132I/ C134L/K140N/C141N/D143S/G152S/P155C/S156N/ F162Y/S163A/Q166K/K169N/E172R/S173A/V175I/N180K/ S219A/I220N/K223D/D257E/Q273G/Q277E/R281A/ V282M/D285V/V288A/I292V/V299P/L300N/N311D/ I312V/Y313H/D314S/T315A/M317L/C318A/Y320L/I323L/ A325V/A339V/T345E/P346F/E347D/F350A/S352G/ A359T/F364L/R365I/A366K/L368A/K369E/L370I/E372D/ D377A | | |
| 65 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76H/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ K223D/Q273G/T275S/V282I/A283S/R284S/D285I/V288M/ F289I/I292V/V299M | t279c/a510t/t511c/ g1023a/a1029t/ g1035t/t1038a/a1054t/ g1055c/a1095g | 2N3/70I71/131G132 |
| 66 | ≥1.0 | S5K/G8S/Q11P/Q13E/P15K/K16D/D19N/S22A/E29D/N33D/ T36K/E39D/H40I/L41M/T64A/Q70E/S71N/D89Q/ Y96F/A112E/D115A/E126A/G129A/D130E/K131T/F132L/ N198D/M199L/S219A/I220N/K223D/V247A/L248I/ K253Q/M262L/A269G/D285V/V288A/N311D/I312V/Y313H/ D314S/T315A/M317L/C318A/Y320L/I323L/A339V/ T345E/P346F/E347D/F350A/S352G/A359T/F364L/R365I/ A366K/L368A/K369E/L370I/E372D/D377A/A381D/ W387Y/N388K/A393K/D394A/I396V/A397D/K399T/ A400T/D401S/F402L/A403E/S404E/K407Q/A409V/E411T/ K412H/G413S/V415P/T416V/A417-/S418-/ L419M/S420Q/M426V/S429T/V434I/S437R/L438- | a27g/c30a/t42c/c51t/ a54c/t60a/g63a/ t69c/a72g/t75c/ t78c/g114a/a126g/ c129t/c133t/a135g/ c138t/c147t/ t156a/c159t/c177t/ a180c/c195t/c201a/ t207c/c216t/ g222t/a225t/g234a/ c237t/t249c/t252a/ c255t/t261c/ c271t/g273a/a274t/ g275c/c306t/c307t/ t309g/a318g/ t321c/c324t/c327t/ a333g/c339a/ t342c/c349t/t360c/ t366c/g381a/g384a/ g399a/t403c/ a405t/c411t/a420g/ t426c/t429c/c432t/ c435a/g438a/ a453t/a456t/a466t/ g467c/t468a/c471g/ t477c/t483a/ t486c/t489a/g495t/ g783a/t1185c/t1224c | 131G132 |
| 67 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ S219A/I220N/K223D/G224C/G249A/D257E/Q273G/Q277E/ R281A/V282M/D285V/V288A/I292V/V299P/L300N/ N311G/I312V/Y313H/D314S/T315A/M317L/C318A/ Y320L/I323L/A339V/T345E/P346F/E347D/F350A/S352G/ A359T/F364L/R365I/A366K/L368A/K369E/L370I/E372D/ D377A/A381D/W387Y/N388K/A393K/D394A/I396V/ A397D/K399T/A400T/D401S/F402L/A403E/S404E/ K407Q/A409V/E411T/K412H/G413S/V415P/T416V/A417-/ S418-/ L419M/S420Q/M426V/S429T/V434I/S437R/L438- | t279c/a510t/t1185c/ t1224c | 2N3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
| 68 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75V/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/R146G/G152S/P155C/S156N/ F162Y/S163A/Q166K/K169N/E172D/S173A/V175I/ N180K/S219A/I220N/K223D/G249A/D257E/Q273G/Q277E/ R281A/V282M/D285V/V288A/I292V/V299P/L300N/ N311D/I312V/Y313H/D314S/T315A/M317L/C318A/ Y320L/I323L/A339V/T345E/P346F/E347D/F350A/S352G/ A359T/F364L/R365I/A366K/L368A/K369E/L370I/E372D/ D377A/A381D/W387Y/N388K/A393K/D394A/I396V/ A397D/K399T/A400T/D401S/F402L/A403E/S404E/ K407Q/A409V/E411T/K412H/G413S/V415P/T416V/A417-/ S418-/ L419M/S420Q/M426V/S429T/V434I/S437R/L438* | t279c/a510t/t990c/ t1185c/t1224c | 2N3/70I71/131G132 |
| 69 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75V/R76H/A84G/I87L/D89T/S92G/D94E/Y95F/Y96F/ R101A/L103I/S104A/Y107G/G108D/S109T/K111E/A112E/ T113S/N114K/D115K/Q116N/D118F/I119E/V120I/ T121V/Q128M/G129D/D130Q/K131T/F132I/C134L/K140N/ C141N/D143S/G152S/P155C/S156N/F162Y/S163A/ Q166K/K169N/E172D/S173A/V175I/N180K/S219A/I220N/ K223D/Q273G/T275S/V282I/A283S/R284S/D285I/ V288M/F289L/I292V/V299M | t279c/t328c/g330c/ a510t/a642t/a645g/ c648t | 2N3/70I71/131G132 |
| 70 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75V/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ K223D/G249A/D257E/Q273G/Q277E/R281A/V282M/D285V/ V288A/I292V/V299P/L300N/N311D/I312V/Y313H/ D314S/T315A/M317L/C318A/Y320L/I323L/T345E/P346F/ E347D/F350A/S352G/A359T/F364L/R365I/A366K/ L368A/K369E/L370I/E372D/D377A/A381D/W387Y/ N388K/A393K/D394A/I396V/A397D/K399T/A400T/D401S/ F402L/A403E/S404E/K407Q/A409V/E411T/K412H/ G413S/V415P/T416V/A417-/S418-/ L419M/S420Q/M426V/S429T/V434I/S437R/L438- | t279c/a510t/t1113c/ t1185c/t1224c | 2N3/70I71/131G132 |
| 71 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/K42P/L45M/S46A/T50N/M51L/G52C/G53A/D54A/ C61R/G62D/T64A/T67S/W68F/Q70E/S71K/D72G/P73S/ A74M/A75V/R76H/A84G/I87F/D89E/S92G/D94K/Y96F/ R101V/S104A/Y107A/G108C/S109D/L110I/A112E/ D115S/Q116N/I119E/V120I/T121S/K125L/Q128K/D130T/ K131D/F132I/K140N/C141M/D143S/H144N/M148V/ H149N/T153S/S154T/P155N/F160Y/A161C/S163A/E172D/ S173I/N180R/N198D/M199L/S219A/T236A/T244A/ V247A/L248I/K253Q/M262L/Q273G/T275S/V282I/A283S/ R284S/D285I/V288M/F289L/I292V/V299M/Q307E/ T310F/N311D/I312V/I323L/A325N/F328L/N330-/ L333F/A339N/G342F/P344Y/P346Y/I349M/S352G/Y353F/ A355L/A359S/F364L/R365I/A366K/L368A/D373E/ R375T/I376L/K378N/V380I/A381D/D382E/A385K/W387F/ N388E/T389S/G390E/A393K/D394K/I396R/A397S/ G398K/K399S/D401S/F402L/A403Q/S404E/E406A/K407A/ L410E/K412M/E414-/ V415A/T416P/S418M/L419P/S420G/M426Y/E428Q/S429A/ I430A/V431N/L433Q/V434N/S437E/L438V | g585a/a642g/g783a/ c924t/t1263a/ a1269g | 2N3/69L70/127M128/ 436G437 |
| 72 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ | t279c/a510t/t558c/ t1185c/t1224c | 2N3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
| | | C61V/G62T/T64V/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ S219A/I220N/K223D/T236M/D257E/Q273G/Q277E/R281A/ V282M/D285V/V288A/I292V/V299P/L300N/N311D/ I312V/Y313H/D314S/T315A/M317L/C318A/Y320L/I323L/ A339V/A359T/F364L/R365I/A366K/L368A/K369E/ L370I/E372D/D377A/A381D/W387Y/N388K/A393K/ D394A/I396V/A397D/K399T/A400T/D401S/F402L/A403E/ S404E/K407Q/A409V/E411T/K412H/G413S/V415P/ T416V/A417-/S418-/ L419M/S420Q/M426V/S429I/V434I/S437R/L438- | | |
| 73 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199V/T236M/T244A/V247A/L248I/K253Q/M262L/ Q273G/Q277E/R281A/V282M/D285V/V288A/I292V/ V299P/L300N/N311D/I312V/Y313H/D314S/T315A/ M317L/C318A/Y320L/I323L/A339V/T345E/P346F/E347D/ I349V/F350A/S352G/A359T/F364L/R365I/A366K/L368A/ K369E/L370I/E372D/D377A/A381D | t279c/a510t/t657c/ g783a | 2N3/70I71/131G132 |
| 74 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ S219A/I220N/K223D/G249A/V299P/L300N/N311D/I312V/ Y313H/D314S/T315A/M317L/C318A/Y320L/I323L/ A339V/T345E/P346F/E347D/F350A/A359T/F364L/R365I/ A366K/L368A/K369E/L370I/E372D/D377A/A381D/ W387Y/N388K/A393K/D394A/I396V/A397D/K399T/A400T/ D401S/F402L/A403E/S404E/K407Q/A409V/E411T/ K412H/G413S/V415P/T416V/A417-/S418-/ L419M/S420Q/M426V/S429I/V434I/S437R/L438- | a219g/t279c/a510t/ c607t/t771c/t1185c/ t1224c | 2N3/70I71/131G132 |
| 75 | ≥1.0 | E2K/F3Y/S5P/I7V/G8P/K9D/I10F/Q11K/Q13E/K16N/D19N/ L21F/S22A/N27D/P28A/E29N/E30K/I32V/N33A/ K35N/T36I/R38K/L41C/K42R/M51L/G52C/G53A/D54G/ T56A/M58P/C61V/G62T/T64M/K66R/W68Y/Q70N/ S71T/A74M/A75E/R76L/A84G/I87L/D89T/S92G/D94E/ Y95F/Y96F/R101A/L103I/S104A/Y107G/G108D/S109T/ L110F/K111E/A112E/T113S/N114K/D115K/Q116N/ D118F/I119E/V120I/T121V/Q128M/G129D/D130Q/K131T/ F132I/C134L/K140N/C141N/D143S/G152S/P155C/ S156N/F162Y/S163A/Q166K/K169N/E172D/S173A/V175I/ N180K/T236M | t279c/a510t | 2N3/70I71/131G132 |
| 76 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ S219A/I220N/G249A/V299P/L300N/A339V/T345E/P346F/ E347D/F350A/S352G/A359T/F364L/R365I/A366K/ L368A/K369E/L370I/E372D/D377A | t279c/a510t | 2N3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
| 77 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/S219A/I220N/K223D/G249A/D257E/V299M/ N311D/I312V/Y313H/D314S/T315A/M317L/C318A/ Y320L/I323L/A339V/T345E/P346F/E347D/F350A/S352G/ A359T/F364L/R365I/A366K/L368A/K369E/L370I/ E372D/D377A/A381D/W387Y/N388K/A393K/D394A/I396V/ A397D/K399T/A400T/D401S/F402L/A403E/S404E/ K407Q/A409V/E411T/K412H/G413S/V415P/T416V/ A417-/S418-/ L419M/S420Q/M426V/S429T/V434I/S437R/L438- | t279c/a510t/t1185c/ t1224c | 2N3/70I71/131G132 |
| 78 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ S219A/I220N/K223D/G249A/N311D/I312V/Y313H/D314S/ T315A/M317L/C318A/Y320L/I323L/A339V/T345E/ P346F/E347D/F350A/S352G/A359T/F364L/R365I/A366K/ L368A/K369E/L370I/E372D/D377A/K378E/A381D/ W387Y/N388K/A393K/D394A/I396V/A397D/K399T/A400T/ D401S/F402L/A403E/S404E/K407Q/A409V/E411T/ K412H/G413S/V415P/T416V/A417-/S418-/ L419M/S420Q/M426V/S429T/V434I/S437R/L438* | t279c/a510t/t1185c/ t1224c | 2N3/70I71/131G132 |
| 79 | ≥1.0 | S5K/G8S/Q11P/Q13E/P15K/K16D/D19N/S22A/E29D/N33D/ T36K/E39D/H40I/L41M/T64A/Q70E/S71N/D89Q/ Y96F/A112D/D115E/A126A/G129A/D130E/K131T/F132L/ N180K/N198D/M199V/T244A/V247A/L248I/K253Q/ Q273G/T275S/V282I/A283S/R284S/D285I/V288M/F289L/ I292V/N311D/I312V/Y313H/D314S/T315A/M317L/ C318A/Y320L/I323L/W387Y/N388K | a27g/c30a/t42c/c51t/ a54c/t60a/g63a/ t69c/a72g/t75c/ t78c/g114a/a126g/ c129t/c133t/a135g/ c138t/c147t/ t156a/c159t/c177t/ a180c/c195t/c201a/ t207c/c216t/ g222t/a225t/g234a/ c237t/t249c/t252a/ c255t/t261c/ c271t/g273a/a274t/ g275c/c306t/c307t/ t309g/a318g/ t321c/c324t/c327t/ a333g/c339a/ t342c/c349t/t360c/ t366c/g381a/g384a/ g399a/t403c/ a405t/c411t/a420g/ t426c/t429c/c432t/ c435a/g438a/ a453t/a456t/a466t/ g467c/t468a/c471g/ t477c/t483a/ t486c/t489a/g495t/ a510t/t511c/a513g/ c625t/a627g/a642t/ a645g/c648t/ t1047c/a1054t/g1055c/ a1095g/a1194c/ c1200t | 131G132 |
| 80 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ | t279c/a510t/c726t | 2S3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
| 81 | ≥1.0 | R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75V/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/V247A/L248I/K253Q/Q273G/Q277E/R281A/ V282M/D285V/V288A/N311D/I312V/Y313H/D314S/ T315A/M317L/C318A/M319T/Y320L/I323L/A339V/ T345E/P346F/E347D/F350A/S352G/A359T/F364L/R365I/ A366K/L368A/K369E/L370I/E372D/D377A/A381D/ W387Y/N388K/A393K/D394A/I396V/A397D/K399T/A400T/ D401S/F402L/A403E/S404E/K407Q/A409V/E411T/ K412H/G413S/V415P/T416V/A417-/S418-/ L419M/S420Q/M426V/S429T/V434I/S437R/L438- | t279c/t483c/a510t/ a606g/t1185c/t1224c | 2N3/70I71/131G132 |
| 82 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64V/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ K253Q/Q273G/T275S | t279c/a510t/a663t/ a1054t/g1055c/ a1194c/c1200t | 2N3/70I71/131G132 |
| 83 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53T/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/E106G/Y107G/G108D/S109T/L110F/ K111E/A112E/T113S/N114K/D115K/Q116N/D118F/ I119E/V120I/T121V/Y123H/Q128M/G129D/D130Q/K131T/ F132I/C134L/K140N/C141N/D143S/G152S/P155C/ S156N/F162Y/S163A/Q166K/K169N/E172D/S173A/ V175I/N180K/G249A/D257E/Q273G/Q277E/R281A/V282M/ D285V/V288A/I292V/V299P/L300N/N311D/I312V/ Y313H/D314S/T315A/M317L/C318A/Y320L/I323L/ A339V/T345E/P346F/E347D/F350A/S352G/A359T/F364L/ R365I/A366K/L368A/K369E/L370I/E372D/D377A/ A381D | t279c/a510t/t873c | 2N3/70I71/131G132 |
| 84 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N198D/ M199L/S219A/I220N/K223D/G249A/D257E/I292V/V299P/ L300N/N311D/I312V/Y313H/D314S/T315A/M317L/ C318A/Y320L/I323L/A339V/T345E/P346F/E347D/F350A/ S352G/A359T/F364L/R365I/A366K/L368A/K369E/ L370I/E372D/D377A/A381D/W387Y/N388K/A393K/D394A/ I396V/A397D/K399T/A400T/D401S/F402L/A403E/ S404E/K407Q/A409V/E411T/K412H/G413S/V415P/ T416V/A417-/S418-/ L419M/S420Q/M426V/S429T/V434I/S437R/L438- | t279c/a510t/t552c/ t735c/t1185c/t1224c | 2N3/70I71/131G132 |
| 85 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ | t279c/a510t/c885t/ c894t/a903g/a906t/ c912t/g915a/ a921g/c924t/c927t/ t936c/t954c/g1035t/ | 2Y3/70I71/131G132 |

TABLE 3-1-continued

Improved Xylose Isomerase Variants

| Var. No. | FI | Active Mutations | Silent Mutations | Insertions wrt RF.XI.4 |
|---|---|---|---|---|
| | | R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/F162Y/S163A/ Q166K/K169N/E172D/S173A/V175I/N180K/N198D/ M199L/V299P | t1038a | |
| 86 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/T236M/T244A/V299P/L300N/N311D/I312V/ Y313H/D314S/T315A/M317L/C318A/Y320L/I323L/ A339V/T345E/P346F/E347D/F350A/S352G/A359T/F364L/ R365I/A366K/L368A/K369E/L370I/E372D/D377A/ A381D/W387Y/N388K/A393K/D394A/I396V/A397D/ K399T/A400T/D401S/F402L/A403E/S404E/K407Q/A409V/ E411T/K412H/G413S/V415P/T416V/A417-/S418-/ L419M/S420Q/M426V/S429T/V434I/S437R/L438- | t279c/a510t/g1023a/ t1185c/t1224c | 2N3/70I71/131G132 |
| 87 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61V/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ V183A/N198D/M199L/S219A/I220N/D257E/N311D/I312V/ Y313H/D314S/T315A/M317L/C318A/Y320L/I323L/ A339V/T345E/P346F/E347D/F350A/S352G/A359T/F364L/ R365I/A366K/L368A/K369E/L370I/E372D/D377A/ A381D/W387Y/N388K/A393K/D394A/I396V/A397D/ K399T/A400T/D401S/F402L/A403E/S404E/K407Q/A409V/ E411T/K412H/G413S/V415P/T416V/A417-/S418-/ L419M/S420Q/M426V/S429T/V434I/S437R/L438- | t279c/t483c/a510t/ a567g/a1029t/t1185c/ t1224c | 2N3/70I71/131G132 |
| 88 | ≥1.0 | E372G | c138a/t150a/g783a/ t1143g/c1146t/ c1155a/t1263a/a1269g | |
| 89 | ≥1.0 | S5K/G8S/Q11P/Q13E/P15K/K16D/D19N/S22A/E29D/N33D/ T36K/E39D/H40I/L41M/T64A/Q70E/S71N/D89Q/ Y96F/A112D/D115A/E126A/G129A/D130E/K131T/F132L/ N180T/N198D/M199L/S219A/I220N/T236M/G249A/ D257E/Q273G/Q277E/R281A/V282M/D285V/V288A/I292V/ N311D/I312V/Y313H/D314S/T315A/M317L/C318A/ Y320L/I323L/A339V/T345E/P346F/E347D/F350A/S352G/ A359T/F364L/R365I/A366K/L368A/K369E/L370I/ E372D/D377A/A381D/W387Y/N388K/A393K/D394A/ I396V/A397D/K399T/A400T/D401S/F402L/A403E/S404E/ K407Q/A409V/E411T/K412H/G413S/V415P/T416V/ A417-/S418-/ L419M/S420Q/M426V/S429T/V434I/S437R/L438- | a27g/c30a/t42c/c51t/ a54c/t60a/g63a/ t69c/a72g/t75c/ t78c/g114a/a126g/ c129t/c133t/a135g/ c138t/c147t/ t156a/c159t/c177t/ a180c/c195t/c201a/ t207c/c216t/ g222t/a225t/g234a/ c237t/t249c/t252a/ c255t/t261c/ c271t/g273a/a274t/ g275c/c306t/c307t/ t309g/a318g/ t321c/c324t/c327t/ a333g/c339a/ t342c/c349t/t360c/ t366c/g381a/g384a/ g399a/t403c/ a405t/c411t/a420g/ t426c/t429c/c432t/ c435a/g438a/ a453t/a456t/a466t/ g467c/t468a/c471g/ t477c/t483a/ t486c/t489a/g495t/ a501c/a510t/t511c/ a513g/c534t/t537a/ t1185c/t1224c | 131G132 |

TABLE 3-1-continued

Improved Xylose Isomerase Variants

| Var. No. | FI | Active Mutations | Silent Mutations | Insertions wrt RF.XI.4 |
|---|---|---|---|---|
| 90 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61G/G62T/T64M/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ N198D/M199L/Q273G/Q277E/R281A/V282M/D285V/ V288A/I292V/V299P/L300N/N311D/I312V/Y313H/D314S/ T315A/M317L/C318A/Y320L/I323L/F328L/A339V/ T345E/P346F/E347D/F350A/S352G/A359T/F364L/R365I/ A366E/L368A/K369E/L370I/W387Y/N388K/A393K/ D394A/I396V/A397D/K399T/A400T/D401S/F402L/A403E/ S404E/K407Q/A409V/E411T/K412H/G413S/V415P/ T416V/A417-/S418-/ L419M/S420Q/M426V/S429T/V434I/S437R/L438* | t279c/a510t/t1185c/ t1224c | 2N3/70I71/131G132 |
| 91 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61G/G62T/T64M/K66R/W68Y/Q70N/S71T/A74M/ A75E/R76H/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ V288M/F289L/I292V | t279c/a510t/c600a/ t601c/a603t/c607t/ c625t/a627g/ a642t/a645g/c648t/ a1194c/c1200t | 2N3/70I71/131G132 |
| 92 | ≥1.0 | E2K/F3Y/S5P/I7V/G8P/K9E/I10V/Q11K/Q13E/K16N/D19N/ L21F/S22A/N27D/P28A/E29N/E30K/I32V/N33A/ R38K/L41C/K42R/M51L/G52C/G53A/D54G/T56A/M58P/ C61G/G62T/T64V/K66R/W68Y/Q70N/S71T/A74M/ A75E/R76L/A84G/I87L/D89T/S92G/D94E/Y95F/Y96F/ R101A/L103I/S104A/Y107G/G108D/S109T/L110F/K111E/ A112E/T113S/N114K/D115K/Q116N/D118F/I119E/ V120I/T121V/Q128M/G129D/D130Q/K131T/F132I/C134L/ K140N/C141N/D143S/G152S/P155C/S156N/F162Y/ S163A/Q166K/K169N/E172D/S173A/V175I/N180K/ K253Q/Q273G/T275S | t279c/a510t/a663t/ a1054t/g1055c/ a1194c/c1200t | 2N3/70I71/131G132 |

The DNA and amino acid sequences of xylose isomerase variants 2, 3, 42, 48, 56, and 62 are provided below.

Variant No 2:
(SEQ ID NO: 22)
ATGAGTGAATTGTTCCAAAACATCCCAAAAATCAAATACGAAAGTGCA

AATTCCAAAAATCCTTTGGCTTTTCATTATTATGATGCTGAAAAAATA

GTCCTCGGTAAGACCATGAAGGAGCATTTGCCATTCGCTATGGCATGG

TGGCACAATTTGTGTGCCGCTGGTACTGATATGTTCGGACGTGATACT

GCGGACAAGTCCCTTGGTTTGGAAAAAGGCTCAATGGAACATGCTAAG

GCCAAAGTTGATGCTGGTTTCGAATTTATGGAAAAGCTGGGCATTAAA

TACTTCTGCTTCCATGATGTAGACCTTGTTCCAGAAGCTTGCGACATT

AAAGAGACCAATTCTCGACTGGACGAAATTTCTGATTACATCTTGGAG

AAGATGAAGGGCACTGATATTAAGTGTTTATGGGGCACTGCTAATATG

TTTTCTAACCCCAGGTTCGTGAACGGTGCAGGATCTACTAATAGTGCC

GATGTTTACTGTTTTGCTGCTGCGCAAATAAAGAAAGCATTAGATATT

ACCGTCAAGTTGGGCGGTAGAGGTTATGTCTTTTGGGGTGGTAGAGAA

GGTTACGAGACCCTGCTGAATACTAACGTTGGCTTAGAACTGGACAAC

ATGGCTAGGCTAATGAAGATGGCCGTAGAATACGGTAGGTCTATTGGA

TTCAAAGGTGACTTCTACATCGAGCCTAAACCCAAGGAACCTGCAAAG

CACCAGTACGACTTCGACACTGCTACCGTATTAGGTTTTTTAAGGAAG

TACGGGTTGGATAAAGACTTCAAGATGAACATCGAAGCCAATCACGCC

ACACTAGCAGGACACTCATTCCAGCATGAGTTACGTATTTCTAGTATT

AACGGTATGTTGGGTTCTGTTGATGCTAACCAAGGTGACATGTTGTTA

GGATGGGACACGGATGAATTTCCCTTTGACGTTTATGATACTACTATG

TGTATGTATGAGGTCCTTAAAAACGGTGGTTTGACAGGCGGCTTTAAC

TTTGATGCGAAAAATCGTAGGCCTTCATACACGTATGAAGATATGTTC

TATGGTTTCATTCTTGGTATGGATTCTTTCGCGTTAGGGTTTAGAGCA

GCTCTTAAATTGATTGAAGACGGTAGAATTGACAAGTTTGTGGCTGAC

AGGTATGCCTCTTGGAATACCGGTATTGGTGCAGATATTATTGCCGGA

AAAGCCGATTTTGCATCATTGGAAAAAATATGCTTTGGAAAAAGGTGAA

GTTACCGCGTCATTGTCTTCTGGTAGACAAGAGATGCTGGAATCTATT

GTCAACAACGTATTGTTTAGTTTGTAA (SEQ ID NO: 23)
MSELFQNIPKIKYESANSKNPLAFHYYDAEKIVLGKTMKEHLPFAMAW

WHNLCAAGTDMFGRDTADKSLGLEKGSMEHAKAKVDAGFEFMEKLGIK

YFCFHDVDLVPEACDIKETNSRLDEISDYILEKMKGTDIKCLWGTANM

FSNPRFVNGAGSTNSADVYCFAAAQIKKALDITVKLGGRGYVFWGGRE

GYETLLNTNVGLELDNMARLMKMAVEYGRSIGFKGDFYIEPKPKEPAK

HQYDFDTATVLGFLRKYGLDKDFKMNIEANHATLAGHSFQHELRISSI

NGMLGSVDANQGDMLLGWDTDEFPFDVYDTTMCMYEVLKNGGLTGGFN

FDAKNRRPSYTYEDMFYGFILGMDSFALGFRAALKLIEDGRIDKFVAD

RYASWNTGIGADIIAGKADFASLEKYALEKGEVTASLSSGRQEMLESI

VNNVLFSL

Variant No 3:

(SEQ ID NO: 24)
ATGGAATTTTTCAAGAACATCTCTAAGATACCATACGAAGGCAAAGAC

TCTACCAATCCATTAGCATTCAAGTACTACAATCCTGACGAAGTAATC

GACGGTAAGAAGATGAGAGACATCATGAAGTTTGCTTTGTCTTGGTGG

CATACTATGGGAGGTGATGGTACTGATATGTTTGGCTGTGGTACTGCT

GATAAGACATGGGCGAGAATGATCCAGCTGCTAGAGCTAAAGCTAAA

GTTGATGCCGCATTTGAAATCATGCAGAAGTTATCCATTGATTACTTC

TGCTTCCATGATAGAGATTTGTCTCCAGAGTACGGTTCTTTGAAGGAC

ACAAACGCTCAATTGGACGTTGTCACTGACTACATCAAGGCTAAACAA

GCTGAAACCGGTTTGAAATGTCTTTGGGGTACTGCTAAGTGCTTCGAC

CATCCAAGATTCATGCACGGTGCTGGTACTTCTCCTTCAGCGGATGTC

TTCGCATTCTCAGCTGCTCAAATCAAGAAAGCTCTGGAATCTACCGTC

AAGTTGGGTGGAACTGGTTATGTCTTTTGGGGTGGTAGAGAAGGTTAC

GAGACCCTGCTGAATACTAACATGGGCTTAGAACTGGACAACATGGCT

AGGCTAATGAAGATGGCCGTAGAATACGGTAGGGCTAATGGATTCAAA

GGTGACTTCTACATCGAGCCTAAACCCAAGGAACCAACTAAGCATCAA

TACGACTTTGACACTGCTACAGTCTTGGGCTTTCTGAGAAAGTACGGC

CTGGACAAAGACTTCAAGATGAACATCGAACCCAATCACACCACACTA

GCAGGACACTCATTCGAGCATGAGTTAGCTATGGCTAGGGTAAACGGT

GCATTCGGTTCTGTTGATGCTAACCAAGGTGACGTATTGTTAGGATGG

GACACGGGTCAATTCCCCACAGACGTTCATTCTGCTACTCTTGCTATG

CTGGAGGTCTTGAAAGCCGGTGGTTTCACAAATGCGGCCTGAACTTT

GATGCGAAAGCTCGTAGGGGTTCATTCGAGTTTGACGATATTGCCTAT

GGTTACATTGCTGGTATGGATACTTTCGCGTTAGGGTTAATTAAAGCT

GCTGAAATCATTGATGACGGTAGAATTGCCAAGTTTGTGGATGACAGG

TATGCCTCTTACAAGACCGGTATTGGTAAAGCGATCGTTGACGGAACT

ACCTCTTTGGAAGAATTGGAACAATACGTGTTGACTCATTCTGAACCT

GTCATGCAATCTGGTGGACAAGAGGTTCTGGAAACTATTGTCAACAAC

GTATTGTTTAGATAA (SEQ ID NO: 25)
MEFFKNISKIPYEGKDSTNPLAFKYYNPDEVIDGKKMRDIMKFALSWW

HTMGGDGTDMFGCTADKTWGENDPAARAKAKVDAAFEIMQKLSIDYF

CFHDRDLSPEYGSLKDTNAQLDVVTDYIKAKQAETGLKCLWGTAKCFD

HPRFMHGAGTSPSADVFAFSAAQIKKALESTVKLGGTGYVFWGGREGY

ETLLNTNMGLELDNMARLMKMAVEYGRANGFKGDFYIEPKPKEPTKHQ

YDFDTATVLGFLRKYGLDKDFKMNIEPNHTTLAGHSFEHELAMARVNG

AFGSVDANQGDVLLGWDTGQFPTDVHSATLAMLEVLKAGGFTNGGLNF

DAKARRGSFEFDDIAYGYIAGMDTFALGLIKAAEIIDDGRIAKFVDDR

YASYKTGIGKAIVDGTTSLEELEQYVLTHSEPVMQSGGQEVLETIVNN

VLFR

Variant No 42:

(SEQ ID NO: 26)
ATGAAGAACTATTTCCCCAACGTCCCAGAAGTCAAATACGAAGGTCCA

AACTCCACAAATCCTTTCGCTTTTAAATATTATGATGCTAATAAAGTA

GTCGCCGGTAAGACCATGAAGGAGCATTGTAGATTCGCTCTATCCTGG

TGGCACACTTTGTGTGCCGGTGGTGCTGATCCATTCGGAGTAACTACT

ATGGACAGGACCTACGGTAACATTACCGACCCAATGGAACTAGCTAAG

GCCAAAGTTGATGCTGGTTTCGAACTGATGACTAAGCTGGGCATCGAG

TTCCTGCTTCCATGATGCCGACATTGCTCCAGAAGGTGACACCTTC

GAAGAGTCCAAGAAGAATCTGTTCGAGATTGTTGATTACATCAAGGAG

AAGATGGACCAAACCGGCATCAAGTTGTTATGGGGCACTGCTAACAAC

TTTAGTCACCCCAGGTTCATGCACGGTGCAGGAACTTCTCCTAGTGCC

GATGTTTTCGCTTATGCTGCTGCGAAAATAAAGAACGCTTTAGATGCG

ACCATCAAGTTGGGCGGTAGAGGTTATGTCTTTTGGGGTGGTAGAGAA

GGTTACGAGACCCTGCTGAATACTAACATGGGCTTAGAACTGGACAAC

ATGGCTAGGTTGATGAAGATGGCCGTTGAGTATGGTAGGTCTATTGGA

TTCAAAGGTGACTTCTACATCGAGCCTAAACCCAAGGAACCTATGAAG

CACCAGTACGACTTCGACACTGCTACCGTATTAGGTTTTTTAAGGCAG

TACGGGTTGGATAAAGACTTCAAATTGAACATCGAAGCCAATCACGCC

ACACTAGCAGGACACTCATTCCAGCATGAGTTACGTATTTCTAGTATT

AACGGTATGTTGGGTTCTGTTGATGCTAACCAAGGTGACGTATTGTTA

GGATGGGACACGGATCAATTCCCCACAAACATTTATGATACTACTATG

TGTATGTATGAGGTCATTAAAGCCGGTGGTTTCACAAATGCGGCCTG

AACTTTGATGCTAAAGCTAGAAGAGGTTCATTCACGCCTGAAGATATT

TTCTATTCTTACATTGCTGGTATGGATGCTTTCGCGTTAGGGTTTAGA

GCAGCTCTTAAATTGATTGAAGACGGTAGAATTGACAAGTTTGTGGCT

GACAGGTATGCCTCTTGGAATACCGGTATTGGTCAGATATTATTGCC

GGAAAAGCCGATTTTGCATCATTGGAAAAATATGCTTTGGAGAAAGGA

-continued

GAGGTTACCGCGTCATTGTCTTCTGGTAGACAAGAGATGCTGGAATCT

ATTGTCAACAACGTATTGTTTAGTTTGTAA (SEQ ID NO: 27)
MKNYFPNVPEVKYEGPNSTNPFAFKYYDANKVVAGKTMKEHCRFALSW

WHTLCAGGADPFGVTTMDRTYGNITDPMELAKAKVDAGFELMTKLGIE

FFCFHDADIAPEGDTFEESKKNLFEIVDYIKEKMDQTGIKLLWGTANN

FSHPRFMHGAGTSPSADVFAYAAAKIKNALDATIKLGGRGYVFWGGRE

GYETLLNTNMGLELDNMARLMKMAVEYGRSIGFKGDFYIEPKPKEPMK

HQYDFDTATVLGFLRQYGLDKDFKLNIEANHATLAGHSFQHELRISSI

NGMLGSVDANQGDVLLGWDTDQFPTNIYDTTMCMYEVIKAGGFTNGGL

NFDAKARRGSFTPEDIFYSYIAGMDAFALGFRAALKLIEDGRIDKFVA

DRYASWNTGIGADIIAGKADFASLEKYALEKGEVTASLSSGRQEMLES

IVNNVLFSL

Variant No 48:
(SEQ ID NO: 28)
ATGAAGAACTATTTCCCCAACGTCCCAGAAGTCAAATACGAAGGTCCA

AACTCCACAAATCCTTTCGCTTTTAAATATTATGATGCTAATAAAGTA

GTCGCCGGTAAGACCATGAAGGAGCATTGTAGATTCGCTCTATCCTGG

TGGCACACTTTGTGTGCCGGTGGTGCTGATCCATTCGGAGTAACTACT

ATGGACAGGACCTACGGTAACATTACCGACCCAATGGAACTAGCTAAG

GCCAAAGTTGATGCTGGTTTCGAACTGATGACTAAGCTGGGCATCGAG

TTCTTCTGCTTCCATGATGCCGACATTGCTCCAGAAGGTGACACCTTC

GAAGAGTCCAAGAAGAATCTGTTCGAGATTGTTGATTACATCAAGGAG

AAGATGGACCAAACCGGCATCAAGTTGTTATGGGGCACTGCTAACAAC

TTTAGTCACCCCAGGTTCATGCACGGTGCATCAACTTCTTGTAATGCC

GATGTTTTCGCTTATGCTGCTGCGAAAATAAAGAACGCTTTAGGTGCG

ACCATCAAGTTGGGCGGTAGAGGTTATGTCTTTTGGGGTGGTAGAGAA

GGATATGAAACGTTGTTGAATACTAACATGGGACTTGAATTGGACAAC

ATGGCTAGGTTGATGAAGATGGCCGTTGAGTATGGTAGGTCTATTGGT

TTCAAAGGTGACTTCTACATCGAGCCTAAACCCAAGGAACCTACTAAG

CACCAGTACGACTTCGACGCTGCTACCGCAATAGGTTTTTTAAGGCAG

TACGGGTTGGACAAAGACTTCAAATTGAACATCGAAGCCAATCACGCC

ACACTAGCAGGACACTCATTCCAGCATGAGTTACGTATTTCTAGTATT

AACGGTATGTTGGGTTCTGTTGATGCTAACCAAGGTGACCCAAACTTA

GGATGGGACACGGATCAATTCCCCACAGACGTTCATTCTGCTACTCTT

GCTATGCTGGAGGTCTTGAAAGCCGGTGGTTTCACAAATGGCGGCCTG

AACTTTGATGCGAAAGTTCGTAGGGGTTCATTCGAGTTTGACGATATT

GCCTATGGTTACATTGCTGGTATGGATGCTTTCGCGTTAGGGTTAATT

AAAGCTGCTGAAATCATTGATGACGGTAGAATTGCCAAGTTTGTGGAT

GACAGGTATGCCTCTTACAAGACCGGCATTGGTAAAGCGATCGTTGAC

GGAACTACCTCTTTGGAAGAATTGGAACAATACGTGTTGACTCATTCT

-continued

GAACCTGTCATGCAATCTGGTAGACAAGAGGTTCTGGAAACTATTGTC

AACAACATATTGTTTAGATAA (SEQ ID NO: 29)
MKNYFPNVPEVKYEGPNSTNPFAFKYYDANKVVAGKTMKEHCRFALSW

WHTLCAGGADPFGVTTMDRTYGNITDPMELAKAKVDAGFELMTKLGIE

FFCFHDADIAPEGDTFEESKKNLFEIVDYIKEKMDQTGIKLLWGTANN

FSHPRFMHGASTSCNADVFAYAAAKIKNALGATIKLGGRGYVFWGGRE

GYETLLNTNMGLELDNMARLMKMAVEYGRSIGFKGDFYIEPKPKEPTK

HQYDFDAATAIGFLRQYGLDKDFKLNIEANHATLAGHSFQHELRISSI

NGMLGSVDANQGDPNLGWDTDQFPTDVHSATLAMLEVLKAGGFTNGGL

NFDAKVRRGSFEFDDIAYGYIAGMDAFALGLIKAAEIIDDGRIAKFVD

DRYASYKTGIGKAIVDGTTSLEELEQYVLTHSEPVMQSGRQEVLETIV

NNILFR

Variant No 56:
(SEQ ID NO: 30)
ATGAAGAACTATTTCCCCAACGTCCCAGAAGTCAAATACGAAGGTCCA

AACTCCACAAATCCTTTCGCTTTTAAATATTATGATGCTAATAAAGTA

GTCGCCGGTAAGACCATGAAGGAGCATTGTAGATTCGCTCTATCCTGG

TGGCACACTTTGTGTGCCGGTGGTGCTGATCCATTCGGAGTAACTACT

ATGGACAGGACCTACGGTAACATTACCGACCCAATGGAACTAGCTAAG

GCCAAAGTTGATGCTGGTTTCGAACTGATGACTAAGCTGGGCATCGAG

TTCTTCTGCTTCCATGATGCCGACATTGCTCCAGAAGGTGACACCTTC

GAAGAGTCCAAGAAGAATCTGTTCGAGATTGTTGATTACATCAAGGAG

AAGATGGACCAAACCGGCATCAAGTTGTTATGGGGCACTGCTAACAAC

TTTAGTCACCCCAGGTTCATGCACGGTGCAGGAACTTCTTGTAATGCC

GATGTTTTCGCTTATGCTGCTGCGAAAATAAAGAACGCTTTAGATGCG

ACCATCAAGTTGGGCGGTAGAGGTTATGTCTTTTGGGGTGGTAGAGAA

GGTTACGAGACCCTGCTGAATACTAACATGGGCTTAGAACTGGACAAC

ATGGCTAGGCTAATGAAGATGGCCGTAGAATACGGTAGGTCTATTGGA

TTCAAAGGTGACTTCTACATTGAACCTAAACCCAAGGAACCTACTAAG

CACCAGTACGACTTCGACACTGCTACCGTATTAGGTTTTTTAAGGAAG

TACGGGTTGGATAAAGACTTCAAGATGAACATCGAAGCCAATCACGCC

ACACTAGCAGGACACTCATTCCAGCATGAGTTACGTGTGGCTAGGGAT

AACGGTGTATTCGGTTCTATTGATGCTAACCAAGGTGACGTATTGTTA

GGATGGGACACGGATCAATTCCCCACAAACATTTATGATACTACTATG

TGTATGTATGAGGTCATTAAAGCCGGCGGTTTCACAAATGGCGGCCTG

AACTTTGATGCGAAAGCTCGTAGGGGTTCATTCACGCCTGAAGATATT

TTCTATAGTTACATTGCTGGTATGGATGCTTTCGCGTTAGGGTTTAGA

GCAGCTCTTAAATTGATTGAAGACGGTAGAATTGACAAGTTTGTGGCT

GACAGGTATGCCTCTTGGAATACCGGTATTGGTGCAGATATTATTGCC

GGAAAAGCCGATTTTGCATCATTGGAAAAATATGCTTTGGAAAAAGGT

GAAGTTGCCGCGTCATTGTCTTCTGGTAGACAAGAGATGCTGGAATCT

ATTGTCAACAACGTATTGTTTAGTTTGTAA (SEQ ID NO: 31)
MKNYFPNVPEVKYEGPNSTNPFAFKYYDANKVVAGKTMKEHCRFALSW

WHTLCAGGADPFGVTTMDRTYGNITDPMELAKAKVDAGFELMTKLGIE

FFCFHDADIAPEGDTFEESKKNLFEIVDYIKEKMDQTGIKLLWGTANN

FSHPRFMHGAGTSCNADVFAYAAAKIKNALDATIKLGGRGYVFWGGRE

GYETLLNTNMGLELDNMARLMKMAVEYGRSIGFKGDFYIEPKPKEPTK

HQYDFDTATVLGFLRKYGLDKDFKMNIEANHATLAGHSFQHELRVARD

NGVFGSIDANQGDVLLGWDTDQFPTNIYDTTMCMYEVIKAGGFTNGGL

NFDAKARRGSFTPEDIFYSYIAGMDAFALGFRAALKLIEDGRIDKFVA

DRYASWNTGIGADIIAGKADFASLEKYALEKGEVAASLSSGRQEMLES

IVNNVLFSL

Variant No 62:
(SEQ ID NO: 32)
ATGAAGAACTATTTCCCCAACGTCCCAGAAGTCAAATACGAAGGTCCA

AACTCCACAAATCCTTTCGCTTTTAAATATTATGATGCTAATAAAGTA

GTCGCCGGTAAGACCATGAAGGAGCATTGTAGATTCGCTCTATCCTGG

TGGCACACTTTGTGTGCCGGTGGTGCTGATCCATTCGGAGTAACTACT

ATGGACAGGACCTACGGTAACATTACCGACCCAATGGAACATGCTAAG

GCCAAAGTTGATGCTGGTTTCGAACTGATGACTAAGCTGGGCATCGAG

TTCTTCTGCTTCCATGATGCCGACATTGCTCCAGAAGGTGACACCTTC

GAAGAGTCCAAGAAGAATCTGTTCGAGATTGTTGATTACATCAAGGAG

AAGATGGACCAAACCGGCATCAAGTTGTTATGGGGCACTGCTAACAAC

TTTAGTCACCCCAGGTTCATGCACGGTGCATCAACTTCTTGTAATGCC

GATGTTTTCGCTTATGCTGCTGCGAAAATAAAGAACGCTCTAGATGCG

ACCATCAAGTTGGGCGGTAAGGGTTATGTCTTTTGGGGTGGTAGAGAA

GGTTACGAGACCCTGCTGAATACTAACATGGGCTTAGAACTGGACAAC

ATGGCTAGGCTAATGAAGATGGCCGTAGAATACGGTAGGTCTATTGGA

TTCGACGGTGACTTCTACATCGAGCCTAAACCCAAGGAACCTACTAAG

CACCAGTACGACTTCGACACTGCTACCGTATTAGGTTTTTTAAGGAAG

TACGGGTTGGATAAAGACTTCAAGATGAACATCGAAGCCAATCACGCC

ACACTAGCAGGACACTCATTCCAGCATGAGTTACGTATTTCTAGTATT

AACGGTATGTTGGGTTCTGTTGATGCTAACCAAGGTGACATGTTGTTA

GGATGGGACACGGATCAATTCCCCACAAACATTTATGATACTACTATG

TGTATGTATGAGGTCATTAAAGCCGGTGGTTTCACAAATGGCGGCCTG

AACTTTGATGCGAAAGCTCGTAGAGGTTCTTTCACTCCAGAAGATATT

TTCTATTCTTACATTGCTGGTATGGATGCTTTCGCGTTAGGGTTTAGG

GCAGCTCTTAAATTGATTGAAGACGGTAGAATTGACAAGTTTGTGGCT

GACAGGTATGCCTCTTGGAATACCGGTATTGGTGCAGATATTATTGCC

GGAAAAGCCGATTTTGCATCATTGGAAAAATATGCTTTGGAAAAAGGT

GAAGTTACCGCGTCATTGTCTTCTGGTAGACAAGAGATGCTGGAATCT

ATTGTCAACAACGTATTGTTTAGTTTGTAA (SEQ ID NO: 3)
MKNYFPNVPEVKYEGPNSTNPFAFKYYDANKVVAGKTMKEHCRFALSW

WHTLCAGGADPFGVTTMDRTYGNITDPMEHAKAKVDAGFELMTKLGIE

FFCFHDADIAPEGDTFEESKKNLFEIVDYIKEKMDQTGIKLLWGTANN

FSHPRFMHGASTSCNADVFAYAAAKIKNALDATIKLGGKGYVFWGGRE

GYETLLNTNMGLELDNMARLMKMAVEYGRSIGFDGDFYIEPKPKEPTK

HQYDFDTATVLGFLRKYGLDKDFKMNIEANHATLAGHSFQHELRISSI

NGMLGSVDANQGDMLLGWDTDQFPTNIYDTTMCMYEVIKAGGFTNGGL

NFDAKARRGSFTPEDIFYSYIAGMDAFALGFRAALKLIEDGRIDKFVA

DRYASWNTGIGADIIAGKADFASLEKYALEKGEVTASLSSGRQEMLES

IVNNVLFSL

Example 4

Fermentation Activity of Improved Xylose Isomerase Genes

Improved xylose isomerase variant numbers 42, 48, 56, and 62, were transformed into *S. cerevisiae* BY474, using methods known in the art. Single colonies of transformed strains were used to inoculate 400 ul of YPD medium containing 1 mM $MgSO_4$ and 200 ug/ml G418. The cultures were grown at 30° C. for 72 hrs at 250 rpm. Forty μl of the saturated cultures were used to inoculate 400 ul of YPD containing 2% xylose supplemented with 1 mM $MgSO_4$ and 200 ug/ml of G418. The cultures were grown at 30° C. for 48 hrs with 250 rpm shaking. At 48 hrs, the cells were spun down at 22° C. for 10 mins.

Figure 3:
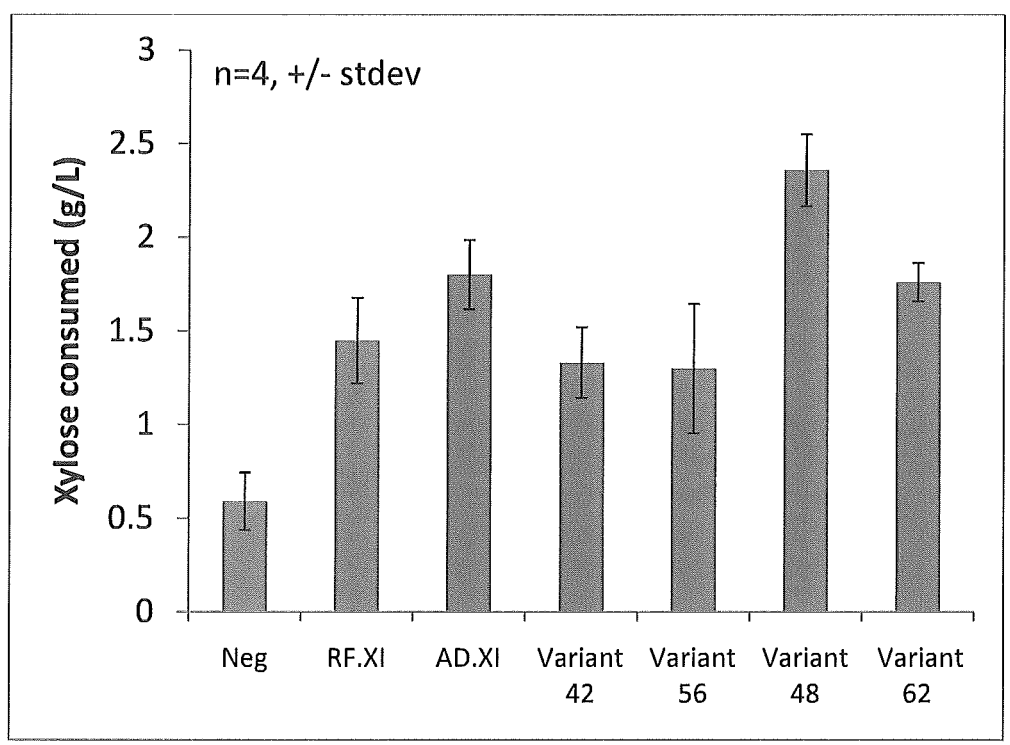
FIG. 3 provides a graph showing the total xylose consumed at the end of 120 hours fermentation by some of the chimeric xylose isomerases provided herein, in comparison with RF_XI and AD_XI wild-type enzymes.

To assay for fermentation, cells were re-suspended in 400 ul of defined medium (55 g/L glucose, 28 g/L xylose, 2.8 g/L arabinose, 1.3 g/L galactose, 0.9 g/L mannose, 4.1g/L acetic acid, 1.1g/L fiurfural, 3 g/L potassium phosphate, 5 g/L ammonium sulphate, 0.5 g/L magnesium sulphate, 100 mM MES buffer, pH 5.5; trace elements and vitamins solution [0.05 g/L biotin, 1g/L pantothenate; 1g/L nicotinic acid, 1g/L myo-inositol, 1g/L thiamine hydrochloride 1g/L, pyridoxal hydrochloride, and 0.2 g/L p-aminobenzoic acid) supplemented with 1 mM $MgSO_4$ and 200 ug/ml of G418. The plates were sealed with mats and incubated at 30° C. with 160 rpm shaking. At 120 hrs, the cells were harvested and the residual sugars and ethanol in the supernatant were measured by HPLC using methods known in the art (See e.g., DuPont et al., Carbohydr. Polym., 68:1-16 [2007], incorporated herein by reference). In some experiments, the residual xylose in the supernatant was measured using a spectrophotometric assay (Megazyme xylose assay; Cat no. K-XYLOSE) performed according to the manufacturer's protocol. FIG. 3 shows the total xylose consumed for some of the chimeric xylose isomerases compared to RF_XI and AD_XI.

While particular embodiments of the present invention have been illustrated and described, it will be apparent to those skilled in the art that various other changes and modifications can be made without departing from the spirit and scope of the present invention. Therefore, it is intended that the present invention encompass all such changes and modifications with the scope of the present invention.

The present invention has been described broadly and generically herein. Each of the narrower species and subgeneric groupings falling within the generic disclosure also form part(s) of the invention. The invention described herein suitably may be practiced in the absence of any element or elements, limitation or limitations which is/are not specifically disclosed herein. The terms and expressions which have been employed are used as terms of description and not of limitation. There is no intention that in the use of such terms and expressions, of excluding any equivalents of the features described and/or shown or portions thereof, but it is recognized that various modifications are possible within the scope of the claimed invention. Thus, it should be understood that although the present invention has been specifically disclosed by some preferred embodiments and optional features, modification and variation of the concepts herein disclosed may be utilized by those skilled in the art, and that such modifications and variations are considered to be within the scope of this invention.

We claim:

1. An isolated chimeric xylose isomerase variant comprised of at least two xylose isomerase fragments obtained from *Ruminococcus* and *Clostridium*, wherein said chimeric xylose isomerase fragments comprise at least a portion of SEQ ID NOS:2, 4, and 8, wherein said variant comprises at least one insertion set selected from 131G132/436G437; 1S2/69L70/127M128/436G437; 2N3/69L70/127M128/436G437; 2S3/70I71/131G132; 2Y3/70I71/131G132, wherein the positions are numbered by correspondence with the amino acid sequence set forth in SEQ ID NO:2, and further, wherein said xylose isomerase variant has xylose isomerase activity.

* * * * *